United States Patent
Kawaminami et al.

(10) Patent No.: US 8,669,246 B2
(45) Date of Patent: Mar. 11, 2014

(54) SUBSTITUTED AMIDE COMPOUND

(75) Inventors: Eiji Kawaminami, Tokyo (JP);
Tatsuhisa Takahashi, Tokyo (JP);
Takatoshi Kanayama, Tokyo (JP); Yuta Fukuda, Tokyo (JP); Hiroyuki Kaizawa, Tokyo (JP); Yutaka Kondoh, Tokyo (JP); Ryushi Seo, Tokyo (JP);
Kazuyuki Kuramoto, Tokyo (JP);
Kazuhiko Take, Tsukuba (JP);
Kazuyuki Sakamoto, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/498,159

(22) PCT Filed: Sep. 24, 2010

(86) PCT No.: PCT/JP2010/066572
§ 371 (c)(1),
(2), (4) Date: Mar. 26, 2012

(87) PCT Pub. No.: WO2011/037192
PCT Pub. Date: Mar. 31, 2011

(65) Prior Publication Data
US 2012/0184521 A1 Jul. 19, 2012

(30) Foreign Application Priority Data
Sep. 25, 2009 (JP) ................. 2009-220316

(51) Int. Cl.
| | |
|---|---|
| A61K 31/341 | (2006.01) |
| A61K 31/381 | (2006.01) |
| A61K 31/401 | (2006.01) |
| A61K 31/415 | (2006.01) |
| C07D 207/34 | (2006.01) |
| C07D 213/81 | (2006.01) |
| C07D 263/34 | (2006.01) |
| C07D 277/56 | (2006.01) |
| C07D 307/68 | (2006.01) |
| C07D 333/38 | (2006.01) |
| C07D 417/12 | (2006.01) |

(52) U.S. Cl.
USPC ......... 514/210.2; 514/227.8; 514/230.5; 514/252.13; 514/274; 514/326; 514/58.2; 514/58.7; 514/105; 514/310; 514/369; 546/169; 546/209; 546/269.7; 548/200

(58) Field of Classification Search
None
See application file for complete search history.

(56) References Cited

U.S. PATENT DOCUMENTS

| | | |
|---|---|---|
| 2003/0114505 A1 | 6/2003 | Ueno et al. |
| 2004/0067908 A1 | 4/2004 | Nakade et al. |
| 2005/0256160 A1 | 11/2005 | Habashita et al. |
| 2006/0135577 A1 | 6/2006 | Nakade et al. |
| 2006/0148830 A1 | 7/2006 | Terakado et al. |
| 2007/0149595 A1 | 6/2007 | Tanaka et al. |
| 2008/0207584 A1 | 8/2008 | Habashita et al. |
| 2010/0197749 A1 | 8/2010 | Cowen et al. |

FOREIGN PATENT DOCUMENTS

| | | |
|---|---|---|
| CN | 101370794 A | 2/2009 |
| EP | 1 695 955 A1 | 8/2006 |
| JP | 2009 523774 | 6/2009 |
| WO | 01 60819 | 8/2001 |
| WO | 02 062389 | 8/2002 |
| WO | 03 099765 | 12/2003 |
| WO | 2004 002530 | 1/2004 |
| WO | 2004 031118 | 4/2004 |
| WO | 2005 058790 | 6/2005 |
| WO | 2006 001463 | 1/2006 |
| WO | WO 2010/051053 A1 | 5/2010 |
| WO | WO 2012/039460 A1 | 3/2012 |

OTHER PUBLICATIONS

Hama, K., et al., "Lysophosphatidic acid (LPA) receptors are activated differentially by biological fluids: possible role of LPA—binding proteins in activation of LPA receptors," FEBS Letters, vol. 523, pp. 187-192, (2002).

Kropp, B.P., et al., "Characterization of Cultured Bladder Smooth Muscle Cells: Assessment of In Vitro Contractility," The Journal of Urology, vol. 162, pp. 1779-1784, (Nov. 1999).

(Continued)

Primary Examiner — Kamal Saeed
Assistant Examiner — Ana Z Muresan
(74) Attorney, Agent, or Firm — Oblon, Spivak, McClelland, Maier & Neustadt, L.L.P.

(57) ABSTRACT

A substituted amide compound is useful as an active ingredient of a pharmaceutical composition, in particular a pharmaceutical composition for treating diseases caused by lysophosphatidic acid (LPA). The compound is of a formula:

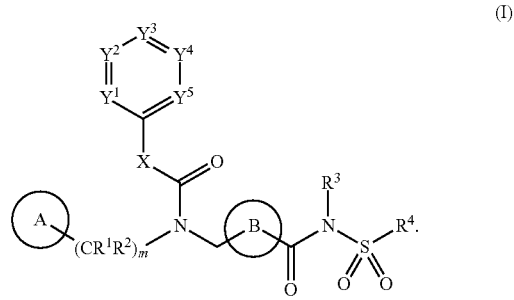

(I)

In this formula, A is an optionally substituted aryl, etc.; B is an optionally substituted 5-membered aromatic hetero ring group; X is a single bond or $-(CR^{X1}R^{X2})_n-$; n is 1, 2, 3, or 4; $R^{X1}$ and $R^{X2}$ are hydrogen, etc.; $Y^1$ to $Y^5$ are each $CR^Y$ or N; each $R^Y$ is hydrogen, etc.; $R^1$ and $R^2$ are hydrogen, etc.; m is 1, 2, or 3; $R^3$ is hydrogen, etc.; and $R^4$ is an optionally substituted lower alkyl, etc.

26 Claims, No Drawings

(56) References Cited

OTHER PUBLICATIONS

Guo, C., et al., "Mitogenic Signaling in Androgen Sensitive and Insensitive Prostate Cancer Cell Lines," The Journal of Urology, vol. 163, pp. 1027-1032, (Mar. 2000).

Allard, J., et al., "A rat G protein-coupled receptor selectively expressed in myelin-forming cells," European Journal of Neuroscience, vol. 10, pp. 1045-1053, (1998).

Weiner, J.A., et al., "Lysophosphatidic Acid Receptor Gene vzg-1/lp$_{A1}$/edg-2 Is Expressed by Mature Oligodendrocytes During Myelination in the Postnatal Murine Brain," The Journal of Comparative Neurology, vol. 398, pp. 587-598, (1998).

Weiner, J.A., et al., "Schwann cell survival mediated by the signaling phospholipid lysophosphatidic acid," Proceedings of the National Academy of Science, vol. 96, pp. 5233-5238, (Apr. 1999).

Inoue, M., et al., "Initiation of neuropathic pain requires lysophosphatidic acid receptor signaling," Nature Medicine, vol. 10, No. 7, pp. 712-718, (Jul. 2004).

Yanase, M., et al., "Lysophosphatidic Acid Enhances Collagen Gel Contraction by Hepatic Stellate Cells: Association with Rho-Kinase," Biochemical and Biophysical Research Communications, vol. 277, No. 1, pp. 72-78, (2000).

Ikeda, H., et al., "Effects of Lysophosphatidic Acid on Proliferation of Stellate Cells and Hepatocytes in Culture," Biochemical and Biophysical Communications, vol. 248, No. 2, pp. 436-440, (1998).

Watanabe, N., et al., "Both Plasma Lysophosphatidic Acid and Serum Autotaxin Levels are Increased in Chronic Hepatitis C," Journal of Clinical Gastroenterology, vol. 41, No. 6, pp. 616-623, (Jul. 2007).

Watanabe, N., et al., "Plasma lysophosphatidic acid level and serum autotaxin activity are increased in liver injury in rats in relation to its severity," Life Sciences, vol. 81, pp. 1009-1015, (2007).

Pradere, J.P., "LPA$_1$ Receptor Activation Promotes Renal Interstitial Fibrosis," Journal of American Society of Nephrology, vol. 18, pp. 3110-3118, (2007).

Tager, A.M., et al., "The lysophosphatidic acid receptor LPA$_1$ links pulmonary fibrosis to lung injury by mediating fibroblast recruitment and vascular leak," Nature Medicine, vol. 14, No. 1, pp. 45-54, (Jan. 2008).

Siess, W., et al., "Lysophosphatidic acid mediates the rapid activation of platelets and endothelial cells by mildly oxidized low density lipoprotein and accumulates in human atherosclerotic lesions," Proceedings of the National Academy of Science, vol. 96, pp. 6931-6936, (Jun. 1999).

Imamura, F., et al., "Induction of In Vitro Tumor Cell Invasion of Cellular Monolayers by Lysophosphatidic Acid or Phospholipase D," Biochemical and Biophysical Research Communications, vol. 193, No. 2, pp. 497-503, (Jun. 15, 1993).

Xu, Y., et al., "Lysophosphatidic Acid as a Potential Biomarker for Ovarian and other Gynecologic Cancers," JAMA, vol. 280, No. 8, pp. 719-723, (Aug. 26, 1998).

Hu, Y.L., et al., "Lysophosphatadic Acid Induction of Vascular Endothelial Growth Factor Expression in Human Ovarian Cancer Cells," Journal of the National Cancer Institute, Nol. 93, No. 10, pp. 762-768, (May 16, 2001).

Kumar, A., et al., "Increased Pro-Nerve Growth Factor and p75 Neurotrophin Receptor Levels in Developing Hypothyroid Rat Cerebral Cortex Are Associated with Enhanced Apoptosis," Endocrinology, vol. 147, No. 10, pp. 4893-4903, (Oct. 2006).

Boucharaba, A., et al., "The type 1 lysophosphatidic acid receptor is a target for therapy in bone metastases," Proceedings of the National Academy of Science, vol. 103, No. 25, pp. 9643-9648, (Jun. 20, 2006).

Jeon, E.S., et al., "Mesenchymal stem cells stimulate angiogenesis in a murine xenograft model of A549 human adenocarcinoma through an LPA1 receptor-dependent mechanism," Biochimica et Biophysica Acta, vol. 1801, pp. 1205-1213, (2010).

International Search Report Issued Nov. 22, 2010 in PCT/JP10/66572 Filed Sep. 24, 2010.

American Urological Association Education and Research, Inc., Guideline on the management of benign prostatic hyperplasia (BPH), (2003).

Zeng et al., Prostate, vol. 69 (2009) pp. 1-10.

Hedlund and Andersson, Scan J Urol Nephrol, vol. 23 (1989) pp. 251-254.

Aoki J., Semin Cell Dev Biol., vol. 15 (2004) pp. 477-489.

Nitti V. W. Reviews in Urology, vol. 7 (2005) pp. S12-S17.

Chang et al., International Journal of Urology, vol. 15 (2008) pp. 981-985.

Boucharaba A. et al., PNAS, vol. 103, No. 25 (2006) pp. 9643-9648.

Pradere et al., J Am Soc Nephrol, vol. 18 (2007) pp. 3110-3118.

Pradere et al., Biochimica et Biophysica Acta 1781, (2008) pp. 582-587.

Tager et al., Nature Medicine, vol. 14, No. 1 (2008) pp. 45-54.

Inoue et al., Nature Medicine, vol. 10 (2004) pp. 1-7.

Ma L. et al., J. Neurochem, vol. 109 (2009) pp. 603-610.

Extended European Search Report issued Feb. 15, 2013, in European Patent Application 10818864.0-1452/2481725 PCT/JP2010/066572, filed Sep. 24, 2010 (with English-language Translation).

International Search Report issued on Dec. 6, 2011, in PCT/JP2011/071635 filed on Sep. 22, 2011.

International Preliminary Report on Patentability and Written Opinion issued Apr. 25, 2013 in PCT/JP2011/071635 filed on Sep. 22, 2011.

Office Action issued Sep. 11, 2013 in Israeli Patent Application No. 218723 (with English-language translation).

Office Action issued Jan. 29, 2013 in Thai Patent Application No. 1201001317 (submitting English Statement of Relevancy).

Office Action issued Apr. 17, 2013 in Mexican Patent Application No. MX/a/2012/003560 (with English language translation).

Combined Office Action and Search Report issued Apr. 19, 2013 in Chinese Patent Application No. 201080042593.8 (with English language translation).

Mexican Office Action issued Jul. 22, 2013 in Patent Application No. MX/a/2012/003560 with English Translation.

SUBSTITUTED AMIDE COMPOUND

TECHNICAL FIELD

The present invention relates to a substituted amide compound which is useful as an active ingredient of a pharmaceutical composition, in particular, a pharmaceutical composition for preventing and/or treating diseases caused by lysophosphatidic acid (hereinafter abbreviated as LPA).

BACKGROUND ART

LPA is a phospholipid, for example, as represented by the following chemical formula, which has a simple structure containing a glycerol unit in which a fatty acid is present at the 1-position or 2-position and a phosphate group is bonded at the 3-position. Examples thereof include 1-acyl LPA, 1-alkyl LPA, 1-alkenyl LPA, 2-acyl LPA, and the like. Further, it has diversity depending on the type of the fatty acid, and may be classified into 18:1-LPA, 18:3-LPA, 16:0-LPA, and the like according to the length of the carbon chain and the degree of unsaturation.

[Chem. 1]

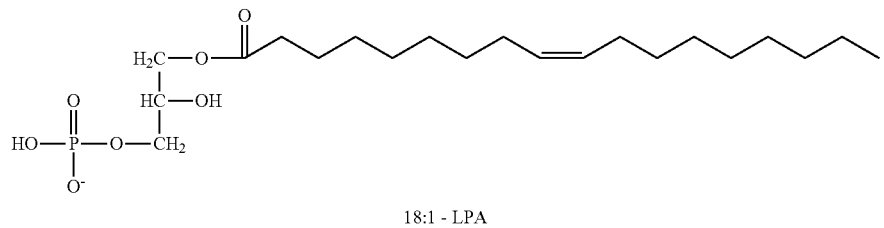

18:1 - LPA

It is known that LPA is produced in various parts of the living body, both inside and outside of the cells, transduces signals into the cell mainly by binding to a G-protein coupled receptor present on the cell surface, and shows various physiological effects. 5 subtypes of LPA receptors are known, LPA1 to LPA5. Among these, three types of receptors, LPA1, LPA2, and LPA3 are also called EDG (Endothelial Differentiation Gene) 2, EDG4, and EDG7, respectively. The LPA receptors subtypes are distributed in various parts in the living body, but the localization tissue varies depending on the subtype, and it is thought that each receptor subtypes are involved in the biological functions of each tissue.

It has been reported that LPA is present in the semen in the lower urinary tract tissue (Non-Patent Document 1), and it has been revealed that LPA induces contraction of isolated urethral and prostate tissue strips in vitro, and increases the urethral pressure in vivo (Patent Document 1).

Furthermore, it has been reported that LPA induces contraction of isolated bladder smooth muscle cells, and LPA also promotes the proliferation of prostate cells obtained from benign prostatic hyperplasia (Non-Patent Documents 2 and 3).

In the nerve cells, LPA1 is highly expressed in oligodendrocytes and Schwann cells in a myelination period, and is expressed in correspondence with the period of myelination (Non-Patent Document 4).

It is also known that in a mouse model with demyelination, the amount of mRNA of LPA1 decreases by about 40% (Non-Patent Document 5).

It has been suggested that LPA inhibits the cell death of Schwann cells and oligodendrocytes, and is involved in the myelination (Non-Patent Document 6).

It has further been reported that LPA and LPA 1 are involved in the expression of neuropathic pain (Non-Patent Document 7).

It has been shown that LPA is involved in various fibrotic diseases. It has been reported that in hepatic fibrosis, LPA promotes the contraction and proliferation of stellate cells which play an important role in the process of hepatic fibrosis and that the LPA concentration increases in patients with chronic hepatitis C and animal models with various hepatic diseases (Non-Patent Documents 8, 9, 10, and 11). It has further been reported that in renal fibrosis, the production of LPA and the expression of LPA1 increase in a mice with unilateral ureteral ligation model, which is an animal model of renal fibrosis, and the progression of fibrosis decreases in LPA1-deficient mice and LPA receptor antagonists (Non-Patent Document 12). It has been reported that with respect to pulmonary fibrosis, the LPA concentration in the bronchoalveolar lavage fluid in patients with idiopathic pulmonary fibrosis increases, that the LPA concentration in the bronchoalveolar lavage fluid increases in model mice with bleomycin-induced lung fibrosis, and that the progression of fibrosis and the death are remarkably inhibited in LPA1-deficient mice (Non-Patent Document 13).

In addition, it has been reported that LPA is accumulated to mediate the activation of platelets and endothelial cells by oxidized LDL in atherosclerosis lesions, and it has been suggested that LPA is involved in cardiovascular diseases (Non-Patent Document 14).

Furthermore, it is known that in the proliferative diseases, LPA promotes the migration of cancer cells (Non-Patent Document 15). It has been reported that the LPA concentration increases in the ascites of patients with ovarian cancer, and actually promotes the proliferation of the ovarian cancer cells (Non-Patent Documents 16 and 17). It has been reported that in prostate cancer, the expression of LPA1 receptor increases in the tumorlesion and the proliferation is enhanced in the prostate cancer cells overexpressing LPA1 (Non-Patent Document 18). It also has been reported that in breast cancer bone metastasis models, overexpression of LPA1 increases tumor proliferation/metastasi and LPA receptor antagonist inhibits the metastasis (Non-Patent Document 19). Further, in recent years, it has been rapidly revealed that various cells surrounding cancer cells assist the survival, growth, and distant metastasis of cancer cells in the cancer tissues. It has been revealed that human fat-derived mesenchymal stem cells differentiate into tumor-associated fibroblasts through the activation of LPA1 in tumor tissues by transplantation with cancer cells, thereby promoting the growth/angiogenesis of tumors (Non-Patent Document 20).

From the findings obtained by various studies on the LPA and LPA receptors, it is thought that an agent which inhibits the physiological activity of LPA, in particular, an antagonist of LPA1, may be useful as a drug for preventing or treating urologic diseases such as urinary dysfunction associated with benign prostatic hyperplasia and the like, central/peripheral nervous system neurological diseases and urological nerve diseases, hepatitis and renal insufficiency, fibrotic diseases such as idiopathic pulmonary fibrosis and the like, cardiovascular diseases such as atherosclerosis and the like, and proliferative diseases such as prostate cancer, breast cancer, ovarian cancer, and the like.

Meanwhile, it is known that a carboxylic acid derivative represented by the formula (A) has an LPA receptor antagonistic action and is useful for various diseases, for example, urinary system diseases, cancer-related diseases, proliferative diseases, inflammatory immune disease, brain-related diseases, chronic diseases, and the like (Patent Document 2).

[Chem. 2]

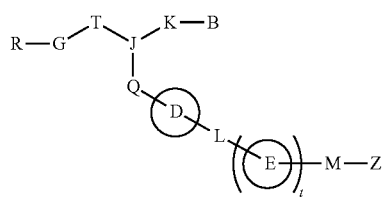

(A)

(wherein Z represents an acidic group, for the others, refer to the publication.)

It is further known that a compound represented by the formula (B) has an LPA receptor antagonistic action and is useful for various diseases, for example, urinary system diseases (symptoms associated with benign prostatic hyperplasia, neurogenic bladder diseases, and the like), cancer-related diseases, proliferative diseases, inflammatory immune diseases, brain-related diseases, chronic diseases, and the like (Patent Document 3).

[Chem. 3]

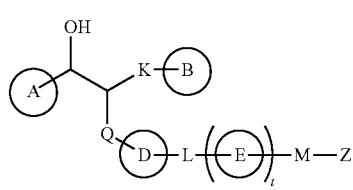

(B)

(for the symbols in the formula, refer to the publication.)

In any of the documents above, there is no specific disclosure of the compound of the present invention.

RELATED ART

Non-Patent Document

[Non-Patent Document 1] FEBS Lett. 2002, 523, 187.
[Non-Patent Document 2] J. Urol. 1999, 162, 1779.
[Non-Patent Document 3] J. Urol. 2000, 163, 1027.
[Non-Patent Document 4] Eur. J. Neurosci. 1998, 10, 1045.
[Non-Patent Document 5] J. Comp. Neurol. 1998, 398, 587.
[Non-Patent Document 6] Proc. Natl. Acad. Sci. U.S.A. 1999, 96, 5233.
[Non-Patent Document 7] Nat. Med. 2004, 10, 712.
[Non-Patent Document 8] Biochem. Biophys. Res. Commun. 2000, 277, 72.
[Non-Patent Document 9] Biochem. Biophys. Res. Commun. 2000, 248, 436.
[Non-Patent Document 10] J. Clin. Gastroenterol. 2007, 41, 616.
[Non-Patent Document 11] Life Sci. 2007, 81, 1009.
[Non-Patent Document 12] J. Am. Soc. Nephrol. 2007, 18, 3110.
[Non-Patent Document 13] Nat. Med. 2008, 14, 45.
[Non-Patent Document 14] Proc. Natl. Acad. Sci. U.S.A. 1999, 96, 6931.
[Non-Patent Document 15] Biochem. Biophysic. Res. Communic. 1993, 193, 497.
[Non-Patent Document 16] JAMA 1998, 280, 719.
[Non-Patent Document 17] J. Natl. Cancer. Inst. 2001, 93, 762.
[Non-Patent Document 18] Endocrinology 2006, 147, 4883.
[Non-Patent Document 19] Proc Natl Acad Sci U.S.A. 2006, 103, 9643.
[Non-Patent Document 20] Biochim Biophys Acta. 2010, 1801, 1205.
[Patent Document 1] Pamphlet of International Publication WO 02/062389
[Patent Document 2] Pamphlet of International Publication WO 2004/031118
[Patent Document 3] Pamphlet of International Publication WO 2005/058790

DISCLOSURE OF INVENTION

Technical Problem

Problems to be Solved by the Invention

The present invention provides a substituted amide compound which is useful as an active component of a pharmaceutical composition, in particular, a pharmaceutical composition for preventing and/or treating diseases caused by LPA.

Means for Solving the Problems

The present inventors have made intensive studies on a compound having an antagonistic action against LPA receptor, and as a result, they have found that a substituted amide compound which is the compound of the present invention has an excellent antagonistic action against LPA receptor and is useful as an agent for preventing and/or treating diseases caused by LPA, thereby completing the present invention.

The present invention relates to a compound of the formula (I) or a salt thereof.

[Chem. 4]

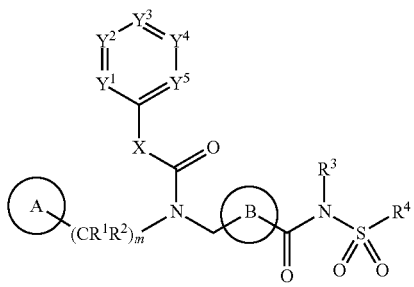

(wherein A is an aryl which may be substituted or an aromatic hetero ring group which may be substituted, B is a 5-membered aromatic hetero ring group which may be substituted, X is a single bond or —$(CR^{X1}R^{X2})_n$—, n is 1, 2, 3, or 4, $R^{X1}$ and $R^{X2}$ are the same as or different from each other, and are H, halogen, OH, —O-(lower alkyl which may be substituted), or lower alkyl which may be substituted, or $R^{X1}$ and $R^{X2}$ are combined with each other to form oxo (=O), or $R^{X1}$ and $R^{X2}$ are combined with each other to form $C_{2-5}$ alkylene which may be substituted, in which when n is 2, 3, or 4, $R^{X1}$ may be combined with adjacent $R^{X1}$ to form a new bond, $Y^1, Y^2, Y^3, Y^4$, and $Y^5$ are the same as or different from each other, and are $CR^Y$ or N, $R^Y$'s are the same as or different from each other, and are H, OH, halogen, —O-(lower alkyl which may be substituted), —S-(lower alkyl which may be substituted), lower alkyl which may be substituted, lower alkenyl which may be substituted, or cycloalkyl which may be substituted, $R^1$ and $R^2$ are the same as or different from each other, and are H, halogen, —O-(lower alkyl which may be substituted), or lower alkyl which may be substituted, m is 1, 2, or 3, $R^3$ is H, or lower alkyl which may be substituted, $R^4$ is lower alkyl which may be substituted, lower alkenyl which may be substituted, cycloalkyl which may be substituted, aryl which may be substituted, a hetero ring group which may be substituted, or $NR^{101}R^{102}$, or $R^3$ and $R^4$ may be combined with each other to form $C_{2-5}$ alkylene which may be substituted, and $R^{101}$ and $R^{102}$ are the same as or different from each other, and are H, OH, —O-(lower alkyl which may be substituted), —C(=O)-(lower alkyl which may be substituted), —C(=O)—O-(lower alkyl which may be substituted), —NH—C(=O)-(lower alkyl which may be substituted), lower alkyl which may be substituted, lower alkenyl which may be substituted, cycloalkyl which may be substituted, aryl which may be substituted, or a hetero ring group which may be substituted, or $R^{101}$ and $R^{102}$ may be combined with nitrogen atoms to which they are bonded to form a nitrogen-containing monocyclic saturated hetero ring group, in which when $R^4$ is $NR^{101}R^{102}$, at least one of $R^3$, $R^{101}$, and $R^{102}$ is H.)

Moreover, unless specified otherwise, in the case where the symbols of the formulae in the present specification are also used in other chemical formulae, the same symbols denote the same meanings.

The present invention relates to a pharmaceutical composition including the compound of the formula (I) or a salt thereof, and an excipient.

Furthermore, the present invention relates to pharmaceutical composition, in particular, a pharmaceutical composition for preventing and/or treating diseases caused by LPA, which includes the compound of the formula (I) or a salt thereof, and an excipient.

In addition, the present invention relates to use of the compound of the formula (I) or a salt thereof for the preparation of a pharmaceutical composition for preventing and/or treating diseases caused by LPA, use of the compound of the formula (I) or a salt thereof for prevention and/or treatment of diseases caused by LPA, the compound of the formula (I) or a salt thereof for prevention and/or treatment of diseases caused by LPA, and a method for preventing and/or treating diseases caused by LPA, including administering to a patient an effective amount of the compound of the formula (I) or a salt thereof.

Effects of the Invention

The compound of the formula (I) or a salt thereof has an antagonistic action against LPA receptor and can be used as an agent for preventing and/or treating diseases caused by LPA.

EMBODIMENTS FOR CARRYING OUT THE INVENTION

Hereinafter, the present invention will be described in detail. Further, "the compound of the formula (I) or a salt thereof" may be hereinafter denoted as "the compound (I) of the present invention" or "the compound (I)" in some cases.

In the present specification, the "lower alkyl" refers to linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, n-hexyl, or the like. In another embodiment, it is $C_{1-4}$ alkyl, and in a still another embodiment, $C_{1-3}$ alkyl.

The "lower alkenyl" refers to linear or branched $C_{2-6}$ alkenyl, for example, vinyl, propenyl, butenyl, pentenyl, 1-methylvinyl, 1-methyl-2-propenyl, 1,3-butadienyl, 1,3-pentadienyl, or the like. In another embodiment, it is $C_{2-4}$ alkenyl, and in a still another embodiment, $C_{2-3}$ alkenyl.

The "lower alkynyl" refers to linear or branched $C_{2-6}$ alkynyl, for example, ethynyl, propynyl, butynyl, pentynyl, 1-methyl-2-propynyl, 1,3-butadiynyl, 1,3-pentadiynyl, or the like. In another embodiment, it is $C_{2-4}$ alkynyl.

The "alkylene" refers to linear or branched alkylene. The "$C_{2-5}$ alkylene" means alkylene having 2 to 5 carbon atoms, for example, methylene, ethylene, trimethylene, tetramethylene, pentamethylene, propylene, methylmethylene, ethylethylene, 1,2-dimethylethylene, or the like. Further, in another embodiment, it is $C_{2-4}$ alkylene, and in a still another embodiment, $C_{2-3}$ alkylene.

The "cycloalkyl" refers to a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like. In an embodiment, it is $C_{3-8}$ cycloalkyl, and in a still another embodiment, $C_{3-6}$ cycloalkyl.

The "aryl" includes a $C_{6-14}$ monocyclic to tricyclic aromatic hydrocarbon ring group, and includes a ring group condensed with $C_{5-8}$ cycloalkene at its double bond site. It is, for example, phenyl, naphthyl, 5-tetrahydronaphthyl, 4-indenyl, 1-fluorenyl, or the like.

The "hetero ring" means a ring group selected from i) a monocyclic 3- to 8-membered, and in another embodiment, a 5- to 7-membered hetero ring, containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by condensation of the monocyclic hetero ring with one or two rings is selected from the group consisting of a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

Examples of the "hetero ring" include the following embodiments.

(1) Monocyclic saturated hetero ring groups (a) those containing 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, hexamethyleneimino, homopiperazinyl, and the like;

(b) those containing 1 to 3 nitrogen atoms and 1 to 2 sulfur atoms and/or 1 to 2 oxygen atoms, for example, thiomorpholinyl, thiazolidinyl, thiadiazolyl, isothiazolidinyl, oxazolidinyl, morpholinyl, and the like;

(c) those containing 1 to 2 sulfur atoms, for example, tetrahydrothiopyranyl and the like;

(d) those containing 1 to 2 sulfur atoms and 1 to 2 oxygen atoms, for example, oxathiolanyl and the like;

(e) those containing 1 to 2 oxygen atoms, for example, oxiranyl, oxetanyl, dioxolanyl, tetrahydrofuranyl, tetrahydropyranyl, 1,4-dioxanyl, and the like;

(2) Monocyclic unsaturated hetero ring groups (a) those containing 1 to 4 nitrogen atoms, for example, pyrrolyl, 2-pyrrolinyl, imidazolyl, 2-imidazolinyl, pyrazolyl, 2-pyrazolinyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;

(c) those containing 1 to 2 sulfur atoms, for example, thienyl, thiepinyl, dihydrodithiopyranyl, dihydrodithionyl, 2H-thiopyranyl, and the like;

(d) those containing 1 to 2 sulfur atoms and 1 to 2 oxygen atoms, specifically, dihydroxathiopyranyl and the like;

(e) those containing 1 to 2 oxygen atoms, for example, furyl, dihydrofuryl, pyranyl, 2H-pyranyl, oxepinyl, dioxolyl, and the like;

(3) Fused polycyclic saturated hetero ring groups (a) those containing 1 to 5 nitrogen atoms, for example, quinuclidinyl, 7-azabicyclo[2.2.1]heptyl, 3-azabicyclo[3.2.2]nonanyl, and the like;

(b) those containing 1 to 4 nitrogen atoms and 1 to 3 sulfur atoms and/or 1 to 3 oxygen atoms, for example, trithiadiazaindenyl, dioxoloimidazolidinyl, and the like;

(c) those containing 1 to 3 sulfur atoms and/or 1 to 3 oxygen atoms, for example, 2,6-dioxabicyclo[3.2.2]oct-7-yl and the like;

(4) Fused polycyclic unsaturated hetero ring groups (a) those containing 1 to 5 nitrogen atoms, for example, indolyl, isoindolyl, indolinyl, indolizinyl, benzoimidazolyl, dihydrobenzoimidazolyl, tetrahydrobenzoimidazolyl, quinolyl, tetrahydroquinolyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, pyridopyrrolidinyl, triazolopiperidinyl, 9,10-dihydroacridine, and the like;

(b) those containing 1 to 4 nitrogen atoms and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxazinyl, benzoxadiazolyl, benzoisothiazolyl, benzoisoxazolyl, thiazolopiperidinyl, 5,6-dihydro-4H-pyrrolo[3,4-d][1,3]thiazol-2-yl, 10H-phenothiazine, and the like;

(c) those containing 1 to 3 sulfur atoms, for example, benzothienyl, benzodithiopyranyl, chromanyl, dibenzo[b,d]thienyl, and the like;

(d) those containing 1 to 3 sulfur atoms and 1 to 3 oxygen atoms, for example, benzoxathiopyranyl, phenoxazinyl, and the like;

(e) those containing 1 to 3 oxygen atoms, for example, benzodioxolyl, benzofuranyl, dihydrobenzofuranyl, isobenzofuranyl, chromanyl, chromenyl, isochromenyl, dibenzo[b,d]furanyl, methylenedioxyphenyl, ethylenedioxyphenyl, xanthenyl, and the like;

etc.

Further, the "hetero ring" in (1) to (4) above is described as a monovalent group, but this may represent a divalent or higher group in some cases.

The "monocyclic hetero ring" refers to a hetero ring which has no fused ring as in (1) and (2), among the "hetero rings" above.

The "nitrogen-containing hetero ring" refers to one containing at least one nitrogen atom, as in (1)(a), (1)(b), (2)(a), (2)(b), (3)(a), (3)(b), (4)(a), (4)(b), and the like, among the "hetero rings" above.

The "aromatic hetero ring" refers to a ring group having an aromatic property, among (2) and (4) of the "hetero rings" above. Examples thereof include pyrrolyl, furyl, imidazolyl, pyrazolyl, oxazolyl, isoxazolyl, thiazolyl, isothiazolyl, pyridyl, pyrimidyl, pyrazinyl, pyridazinyl, quinolyl, isoquinolyl, and the like.

The "5-membered aromatic hetero ring" refers to a ring group having a 5-membered ring structure, among the "aromatic hetero rings" above. Examples thereof include pyrrolyl, furyl, thiophenyl, imidazolyl, pyrazolyl, oxazolyl, isoxazolyl, thiazolyl, isothiazolyl, and the like.

The "aromatic nitrogen-containing hetero ring" refers to a ring group having an aromatic property, among the nitrogen-containing hetero rings" above. Examples thereof include pyridyl, pyrimidinyl, pyrazinyl, pyridazinyl, and the like.

The "nitrogen-containing monocyclic saturated hetero ring" refers to those having at least one nitrogen atom, among the "monocyclic saturated hetero rings" above as in (1)(a), (1)(b), and the like.

The "5-membered aromatic nitrogen-containing hetero ring" refers to those having at least one nitrogen atom, among the "5-membered aromatic hetero rings" above. Examples thereof include pyrrolyl, imidazolyl, pyrazolyl, oxazolyl, isoxazolyl, thiazolyl, isothiazolyl, and the like.

The expression "$R^{X1}$ and $R^{X2}$ are combined with each other to form $C_{2-5}$ alkylene" indicates that $R^{X1}$ and $R^{X2}$ are combined with carbon atoms to which they are bonded to form a $C_{3-6}$ saturated hydrocarbon ring. Examples of the saturated hydrocarbon ring include cyclopropane, cyclobutane, cyclopentane, cyclohexane, and the like, in another embodiment, $C_{2-4}$ alkylene, and in a still another embodiment, $C_{2-3}$ alkylene.

The expression "$R^3$ and $R^4$ are combined with each other to form $C_{2-5}$ alkylene" indicates that $R^3$ and $R^4$ are combined with nitrogen atoms and sulfur atoms to which they are bonded to form a nitrogen-containing hetero ring having a —N—SO$_2$—moiety structure and having 2 to 5 carbon atoms. Examples of the nitrogen-containing hetero ring include 1,1-dioxoisothiazolidinyl.

The expression "$R^{101}$ and $R^{102}$ may be combined with nitrogen atoms to which they are bonded to form a nitrogen-containing monocyclic saturated hetero ring" indicates that $R^{101}$ and $R^{102}$ are combined to form a ring containing nitrogen atom to which they are bonded, and represents a ring group such as a nitrogen-containing monocyclic saturated hetero ring.

The expression "$R^{X1}$ may be combined with adjacent $R^{X1}$ to form a new bond" indicates that $R^{X1}$ is combined with adjacent $R^{X1}$ to form a double bond, and represents, for example, —$(CR^{X2})$=$(CR^{X2})$—.

The "halogen" means F, Cl, Br, or I, and preferably F.

In the present specification, the "diseases caused by LPA" refers to, for example, diseases such as urinary system diseases (benign prostatic hyperplasia (urinary dysfunction associated with benign prostatic hyperplasia, and the like), overactive bladder, neurogenic bladder, bladder neck sclerosis, underactive bladder, and the like), central/peripheral neuropathy (neurogenic pain, painful peripheral diabetic neuropathy, nerve cell degeneration/nerve cell death after stroke, and the like), cancer-related diseases (prostate cancer, breast cancer, ovarian cancer, lung cancer, colon cancer, and the like), inflammatory diseases (rheumatoid arthritis, knee osteoarthritis, hepatitis C, and non-alcoholic steatohepatitis), diseases associated with fibrosis (chronic renal diseases, idiopathic pulmonary fibrosis, and chronic rejection after non-organ transplantation), cardiovascular diseases such as arteriosclerosis and the like. In another embodiment, examples of the diseases caused by LPA include urinary system diseases (benign prostatic hyperplasia (urinary dysfunction associated with benign prostatic hyperplasia, and the like), overactive bladder, neurogenic bladder, bladder neck sclerosis, underactive bladder, and the like).

The expression "which may be substituted" represents non-substitution or substitution with 1 to 5 substituents". Further, if it has a plurality of substituents, the substituents may be the same as or different from one other. For example, —N(lower alkyl)$_2$ includes an ethylmethylamino group.

Examples of the substituent in "lower alkyl which may be substituted" and "lower alkenyl which may be substituted" in $R^{101}$ and $R^{102}$ include the groups shown in (a) to (k) below.

(a) halogen.

(b) —OH, —O-lower alkyl (in which the lower alkyl may be substituted with 1 to 3 OH, halogen, —O-lower alkyl, or aryl groups).

(c) amino which may be substituted with one or two lower alkyl groups or nitro.

(d) —SH, —S-lower alkyl (in which the lower alkyl may be substituted with 1 to 3 halogen atoms).

(e) —SO$_2$-lower alkyl, —SO$_2$-cycloalkyl, —SO$_2$-hetero ring, —SO$_2$-aryl, sulfamoyl which may be substituted with one or two lower alkyl groups.

(f) —CHO, —CO-lower alkyl (in which the lower alkyl may be substituted with 1 to 3 halogen atoms), —CO-cycloalkyl (in which cycloalkyl may be substituted with one or more —O-lower alkyl groups), —CO-monocyclic saturated hetero ring, cyano.

(g) aryl or cycloalkyl; further, these groups may be substituted with 1 to 5 halogen atoms or one or more —O-lower alkyl groups.

(h) a hetero ring, and in another embodiment, a monocyclic hetero ring; further, these hetero rings and monocyclic hetero rings may be substituted with halogen or lower alkyl (in which the lower alkyl may be substituted with one or more aryl groups).

(i) —COOH, —COO-lower alkyl (in which the lower alkyl may be substituted with 1 to 3 halogen atoms).

(j) —CONH$_2$, —CONH(lower alkyl) (in which the lower alkyl may be substituted with 1 to 3 halogen atoms), —CONH(lower alkyl)$_2$ (in which the lower alkyl may be substituted with 1 to 3 halogen atoms).

(k) —O—CO-lower alkyl (in which the lower alkyl may be substituted with 1 to 3 halogen atoms), —O—CO—O-lower alkyl (in which the lower alkyl may be substituted with 1 to 3 halogen atoms).

(l) lower alkyl which may be substituted with one or more groups selected from the substituents shown in (a) to (k).

Examples of the substituents that can be used in the "aryl which may be substituted" and the "aromatic hetero ring which may be substituted" in A include the groups shown in (a) to (l) above, lower alkenyl (in which the lower alkenyl may be substituted with 1 to 3 halogen atoms) and lower alkynyl (in which the lower alkynyl may be substituted with 1 to 3 halogen atoms), and in another embodiment, the groups shown in (a), (b), (f), (k), and (l) above.

Examples of the substituents that can be used in the "5-membered aromatic hetero ring" in B include the groups shown in (a) to (l) above, lower alkenyl (in which the lower alkenyl may be substituted with 1 to 3 halogen atoms) and lower alkynyl (in which the lower alkynyl may be substituted with 1 to 3 halogen atoms), and in another embodiment, the groups shown in (a), (b), (f), (k), and (l) above.

Examples of the substituents that can be used in the "lower alkyl which may be substituted" and the "lower alkenyl which may be substituted" in $R^Y$ include the groups shown in (a) to (k) above, and in another embodiment, the groups shown in (a) and (b) above.

Examples of the substituents that can be used in the "cycloalkyl which may be substituted" in $R^Y$ include the groups shown in (a) to (l) above, and in another embodiment, the groups shown in (a) and (b) above.

Examples of the substituents that can be used in the "lower alkyl which may be substituted" in $R^{X1}$ and $R^{X2}$ and "$R^{X1}$ and $R^{X2}$ are combined with each other to form C$_{2-5}$ alkylene which may be substituted" include the groups shown in (a) to (k) above, and in another embodiment, the groups shown in (a).

Examples of the substituents that can be used in the "$R^3$ and $R^4$ are combined with each other to form C$_{2-5}$ alkylene which may be substituted" include the groups shown in (a) to (k) above, and in another embodiment, the groups shown in (a) above and oxo (=O).

Examples of the substituents that can be used in the "lower alkyl which may be substituted" and the "lower alkenyl which may be substituted" in $R^4$ include the groups shown in (a) to (k) above, and in another embodiment, the groups shown in (a), (b), (g), and (j) above.

Examples of the substituents that can be used in the "aryl which may be substituted" in $R^4$ include the groups shown in (a) to (k) above, and in another embodiment, the groups shown in (a), (b), (g), (k), and (l) above.

Examples of the substituents that can be used in the "cycloalkyl which may be substituted" and the "hetero ring which may be substituted" in $R^4$ include the groups shown in (a) to (l) above and oxo (=O), and in another embodiment, the groups shown in (a), (b), (g), (k), and (l) above and oxo (=O).

Examples of the substituents that can be used in the "lower alkyl which may be substituted" in $R^1$ and $R^2$ include the groups shown in (a) to (k) above, and in another embodiment, the groups shown in (a) above.

Examples of the substituents that can be used in the "lower alkyl which may be substituted" in $R^3$ include the groups shown in (a) to (k) above, and in another embodiment, the groups shown in (a) above.

Examples of the substituents that can be used in the "aryl which may be substituted" in $R^{101}$ and $R^{102}$ include the groups shown in (a) to (l) above, and in another embodiment, the groups shown in (a), (b), and (l) above.

Examples of the substituents that can be used in the "cycloalkyl which may be substituted" and the "hetero ring which may be substituted" in $R^{101}$ and $R^{102}$ include the groups shown in (a) to (l) above and oxo (=O), and in another embodiment, the groups shown in (a), (b), and (l) above.

Embodiments of the compound (I) of the present invention include a compound of the formula (I') or a salt thereof.

[Chem. 5]

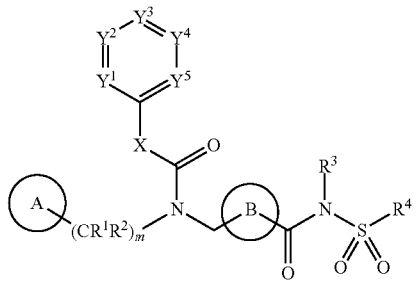

(I')

(wherein
A is aryl which may be substituted, or an aromatic hetero ring group which may be substituted,
B is a 5-membered aromatic hetero ring group which may be substituted,
X is a single bond or $-(CR^{X1}R^{X2})_n-$,
n is 1, 2, 3, or 4,
$R^{X1}$ and $R^{X2}$ are the same as or different from each other, and are H, halogen, OH, —O-(lower alkyl which may be substituted), or lower alkyl which may be substituted, or
$R^{X1}$ and $R^{X2}$ are combined with each other to form oxo (=O), or
$R^{X1}$ and $R^{X2}$ are combined with each other to form $C_{2-5}$ alkylene which may be substituted,
in which n is 2, 3, or 4, $R^{X1}$ may be combined with adjacent $R^{X1}$ to form a new bond,
$Y^1$, $Y^2$, $Y^3$, $Y^4$ and $Y^5$ are the same as or different from each other, and are $CR^Y$ or N,
$R^Y$'s are the same as or different from each other, and are H, OH, halogen, —O-(lower alkyl which may be substituted), lower alkyl which may be substituted, lower alkenyl which may be substituted, or cycloalkyl which may be substituted,
$R^1$ and $R^2$ are the same as or different from each other, and are H, halogen, —O-(lower alkyl which may be substituted), or lower alkyl which may be substituted,
m is 1, 2, or 3,
$R^3$ is H, or lower alkyl which may be substituted,
$R^4$ is lower alkyl which may be substituted, lower alkenyl which may be substituted, cycloalkyl which may be substituted, aryl which may be substituted, a hetero ring group which may be substituted, or $NR^{101}R^{102}$, or
$R^3$ and $R^4$ may be combined with each other to form $C_{2-5}$ alkylene which may be substituted, and
$R^{101}$ and $R^{102}$ are the same as or different from each other, and are H, OH, —O-(lower alkyl which may be substituted), —C(=O)-(lower alkyl which may be substituted), —C(=O)—O-(lower alkyl which may be substituted), —NH—C(=O)-(lower alkyl which may be substituted), lower alkyl which may be substituted, lower alkenyl which may be substituted, cycloalkyl which may be substituted, aryl which may be substituted, or a hetero ring group which may be substituted, or
$R^{101}$ and $R^{102}$ may be combined with nitrogen atoms to which they are bonded to form a nitrogen-containing monocyclic saturated hetero ring group,
in which when $R^4$ is $NR^{101}R^{102}$, at least one of $R^3$, $R^{101}$, and $R^{102}$ is H.)

Embodiments of the compounds (I) and (I') include the following compounds or salts thereof.

(1) The compound, wherein A is aryl which may be substituted with halogen or an aromatic hetero ring which may be substituted with halogen.

(2) The compound, wherein A is phenyl.

(3) The compound, wherein B is thiazole-2,4-diyl which is bonded with —C(=O)—$NR^3$— at the 2-position, thiazole-2,4-diyl which is bonded with —C(=O)—$NR^3$— at the 4-position, pyrazole-1,3-diyl which is bonded with —C(=O)—$NR^3$— at the 3-position, pyrazole-1,4-diyl which is bonded with —C(=O)—$NR^3$— at the 4-position, oxazole-2,4-diyl which is bonded with —C(=O)—$NR^3$— at the 2-position, thiophene-2,5-diyl which is bonded with —C(=O)—$NR^3$— at the 2-position, thiophene-2,4-diyl which is bonded with —C(=O)—$NR^3$— at the 2-position, furan-2,5-diyl which is bonded with —C(=O)—$NR^3$— at the 2-position, furan-2,4-diyl which is bonded with —C(=O)—$NR^3$— at the 2-position, isoxazole-3,5-diyl which is bonded with —C(=O)—$NR^3$— at the 5-position, or pyrrole-2,5-diyl which is bonded with —C(=O)—$NR^3$— at the 2-position, each of which may be substituted.

(4) The compound, wherein B is thiazole-2,4-diyl which is bonded with —C(=O)—$NR^3$— at the 2-position, thiazole-2,4-diyl which is bonded with —C(=O)—$NR^3$— at the 4-position, pyrazole-1,3-diyl which is bonded with —C(=O)—$NR^3$— at the 3-position, oxazole-2,4-diyl which is bonded with —C(=O)—$NR^3$— at the 2-position, thiophene-2,5-diyl which is bonded with —C(=O)—$NR^3$— at the 2-position, thiophene-2,4-diyl which is bonded with —C(=O)—$NR^3$— at the 2-position, 5-methoxymethylthiophene-2,4-diyl which is bonded with —C(=O)—$NR^3$— at the 2-position, 5-chlorothiophene-2,4-diyl which is bonded with —C(=O)—$NR^3$— at the 2-position, furan-2,5-diyl which is bonded with —C(=O)—$NR^3$— at the 2-position, 5-chlorothiazole-2,4-diyl which is bonded with —C(=O)—$NR^3$— at the 2-position, or 5-methylthiazole-2,4-diyl which is bonded with —C(=O)—$NR^3$— at the 2-position (5) The compound, wherein X is a single bond.

(6) The compound, wherein X is $-(CR^{X1}R^{X2})_n-$, n is 1, $R^{X1}$ and $R^{X2}$ are the same as or different from each other, and are H, OH, —O-(lower alkyl which may be substituted), or $R^{X1}$ and $R^{X2}$ are combined with each other to form oxo (=O), or $C_{2-5}$ alkylene which may be substituted.

(7) The compound, wherein X is $-(CR^{X1}R^{X2})_n-$, n is 1, $R^{X1}$ is H, and $R^{X2}$ is OH or methoxy.

(8) The compound, wherein X is $-(CR^{X1}R^{X2})_n-$, n is 1, $R^{X1}$ and $R^{X2}$ are combined with each other to form oxo (=O), trimethylene, or ethylene.

(9) The compound, wherein $Y^1$, $Y^2$, $Y^3$, $Y^4$, and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl.

(10) The compound, wherein $Y^2$ and $Y^4$ is $CR^{Y11}$, $R^{Y11}$'s are the same as or different from each other, and are H, F, methyl, or methoxy, $Y^1$, $Y^3$, and $Y^5$ are $CR^{Y21}$, $R^{Y21}$'s are the same as or different from each other, and are H, OH, bromo, methyl, difluoromethyl, ethyl, ethenyl, isopropenyl, methoxy, methoxymethyl, 2-fluoroethoxy, or cyclopropyl.

(11) The compound, wherein $Y^2$ and $Y^4$ is C—CH$_3$, $Y^3$ is C—O—CH$_3$, $Y^1$ and $Y^5$ are CH.

(12) The compound, wherein m is 3, $R^1$ and $R^2$ are the same as or different from each other, and are H, halogen, —O-(lower alkyl which may be substituted with halogen), or lower alkyl which may be substituted with halogen.

(13) The compound, wherein m is 3, $R^1$ and $R^2$ are the same as or different from each other, and are H, F, methyl, or methoxy.

(14) The compound, wherein $R^3$ is H, $R^4$ is lower alkyl which may be substituted with —OH, —O—C(=O)-lower alkyl, —O—C(=O)—O-lower alkyl, O-lower alkyl, or aryl; lower alkenyl which may be substituted with halogen; aryl which may be substituted with halogen or lower alkyl; hetero ring which may be substituted with halogen or lower alkyl; or cycloalkyl which may be substituted with halogen or lower alkyl, or $R^3$ and $R^4$ may be combined with each other to form C$_{2-5}$ alkylene which may be substituted with halogen or oxo (=O).

(15) The compound, wherein $R^3$ is H, $R^4$ is lower alkyl which may be substituted with —OH, —O—C(=O)-lower alkyl, —O—C(=O)—O-lower alkyl, O-lower alkyl, or aryl; vinyl which may be substituted with halogen; aryl which may be substituted with halogen or methyl; pyridine which may be substituted with halogen or methyl; thiophene; thiazole; imidazole; oxazole; or cycloalkyl which may be substituted with halogen or methyl, or $R^3$ and $R^4$ may be combined with each other to form ethylene which may be substituted with halogen.

(16) The compound, wherein $R^3$ is H, $R^4$ is vinyl, methyl, trifluoromethyl, benzyl, 2-hydroxy-2-methyl-ethyl, ethyl, 2-(acetoxy)ethyl, 2-methoxyethyl, 2-(ethoxycarbonyloxy)ethyl, 2-hydroxy-2,2-dimethyl-ethyl, isopropyl, 4-(acetoxy) butyl, 4-hydroxybutyl, phenyl, 5-methylpyridin-2-yl, 4-chloropyridin-3-yl, thiophen-3-yl, 2-methylthiazol-4-yl, 2-methylimidazol-4-yl, 3,5-dimethyloxazol-4-yl, or cyclopropyl, or $R^3$ and $R^4$ may be combined with each other to form ethylene.

(17) The compound, wherein $R^3$ is H, $R^4$ is $NR^{101}R^{102}$, $R^{101}$, and $R^{102}$ are the same as or different from each other, and are H, —O-(lower alkyl which may be substituted with halogen), —C(=O)-(lower alkyl which may be substituted with halogen), —C(=O)—O-(lower alkyl which may be substituted with halogen), lower alkyl which may be substituted with halogen or OH, or hetero ring which may be substituted with halogen or OH, or $R^{101}$ and $R^{102}$ are combined with nitrogen atoms to which they are bonded to form a nitrogen-containing monocyclic saturated hetero ring which may be substituted with halogen or oxo (=O).

(18) The compound, wherein $R^3$ is H, $R^4$ is $NR^{102}$, $R^{101}$ is H, and $R^{102}$ is H, methoxy, acetyl, methoxycarbonyl, methyl, ethyl, 2-fluoroethyl, 2-hydroxyethyl, or pyridin-2-yl.

Other embodiments of the compounds (I) and (I') include the following compounds or salts thereof.

(19) The compound, wherein A is phenyl which may be substituted with halogen, or a 5-membered aromatic hetero ring which may be substituted with halogen or lower alkyl.

(20) The compound, wherein A is 2-fluorophenyl, 3-fluorophenyl, 4-fluorophenyl, 3-methylphenyl, 3-difluoromethylphenyl, 2-fluoro-4-trifluoromethylphenyl, 3-methylphenyl, 3-ethylphenyl, 3-butylphenyl, 2-fluoro-5-methylphenyl, 2-fluoro-3-methylphenyl, 3-bromophenyl, 3-chlorophenyl, or phenyl.

(21) The compound, wherein A is furyl which may be substituted with halogen or lower alkyl, or thiophenyl which may be substituted with halogen or lower alkyl.

(22) The compound, wherein A is furan-2-yl, 5-methylfuran-2-yl, 4,5-dimethylfuran-2-yl, 5-chlorofuran-2-yl, 5-ethylthiophen-2-yl, thiophen-2-yl, 2-methylthiophen-2-yl, 3-methylthiophen-2-yl, 4-methylthiophen-2-yl, 4,5-dimethylthiophen-2-yl, or 5-chlorothiophen-2-yl.

(23) The compound, wherein B is a 5-membered aromatic nitrogen-containing hetero ring.

(24) The compound, wherein B is

[Chem. 6]

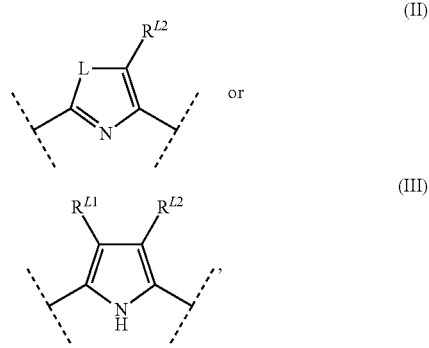

L is O or S, $R^{L1}$ is H, halogen, lower alkyl which may be substituted, lower alkenyl which may be substituted, lower alkynyl which may be substituted, or cycloalkyl which may be substituted, $R^{L2}$ is H, halogen, lower alkyl which may be substituted, lower alkenyl which may be substituted, lower alkynyl which may be substituted, or cycloalkyl which may be substituted.

(25) The compound as described in (24), wherein B is the formula (III).

(26) The compound as described in (24), wherein $R^{L1}$ are H, halogen, or lower alkyl which may be substituted with halogen or OH.

(27) The compound as described in (24), wherein $R^{L1}$ is H.

(28) The compound as described in (24), wherein B is the formula (II) and L is O.

(29) The compound as described in (24), wherein B is the formula (II) and L is S.

(30) The compound as described in (24), wherein $R^{L2}$ are H, halogen, or lower alkyl which may be substituted with halogen or OH.

(31) The compound as described in (24), wherein $R^{L2}$ are H, Cl, or methyl.

(32) The compound, wherein X is —$(CR^{X1}R^{X2})_n$—, n is 1, $R^{X1}$ is H, and $R^{X2}$ is OH.

(33) The compound, wherein X is —$(CR^{X1}R^{X2})_n$—, n is 1, and $R^{X1}$ and $R^{X2}$ are combined with each other to form ethylene.

(34) The compound, wherein $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl.

(35) The compound, wherein $R^Y$'s are the same as or different from each other, and are H, OH, halogen, lower alkyl, or —O-(lower alkyl).

(36) The compound, wherein $R^Y$'s are the same as or different from each other, and are H, OH, halogen, methyl, or methoxy.

(37) The compound, wherein $Y^2$, $Y^3$, $Y^4$, and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, and $Y^1$ is N.

(38) The compound, wherein $Y^2$, $Y^3$, $Y^4$, and $Y^5$ are $CR^Y$, $R^Y$'s are the same as or different from each other, and are H, or —O-(lower alkyl), and $Y^1$ is N.

(39) The compound, wherein $Y^2$, $Y^4$, and $Y^5$ are CH, and $Y^3$ is C—O—$CH_3$, and $Y^1$ is N.

(40) The compound, wherein $Y^1$, $Y^3$, $Y^4$, and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, and $Y^2$ is N.

(41) The compound, wherein $Y^1$, $Y^3$, $Y^4$, and $Y^5$ are $CR^Y$, $R^Y$'s are the same as or different from each other, and are H, or —O-(lower alkyl), and $Y^2$ is N.

(42) The compound, wherein $Y^1$, $Y^4$, and $Y^5$ are CH, $Y^3$ is C—O—$CH_3$, and $Y^2$ is N.

(43) The compound, wherein $Y^1$, $Y^2$, $Y^3$, $Y^4$, and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl.

(44) The compound, wherein $Y^1$, $Y^2$, $Y^3$, $Y^4$, and $Y^5$ are $CR^Y$, and $R^Y$'s are the same as or different from each other, and are H, lower alkyl, or —O-(lower alkyl).

(45) The compound, wherein $Y^1$, $Y^2$, $Y^4$, and $Y^5$ are CH, $Y^3$ is C—O—$CH_3$.

(46) The compound, wherein $Y^2$ and $Y^4$ are C—O—$CH_3$, $Y^3$ is C—$CH_3$, and $Y^1$ and $Y^5$ are CH.

(47) The compound, wherein $R^3$ is H.

(48) The compound, wherein $R^3$ is methyl.

(49) The compound, wherein $R^4$ is lower alkyl which may be substituted, cycloalkyl which may be substituted, aryl which may be substituted, or a nitrogen-containing hetero ring group which may be substituted, or $NR^{101}R^{102}$.

(50) The compound, wherein $R^4$ is lower alkyl (in which the lower alkyl may be substituted with halogen, OH, or —O—C(O)-lower alkyl), cycloalkyl which may be substituted with a group selected from Group $G^1$, aryl which may be substituted with a group selected from Group $G^1$, a 5-membered nitrogen-containing hetero ring group which may be substituted with a group selected from Group $G^1$, or $NR^{101}R^{102}$, in which Group $G^1$ is halogen, OH, lower alkyl, or —O—C(O)-lower alkyl, $R^{101}$ and $R^{102}$ are the same as or different from each other, and are H, OH, —C(=O)-halogen, —O-(lower alkyl which may be substituted), —C(=O)-(lower alkyl which may be substituted), —C(=O)—O-(lower alkyl which may be substituted), —NH—C(=O)-(lower alkyl which may be substituted), lower alkyl which may be substituted, lower alkenyl which may be substituted, cycloalkyl which may be substituted, aryl which may be substituted, or a hetero ring group which may be substituted.

(51) The compound, wherein $R^4$ is lower alkyl (in which the lower alkyl may be substituted with halogen, OH, or —O—C(O)-lower alkyl), a 5-membered nitrogen-containing hetero ring group which may be substituted with lower alkyl, cycloalkyl, aryl, or $NR^{101}R^{102}$, $R^{101}$ and $R^{102}$ are the same as or different from each other, and are H, halogen, OH, COOH, —COO-lower alkyl, C(=O)—$NH_2$, O-(lower alkyl which may be substituted with halogen), lower alkyl (in which the lower alkyl may be substituted with halogen, OH, S-lower alkyl, or a hetero ring group), —C(=O)—O-(lower alkyl which may be substituted with aryl), a hetero ring group which may be substituted with lower alkyl, or lower alkenyl.

(52) The compound, wherein $R^4$ is ethyl which may be substituted with a group selected from Group $G^1$, methyl which may be substituted with halogen, propyl which may be substituted with OH, oxazole which may be substituted with lower alkyl, imidazole which may be substituted with lower alkyl, isopropyl, cyclopropyl, phenyl, or $NR^{101}R^{102}$, in which Group $G^1$ is halogen, OH, or —O—C(O)-lower alkyl, and $R^{101}$ and $R^{102}$ are the same as or different from each other, and are lower alkyl (in which the lower alkyl may be substituted with H, halogen, OH, S-lower alkyl, or a hetero ring group.

(53) The compound, wherein $R^4$ is methyl, trifluoromethyl, halogen, 2-hydroxyethyl, 2-acetoxyethyl, propyl, 2-hydroxypropyl, 3-hydroxypropyl, isopropyl, cyclopropyl, phenyl, 3,5-dimethylisoxazol-4-yl, 1-methyl-1H-imidazol-4-yl, or $NR^{101}R^{102}$, $R^{101}$, and $R^{102}$ are the same as or different from each other, and are H, methyl which may be substituted with, halogen, or OH, ethyl which may be substituted with halogen or OH, or propyl which may be substituted with halogen or OH.

(54) The compound, wherein $R^4$ is lower alkyl (in which the lower alkyl may be substituted with halogen, OH, or —O—C(O)-lower alkyl), or cycloalkyl which may be substituted with a group selected from Group $G^1$, aryl which may be substituted with a group selected from Group $G^1$, or a 5-membered nitrogen-containing hetero ring group which may be substituted with a group selected from Group $G^1$, in which Group $G^1$ is halogen, OH, lower alkyl, or —O—C(O)-lower alkyl.

(55) The compound, wherein $R^4$ is lower alkyl (in which the lower alkyl may be substituted with halogen, OH, or —O—C(O)-lower alkyl), a 5-membered nitrogen-containing hetero ring group which may be substituted with lower alkyl, cycloalkyl, or aryl.

(56) The compound, wherein $R^4$ is methyl which may be substituted with halogen, ethyl (in which ethyl may be substituted with halogen, OH, or —O—C(O)-lower alkyl), propyl which may be substituted with OH, oxazole which may be substituted with lower alkyl, imidazole which may be substituted with lower alkyl, isopropyl, cyclopropyl, or phenyl.

(57) The compound, wherein $R^4$ is methyl, trifluoromethyl, halogen, 2-hydroxyethyl, 2-acetoxyethyl, propyl, 2-hydroxypropyl, 3-hydroxypropyl, isopropyl, cyclopropyl, phenyl, 3,5-dimethylisoxazol-4-yl, or 1-methyl-1H-imidazol-4-yl.

(58) The compound, wherein $R^4$ is methyl, trifluoromethyl, halogen, 2-hydroxyethyl, 2-acetoxyethyl, propyl, 2-hydroxypropyl, 3-hydroxypropyl, or isopropyl.

(59) The compound, wherein $R^4$ is cyclopropyl, phenyl, 3,5-dimethylisoxazol-4-yl, 2,4-dimethylthiazol-5-yl, or 1-methyl-1H-imidazol-4-yl.

(60) The compound, wherein $R^4$ is $NR^{101}R^{102}$, $R^{101}$ is H, and $R^{102}$ is H, O-(lower alkyl which may be substituted), lower alkyl which may be substituted, —C(=O)—O-(lower alkyl which may be substituted), a hetero ring group which may be substituted, or lower alkenyl which may be substituted.

(61) The compound, wherein $R^4$ is $NR^{101}R^{102}$, $R^{101}$ is H, and $R^{102}$ is H, O-(lower alkyl which may be substituted with halogen), lower alkyl (in which the lower alkyl may be substituted with halogen, OH, S-lower alkyl, or a hetero ring group), —C(═O)—O-(lower alkyl which may be substituted with aryl), a hetero ring group which may be substituted with lower alkyl, or lower alkenyl.

(62) The compound, wherein $R^4$ is $NR^{101}R^{102}$, $R^{101}$ is H, and $R^{102}$ is lower alkyl (in which the lower alkyl may be substituted with halogen, OH, S-lower alkyl, or a hetero ring group).

(63) The compound, wherein $R^4$ is $NR^{101}R^{102}$, $R^{101}$ is H, and $R^{102}$ is methyl which may be substituted with a group selected from Group $G^2$, ethyl which may be substituted with a group selected from Group $G^2$, or propyl which may be substituted with a group selected from Group $G^2$, in which Group $G^2$ is halogen, OH, S-lower alkyl, or a hetero ring group.

(64) The compound, wherein $R^4$ is $NR^{101}$, $R^{102}$, $R^{101}$ is H, and $R^{102}$ is methyl, ethyl, or propyl.

(65) The compound, wherein $R^4$ is $NR^{101}R^{102}$, and $R^{101}$ and $R^{102}$ are the same as or different from each other, and are O-(lower alkyl which may be substituted with halogen), lower alkyl (in which the lower alkyl may be substituted with halogen, OH, S-lower alkyl, or a hetero ring group), —C(═O)—O-(lower alkyl which may be substituted with aryl), a hetero ring group which may be substituted with lower alkyl, or lower alkenyl.

(66) The compound, wherein $R^4$ and $NR^{101}R^{102}$, and $R^{101}$ and $R^{102}$ are the same as or different from each other, and are lower alkyl (in which the lower alkyl may be substituted with halogen, OH, S-lower alkyl, or a hetero ring group).

(67) The compound, wherein $R^4$ and $NR^{101}R^{102}$, and $R^{101}$ and $R^{102}$ are the same as or different from each other, and are lower alkyl which may be substituted with halogen or OH.

(68) $R^4$ and $NR^{101}R^{102}$, and $R^{101}$ and $R^{102}$ are the same as or different from each other, and are methyl which may be substituted with halogen or OH, ethyl which may be substituted with halogen or OH, or propyl which may be substituted with halogen or OH.

Furthermore, still other embodiments of the compounds (I) and (I') of the present invention include the compounds or salts thereof including the combinations of two or more of the groups as described in (1) to (18), and specifically the following compounds or salts thereof.

(69) The compound as described in (14) to (18), wherein A is aryl which may be substituted with halogen, or an aromatic hetero ring which may be substituted with halogen, B is a monocyclic aromatic hetero ring which may be substituted, $Y^1$, $Y^2$, $Y^3$, $Y^4$ and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, m is 3, and $R^1$ and $R^2$ are the same as or different from each other, and are H, halogen, —O-(lower alkyl which may be substituted with halogen), or lower alkyl which may be substituted with halogen.

(70) The compound as described in (69), wherein B is thiazole-2,4-diyl which is bonded with —C(═O)—NR³— at the 2-position, thiazole-2,4-diyl which is bonded with —C(═O)—NR³— at the 4-position, pyrazole-1,3-diyl which is bonded with —C(═O)—NR³— at the 3-position, pyrazole-1,4-diyl which is bonded with —C(═O)—NR³— at the 4-position, oxazole-2,4-diyl which is bonded with —C(═O)—NR³— at the 2-position, thiophene-2,5-diyl which is bonded with —C(═O)—NR³— at the 2-position, thiophene-2,4-diyl which is bonded with —C(═O)—NR³— at the 2-position, furan-2,5-diyl which is bonded with —C(═O)—NR³— at the 2-position, furan-2,4-diyl which is bonded with —C(═O)—NR³— at the 2-position, isoxazole-3,5-diyl which is bonded with —C(═O)—NR³— at the 5-position, or pyrrole-2,5-diyl which is bonded with —C(═O)—NR³— at the 2-position, each of which may be substituted.

(71) The compound as described in (69), wherein B is thiazole-2,4-diyl which is bonded with —C(═O)—NR³— at the 2-position, thiazole-2,4-diyl which is bonded with —C(═O)—NR³— at the 4-position, pyrazole-1,3-diyl which is bonded with —C(═O)—NR³— at the 3-position, oxazole-2,4-diyl which is bonded with —C(═O)—NR³— at the 2-position, thiophene-2,5-diyl which is bonded with —C(═O)—NR³— at the 2-position, thiophene-2,4-diyl which is bonded with —C(═O)—NR³— at the 2-position, 5-methoxymethylthiophene-2,4-diyl which is bonded with —C(═O)—NR³— at the 2-position, 5-chlorothiophene-2,4-diyl which is bonded with —C(═O)—NR³— at the 2-position, furan-2,5-diyl which is bonded with —C(═O)—NR³— at the 2-position, 5-chlorothiazole-2,4-diyl which is bonded with —C(═O)—NR³— at the 2-position, or 5-methylthiazole-2,4-diyl which is bonded with —C(═O)—NR³— at the 2-position.

(72) The compound as described in (69), (70), or (71), wherein A is phenyl.

(73) The compound as described in (69) to (72), wherein $Y^2$ and $Y^4$ are $CR^{Y11}$, $R^{Y11}$'s are the same as or different from each other, and are H, F, methyl, or methoxy, $Y^1$, $Y^3$, and $Y^5$ are $CR^{Y21}$, and $R^{Y21}$'s are the same as or different from each other, and are H, OH, bromo, methyl, difluoromethyl, ethyl, ethenyl, isopropenyl, methoxy, methoxymethyl, 2-fluoroethoxy, or cyclopropyl.

(74) The compound as described in (69) to (72), wherein $Y^2$ and $Y^4$ are C—CH₃, $Y^3$ is C—O—CH₃, and $Y^1$ and $Y^5$ are CH.

(75) The compound as described in (69) to (74), wherein X is a single bond.

(76) The compound as described in (69) to (74), wherein X is —(CR$^{X1}$R$^{X2}$)$_n$—, n is 1, $R^{X1}$ and $R^{X2}$ are the same as or different from each other, and are H, OH, —O-(lower alkyl which may be substituted), or $R^{X1}$ and $R^{X2}$ are combined with each other to form oxo (═O) or $C_{2-5}$ alkylene which may be substituted.

(77) The compound as described in (69) to (74), wherein X is —(CR$^{X1}$R$^{X2}$)$_n$—, n is 1, $R^{X1}$ is H, $R^{X2}$ is OH or methoxy.

(78) The compound as described in (69) to (74), wherein X is —(CR$^{X1}$R$^{X2}$)n-, n is 1, and $R^{X1}$ and $R^{X2}$ are combined with each other to form oxo (═O), trimethylene or ethylene.

(79) The compound as described in (69) to (78), wherein m is 3, $R^1$ and $R^2$ are the same as or different from each other, and are H, F, methyl, or methoxy.

(80) The compound as described in (69) to (79), wherein L is a single bond.

(81) The compound as described in (69) to (79), wherein L is —(CR$^{L1}$R$^{L2}$)$_p$—, J-(O)$_q$—(CR$^{L3}$R$^{L4}$)$_r$—, p is 1, J is a single bond, q is 0, r is 0, and $R^{L1}$ and $R^{L2}$ are both H.

(82) The compound as described in (69) to (79), wherein L is —(CR$^{L1}$R$^{L2}$)$_p$-J-(O)$_q$—(CR$^{L3}$R$^{L4}$)$_r$—, p is 1, J is a single bond, q is 0, r is 0, $R^{L1}$ is H, and $R^{L2}$ is 2-methoxyethyl, methoxy, cyclopropyl, or —C(═O)—O—CH₃.

(83) The compound as described in (69) to (82), wherein B is thiazole-2,4-diyl which is bonded with —C(═O)—NR³— at the 2-position, or 5-methylthiazole-2,4-diyl which is bonded with —C(═O)—NR³— at the 2-position.

(84) The compound as described in (69) to (82), wherein B is pyrazole-1,3-diyl which is bonded with —C(=O)—NR³— at the 3-position, pyridine-2,6-diyl which is bonded with —C(=O)—NR³— at the 2-position, oxazole-2,4-diyl which is bonded with —C(=O)—NR³— at the 2-position, thiophene-2,5-diyl which is bonded with —C(=O)—NR³— at the 2-position, thiophene-2,4-diyl which is bonded with —C(=O)—NR³— at the 2-position, 5-methoxymethylthiophene-2,4-diyl which is bonded with —C(=O)—NR³— at the 2-position, 5-chlorothiophene-2,4-diyl which is bonded with —C(=O)—NR³— at the 2-position, furan-2,5-diyl which is bonded with —C(=O)—NR³— at the 2-position, or pyrazine-2,6-diyl which is bonded with —C(=O)—NR³— at the 2-position.

In addition, further still other embodiments of the compounds (I) and (I') of the present invention include the compounds or salts thereof including the combinations of two or more of the groups as described in (1) to (68), and specifically the following compounds or salts thereof.

(85) The compound as described in (14) to (18), or (49) to (68), wherein A is aryl which may be substituted with halogen, or an aromatic hetero ring which may be substituted with halogen.

(86) The compound as described in (14) to (18), or (49) to (68), wherein A is phenyl.

(87) The compound as described in (14) to (18), or (49) to (68), wherein A is phenyl which may be substituted with halogen, or a 5-membered aromatic hetero ring which may be substituted with halogen or lower alkyl.

(88) The compound as described in (14) to (18), or (49) to (68), wherein A is 2-fluorophenyl, 3-fluorophenyl, 4-fluorophenyl, 3-methylphenyl, 3-difluoromethylphenyl, 2-fluoro-4-trifluoromethylphenyl, 3-methylphenyl, 3-ethylphenyl, 3-butylphenyl, 2-fluoro-5-methylphenyl, 2-fluoro-3-methylphenyl, 3-bromophenyl, 3-chlorophenyl, or phenyl.

(89) The compound as described in (14) to (18), or (49) to (68), wherein A is furyl which may be substituted with halogen or lower alkyl, or thiophenyl which may be substituted with halogen or lower alkyl.

(90) The compound as described in (14) to (18), or (49) to (68), wherein A is furan-2-yl, 5-methylfuran-2-yl, 4,5-dimethylfuran-2-yl, 5-chlorofuran-2-yl, 5-ethylthiophen-2-yl, thiophen-2-yl, 2-methylthiophen-2-yl, 3-methylthiophen-2-yl, 4-methylthiophen-2-yl, 4,5-dimethylthiophen-2-yl, or 5-chlorothiophen-2-yl.

(91) The compound as described in (14) to (18), (49) to (68), or (85) to (90), wherein B is thiazole-2,4-diyl which is bonded with —C(=O)—NR³— at the 2-position, thiazole-2,4-diyl which is bonded with —C(=O)—NR³— at the 4-position, pyrazole-1,3-diyl which is bonded with —C(=O)—NR³— at the 3-position, pyrazole-1,4-diyl which is bonded with —C(=O)—NR³— at the 4-position, oxazole-2,4-diyl which is bonded with —C(=O)—NR³— at the 2-position, thiophene-2,5-diyl which is bonded with —C(=O)—NR³— at the 2-position, thiophene-2,4-diyl which is bonded with —C(=O)—NR³— at the 2-position, furan-2,5-diyl which is bonded with —C(=O)—NR³— at the 2-position, furan-2,4-diyl which is bonded with —C(=O)—NR³— at the 2-position, isoxazole-3,5-diyl which is bonded with —C(=O)—NR³— at the 5-position, or pyrrole-2,5-diyl which is bonded with —C(=O)—NR³— at the 2-position, each of which may be substituted.

(92) The compound as described in (14) to (18), (49) to (68), or (85) to (90), wherein B is thiazole-2,4-diyl which is bonded with —C(=O)—NR³— at the 2-position, thiazole-2,4-diyl which is bonded with —C(=O)—NR³— at the 4-position, pyrazole-1,3-diyl which is bonded with —C(=O)—NR³— at the 3-position, oxazole-2,4-diyl which is bonded with —C(=O)—NR³— at the 2-position, thiophene-2,5-diyl which is bonded with —C(=O)—NR³— at the 2-position, thiophene-2,4-diyl which is bonded with —C(=O)—NR³— at the 2-position, 5-methoxymethylthiophene-2,4-diyl which is bonded with —C(=O)—NR³— at the 2-position, 5-chlorothiophene-2,4-diyl which is bonded with —C(=O)—NR³— at the 2-position, furan-2,5-diyl which is bonded with —C(=O)—NR³— at the 2-position, 5-chlorothiazole-2,4-diyl which is bonded with —C(=O)—NR³— at the 2-position, or 5-methylthiazole-2,4-diyl which is bonded with —C(=O)—NR³— at the 2-position.

(93) The compound as described in (14) to (18), (49) to (68), or (85) to (90), wherein B is a 5-membered aromatic nitrogen-containing hetero ring.

(94) The compound as described in (14) to (18), (49) to (68), or (85) to (90), wherein B is

[Chem. 7]

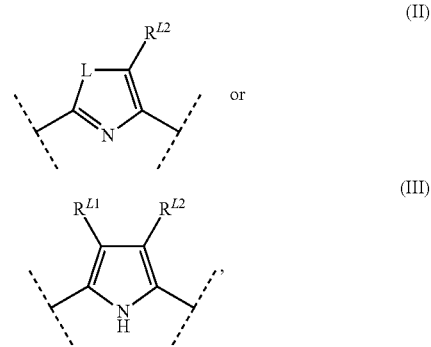

L is O, or S, $R^{L1}$ are H, halogen, lower alkyl which may be substituted, lower alkenyl which may be substituted, lower alkynyl which may be substituted, or cycloalkyl which may be substituted, $R^{L2}$ are H, halogen, lower alkyl which may be substituted, lower alkenyl which may be substituted, lower alkynyl which may be substituted, or cycloalkyl which may be substituted.

(95) The compound as described in (94), wherein B is the formula (III).

(96) The compound as described in (94) or (95), wherein $R^{L1}$ is H, halogen, or lower alkyl which may be substituted with halogen or OH.

(97) The compound as described in (94) or (95), wherein $R^{L1}$ is H.

(98) The compound as described in (94), wherein B is the formula (II) and L is O.

(99) The compound as described in (94), wherein B is the formula (II) and L is S.

(100) The compound as described in (94) to (99), wherein $R^{L2}$ are H, halogen, or lower alkyl which may be substituted with halogen or OH.

(101) The compound as described in (94) to (99), wherein $R^{L2}$ is H, Cl, or methyl.

(102) The compound as described in (14) to (18), (49) to (68), or (85) to (101), wherein X is a single bond.

(103) The compound as described in (14) to (18), (49) to (68), or (85) to (101), wherein X is n is —$(CR^{X1}R^{X2})_n$—, $R^{X1}$ and $R^{X2}$ are the same as or different from each other, and are H, OH, —O-(lower alkyl which may be substituted), or $R^{X1}$ and $R^{X2}$ are combined with each other to form oxo (=O) or $C_{2-5}$ alkylene which may be substituted.

(104) The compound as described in (14) to (18), (49) to (68), or (85) to (101), wherein X is $—(CR^{X1}R^{X2})_n—$, n is 1, $R^{X1}$ is H, and $R^{X2}$ is OH or methoxy.

(105) The compound as described in (14) to (18), (49) to (68), or (85) to (101), wherein X is $—(CR^{X1}R^{X2})_n—$, n is 1, and $R^{X1}$ and $R^{X2}$ are combined with each other to form oxo (=O), trimethylene or ethylene.

(106) The compound as described in (14) to (18), (49) to (68), or (85) to (101), wherein X is $—(CR^{X1}R^{X2})_n—$, n is 1, $R^{X1}$ is H, and $R^{X2}$ is OH.

(107) The compound as described in (14) to (18), (49) to (68), or (85) to (101), wherein X is $—(CR^{X1}R^{X2})_n—$, n is 1, and $R^{X1}$ and $R^{X2}$ are combined with each other to form ethylene.

(108) The compound as described in (14) to (18), (49) to (68), or (85) to (107), wherein $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl.

(109) The compound as described in (14) to (18), (49) to (68), or (85) to (107), wherein $R^Y$'s are the same as or different from each other, and are H, OH, halogen, lower alkyl, or —O-(lower alkyl).

(110) The compound as described in (14) to (18), (49) to (68), or (85) to (107), wherein $R^Y$'s are the same as or different from each other, and are H, OH, halogen, methyl, or methoxy.

(111) The compound as described in (14) to (18), (49) to (68), or (85) to (107), wherein $Y^1, Y^2, Y^3, Y^4$, and $Y^5$ are $CR^Y$, and $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl.

(112) The compound as described in (14) to (18), (49) to (68), or (85) to (107), wherein $Y^2$ and $Y^4$ are $CR^{Y11}$, $R^{Y11}$'s are the same as or different from each other, and are H, F, methyl, or methoxy, $Y^1, Y^3$, and $Y^5$ are $CR^{Y21}$, and $R^{Y21}$'s are H, OH, bromo, methyl, difluoromethyl, ethyl, ethenyl, isopropenyl, methoxy, methoxymethyl, 2-fluoroethoxy, or cyclopropyl.

(113) The compound as described in (14) to (18), (49) to (68), or (85) to (107), wherein $Y^2$ and $Y^4$ are $C—CH_3$, $Y^3$ is $C—O—CH_3$, and $Y^1$ and $Y^5$ are CH.

(114) The compound as described in (14) to (18), (49) to (68), or (85) to (107), wherein $Y^2, Y^3, Y^4$, and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, and $Y^1$ is N.

(115) The compound as described in (14) to (18), (49) to (68), or (85) to (107), wherein $Y^2, Y^3, Y^4$, and $Y^5$ are $CR^Y$, $R^Y$'s are the same as or different from each other, and are H, or —O-(lower alkyl), and $Y^1$ is N.

(116) The compound as described in (14) to (18), (49) to (68), or (85) to (107), wherein $Y^2, Y^4$, and $Y^5$ are CH, $Y^3$ is $C—O—CH_3$, and $Y^1$ is N.

(117) The compound as described in (14) to (18), (49) to (68), or (85) to (107), wherein $Y^1, Y^3, Y^4$, and $Y^5$ are $CR^Y$, $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, and $Y^2$ is N.

(118) The compound as described in (14) to (18), (49) to (68), or (85) to (107), wherein $Y^1, Y^3, Y^4$, and $Y^5$ are $CR^Y$, $R^Y$'s are the same as or different from each other, and are H, or —O-(lower alkyl), and $Y^2$ is N.

(119) The compound as described in (14) to (18), (49) to (68), or (85) to (107), wherein $Y^1, Y^4$, and $Y^5$ are CH, $Y^3$ is $C—O—CH_3$, and $Y^2$ is N.

(120) The compound as described in (14) to (18), (49) to (68), or (85) to (107), wherein $Y^1, Y^2, Y^3, Y^4$, and $Y^5$ are $CR^Y$, and $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl.

(121) The compound as described in (14) to (18), (49) to (68), or (85) to (107), wherein $Y^1, Y^2, Y^3, Y^4$, and $Y^5$ are $CR^Y$, and $R^Y$'s are the same as or different from each other, and are H, lower alkyl, or —O-(lower alkyl).

(122) The compound as described in (14) to (18), (49) to (68), or (85) to (107), wherein $Y^1, Y^2, Y^4$, and $Y^5$ are CH, and $Y^3$ is $C—O—CH_3$.

(123) The compound as described in (14) to (18), (49) to (68), or (85) to (107), wherein $Y^2$ and $Y^4$ are $C—O—CH_3$, $Y^3$ is $C—CH_3$, and $Y^1$ and $Y^5$ are CH.

(124) The compound as described in (14) to (18), (49) to (68), or (85) to (107), wherein m is 3, and $R^1$ and $R^2$ are the same as or different from each other, and are H, halogen, —O-(lower alkyl which may be substituted with halogen), or lower alkyl which may be substituted with halogen.

(125) The compound as described in (14) to (18), (49) to (68), or (85) to (123), wherein m is 3, and $R^1$ and $R^2$ are the same as or different from each other, and are H, F, methyl, or methoxy.

(126) The compound as described in (14) to (18), (49) to (68), or (85) to (125), wherein $R^3$ is H.

(127) The compound as described in (14) to (18), (49) to (68), or (85) to (125), wherein $R^3$ is methyl.

Specific examples of the compound included in the present invention include the following compounds or salts thereof:

2-{[(3,5-dimethoxy-4-methylbenzoyl)(3-phenylpropyl)amino]methyl}-N-(methylsulfonyl)-1,3-thiazole-4-carboxamide, 2-{[(3,5-dimethoxy-4-methylbenzoyl)(3-phenylpropyl)amino]methyl}-N-(2-thienylsulfonyl)-1,3-thiazole-4-carboxamide, N-(aminosulfonyl)-2-{[(3,5-dimethoxy-4-methylbenzoyl)(3-phenylpropyl)amino]methyl}-1,3-thiazole-4-carboxamide, 5-chloro-2-{[(3,5-dimethoxybenzoyl)(3-phenylpropyl)amino]methyl}-N-(methylsulfonyl)-1,3-thiazole-4-carboxamide, N-(aminosulfonyl)-5-chloro-2-{[(4-hydroxy-3,5-dimethylbenzoyl)(3-phenylpropyl)amino]methyl}-1,3-thiazole-4-carboxamide, N-(aminosulfonyl)-2-{[(3,5-dimethoxy-4-methylbenzoyl)(3-phenylpropyl)amino]methyl}-1,3-oxazol-4-carboxamide, N-(aminosulfonyl)-2-{[(4-cyclopropyl-3,5-dimethoxybenzoyl)(3-phenylpropyl)amino]methyl}-1,3-thiazole-4-carboxamide, N-(aminosulfonyl)-2-{[(4-bromo-3,5-dimethoxybenzoyl)(3-phenylpropyl)amino]methyl}-1,3-thiazole-4-carboxamide, N-(acetamidesulfonyl)-2-{[(3,5-dimethoxy-4-methylbenzoyl)(3-phenylpropyl)amino]methyl}-1,3-thiazole-4-carboxamide, 2-{[(3,5-dimethoxy-4-methylbenzoyl)(3-phenylpropyl)amino]methyl}-N-[(ethylamino)sulfonyl]-1,3-thiazole-4-carboxamide, N-(aminosulfonyl)-2-({[3-(5-chloro-2-thienyl)propyl](3,5-dimethoxy-4-methylbenzoyl)amino}methyl)-1,3-thiazole-4-carboxamide, N-(aminosulfonyl)-2-({(3,5-dimethoxy-4-methylbenzoyl)[3-(5-methyl-2-furyl)propyl]amino}methyl)-1,3-thiazole-4-carboxamide, N-(aminosulfonyl)-2-({(3,5-dimethoxy-4-methylbenzoyl)[3-(2-fluorophenyl)propyl]amino}methyl)-1,3-thiazole-4-carboxamide, N-(aminosulfonyl)-2-({[3-(2,5-difluorophenyl)propyl](3,5-dimethoxy-4-methylbenzoyl)amino}methyl)-1,3-thiazole-4-carboxamide, N-(aminosulfonyl)-4-{[(3,5-dimethoxy-4-methylbenzoyl)(3-phenylpropyl)amino]methyl}-1,3-thiazole-2-carboxamide, 2-{[(3,5-dimethoxybenzoyl)(3-phenylpropyl)amino]methyl}-5-methyl-N-[(methylamino)sulfonyl]-1,3-thiazole-4-carboxamide, 2-{[(4-ethyl-3,5-dimethoxybenzoyl)(3-phenylpropyl)amino]methyl}-5-methyl-N-[(methylamino)sulfonyl]-1,3-thiazole-4-carboxamide, 2-({(3,5-dimethoxy-4-methylbenzoyl)[3-(3-thienyl)propyl]amino}methyl)-N-[(methylamino)sulfonyl]-1,3-thiazole-4-carboxamide, N-(aminosulfonyl)-2-{[(3,5-dimethoxy-4-methylbenzoyl)(3-phenylpropyl)amino]methyl}-N-methyl-1,3-thiazole-4-carboxamide, 2-{[(4-cyclopropyl-3,5-dimethoxybenzoyl)(3-phenylpropyl)amino]methyl}-5-methyl-N-[(methylamino)sulfonyl]-1,3-thiazole-4-carboxamide, methyl ({[(2-{[(3,5-dimethoxy-4-methylbenzoyl)(3-phenylpropyl)amino]methyl}-1,3-thiazol-4-yl)carbonyl]amino}sulfonyl)methylcarbamate, 2-{[(3,5-dimethoxy-4-methylbenzoyl)(3-phenylpropyl)amino]methyl}-N-{[(2-fluoroethyl)(methyl)amino]sulfonyl}-5-methyl-1,3-thiazole-4-carboxamide, 2-{[(3,5-dimethoxy-4-methylbenzoyl)(3-phenylpropyl)amino]methyl}-N-[(pyridin-2-yl amino)sulfonyl]-1,3-thiazole-4-carboxamide, 2-{[(3,5-dimethoxy-4-methylbenzoyl)(3-phenylpropyl)amino]methyl}-N-{[ethyl(2-hydroxyethyl)amino]sulfonyl}-1,3-thiazole-4-carboxamide, 2-{[(3,5-dimethoxybenzoyl)(3-phenylpropyl)amino]methyl}-N-[(methoxyamino)sulfonyl]-5-methyl-1,3-thiazole-4-carboxamide, 2-{[(3,5-dimethoxy-4-methylbenzoyl)(3-phenylpropyl)amino]methyl}-N-{[(2-fluoroethyl)(2-hydroxyethyl)amino]sulfonyl}-1,3-thiazole-4-carboxamide, 2-{[(3,5-dimethoxy-4-methylbenzoyl)(3-phenylpropyl)amino]methyl}-5-methyl-N-(methylsulfonyl)-1,3-thiazole-4-carboxamide, 2-({[(2,4-dimethoxyphenyl)acetyl] (3-phenylpropyl)amino}methyl)-N-[(dimethylamino)sulfonyl]-5-methyl-1,3-thiazole-4-carboxamide, 2-{[(3,5-dimethoxy-4-methylbenzoyl)(3-phenylpropyl)amino]methyl}-N-[(2-hydroxypropyl)sulfonyl]-1,3-thiazole-4-carboxamide, 2-({[3,5-dimethoxy-4-(methoxymethyl)benzoyl](3-phenylpropyl)amino}methyl)-N-[(methoxyamino)sulfonyl]-5-methyl-1,3-thiazole-4-carboxamide, 2-({(3,5-dimethoxy-4-methylbenzoyl)[3-(2-fluorophenyl)propyl]amino}methyl)-N-[(dimethylamino)sulfonyl]-1,3-thiazole-4-carboxamide, 2-({[hydroxy(4-methoxyphenyl)acetyl] (3-phenylpropyl)amino}methyl)-5-methyl-N-(methylsulfonyl)-1,3-thiazole-4-carboxamide, N-aminosulfonyl-2-({[hydroxy(4-methoxyphenyl)acetyl](3-phenylpropyl)amino}methyl)-5-methyl-1,3-thiazole-4-carboxamide, N-[(dimethylamino)sulfonyl]-2-({[(2-fluoro-4-methoxyphenyl)(hydroxy)acetyl](3-phenylpropyl)amino}methyl)-5-methyl-1,3-thiazole-4-carboxamide, N-[(dimethylamino)sulfonyl]-2-({[hydroxy(6-methoxypyridin-3-yl)acetyl](3-phenylpropyl)amino}methyl)-5-methyl-1,3-thiazole-4-carboxamide, N-(dimethylsulfamoyl)-2-{[{[1-(5-methoxypyridin-2-yl)cyclopropyl]carbonyl}(3-phenylpropyl)amino]methyl}-5-methyl-1,3-thiazole-4-carboxamide, 5-chloro-N-(dimethylsulfamoyl)-2-{[{[1-(6-methoxypyridin-3-yl)cyclopropyl]carbonyl}(3-phenylpropyl)amino]methyl}-1,3-thiazole-4-carboxamide, N-(dimethylsulfamoyl)-2-[({[1-(5-methoxypyridin-2-yl)cyclopropyl]carbonyl}[3-(5-methyl-2-furyl)propyl]amino)methyl]-5-methyl-1,3-thiazole-4-carboxamide, 2-({[(2R)-2-hydroxy-2-(4-methoxyphenyl)acetyl] (3-phenylpropyl)amino}methyl)-5-methyl-N-(methylsulfonyl)-1,3-thiazole-4-carboxamide, N-(dimethylsulfamoyl)-2-{[(3-fluoro-3-phenylpropyl) {[1-(4-methoxyphenyl)cyclopropyl]carbonyl}amino]methyl}-5-methyl-1,3-thiazole-4-carboxamide, N-(dimethylsulfamoyl)-2-[([3-(3-fluorophenyl)propyl]{[1-(5-methoxypyridin-2-yl)cyclopropyl]carbonyl}amino)methyl]-5-methyl-1,3-thiazole-4-carboxamide, N-(dimethylsulfamoyl)-2-({[(2R)-2-hydroxy-2-(4-methoxyphenyl)acetyl](3-phenylpropyl)amino}methyl)-5-methyl-1,3-thiazole-4-carboxamide, N-(dimethylsulfamoyl)-2-[({[1-(5-methoxypyridin-2-yl)cyclopropyl]carbonyl}[3-(2-thienyl)propyl]amino)methyl]-5-methyl-1,3-thiazole-4-carboxamide, N-(dimethylsulfamoyl)-2-[([3-(2-furyl)propyl]{[1-(5-methoxypyridin-2-yl)cyclopropyl]carbonyl}amino)methyl]-5-methyl-1,3-thiazole-4-carboxamide, N-(dimethylsulfamoyl)-2-({[hydroxy(4-methoxy-2-methylphenyl)acetyl] (3-phenylpropyl)amino}methyl)-5-methyl-1,3-thiazole-4-carboxamide, 2-({[3-(3-fluorophenyl)propyl][(2R)-2-hydroxy-2-(4-methoxyphenyl)acetyl]amino}methyl)-5-methyl-N-sulfamoyl-1,3-thiazole-4-carboxamide, 2-({[(2R)-2-hydroxy-2-(4-methoxyphenyl)acetyl](3-phenylpropyl)amino}methyl)-5-methyl-N-(methylsulfamoyl)-1,3-thiazole-4-carboxamide, N-(dimethylsulfamoyl)-2-({[(2R)-2-hydroxy-2-(4-methoxyphenyl)acetyl][3-(2-thienyl)propyl]amino}methyl)-5-methyl-1,3-thiazole-4-carboxamide, 5-bromo-N-(dimethylsulfamoyl)-2-({[(R2)-2-hydroxy-2-(4-methoxyphenyl)acetyl](3-phenylpropyl)amino}methyl)-1,3-thiazole-4-carboxamide, N-(ethylsulfonyl)-2-({[(2R)-2-hydroxy-2-(4-methoxyphenyl)acetyl](3-phenylpropyl)amino}methyl)-5-methyl-1,3-thiazole-4-carboxamide, N-(dimethylsulfamoyl)-2-[([3-(2-furyl)propyl]{[1-(4-methoxyphenyl)cyclopropyl]carbonyl}amino)methyl]-5-methyl-1,3-thiazole-4-carboxamide, N-(dimethylsulfamoyl)-2-[([3-(3-ethynylphenyl)propyl]{[1-(5-methoxypyridin-2-yl)cyclopropyl]carbonyl}amino)methyl]-5-methyl-1,3-thiazole-4-carboxamide, 2-({[3-(3-fluorophenyl)propyl][(2R)-2-hydroxy-2-(4-methoxyphenyl)acetyl]amino}methyl)-5-methyl-N-(methylsulfonyl)-1,3-thiazole-4-carboxamide,
N-(ethylsulfonyl)-2-({[3-(3-fluorophenyl)propyl][(2R)-2-hydroxy-2-(4-methoxyphenyl)acetyl]amino}methyl)-5-methyl-1,3-thiazole-4-carboxamide,
N-(ethylsulfonyl)-2-({[(2R)-2-hydroxy-2-(4-methoxyphenyl)acetyl][3-(2-thienyl)propyl]amino}methyl)-5-methyl-1,3-thiazole-4-carboxamide,
2-({[(2R)-2-(2-fluoro-4-methoxyphenyl)-2-hydroxyacetyl](3-phenylpropyl)amino}methyl)-5-methyl-N-(methylsulfonyl)-1,3-thiazole-4-carboxamide,
2-({[(2R)-2-hydroxy-2-(4-methoxyphenyl)acetyl][3-(2-thienyl)propyl]amino}methyl)-5-methyl-N-(methylsulfamoyl)-1,3-thiazole-4-carboxamide,
2-({[(2R)-2-(2-fluoro-4-methoxyphenyl)-2-hydroxyacetyl](3-phenylpropyl)amino}methyl)-5-methyl-N-(methylsulfamoyl)-1,3-thiazole-4-carboxamide, or
2-({[(2R)-2-hydroxy-2-(4-methoxyphenyl)acetyl](3-phenylpropyl)amino}methyl)-N-(isopropylsulfonyl)-5-methyl-1,3-thiazole-4-carboxamide.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Drug Design, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystalline substances of the compound of the formula (I) and a salt thereof. In addition, the present invention also includes compounds labeled with various radioactive or non-radioactive isotopes.

(Preparation Methods)
The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4th edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

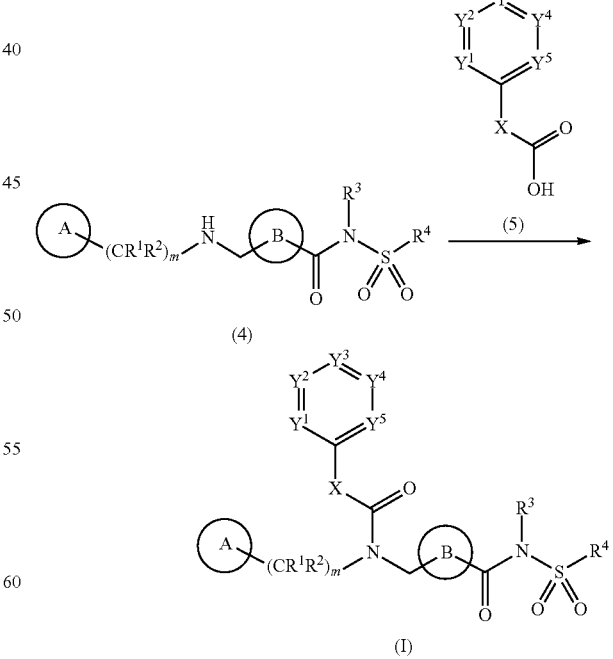

[Chem. 8]

The compound (I) of the present invention can be obtained by the condensation of a compound (4) with a carboxylic acid (5) or a derivative thereof.

For the reaction, the compound (4) and the carboxylic acid (5) in an equivalent amount, or in an excess amount are used, and a mixture thereof is stirred in a range of from cooling to heating, preferably at a temperature from −20° C. to 60° C., usually for about 0.1 hours to 5 days, in a solvent which is inert to the reaction, in the presence of a condensing agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, DMF, DMSO, EtOAc, acetonitrile, or water, and a mixture thereof. Examples of the condensing agent include, but are not limited to, CDI, diphenylphosphonyl azide, phosphorus oxychloride, and WSC (Water-Soluble Condensing agent, trademark, 1-(3-dimethylaminopropyl)-3-ethylcarbodiimide, dicyclohexylcarbodiimide, and the like). It may be in some cases preferable for the reaction to use an additive (for example, 1-hydroxybenzotriazole). It is in some cases advantageous for smooth progress of the reaction to carry out the reaction in the presence of organic bases such as triethylamine, N,N-diisopropylethylamine, N-methylmorpholine, DBU, DMAP, and the like, or inorganic bases such as potassium carbonate, sodium carbonate, potassium hydroxide, and the like.

Furthermore, it is also possible to use a method in which a reactive derivative of the carboxylic acid (5) is used, and reacted with the compound (4). Examples of the reactive derivative of the carboxylic acid include acid halides that can be obtained by the reaction with a halogenating agent such as phosphorus oxychloride, thionyl chloride, and the like, mixed acid anhydrides that can be obtained by the reaction with isobutyl chloroformate or the like, active esters that can be obtained by condensation with 1-hydroxybenzotriazole or the like, etc. The reaction of the reactive derivative with the compound (4) can be carried out in a range of from cooling to heating, and preferably from −20° C. to 60° C., in a solvent which is inert to the reaction, such as halogenated hydrocarbons, aromatic hydrocarbons, ethers, and the like.

DOCUMENTS

"Organic Functional Group Preparations", S. R. Sandler and W. Karo, 2$^{nd}$ edition, Vol. 1, Academic Press Inc., 1991

The Chemical Society of Japan, "Courses in Experimental Chemistry (5$^{th}$ edition)" Vol. 16 (2005) (Maruzen)

(Production Process 2)

[Chem. 9]

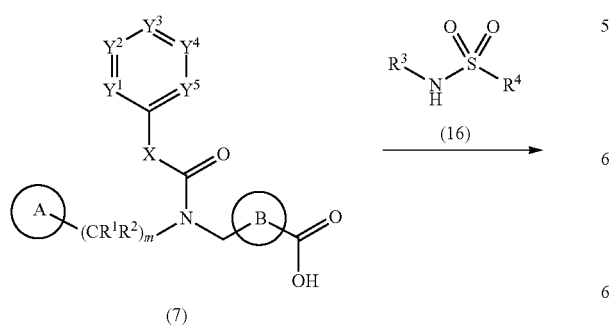

(16)

(7)

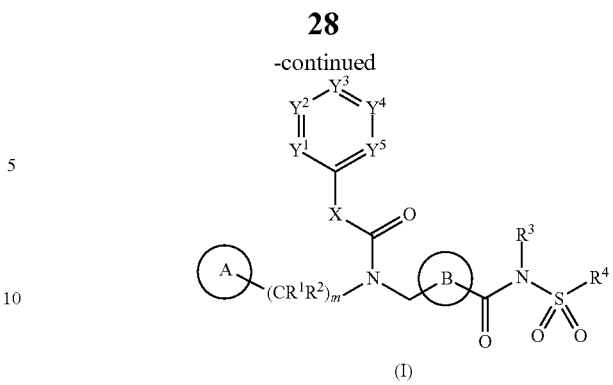

(I)

The compound (I) of the present invention can be obtained by the condensation of a compound (16) with a compound (7).

The present reaction can be carried out using the reaction condition as described in (Production Process 1).

(Other Production Processes)

Furthermore, various substituents in the formula (I) can also be easily converted into other functional groups by using the compound (I) of the present invention as a starting material by means of reactions apparent to a skilled person in the art, or modified methods thereof. The reaction can be carried out by any combination of the processes that can be usually employed by a skilled person in the art, such as hydrolysis, alkylation, halogenation, hydrogenation, and the like. Examples thereof are presented below.

(Production Process 3)

[Chem. 10]

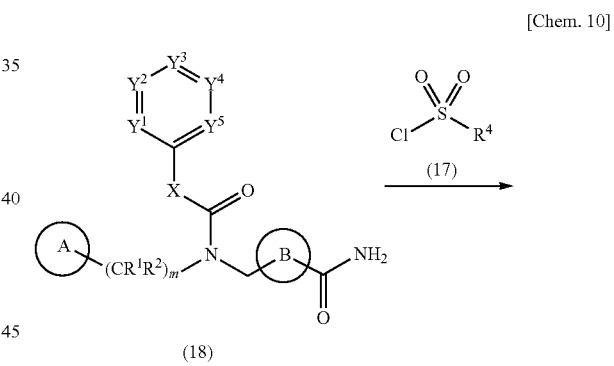

(18)

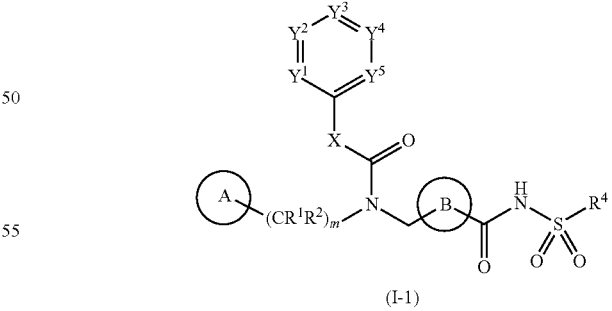

(I-1)

(wherein R is $R^{Z11}$ or $NR^{Z13}R^{Z14}$.)

The compound (1-1) of the present invention can be obtained by the substitution reaction of a compound (18) and a compound (17).

In this reaction, the compound (18) and the compound (17) in an equivalent amount, or in an excess amount are used, a mixture thereof is stirred in a range of from cooling to heating and refluxing, preferably at 0° C. to 200° C., and preferably at 150° C. to 200° C., usually for 0.1 hours to 5 days in a solvent which is inert to the reaction or without a solvent. It is in some cases advantageous for smooth progress of the reaction to carry out the reaction under irradiation with microwaves. The solvent used herein is not particularly limited, but examples thereof include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as sodium tert-butoxide, potassium carbonate, sodium bis(methylsilyl)amide, sodium carbonate, potassium hydroxide, and the like.

Furthermore, the reaction may be carried out using a catalyst which is not particularly limited, but includes catalysts used for an Ullmann reaction, a Buchwald-Hartwig reaction, or the like. The catalyst as used herein is not particularly limited, but a suitable combination of tris(dibenzylideneacetone) palladium, tetrakis(triphenylphosphine) palladium, or the like with 4,5-bis(diphenylphosphino)-9,9'-dimethylxanthene (Xantphos), 2-dicyclohexylphosphino-2',6'-dimethoxybiphenyl (SPhos), 2-dicyclohexylphosphino-2',4',6'-triisopropylbiphenyl (XPhos), and the like can be used.

DOCUMENTS

"Organic Functional Group Preparations", S. R. Sandler and W. Karo, 2nd edition, Vol. 1, Academic Press Inc., 1991
The Chemical Society of Japan, "Courses in Experimental Chemistry (5th edition)" Vol. 14 (2005) (Maruzen)
Synthesis 2006, 4, 629-632
(Starting Material Synthesis 1)

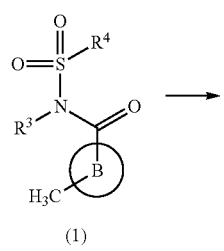

First, the compound (1) can be converted to the compound (2), for example, by reacting a brominating agent used for a Wohl-Ziegler reaction, such as N-bromoacetamide and N-bromosuccinimide in the presence of a radical initiator.

In this reaction, the compound (1) is treated with a brominating agent in an equivalent amount or in an excess amount in a range of from cooling to heating, preferably at 0° C. to 150° C., and preferably at 0° C. to 120° C., usually for 0.1 hours to 5 hours, and preferably 1 to 2 hours, in a solvent which is inert to the reaction, in the presence of a radical initiator. It is in some cases advantageous for smooth progress of the reaction to carry out the reaction under irradiation with microwaves.

The solvent used herein is not particularly limited, but examples thereof include aromatic hydrocarbons such as benzene, toluene, xylene, and the like, halogenated hydrocarbons such as 1,2-dichloroethane, chloroform, carbon tetrachloride, and the like, and a mixture thereof. Further, examples of the radical initiator are not particularly limited, but include benzoyl peroxide and azoisobutyronitrile.

Next, the compound (2) can be converted to the compound (4) by the nucleophilic substitution reaction of the amine compound (3).

In this reaction, the compound (2) and the amine compound (3) in equivalent amounts, or with either thereof in an excess amount are used, and a mixture thereof is stirred in a range of from cooling to heating and refluxing, and preferably at −20° C. to 80° C., usually for 0.1 hours to 5 days in a solvent which is inert to the reaction or without a solvent. The solvent used herein is not particularly limited, but examples thereof include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, DMF, DMSO, EtOAc, acetonitrile, and a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as potassium carbonate, sodium carbonate, potassium hydroxide, and the like.

(Starting Material Synthesis 2)

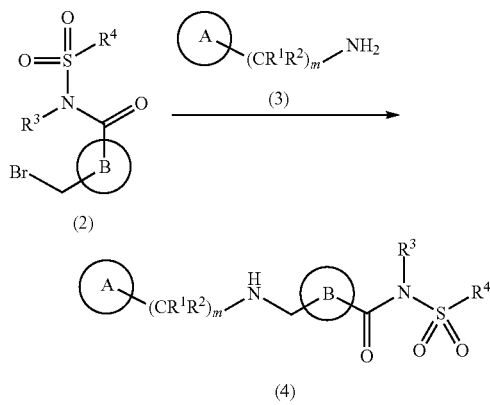

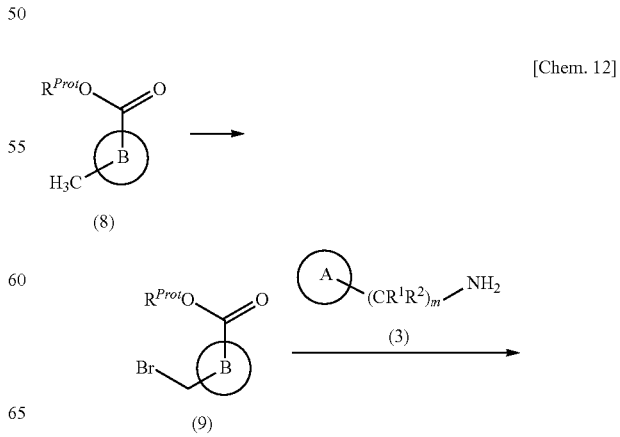

-continued

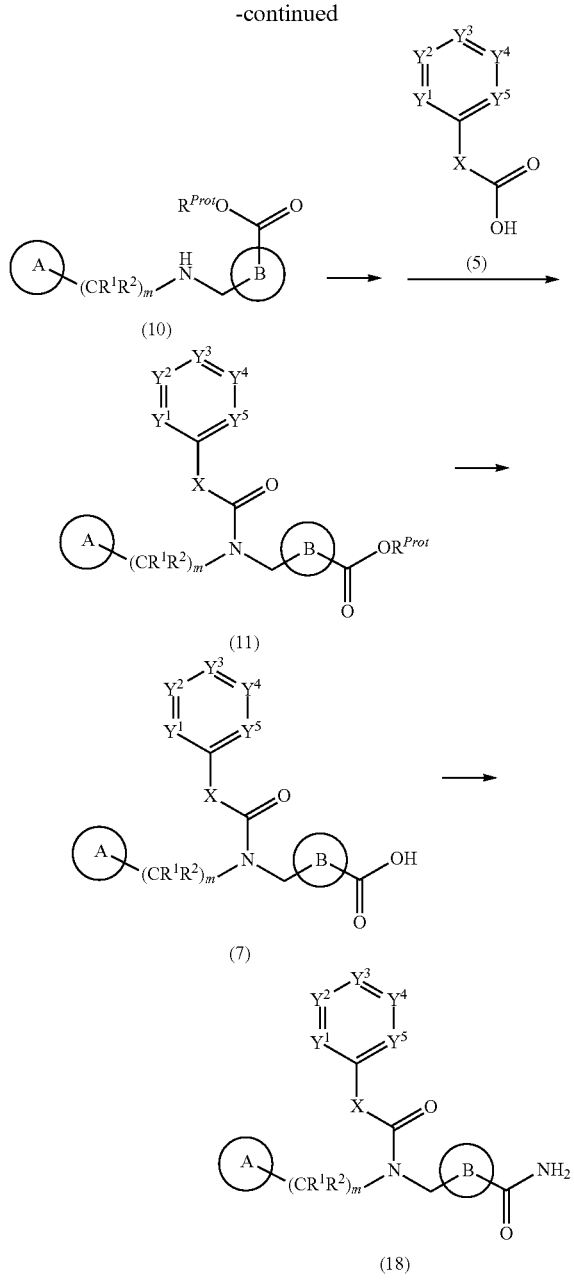

(wherein $R^{Prot}$ represents lower alkyl or aryl.)

The compound (10) can be prepared by treating the compound (8) using the same condition as for the reaction described in (Starting Material Synthesis 1).

Next, the compound (11) can be prepared by the reaction of the compound (10) and the carboxylic acid (5) using the same condition as for the reaction described in (Production Process 1) as described above.

The compound (7) can be obtained by the hydrolysis reaction of the compound (11). Herein, the hydrolysis reaction can be carried out with reference to documents such as Greene, and the like.

The compound (18) can be obtained by the condensation reaction of the compound (7) with $NH_3$ using the same condition as for the reaction described in (Production Process 1) as described above.

DOCUMENTS

"Organic Functional Group Preparations", S. R. Sandler and W. Karo, 2$^{nd}$ edition, Vol. 1, Academic Press Inc., 1991

The Chemical Society of Japan, "Courses in Experimental Chemistry (5$^{th}$ edition)" Vol. 14 (2005) (Maruzen)

"Greene's Protective Groups in Organic Synthesis (4$^{th}$ edition, 2006)", P. G. M. Wuts and T. W. Greene (Starting Material Synthesis 3)

[Chem. 13]

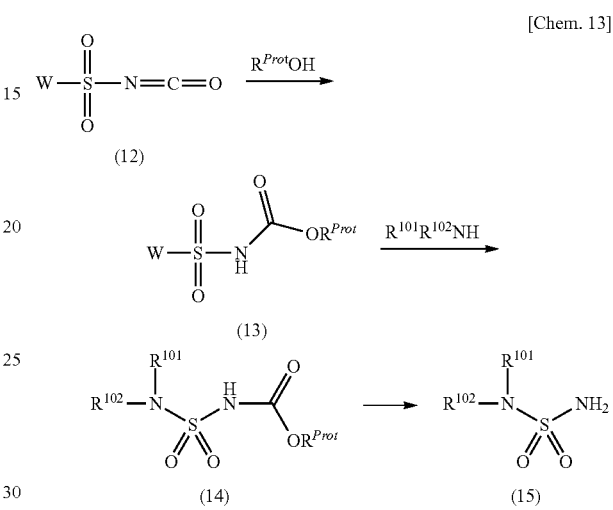

(wherein W represents a leaving group, and $R^{Prot}$ represents lower alkyl or aryl.)

The compound (15) is prepared by three steps from the isocyanate (12). Here, examples of the leaving group X include halogen.

First, the compound (13) can be obtained by the addition reaction of the isocyanate (12) and an alcohol, $R^{Prot}OH$.

In this reaction, a mixture of the isocyanate (12) and the alcohol, $R^{Prot}OH$ in an equivalent amount or in an excess amount are reacted in a range of from cooling to heating, and preferably at −50° C. to 100° C., and preferably at −20° C. to 90° C., usually for 0.1 hours to 10 hours, and preferably for about 1 hour to 3 hours, in a solvent which is inert to the reaction or without a solvent. The solvent used in this step is not particularly limited, but examples thereof include halogenated hydrocarbons such as dichloromethane, 1,2-dichloroethane, chloroform, and the like, ethers such as diethyl ether, tetrahydrofuran, dioxane, dimethoxyethane, and the like, alcohols such as MeOH, EtOH, tert-butanol, and the like, DMF, DMSO, EtOAc, water, and acetonitrile.

Next, the compound (13) can be converted to the compound (14) by the nucleophilic substitution reaction of an amine, $R^{101}R^{102}NH$, using the same method as for (Starting Material Synthesis 1) as described above.

Lastly, an aminosulfonamide compound (15) can be obtained by the deprotection reaction of the compound (14) with reference to documents such as Greene, and the like.

DOCUMENT

Pamphlet of International Publication WO 2002/053557

The compounds of the formula (I) can be isolated and purified as their free compounds, salts, hydrates, solvates, or polymorphic crystalline substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

Test Example 1

Antagonistic Action of Compound of Formula (I) on Human LPA1

The antagonistic action on a human LPA 1 was evaluated with an index of an inhibitory action on the LPA-stimulated increase in intracellular calcium ion concentration, using human LPA 1-CHO cells [cells in which human LPA1 receptors are stably expressed in CHO (dhfr gene-deficient) cell lines].

Establishment of human LPA1-CHO cells was performed based on the basic genetic engineering techniques.

The established cells were maintained by passage in a nucleic acid-free α-MEM medium (Invitrogen) containing 10% FBS, 1% penicillin/streptomycin (Invitrogen), and 100 nM methotrexate, and before experiment, the medium was replaced with a medium that had been reduced to 1% of the PBS concentration, then seeded in 96-well plates to $1.5 \times 10e^5$ cells/100 μL/well, and incubated overnight.

On the day of experiment, a 0.5 μM Fluo-4 solution [a solution prepared by adding 20 mM HEPES (Sigma), 250 mM probenecid (Nacalai Tesque), 0.05% BSA, 0.5 μM Fluo-4 AM (Dojindo Laboratories), and 0.1% Pluronic F217 (Molecular Probe Co.) to a Hanks Balanced Solt Solution (Invitrogen)] was added to the cells, and Fluo-4 was loaded on the cells by incubating for 2 hours at room temperature.

After loading Fluo-4, the Fluo-4 solution was replaced with a reaction solution [a solution obtained by adding 20 mM HEPES, 250 mM probenecid, and 0.05% BSA to a Hanks Balanced Solt Solution], and then measurement was performed using a device for measuring an intracellular calcium concentration (FLIPR tetra, Molecular Devices Inc.).

A reaction solution in which the compound of the formula (I) (with a final concentration of 0.1 nM to 10 μM) had been dissolved was added to each of the wells, the signals were measured over time for 4 minutes, then a reaction solution in which LPA (final concentration 100 nM) had been dissolved was added thereto, and the signals were measured over time for 2 minutes. The difference between the maximum and minimum response during one minute from addition of LPA was calculated. The inhibitory activity was calculated, with a response when LPA only (not including the compound) was added was taken as 0% inhibition, and a response when a reaction solution not including both of the compound and LPA was added was taken as 100% inhibition. Then the 50% inhibitory concentration was calculated as an $IC_{50}$ value (nM). The results are shown in Table 1.

Human LPA1-CHO cells used in the present test were the cells with the same sequence as described in the pamphlet of International Publication WO 99/19513 were used. Further, Ex represents Example No. as denoted below.

TABLE 1

| Ex | $IC_{50}$ (nM) |
|---|---|
| 5 | 7.8 |
| 69 | 8.8 |
| 22 | 24 |
| 27 | 14 |
| 56 | 29 |
| 62 | 11 |
| 71 | 16 |
| 79 | 16 |
| 89 | 17 |
| 108 | 11 |
| 109 | 22 |
| 110 | 11 |
| 111 | 6.6 |
| 113 | 12 |
| 115 | 16 |
| 121 | 19 |
| 123 | 7.5 |
| 126 | 20 |
| 131 | 7.2 |
| 134 | 25 |
| 137 | 9.9 |
| 145 | 23 |
| 147 | 16 |
| 153 | 21 |
| 154 | 34 |
| 156 | 15 |
| 167 | 12 |
| 168 | 17 |
| 170 | 34 |
| 175 | 23 |
| 176 | 24 |
| 200 | 33 |
| 208 | 40 |
| 233 | 22 |
| 266 | 65 |
| 272 | 44 |
| 277 | 12 |
| 283 | 29 |
| 285 | 32 |
| 290 | 33 |

Further, as a result of the present test on the compound of Example 10 (5) in the pamphlet of WO 2004/031118, the $IC_{50}$ value of the relevant compound was 99 nM. Accordingly, it became apparent that the compound of the present invention has an excellent LPA1 receptor antagonistic action, as compared with the relevant compound.

Test Example 2

Inhibitory Action of Compound of Formula (I) on LPA-Induced Increase in Urethral Pressure in Rats Under Anesthesia (with Intravenous Administration at 0.1 mg/kg)

Male Wistar rats (Charles River, 9- to 12-week old) were anesthetized with urethane (1.2 g/kg ip), and held in the supine position on an operating table kept at 37° C. The lower abdominal portion was midline-incised and the bladder was thus exposed. A small portion of the bladder apex was incised, a microchip pressure transducer (Millar) was inserted antegrade, and then placed in the urethra, and the urethral pressure was recorded continuously. In addition, a cannula for administration of a drug was placed into the femoral vein. After about 1 hour of stabilization, the compound of formula (I) (0.1 mg/kg) was administered intravenously. After 5 minutes, LPA (1-oleoyl) was administered intravenously at 3 mg/kg, and the changes in the urethral pressure were recorded. The inhibitory rates (%) of the compound of the formula (I) on the LPA-stimulated increase in the urethral pressure compared with those after administration of the solvent of the compound of the formula (I) were recorded. The results are shown in Table 2.

TABLE 2

| Ex | Inhibitory rate (%) |
|---|---|
| 69 | 33 |
| 9 | 28 |
| 63 | 28 |
| 71 | 18 |
| 111 | 56 |
| 123 | 39 |
| 130 | 39 |
| 131 | 38 |
| 132 | 42 |
| 137 | 17 |
| 145 | 16 |
| 153 | 21 |
| 154 | 28 |
| 162 | 21 |
| 167 | 35 |
| 200 | 31 |
| 208 | 14 |
| 233 | 38 |
| 266 | 15 |
| 277 | 42 |

Test Example 3

Estimation of Concentration in Plasma (2 Hours after Oral Administration) after Administration of Compound of Formula (I) in Rats Using Ex Vivo Bioassay Method The concentration in the plasma after administration of the compound of the formula (I) in rats was estimated according to a bioassay method. That is, test compounds were orally administered to male Wistar rats (Charles River, 6-week old, and fasted), and after a certain period of time, blood was collected from the ophthalmic basilar plexus to give plasma. The compound was extracted from the plasma, and the extracted compound was dissolved in a certain amount of DMSO. Further, for the standard curve, the plasma in which the compounds at various concentrations had been dissolved was prepared separately, and the same extraction procedure was conducted.

The inhibitory action on the LPA-stimulated increase in the intracellular calcium ion concentration in LPA1-expressing cells in the DMSO extract was measured, and the plasma concentration in the individual after administration was estimated from the standard curve. The results are shown in Table 3.

TABLE 3

| Ex | Concentration in plasma (µM) |
|---|---|
| 9 | 8.3 |
| 22 | 1.3 |
| 27 | 6.5 |
| 56 | 1.8 |
| 71 | 2.1 |
| 89 | 2.4 |
| 100 | 6.7 |
| 126 | 8.9 |
| 134 | 1.4 |
| 145 | 5.6 |
| 153 | 5.2 |
| 154 | 3.1 |
| 156 | 2.1 |
| 170 | 1.8 |
| 171 | 2.2 |
| 176 | 4.5 |

As a result of the test, it was confirmed that the compound of the formula (I) has an excellent LPA receptor antagonistic action and an excellent inhibitory action on an LPA-induced increase in the urethral pressure in rats under anesthesia. Further, by an ex vivo bioassay method, it was confirmed that the compound of the formula (I) has excellent oral absorption, and thus, it can be used for treatment of diseases caused by LPA, or the like.

A pharmaceutical composition containing one or or two more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, inhalers, and the like.

The solid composition for use in the oral administration is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound of the formula (I) can be used in combination with various therapeutic or prophylactic agents for the diseases for which the compound of the formula (I) is considered to be effective, as described above. The combined preparation may be administered simultaneously, or separately and continuously, or at a desired time interval. The preparations to be administered simultaneously may be a blend, or may be prepared individually.

EXAMPLES

Hereinbelow, the preparation methods for the compound of the formula (I) will be described in more detail with reference to Examples. Further, the present invention is not limited to only the preparation methods of the specific Examples and Preparation Examples below, but the compound of the formula (I) can be prepared by a combination of the preparation methods or a method apparent to a person skilled in the art.

Moreover, the following abbreviations may be used in some cases in the Examples, Preparation Examples, and Tables as described later.

Rf: Preparation Example No.,
Ex: Example No.,
Data: Physicochemical data,
ESI+: representing m/z values in ESI-MS (positive ions), and representing [M+H]$^+$ peaks unless otherwise specified,
ESI−: representing m/z values in ESI-MS (negative ions), and representing [M−H]$^-$ peaks unless otherwise specified,
APCI+: representing m/z values in APCI-MS (positive ions), and representing [M+H]$^+$ peaks unless otherwise specified,
APCI−: representing m/z values in APCI-MS (negative ions), and representing [M−H]$^-$ peaks unless otherwise specified,
FAB+: representing m/z values in FAB-MS (positive ions), and representing [M+H]$^+$ peaks unless otherwise specified,
FAB−: representing m/z values in FAB-MS (negative ions), and representing [M−H]$^-$ peaks unless otherwise specified,
EI+: representing m/z values in EI-MS (positive ions), and representing [M]$^+$ peaks unless otherwise specified,
CI+: representing m/z values in CI-MS (positive ions), and representing [M+H]$^+$ peaks unless otherwise specified,
NMR-DMSO-$d_6$: δ (ppm) in $^1$H NMR in DMSO-$d_6$,
NMR-CDCl$_3$: δ (ppm) in $^1$H NMR in CDCl$_3$,
Structure: Structural formula,
Syn: Preparation method (in which the numeral shows that the compound is prepared by the same preparation method as the compound having the Example No. and R prefixed before the numeral shows that the compound is prepared by the same preparation method as the compound having the Preparation Example No.),
D-Arg: D-arginate,
HCl: hydrochloride,
brine: saturated brine,
DMSO: dimethylsulfoxide,
THF: tetrahydrofuran,
EtOH: ethanol,
DME: 1,2-dimethoxyethane,
DMF: N,N-dimethylformamide,
MeOH: methanol,
CHCl$_3$: chloroform,
CDI: 1,1'-carbonyldiimidazole,
DBU: 1,8-diazabicyclo[5.4.0]undec-7-ene,
DEAD: diethyl azodicarboxylate,
DMAP: 4-dimethylaminopyridine,
HOBT: 1-hydroxybenzotriazole,
WSCD HCl: 1-ethyl-3-(3-dimethylaminopropyl)carbodiimide hydrochloride,
TBAF: tetrabutylammonium fluoride,
NBS: N-bromosuccinimide,
AIBN: 2,2'-azobis(isobutyronitrile),
LHMDS: lithium bis(trimethylsilyl)amide,
Pd (PPh$_3$)$_4$: tetrakis(triphenylphosphine) palladium (0),
Zn(CN)$_2$: dicyanozinc,
ADDP: 1,1'-(azodicarbonyl)dipiperidine,
HATU: O-(7-azabenzotriazol-1-yl)-N,N,N',N'-tetramethyluronium hexafluorophosphate,
DBAD: di-tert-butylazodicarboxylate,
DAST: (diethylamino)sulfur trifluoride,
MgSO$_4$: anhydrous magnesium sulfate,
Na$_2$SO$_4$: anhydrous sodium sulfate,
n-Bu: normal butyl,
M: mol/L.

Preparation Example 1 tert-Butyl 4-formyl-3,5-dimethoxybenzoate (1.43 g) and anisole (0.85 g) were added to methylene chloride (30 mL), and trifluoroacetic acid (15 mL) was slowly added dropwise thereto under ice-cooling, followed by stirring at room temperature for about 2 hours. The solvent was evaporated under reduced pressure and an appropriate amount of ice water was poured into the obtained residue. The resulting pale orange precipitate was collected by filtration and dried to prepare 4-formyl-3,5-dimethoxybenzoic acid (1.11 g).

Preparation Example 2 tert-Butyl 5-(acetoxymethyl)-2-{[(3,5-dimethoxy-4-methylbenzoyl)(3-phenylpropyl)amino]methyl}-1,3-thiazole-4-carboxylate (150 mg) was added to methylene chloride (2 mL), followed by ice-cooling. To this mixture was slowly added dropwise trifluoroacetic acid (0.67 mL), followed by stirring at room temperature for about 14 hours. The solvent was evaporated under reduced pressure, and an appropriate amount of toluene was poured into the obtained residue. The solvent was evaporated again under reduced pressure. This procedure was repeated twice and azeotroped with trifluoroacetic acid to prepare 5-(acetoxymethyl)-2-{[(3,5-dimethoxy-4-methylbenzoyl)(3-phenylpropyl)amino]methyl}-1,3-thiazole-4-carboxylic acid (135 mg).

Preparation Example 3

Ethyl 3,5-dimethoxy-4-vinylbenzoate (150 mg) was added to an EtOH/THF (1:1) solution (4 mL), and a 1 M aqueous sodium hydroxide solution (1.25 mL) was added dropwise thereto, followed by stirring at room temperature for about 12 hours. The solvent was evaporated under reduced pressure, and to the obtained residue was added purified water. To this mixture was added dropwise 1 M hydrochloric acid (1.25 mL) under ice-cooling, and the precipitated white solid was collected by filtration and dried under reduced pressure to prepare 3,5-dimethoxy-4-vinylbenzoic acid (111 mg).

Preparation Example 4

Ethyl 2-{[(tert-butoxycarbonyl)(3-phenylpropyl)amino]methyl}-1,3-thiazole-4-carboxylate (1.27 g) was added to a THF/MeOH (2:1) solution (13.2 mL), and a 1 M aqueous sodium hydroxide solution (4.4 mL) was added dropwise thereto, followed by stirring at room temperature for about 2 hours. Ice water (about 50 g) including 1 M hydrochloric acid (7 mL) was poured into the reaction mixture, followed by extraction with an appropriate amount of ethyl acetate twice. The organic layer was washed with brine and then dried over $MgSO_4$, and the solvent was evaporated to prepare 2-{[(tert-butoxycarbonyl)(3-phenylpropyl)aminomethyl}-1,3-thiazole-4-carboxylic acid (1.15 g).

Preparation Example 5

Ethyl 2-{[(3,5-dimethoxy-4-methylbenzoyl)(3-phenylpropyl)amino]methyl}-1,3-thiazole-4-carboxylate (3.5 g) was added to a THF/EtOH (2:1) solution (45 mL), and a 1 M aqueous sodium hydroxide solution (15 mL) was added dropwise thereto, followed by stirring at room temperature for about 2 hours. An appropriate amount of a saturated aqueous ammonium chloride solution including 1 M hydrochloric acid (30 mL) and ice water were poured into the reaction mixture, followed by extraction with ethyl acetate twice. The obtained organic layer was washed with brine and dried over $MgSO_4$, and the solvent was evaporated under reduced pressure to obtain a white foam. The obtained white foam was crystallized from a small amount of ethyl acetate-hexane (3:1), washed with diethyl ether, and collected by filtration to prepare 2-{[(3,5-dimethoxy-4-methylbenzoyl)(3-phenylpropyl)amino]methyl}-1,3-thiazole-4-carboxylic acid (3.11 g) as a white powder.

Preparation Example 6 tert-Butyl {[(2-fluoroethyl)(methyl)amino]sulfonyl}carbamate (412 mg) and trifluoroacetic acid (5 mL) were added to methylene chloride (5 mL), followed by stirring at room temperature for about 1 hour, and then the solvent was evaporated under reduced pressure to prepare N-(2-fluoroethyl)-N-methylsulfamide (156 mg).

Preparation Example 7

N-Methyl-N-[2-(methylsulfanyl)ethyl]sulfamide was prepared from N-methyl-2-(methylsulfanyl)ethanamine by carrying out the same reactions as in Preparation Example 54 and Preparation Example 6, successively.

Preparation Example 8

1-(5-Methoxypyridin-2-yl)cyclopropanecarbonitrile (100 mg) and a 5 M aqueous potassium hydroxide solution (2 mL) were added to ethylene glycol (2 mL), followed by heating at 120° C. overnight. To the reaction mixture was added an appropriate amount of ice water, and 1 M hydrochloric acid was further added thereto to adjust the mixture to be weakly acidic, followed by extraction with ethyl acetate. The organic layer was washed with brine, dried over $Na_2SO_4$, and then concentrated under reduced pressure to prepare 1-(5-methoxypyridin-2-yl)cyclopropanecarboxylic acid (55 mg).

Preparation Example 9

4-Formyl-3,5-dimethoxybenzoic acid (1.38 g) was added to DMF (12 mL), followed by adding potassium carbonate (1.82 g) and methyl iodide (0.61 mL) sequentially and stirring at room temperature for about 15 hours. Ice water (120 mL) was poured into the reaction mixture, followed by stirring for about 30 minutes, and then the resulting insoluble material was collected by filtration while washing with purified water, and then dried under reduced pressure at 40° C. to prepare methyl 4-formyl-3,5-dimethoxybenzoate (1.24 g).

Preparation Example 10

5-({[tert-Butyl (dimethyl)silyl]oxy}methyl)-2-{[(3,5-dimethoxy-4-methylbenzoyl)(3-phenylpropyl)amino]methyl}-1,3-thiazole-4-carboxylic acid (0.83 g) was added to benzene (10 mL), and 1,1-di-tert-butoxy N,N-dimethylmethane (2 mL) was further slowly added dropwise thereto, followed by heating at 70 to 80° C. for about 30 minutes. Subsequently, 0.5 equivalents of 1,1-di-tert-butoxy-N,N-dimethylmethane was added again thereto, followed by further heating for 30 minutes. The reaction mixture was left to be cooled, and ethyl acetate was added thereto. The mixture was washed with a saturated aqueous sodium chloride solution including a small amount of 1 M hydrochloric acid, and then the organic layer was dried over $MgSO_4$. The residue obtained by evaporating the solvent was purified by silica gel column chromatography (ethyl acetate:hexane=2:1) to prepare tert-butyl 5-({[tert-butyl (dimethyl)silyl]oxy}methyl)-2-{[(3,5-dimethoxy-4-methylbenzoyl)(3-phenylpropyl)amino]methyl}-1,3-thiazole-4-carboxylate (500 mg).

Preparation Example 11

Ethyl 4-bromo-3,5-dimethoxybenzoate (2.13 g) was added to toluene (60 mL), and subsequently, tris(2-methylphenyl)phosphine (0.9 g), (1E,4E)-1,5-diphenylpenta-1,4-dien-3- one.palladium (3:2) (1.35 g), and tributyl(vinyl)tin (2.57 g) were sequentially added thereto, followed by heating at 140° C. for about 36 hours. The reaction mixture was left to be cooled, and then an appropriate amount of ethyl acetate and 0.2 M hydrochloric acid were poured thereinto. The resulting insoluble material was removed by filtration through Celite, and then subjected to a liquid separation operation to separate the organic layer. The organic layer was sequentially washed with an appropriate amount of an aqueous sodium hydrogen carbonate solution and brine, and dried over $MgSO_4$, and then the solvent was evaporated. The obtained residue was purified by silica gel column chromatography (ethyl acetate:hexane=9:1) to prepare ethyl 3,5-dimethoxy-4-vinylbenzoate (1.2 g).

Preparation Example 12

Ethyl 4-bromo-3,5-dimethoxybenzoate (2.0 g) was added to water-containing toluene (toluene (30 mL), purified water (1.56 mL)), and subsequently, cyclopropyl boric acid (772 mg), tricyclohexylphosphine (194 mg), potassium phosphate tribasic (5.14 g), and palladium(II) acetate (78 mg) were sequentially added thereto, followed by heating at 100° C. for about 12 hours. The reaction mixture was left to be cooled, and then the insoluble material was collected by filtration by washing it with an appropriate amount of ethyl acetate, and the filtrate was sequentially washed with purified water and brine. The organic layer was dried over $MgSO_4$, the solvent was evaporated under reduced pressure, and the obtained residue was purified by silica gel column chromatography (ethyl acetate:hexane=1:10) to prepare ethyl 4-cyclopropyl-3,5-dimethoxybenzoate (1.24 g).

Preparation Example 13

Ethyl 3,5-dimethoxy-4-vinylbenzoate (1.3 g) was added to MeOH (39 mL), followed by cooling to −78° C. To the mixture was added an appropriate amount of $CHCl_3$, followed by stirring for 20 minutes under an ozone atmosphere while maintaining the same temperature. Thereafter, the reaction mixture was held under an oxygen atmosphere, and dimethyl sulfide (0.48 mL) was added to the reaction mixture, followed by stirring at −78° C. for 30 minutes. To the reaction mixture was added an appropriate amount of ethyl acetate, followed by sequentially washing with an aqueous sodium hydrogen carbonate solution and brine. The obtained organic layer was dried over $Na_2SO_4$, and then the solvent was evaporated. The obtained residue was purified by silica gel column chromatography (ethyl acetate:hexane=4:1) to prepare ethyl 3,5-dimethoxy-4-formylbenzoate (1.0 g) as a white solid.

Preparation Example 14

According to the method of Falck, et al. (Tetrahedron Lett., 1994 35, 5997), methyl 3,5-dimethoxy-4-(hydroxymethyl) benzoate (0.34 g) and ADDP (0.76 g) were added to anhydrous benzene (15 mL), and subsequently, tri-n-butylphosphine (0.74 mL) was slowly added dropwise thereto, followed by stirring at room temperature for about 15 minutes. To this mixture was added dropwise an excess amount of trifluoroethanol (0.86 mL), followed by stirring at room temperature for about 13 hours. The reaction mixture was evaporated under reduced pressure, and the obtained residue was purified by silica gel column chromatography (hexane:ethyl acetate=1:3) to prepare methyl 3,5-dimethoxy-4-[(2,2,2-trifluoroethoxy)methyl]benzoate (0.45 g) as a white solid.

Preparation Example 15

Ethyl 2-{[(3,5-dimethoxy-4-methylbenzoyl)(3-phenylpropyl)amino]methyl}-5-(hydroxymethyl)-1,3-thiazole-4-carboxylate (300 mg) was added to methyl iodide (9 mL), and subsequently, silver(I) oxide (149 mg), and $MgSO_4$ (239 mg) were added thereto, followed by stirring at room temperature for about 2 days in a sealed tube. To the reaction mixture was added silver(I) oxide (75 mg), followed by stirring at room temperature for additional 3 days. The insoluble material of the reaction mixture was collected by filtration through Celite while washing with an appropriate amount of $CHCl_3$. The filtrate was washed with water and dried over $MgSO_4$, and then the solvent was evaporated under reduced pressure. The obtained residue was purified by silica gel column chromatography (ethyl acetate:hexane=1:1) to prepare ethyl 2-{[(3, 5-dimethoxy-4-methylbenzoyl)(3-phenylpropyl)amino]methyl}-5-(methoxymethyl)-1,3-thiazole-4-carboxylate (248 mg).

Preparation Example 16

Ethyl 3,5-dimethoxy-4-vinylbenzoate (1.3 g) was added to MeOH (39 mL), followed by cooling to −78° C. To the mixture was added an appropriate amount of $CHCl_3$, followed by stirring for 20 minutes under an ozone atmosphere while maintaining the same temperature. Thereafter, the reaction mixture was held under an oxygen atmosphere, and dimethyl sulfide (0.48 mL) was added to the reaction mixture, followed by stirring at −78° C. for 30 minutes. To the reaction mixture was added an appropriate amount of ethyl acetate, followed by sequentially washing with an aqueous sodium hydrogen carbonate solution and brine. The obtained organic layer was dried over $Na_2SO_4$, and then the solvent was evaporated. The obtained residue was purified by silica gel column chromatography (ethyl acetate:hexane=4:1) to prepare ethyl 3,5-dimethoxy-4-formylbenzoate (1.0 g) as a white solid.

Preparation Example 17

Ethyl 2-{[(3,5-dimethoxy-4-methylbenzoyl)(3-phenylpropyl)amino]methyl}-5-vinyl-1,3-thiazole-4-carboxylate (2.0 g) was added to an acetone/tert-butanol/water (1:1:1) solution (45 mL), and subsequently a 0.1 M osmium tetraoxide (1.97 L) and sodium periodate (1.85 g) were sequentially added thereto, followed by stirring at room temperature for about 14 hours. About 200 g of ice water was poured into the reaction mixture, followed by extraction with an appropriate amount of ethyl acetate several times. The organic layer was washed with brine and dried over $MgSO_4$, and then the solvent was evaporated. The obtained residue was purified by silica gel column chromatography (ethyl acetate:hexane=3:2) to prepare ethyl 2-{[(3,5-dimethoxy-4-methylbenzoyl)(3-phenylpropyl)amino]methyl}-5-formyl-1,3-thiazole-4-carboxylate (1.83 g).

Preparation Example 18

N-{[4-(Hydroxymethyl)-1,3-thiazol-2-yl]methyl}-3,5-dimethoxy-4-methyl-N-(3-phenylpropyl)benzamide (0.75 g) and triethylamine (0.71 mL) were added to methylene chloride (7.5 mL), and a mixture of a sulfur trioxide-pyridine complex (0.83 g) and DMSO (1.5 mL) was slowly added dropwise thereto under ice-cooling, followed by stirring under ice-cooling about 4 hours. A small amount of a 1 M hydrochloric acid solution and a saturated aqueous ammonium chloride solution were poured into the reaction mixture, followed by extraction with CHCl₃. The organic layer was washed with water and dried, and then the solvent was evaporated. The obtained residue was purified by silica gel column chromatography (ethyl acetate:hexane=3:1) to prepare N-[(4-formyl-1,3-thiazol-2-yl)methyl]-3,5-dimethoxy-4-methyl-N-(3-phenylpropyl)benzamide (0.69 g).

Preparation Example 19

2-(Chloromethyl)-5-methoxypyridine (125 mg) was added to DMSO (5 mL), and subsequently, an aqueous potassium cyanide solution (potassium cyanide (155 mg) and water (1 mL)) was added thereto, followed by stirring at room temperature overnight. An appropriate amount of purified water was poured into the reaction mixture under ice-cooling, followed by extraction with ethyl acetate. The obtained organic layer was sequentially washed with purified water and brine, and dried over MgSO₄, and then the solvent was evaporated under reduced pressure to prepare (5-methoxypyridin-2-yl)acetonitrile (110 mg).

Preparation Example 20

To a mixture of (5-methoxypyridin-2-yl)acetonitrile (0.11 mg), 1-bromo-2-chloroethane (0.2 mL), and N-benzyl-N,N,N-triethylammonium chloride (20 mg) was slowly added dropwise a 50% aqueous sodium hydroxide solution (2 mL) under ice-cooling, followed by stirring at room temperature for about 5 hours. Ice water was poured into the reaction mixture, followed by extraction with diethyl ether. The organic layer was washed with brine, dried over Na₂SO₄, and then concentrated under reduced pressure. The obtained residue was purified by silica gel column chromatography (ethyl acetate:hexane=1:2) to prepare 1-(5-methoxypyridin-2-yl)cyclopropanecarbonitrile (100 mg) as a white solid.

Preparation Example 21 tert-Butyl 4-formyl-3,5-dimethoxybenzoate (0.3 g) was added to methylene chloride (10 mL), and subsequently, DAST (0.25 mL) was added dropwise thereto at 0° C., followed by stirring at room temperature overnight. To the reaction mixture was carefully added a saturated aqueous sodium hydrogen carbonate solution, followed by extraction with CHCl₃. The organic layer was washed with brine and dried over MgSO₄, and then the solvent was evaporated. The obtained residue was purified by silica gel column chromatography (hexane:ethyl acetate=7:3 to 5:5) to obtain a colorless oily substance. The obtained oily substance was dissolved in 4 M hydrochloric acid/ethyl acetate (10 mL), followed by stirring at room temperature for 3 hours. Thereafter, the solvent was evaporated to prepare 4-(difluoromethyl)-3,5-dimethoxybenzoic acid (0.22 g) as a white solid.

Preparation Example 22

The following products were prepared with a partial modification of the method of Liu, et al. (Synthesis, 2001 14, 2078-2080).
Ethyl (2-methyl-1,3-thiazol-4-yl)carboxylate (25 g) was added to carbon tetrachloride (500 mL), and subsequently, NBS (53 g), and benzoyl peroxide (4.7 g) (wetted with 75% water) were sequentially added thereto, followed by heating to reflux for 100 minutes under close irradiation with a 300 W lamp. The reaction mixture was left to be cooled, then the insoluble material was collected by filtration, and the obtained filtrate was washed with water, followed by extraction with an appropriate amount of CHCl₃. The organic layer was sequentially washed with a 5% (W/W) aqueous sodium thiosulfate solution (600 g) and brine, and dried over MgSO₄, and then the solvent was evaporated. To the obtained residue was added THF (300 mL), followed by sequential addition dropwise of diethyl phosphite (18.9 mL) and a Hunig's base (25.4 mL) at about 0° C. under an argon atmosphere. Thereafter, the temperature was slowly elevated, and the mixture was stirred at room temperature for about 2 hours. An appropriate amount of ice water was poured into the reaction mixture, followed by extraction with ethyl acetate several times. The organic layer was sequentially washed with 0.3 M hydrochloric acid (1 L) and brine, and dried over MgSO₄, and then the solvent was evaporated under reduced pressure. The obtained residue was purified by silica gel column chromatography (hexane:ethyl acetate=3:1 to 2:1) to prepare ethyl [2-(bromomethyl)-1,3-thiazol-4-yl]carboxylate (26.82 g).

Preparation Example 23

Ethyl 2-methyl-1,3-thiazole-4-carboxylate (10 g) was added to acetonitrile (100 mL), and subsequently, NBS (11.4 g) was added thereto, followed by stirring for 3 hours under heating to reflux. To the reaction mixture was added NBS (5.0 g), followed by stirring for 2 hours under refluxing, and then NBS (5.0 g) was further added thereto, followed by stirring for about 12 hours under the same condition. An appropriate amount of a saturated aqueous sodium hydrogen carbonate solution was slowly poured into the reaction mixture under cooling, followed by extraction with ethyl acetate. The organic layer was washed with brine and dried over MgSO₄, and then the solvent was evaporated. The obtained residue was purified by silica gel column chromatography (hexane:ethyl acetate=3:2) to prepare ethyl 5-bromo-2-methyl-1,3-thiazole-4-carboxylate (8.86 g).

Preparation Example 24

Ethyl 5-bromo-2-methyl-1,3-thiazole-4-carboxylate (6.84 g) was added to carbon tetrachloride (114 mL), and subsequently, NBS (5.35 g) and AIBN (2.25 g) were added thereto, followed by stirring at about 90° C. for 2 hours, and then NBS (5.0 g) and AIBN (0.9 g) were added thereto, followed by heating to reflux for additional 1 hour. The reaction mixture was left to be cooled, then the insoluble material was collected by filtration, and the filtrate was concentrated under reduced pressure. The obtained residue was purified by silica gel column chromatography (hexane:ethyl acetate=3:2) to prepare ethyl 5-bromo-2-(bromomethyl)-1,3-thiazole-4-carboxylate (5.55 g).

Preparation Example 25

Ethyl 2-methyl-1,3-thiazole-4-carboxylate (10 g) was added to DMF (100 mL) under ice-cooling, and subsequently, trichloroisocyanuric acid (13.6 g) was slowly added thereto, followed by stirring at room temperature overnight. Thereafter, an equivalent amount of trichloroisocyanuric acid was added thereto several times in divided portions, followed by stirring at room temperature for one day. The insoluble material in the reaction mixture was collected by filtration through Celite, and to the filtrate was added ice water including an appropriate amount of a 1 M aqueous sodium hydroxide solution, followed by extraction with ethyl acetate. The organic layer was washed with brine and dried over MgSO₄, and then the solvent was evaporated. The obtained residue was purified by silica gel column chromatography (hexane:

ethyl acetate=7:3→1:1) to prepare ethyl 5-chloro-2-methyl-1,3-thiazole-4-carboxylate (6.7 g).

Preparation Example 26

3-Phenylpropan-1-amine (11.33 g) and potassium carbonate (11.58 g) were added to acetonitrile (300 mL), and a solution of ethyl 2-(bromomethyl)-1,3-thiazole-4-carboxylate (11.64 g) in acetonitrile (30 mL) were slowly added dropwise thereto in an MeOH/ice bath, followed by stirring at room temperature for about 1 hour. To the reaction mixture was added an appropriate amount of ice water, followed by extraction with ethyl acetate several times. The organic layer was washed with brine and dried over $MgSO_4$, and then the solvent was concentrated under reduced pressure. The obtained residue was purified by silica gel column chromatography (ethyl acetate:hexane=3:1 to 5:1) to prepare ethyl 2-{[(3-phenylpropyl)amino]methyl}-1,3-thiazole-4-carboxylate (13.17 g).

Preparation Example 27

Ethyl 5-(chloromethyl)isoxazole-3-carboxylate (1.0 g) was added to acetonitrile (20 mL), and subsequently, 3-phenylpropyl amine (1.5 mL) and potassium carbonate (1.46 g) were added thereto under ice-cooling, followed by stirring at 60° C. overnight. The reaction mixture was left to be cooled, and then the solvent was evaporated under reduced pressure. To the obtained residue was added an appropriate amount of ethyl acetate, followed by stirring for a while. Thereafter, the insoluble material was collected by filtration and the filtrate was concentrated under reduced pressure. The obtained residue was purified by silica gel column chromatography (ethyl acetate:hexane=1:1) to prepare ethyl 5-{[(3-phenylpropyl)amino]methyl}isoxazole-3-carboxylate (0.94 g).

Preparation Example 28

Ethyl 2-{[(3-phenylpropyl)amino]methyl}-1,3-thiazole-4-carboxylate (1 g) was added to THF (12 mL), and subsequently, di-tert-butyl dicarbonate (0.72 g) was slowly added thereto under ice-cooling, followed by stirring at room temperature for about 2 hours. The reaction mixture was concentrated under reduced pressure, and the obtained colorless oily substance was purified by silica gel column chromatography (hexane:ethyl acetate=2:1) to prepare ethyl 2-{[(tert-butoxycarbonyl)(3-phenylpropyl)amino]methyl}-1,3-thiazole-4-carboxylate (1.31 g).

Preparation Example 29

Ethyl 2-{[(3,5-dimethoxy-4-methylbenzoyl)(3-phenylpropyl)amino]methyl}-5-(hydroxymethyl)-1,3-thiazole-4-carboxylate (1.24 g) was added to methylene chloride (25 mL), and subsequently, tert-butyldimethylchlorosilane (0.4 g), triethylamine (0.34 mL), and DMAP (0.15 g) were sequentially added thereto, followed by stirring for about 3 hours. To the reaction mixture was added $CHCl_3$, followed by sequentially washing with an appropriate amount of an aqueous ammonium chloride solution and brine. The organic layer was dried over $MgSO_4$ and concentrated under reduced pressure. The obtained residue was purified by silica gel column chromatography (ethyl acetate:hexane=1:1) to prepare ethyl 5-({[tert-butyl (dimethyl)silyl]oxy}methyl)-2-{[(3,5-dimethoxy-4-methylbenzoyl)(3-phenylpropyl)amino]methyl}-1,3-thiazole-4-carboxylate (1.46 g).

Preparation Example 30 tert-Butyl [(4-{[(dimethylamino)sulfonyl]carbamoyl}-1,3-thiazol-2-yl)methyl](3-phenylpropyl)carbamate (0.87 g) was added to ethyl acetate (1 mL), and subsequently, a 4 M hydrochloric acid/ethyl acetate solution (4 mL) was poured thereinto, followed by stirring at room temperature for about 12 hours under a sealed argon gas atmosphere. After diluting and subsequently washing the reaction mixture with an appropriate amount of diethyl ether, a white precipitate was collected by filtration/dried to prepare N-[(dimethylamino)sulfonyl]-2-{[(3-phenylpropyl)amino]methyl}-1,3-thiazole-4-carboxamide hydrochloride (0.74 g) as a white solid.

Preparation Example 31

5-Formyl-furan-2-carboxylic acid (3.5 g) was added to DMF (35 mL), and subsequently, potassium carbonate and ethyl iodide (2.22 mL) were added thereto under ice-cooling, followed by stirring at room temperature overnight. To the reaction mixture was added an appropriate amount of ice water, followed by extraction with ethyl acetate several times. The organic layer was dried over $Na_2SO_4$, and the solvent was evaporated to prepare ethyl 5-formyl-furan-2-carboxylate (2.56 g).

Subsequently, ethyl 5-{[(3-phenylpropyl)amino]methyl}-2-furoate (0.64 g) was prepared from ethyl 5-formyl-furan-2-carboxylate (500 mg) and 3-phenylpropylamine (0.85 mL) in the same manner as in Preparation Example 52.

Next, ethyl 5-{[(3,5-dimethoxy-4-methylbenzoyl)(3-phenylpropyl)amino]methyl}-2-furoate (454 mg) was prepared from ethyl 5-{[(3-phenylpropyl)amino]methyl}-2-furoate (330 mg) in the same manner as in Preparation Example 56.

Preparation Example 32 tert-Butyl 5-({[tert-butyl (dimethyl)silyl]oxy}methyl)-2-{[(3,5-dimethoxy-4-methylbenzoyl)(3-phenylpropyl)amino]methyl}-1,3-thiazole-4-carboxylate (0.49 g) was added to THF (6 mL), and subsequently, a 1 M TBAF/THF solution (3 mL) was added dropwise thereto, followed by stirring at room temperature for about 5 hours. The reaction mixture was concentrated, and to the obtained residue was added a cooled mixed aqueous solution of 1 M hydrochloric acid/saturated ammonium chloride (1:1), followed by extraction with an appropriate amount of ethyl acetate twice. The organic layer was washed with brine and dried over $MgSO_4$, and then the solvent was evaporated. The obtained pale brown oily substance was purified by silica gel column chromatography (ethyl acetate:hexane=3:2) to prepare tert-butyl 2-{[(3,5-dimethoxy-4-methylbenzoyl)(3-phenylpropyl)amino]methyl}-5-(hydroxymethyl)-1,3-thiazole-4-carboxylate (0.33 g).

Preparation Example 33

Ethyl 2-(diethoxymethyl)-5-methyl-1,3-thiazole-4-carboxylate (12.1 g) was added to acetone (300 mL), and subsequently, 1 M hydrochloric acid (150 mL) was added thereto, followed by stirring at 55° C. for about 5 hours. The reaction mixture was concentrated, neutralized by the addition of an appropriate amount of a saturated aqueous sodium hydrogen carbonate solution, and then extracted with ethyl acetate several times. The organic layer was dried over $MgSO_4$, and the solvent was evaporated under reduced pressure to prepare ethyl 2-formyl-5-methyl-1,3-thiazole-4-carboxylate (8.25 g).

Preparation Example 34

2-{[(tert-Butoxycarbonyl)(3-phenylpropyl)amino]methyl}-1,3-thiazole-4-carboxylic acid (0.8 g) was added to anhydrous THF (30 mL), and subsequently, CDI (0.52 g) was added thereto, followed by stirring at about 60° C. for 1 hour under an argon atmosphere. The reaction mixture was ice-cooled, and N,N-dimethylsulfamide (0.53 g) and DBU (0.42 g) were sequentially added thereto, followed by stirring at room temperature for about 6 hours. To the reaction mixture was added an appropriate amount of 1 M hydrochloric acid and ice water, followed by extraction with ethyl acetate several times. The organic layer was washed with brine and dried over $MgSO_4$, and then the solvent was evaporated under reduced pressure. The obtained residue was purified by silica gel column chromatography ($CHCl_3$:MeOH=200:1) to prepare tert-butyl [(4-{[(dimethylamino)sulfonyl]carbamoyl}-1,3-thiazol-2-yl)methyl](3-phenylpropyl)carbamate (0.9 g).

Preparation Example 35

Benzyl [(3-hydroxypyrrolidin-1-yl)sulfonyl]carbamate (2.55 g) was added to MeOH, and subsequently, 10% palladium carbon (657 mg, 55% wet) was added thereto, followed by stirring at a normal temperature/a normal pressure for about 3 hours under a hydrogen atmosphere. The catalyst was collected by filtration through Celite, and the filtrate was concentrated under reduced pressure to obtain 3-hydroxypyrrolidin-1-sulfonamide (1.4 g) as a colorless oily substance.

Preparation Example 36

2,2-diethoxyethanethioamide (9.21 g), calcium carbonate (3.39 g), and an appropriate amount of powder Molecular Sieves (4 Angstrom, about 2 times a medicinal spoon) were added to EtOH (220 mL), and subsequently, ethyl 3-bromo-2-oxobutanoate (13.1 g) prepared by the method by Plouvier, et al. (Heterocycles, 1991 32, 693.) was added dropwise thereto over about 5 minutes, followed by stirring at room temperature for about 30 minutes. Thereafter, the mixture was further warmed to 55° C. for about 6 hours. The reaction mixture was left to be cooled, then the insoluble material was collected by filtration, and the filtrate was concentrated under reduced pressure. To the obtained residue was added an appropriate amount of water, followed by extraction with ethyl acetate twice. The organic layer was washed with brine and dried over $MgSO_4$, and then the solvent was evaporated. The obtained residue was purified by silica gel column chromatography (hexane:ethyl acetate=7:3) to prepare ethyl 2-(diethoxymethyl)-5-methyl-1,3-thiazole-4-carboxylate (12.1 g).

Preparation Example 37

Methyl 4-formyl-3,5-dimethoxybenzoate (3.01 g) was added to a MeOH/THF (1:1) solution (30 mL), and subsequently, 0.3 g of sodium borohydride was added thereto under ice-cooling, followed by stirring at the same temperature for about 30 minutes. The reaction mixture was concentrated, and 0.5 M hydrochloric acid (24 mL) was poured into the obtained residue, followed by stirring at room temperature for about 30 minutes. The resulting insoluble material was collected by filtration to prepare methyl 3,5-dimethoxy-4-(hydroxymethyl)benzoate (2.78 g) as a white solid.

Preparation Example 38

Ethyl 2-{[(3,5-dimethoxy-4-methylbenzoyl)(3-phenylpropyl)amino]methyl}-5-formyl-1,3-thiazole-4-carboxylate (1.57 g) was added to methylene chloride (25 mL), and subsequently, sodium triacetoxyborohydride (1.96 g) was added thereto in an ice bath, followed by stirring at room temperature for about 14 hours. Thereafter, sodium triacetoxyborohydride (1.5 g) was further added thereto, followed by stirring at room temperature for 5 hours. To the reaction mixture was added an appropriate amount of $CHCl_3$, and an appropriate amount of an aqueous sodium hydrogen carbonate solution was added thereto, followed by stirring for a while. The reaction mixture was subjected to liquid separation, subsequently, the organic layer was washed with brine and dried over $MgSO_4$, and then the solvent was evaporated. The obtained residue was purified by silica gel column chromatography (ethyl acetate:hexane=3:1) to prepare ethyl 2-{[(3,5-dimethoxy-4-methylbenzoyl)(3-phenylpropyl)amino]methyl}-5-(hydroxymethyl)-1,3-thiazole-4-carboxylate (1.25 g).

Preparation Example 39

3-Phenylpropan-1-amine (1.3 g) was added to methylene chloride (30 mL), and subsequently, ethyl 2-formyl-5-methyl-1,3-thiazole-4-carboxylate (1.2 g) and acetic acid (1.5 mL) were sequentially added thereto, followed by stirring at room temperature for about 20 minutes. Thereafter, sodium triacetoxyborohydride (2.69 g) was added thereto under ice-cooling, followed by stirring at room temperature for about 1 hour. To the reaction mixture was added $CHCl_3$, and an appropriate amount of a saturated aqueous sodium hydrogen carbonate solution was further added thereto, followed by stirring and then performing liquid-separation. The organic layer was dried over $MgSO_4$, and then the solvent was evaporated under reduced pressure. The obtained yellow oily substance was purified by silica gel column chromatography ($CHCl_3$:MeOH=250:1) to prepare ethyl 5-methyl-2-{[(3-phenylpropyl)amino]methyl}-1,3-thiazole-4-carboxylate (1.56 g).

Preparation Example 40

Under an argon atmosphere, chlorosulfonylisocyanate (0.15 mL) was added to methylene chloride (9.5 mL), followed by cooling in an MeOH/ice bath. Subsequently, tert-butanol (0.18 mL) was added dropwise thereto, followed by stirring for about 30 minutes under cooling. To the reaction mixture were slowly sequentially added triethylamine (0.61 mL) and 2-fluoro-N-methyl ethanamine hydrochloride (197 mg), followed by stirring for 30 minutes under cooling, warming to room temperature, and then further stirring overnight. The solvent was evaporated under reduced pressure, and to the obtained residue was added an appropriate amount of purified water, followed by acidification with 1 M hydrochloric acid, and then extraction with ethyl acetate. The organic layer was washed with brine and dried over $MgSO_4$, and then the solvent was evaporated under reduced pressure to prepare tert-butyl {[(2-fluoroethyl)(methyl)amino]sulfonyl}carbamate (412 mg) as a colorless oily substance.

Preparation Example 41

Under an argon atmosphere, chlorosulfonylisocyanate (1 mL) was added to methylene chloride (67 mL), and the mixture was cooled in an MeOH/ice bath. Subsequently, benzyl alcohol (1.26 mL) was added dropwise thereto, followed by stirring for about 30 minutes under cooling. To the reaction mixture were slowly sequentially added triethylamine (2.42 mL) and 3-hydroxypyrrolidine (1.22 mL), followed by stirring for 30 minutes under cooling, then warming to room temperature, and further stirring overnight. The solvent was evaporated under reduced pressure, and to the obtained residue was added an appropriate amount of purified water, followed by acidification with 1 M hydrochloric acid, and then extraction with ethyl acetate. The organic layer was washed with brine and dried over MgSO$_4$, and then the solvent was evaporated under reduced pressure. The obtained residue was purified by silica gel column chromatography (hexane:ethyl acetate=3:1 to 2:1) to prepare benzyl [(3-hydroxypyrrolidin-1-yl)sulfonyl]carbamate (2.55 g) as a white solid.

Preparation Example 42

Ethyl 2-{[(3-phenylpropyl)amino]methyl}-1,3-thiazole-4-carboxylate (3.2 g) and triethylamine (1.61 mL) were added to acetonitrile (70 mL), and the mixture was sufficiently cooled in an MeOH/ice bath. Subsequently, 3,5-dimethoxy-4-methylbenzoyl chloride (2.48 g) was slowly added thereto, followed by stirring at room temperature for 1 hour. The solvent was evaporated, and to the obtained residue was added an appropriate amount of a saturated aqueous sodium hydrogen carbonate solution, followed by stirring for 2 to 3 minutes and then extraction with ethyl acetate several times. The organic layer was sequentially washed with 1 M hydrochloric acid/a saturated aqueous ammonium chloride solution and brine, and dried over MgSO$_4$, and then the solvent was evaporated under reduced pressure. The obtained colorless oily substance was purified by silica gel column chromatography (ethyl acetate:hexane=1:1) to prepare ethyl 2-{[(3,5-dimethoxy-4-methylbenzoyl)(3-phenylpropyl)amino]methyl}-1,3-thiazole-4-carboxylate (4.93 g).

Preparation Example 43

Anhydrous acetic acid (0.5 mL) was added to pyridine (2 mL), and subsequently tert-butyl 2-{[(3,5-dimethoxy-4-methylbenzoyl)(3-phenylpropyl)amino]methyl}-5-(hydroxymethyl)-1,3-thiazole-4-carboxylate (140 mg) was added thereto under ice-cooling, followed by stirring at room temperature for about 1.5 hours. To the reaction mixture was added an appropriate amount of toluene, followed by concentration under reduced pressure. This procedure was repeated twice, and to the obtained residue was added 0.5 M hydrochloric acid that had been cooled, followed by extraction with ethyl acetate several times. The organic layer was washed with brine and dried over MgSO$_4$, and then the solvent was evaporated under reduced pressure to prepare tert-butyl 5-(acetoxymethyl)-2-{[(3,5-dimethoxy-4-methylbenzoyl)(3-phenylpropyl)amino]methyl}-1,3-thiazole-4-carboxylate (150 mg).

Preparation Example 44

Ethyl 2-({[(2,4-dimethoxyphenyl)acetyl](3-phenylpropyl)amino}methyl)-5-methyl-1,3-thiazole-4-carboxylate was prepared from ethyl 5-methyl-2-{[(3-phenylpropyl)amino]methyl}-1,3-thiazole-4-carboxylate in the same manner as the method of Example 1 as described later.

Preparation Example 45

3,5-Dimethoxy-4-bromobenzoic acid (10 g) was added to DMF (100 mL), and subsequently, CDI (9.32 g) was slowly added thereto at room temperature, followed by stirring at about 40° C. for 1 hour. Further, to the reaction mixture were sequentially added dropwise tert-butanol (7.4 mL) and DBU (6.3 mL), followed by stirring at about 40° C. for about 3 days. An appropriate amount of ethyl acetate was poured into the reaction mixture, followed by sequentially washing with diluted hydrochloric acid, an aqueous sodium hydrogen carbonate solution, and brine. The organic layer was dried over MgSO$_4$, and then the solvent was evaporated under reduced pressure to prepare tert-butyl 4-bromo-3,5-dimethoxybenzoate (11 g) as a white solid.

tert-Butyl 4-bromo-3,5-dimethoxybenzoate (2.22 g) was added to anhydrous TI-IF (50 mL), followed by cooling to around −78° C. under an argon atmosphere, and to the mixture was added dropwise a 2.73 M n-butyl lithium/n-hexane solution (3.1 mL), followed by stirring for about 30 minutes under cooling (about −78° C.). To the reaction mixture was added dropwise DMF (1.1 mL), followed by stirring at the same temperature for about 10 minutes, and then a saturated aqueous ammonium chloride solution was poured thereinto, followed by extraction with an appropriate amount of ethyl acetate twice. The organic layer was washed with brine and dried over MgSO$_4$, and then the solvent was evaporated under reduced pressure. The obtained residue was purified by silica gel column chromatography (hexane:ethyl acetate=3:2) to prepare tert-butyl 4-formyl-3,5-dimethoxybenzoate (1.44 g) as a white powder.

Preparation Example 46

Ethyl 3,5-dimethoxy-4-vinylbenzoate (1.05 g) and 10% palladium/carbon (100 mg) were added to ethyl acetate (20 mL), followed by stirring at a normal temperature/a normal pressure for about 12 hours under a hydrogen atmosphere. The catalyst was collected by filtration through Celite and the filtrate was concentrated under reduced pressure. The obtained residue was purified by silica gel column chromatography (ethyl acetate:hexane=1:1) to prepare 3,5-dimethoxy-4-ethylbenzoate (902 mg).

Ethyl 3,5-dimethoxy-4-ethylbenzoate (0.35 g) was added to an EtOH/THF (1:2)(6 mL) solution, and subsequently, a 1 M aqueous sodium hydroxide solution (3.7 mL) was added dropwise thereto, followed by stirring at room temperature for about 15 hours. The reaction mixture was concentrated under reduced pressure to a half amount, and ice water (about 20 to 30 g) including 1 M hydrochloric acid (6 mL) was added thereto, followed by extraction with CHCl$_3$ several times. The organic layer was washed with water and dried over MgSO$_4$, and then the solvent was evaporated under reduced pressure to prepare 3,5-dimethoxy-4-ethylbenzoic acid (0.28 g).

Preparation Example 47

Ethyl 2-{[(3,5-dimethoxy-4-methylbenzoyl)(3-phenylpropyl)amino]methyl}-5-vinyl-1,3-thiazole-4-carboxylate (235 mg) and 10% palladium/carbon (48 mg) were added to EtOH/THF (1:1) (8 mL), followed by stirring at a normal temperature/a normal pressure for 4 hours under a hydrogen atmosphere. The reaction mixture was filtered through Celite, and the filtrate was concentrated under reduced pressure. The obtained residue was purified by silica gel column chromatography (ethyl acetate:hexane=2:3) to prepare ethyl 2-{[(3,5-dimethoxy-4-methylbenzoyl)(3-phenylpropyl)amino]methyl}-5-ethyl-1,3-thiazole-4-carboxylate (198 mg).

Subsequently, 2-{[(3,5-dimethoxy-4-methylbenzoyl)(3-phenylpropyl)amino]methyl}-5-ethyl-1,3-thiazole-4-carboxylic acid (110 mg) was prepared from ethyl 2-{[(3,5-dimethoxy-4-methylbenzoyl)(3-phenylpropyl)amino]methyl}-5-ethyl-1,3-thiazole-4-carboxylate (118 mg) in the same manner as the method of Preparation Example 5.

Preparation Example 48

Ethyl (2,4-dimethoxybenzoyl)formate (0.78 g) and bis(2-methoxyethyl)aminosulfur-trifluoride (1.8 g) were added to an appropriate amount of dichloroethane, followed by stirring at 60° C. overnight. To the reaction mixture were added bis(2-methoxyethyl)aminosulfur-trifluoride (1.8 g), followed by stirring at 60° C. overnight. The reaction mixture was neutralized by the addition of an appropriate amount of a saturated aqueous sodium hydrogen carbonate solution under ice-cooling, followed by extraction with $CHCl_3$. The organic layer was dried over $Na_2SO_4$, and then the solvent was evaporated under reduced pressure. The obtained residue was purified by silica gel column chromatography (ethyl acetate:hexane=1:2) to prepare ethyl (2,4-dimethoxyphenyl)(difluoro)acetate (852 mg).

Subsequently, (2,4-dimethoxyphenyl)(difluoro)acetic acid (214 mg) was prepared from ethyl (2,4-dimethoxyphenyl)(difluoro)acetate (0.24 g) in the same manner as the method of Preparation Example 3.

Preparation Example 49

2-Fluoro-4-methoxybenzaldehyde (1.0 g), triethylamine (0.2 mL), and trimethylsilylcyanide (0.9 mL) were added to methylene chloride (10 mL), followed by stirring at room temperature for 3 hours. The reaction mixture was concentrated under reduced pressure, and to the obtained residue were added EtOH (12 mL) and chlorotrimethylsilane (12 mL), followed by stirring at room temperature overnight. The reaction mixture was left to be cooled, and then the solvent was evaporated. Dichloroethane (20 mL), EtOH (10 mL), and a saturated aqueous sodium hydrogen carbonate solution (20 mL) were poured into the obtained residue, followed by severely stirring at room temperature for about 3 hours. The reaction mixture was extracted with an appropriate amount of $CHCl_3$, the organic layer was dried over $MgSO_4$, and then the solvent was evaporated under reduced pressure to prepare ethyl (2-fluoro-4-methoxyphenyl)(hydroxy)acetate (0.67 g).

Subsequently, (2-fluoro-4-methoxyphenyl)(hydroxy)acetic acid (0.35 g) was prepared from ethyl (2-fluoro-4-methoxyphenyl)(hydroxy)acetate (0.67 g) in the same manner as the method of Preparation Example 3.

Preparation Example 50

Under ice-cooling, a Burgess reagent (3,3,3-triethyl-1-(methoxycarbonyl)diazathia-3-ium-1-iodo-2,2-dioxide) (2.0 g) and concentrated aqueous ammonia (to 30%) (1.6 mL) were added to toluene (20 mL), followed by stirring at room temperature for 3 hours. The mixture was neutralized with 0.5 M hydrochloric acid and then extracted with an appropriate amount of ethyl acetate. The organic layer was washed with brine and dried over $MgSO_4$, and then the solvent was evaporated under reduced pressure to prepare methyl (aminosulfonyl)carbamate (650 mg).

Subsequently, methyl (aminosulfonyl)carbamate (160 mg), benzyl alcohol (0.14 mL), and triphenylphosphine (354 mg) were added to THF (4.9 mL), and subsequently, a 2.2 M DEAD/toluene solution (0.61 mL) was added thereto under ice-cooling, followed by stirring at room temperature for 3 hours. The solvent was evaporated under reduced pressure, and the obtained residue was purified by silica gel column chromatography (hexane:ethyl acetate=10:1 to 2:1) to prepare methyl (aminosulfonyl)benzylcarbamate (214 mg).

Preparation Example 51

Under ice-cooling, to DMF (31 mL) was slowly added dropwise phosphorous oxychloride (4.47 mL), followed by stirring at the same temperature for about 15 minutes. To the reaction mixture was added methyl 1H-pyrrole-2-carboxylate (5.0 g), followed by slowly warming to 60° C. and stirring for about 5 hours. The reaction mixture was neutralized by the addition of a 8 M aqueous sodium hydroxide solution under ice-cooling, followed by extraction with ethyl acetate several times. The organic layer was washed with brine and dried over $MgSO_4$, and then the solvent was evaporated under reduced pressure. The obtained residue was purified by silica gel column chromatography (ethyl acetate:hexane=1:1) to prepare methyl 5-formyl-1H-pyrrole-2-carboxylate (2.53 g).

Subsequently, methyl 5-{[(3-phenylpropyl)amino]methyl}-1H-pyrrole-2-carboxylate (1.28 g) was prepared from methyl 5-formyl-1H-pyrrole-2-carboxylate (1.0 g) in the same manner as the method of Preparation Example 52.

Preparation Example 52

Ethyl 3,5-dimethoxy-4-formylbenzoate (0.6 g) was added to a MeOH/THF (1:1) (30 mL) solution, and sodium borohydride (0.19 g) was added thereto under ice-cooling, followed by stirring at room temperature for 3 hours. The solvent was evaporated, and the obtained residue was dissolved in an appropriate amount of ethyl acetate, followed by sequentially washing with appropriate amounts of 1 M hydrochloric acid, an aqueous sodium hydrogen carbonate solution, and brine, and performing liquid-separation. The organic layer was dried over $MgSO_4$, and then the solvent was evaporated to prepare ethyl 3,5-dimethoxy-4-(hydroxymethyl)benzoate (0.55 g) as a white solid.

Subsequently, ethyl 3,5-dimethoxy-4-(hydroxymethyl)benzoate (300 mg) was added to DMF (3 mL), and sodium hydride (60 mg) and methyl iodide (0.16 mL) were sequentially added thereto, followed by stirring at room temperature for about 6 hours. To the reaction mixture was added an appropriate amount of ethyl acetate, and the insoluble material was collected by filtration and then washed with purified water and brine. The organic layer was dried over $Na_2SO_4$, and then the solvent was evaporated to prepare ethyl 3,5-dimethoxy-4-(methoxymethyl)benzoate (300 mg).

Furthermore, ethyl 3,5-dimethoxy-4-(methoxymethyl)benzoate (300 mg) was added to an EtOH/THF (1:2) solution (7.5 mL), and subsequently, a 1 M aqueous sodium hydroxide solution (2.3 mL) was added dropwise thereto, followed by stirring at room temperature for about 15 hours. The solvent was evaporated under reduced pressure to about a half amount, the reaction mixture was concentrated, and ice water (about 20 to 30 g) including 1 M hydrochloric acid (6 mL) was poured into the obtained residue, followed by extraction with $CHCl_3$ several times. The organic layer was washed with water and dried over $Na_2SO_4$, and then the solvent was evaporated to prepare 3,5-dimethoxy-4-(methoxymethyl)benzoic acid (240 mg).

Preparation Example 53

1-(4-Hydroxyphenyl)cyclopropanecarboxylic acid (1.07 g) was added to EtOH (20 mL), and concentrated sulfuric acid (0.1 mL) was added dropwise thereto, followed by stirring at 70° C. for 2 days. The solvent was evaporated under reduced pressure, and to the obtained residue was added a saturated aqueous sodium hydrogen carbonate solution, followed by extraction with an appropriate amount of ethyl acetate. The organic layer was washed with brine and dried over $Na_2SO_4$, and then the solvent was evaporated under reduced pressure. The obtained residue was purified by silica gel column chromatography (hexane:ethyl acetate-2:1) to prepare ethyl 1-(4-hydroxyphenyl)cyclopropanecarboxylate (1.15 g) as a pale yellow solid.

Subsequently, ethyl 1-(4-hydroxyphenyl)cyclopropanecarboxylate (200 mg), triphenylphosphine (382 mg), and 2-fluoroethanol (93 mg) were added to THF, and subsequently, DBAD (335 mg) was added thereto under ice-cooling, followed by stirring at room temperature overnight. The solvent was evaporated under reduced pressure, and the obtained residue was purified by silica gel column chromatography (hexane:ethyl acetate=2:1) to prepare ethyl 1-[4-(2-fluoroethoxy)phenyl]cyclopropanecarboxylate (190 mg) as a colorless oily substance.

Furthermore, ethyl 1-[4-(2-fluoroethoxy)phenyl]cyclopropanecarboxylate (190 mg) was added to an EtOH/THF (1:1) solution (10 mL), and subsequently, a 1 M aqueous sodium hydroxide solution (2 mL) was added dropwise thereto, followed by stirring at room temperature overnight. The reaction mixture was concentrated under reduced pressure and neutralized by the addition of purified water and 1 M hydrochloric acid, and then resulting insoluble material was collected by filtration to prepare 1-[4-(2-fluoroethoxy)phenyl]cyclopropanecarboxylic acid (152 mg) as a white solid.

Preparation Example 54

The following products were prepared with a partial modification of the method of Johnson, et al. (Tetrahedron Lett., 2004 45, 8483-8487.).

N-Benzylmethane sulfonamide (2.0 g) was added to THF (40 mL), and subsequently, a 1.66 M solution of n-butyl lithium in n-hexane (13.1 mL) was added dropwise thereto under cooling at −78° C., followed by stirring for 5 minutes and then warming to 0° C. To the reaction mixture was slowly added dropwise a mixture prepared by adding acetaldehyde (2.4 mL) to THF (20 mL), followed by stirring for 2 hours while warming to room temperature. To the reaction mixture was added an aqueous ammonium chloride solution, followed by extraction with $CHCl_3$, the aqueous layer was separated with a phase separator, and the solvent of the organic layer was evaporated. The obtained residue was purified by silica gel column chromatography ($CHCl_3$:MeOH=20:1) to prepare N-benzyl-2-hydroxypropane-1-sulfonamide (1.94 g) as a white solid.

Subsequently, N-benzyl-2-hydroxypropane-1-sulfonamide (1.94 g), DMAP (0.52 g), triethylamine (1.77 mL), and tert-butyldimethylchlorosilane (1.91 g) were added to methylene chloride (50 mL), followed by stirring at room temperature overnight. To the reaction mixture was added an aqueous ammonium chloride solution, followed by extraction with ethyl acetate. The organic layer was washed with brine and dried by the addition of $MgSO_4$, and the solvent was evaporated. The obtained residue was purified by silica gel column chromatography (hexane:ethyl acetate=2:1) to prepare N-benzyl-2-{[tert-butyl (dimethyl)silyl]oxy}propane-1-sulfonamide (1.84 g).

Furthermore, N-benzyl-2-{[tert-butyl (dimethyl)silyl]oxy}propane-1-sulfonamide (1.8 g) and 10% palladium hydroxide (0.5 g) were added to ethyl acetate (30 mL), followed by stirring at room temperature for 3 hours under a hydrogen atmosphere. The reaction mixture was filtered through Celite and the solvent was evaporated. The obtained residue was purified by silica gel column chromatography ($CHCl_3$:MeOH=10:1) to prepare 2-{[tert-butyl (dimethyl)silyl]oxy}propane-1-sulfonamide (1.04 g) as a white solid.

Preparation Example 93

2-{[(3,5-Dimethoxy-4-methylbenzoyl)(3-phenylpropyl)amino]methyl}-1,3-thiazole-4-carboxylic acid (500 mg) and CDI (268 mg) were added to THF (30 mL), followed by stirring at 60° C. for 1 hour. To the reaction mixture were added 3-{[tert-butyl (dimethyl)silyl]oxy}pyrrolidin-1-sulfonamide (370 mg) and DBU (251 mg) under ice-cooling, followed by stirring at room temperature overnight. The solvent was evaporated under reduced pressure and neutralized by the addition of an appropriate amount of purified water and 1 M hydrochloric acid, followed by extraction with $CHCl_3$ several times. The organic layer was washed with brine and then dried over $MgSO_4$, and the solvent was evaporated under reduced pressure. The obtained residue was purified by silica gel column chromatography (hexane:ethyl acetate=1:2) to prepare N-[(3-{[tert-butyl (dimethyl)silyl]oxy}pyrrolidin-1-yl)sulfonyl]-2-{[(3,5-dimethoxy-4-methylbenzoyl)(3-phenylpropyl)amino]methyl}-1,3-thiazole-4-carboxamide (580 mg).

Preparation Example 106

To a mixture of ethyl 2-formyl-1,3-thiazole-4-carboxylate (7.4 mg), 2-phenethylamine (4.8 mg), acetic acid (50 μL), and DMF (0.45 mL) was added MP-Triacetoxyborohydride (Biotage) (75 mg), followed by stirring at room temperature overnight. To the reaction mixture was added PS-Benzaldehyde (Biotage) (50 mg), followed by stirring at room temperature for 4 hours, and the insoluble material was collected by filtration. The filtrate was purified by solid-phase extraction using BondElut SCX (Varian) (eluent, concentrated aqueous ammonia:MeOH=1:9). To the obtained crude purified product was added a mixture of 3,5-dimethoxybenzoic acid (7.3 mg), HOBT (5.4 mg), and DMF (1.0 mL), and PS-Carbodiimide (Biotage) (100 mg) was added thereto, followed by stirring at room temperature overnight. To the reaction mixture were added MP-Carbonate (Biotage) (50 mg) and PS-Isocyanate (Biotage) (50 mg), followed by stirring at room temperature for 4 hours, and the insoluble material was collected by filtration. The filtrate was concentrated under reduced pressure, and to the obtained residue were sequentially added EtOH (0.4 mL), THF (0.4 mL), and 1 M aqueous sodium hydroxide solution (0.4 mL), followed by stirring at room temperature overnight. To the reaction mixture was added 1 M hydrochloric acid (0.4 mL), and the solvent was evaporated under reduced pressure. The obtained residue was purified by preparative liquid chromatography/mass spectroscopy device (MeOH/0.1% aqueous formic acid solution) to prepare 2-{[(3,5-dimethoxybenzoyl)(2-phenyl ethyl)amino]methyl}-1,3-thiazole-4-carboxylic acid (6.4 mg).

Preparation Example 216

Ethyl 2-{[(3,5-dimethoxy-4-methylbenzoyl)(3-phenylpropyl)amino]methyl}-5-vinyl-1,3-thiazole-4-carboxylate (235 mg) and 10% palladium/carbon (48 mg) were added to an EtOH/THF (1:1) solution (7.8 mL), followed by stirring at a normal temperature/a normal pressure for 4 hours under a hydrogen atmosphere. The catalyst was filtered through Celite, the filtrate was concentrated under reduced pressure, and the obtained residue was purified by silica gel column chromatography (ethyl acetate:hexane=2:3) to prepare ethyl 2-{[(3,5-dimethoxy-4-methylbenzoyl)(3-phenylpropyl)amino]methyl}-5-ethyl-1,3-thiazole-4-carboxylate (198 mg) as a colorless oily substance.

Preparation Example 219

Ethyl 2-{[(3,5-dimethoxy-4-methylbenzoyl)(3-phenylpropyl)amino]methyl}-1,3-thiazole-4-carboxylic acid (1.5 g), WSCD HCl (0.76 g), HOBT (0.54 g), and ammonium chloride (0.53 g) were added to DMF (50 mL), and subsequently, triethylamine (1.38 mL) was added dropwise thereto, followed by stirring at room temperature overnight. To the reaction mixture was added a saturated aqueous sodium hydrogen carbonate solution, followed by extraction with ethyl acetate. The organic layer was washed with brine and dried over MgSO$_4$, and then the solvent was evaporated under reduced pressure. The obtained residue was purified by silica gel column chromatography (CHCl$_3$:MeOH=10:1) to prepare 2-{[(3,5-dimethoxy-4-methylbenzoyl)(3-phenylpropyl) amino]methyl}-1,3-thiazole-4-carboxamide (1.35 g).

Preparation Example 400

To a solution containing tert-butyl 1-(4-bromophenyl)cyclopropanecarboxylate (2.0 g) in THF (50 mL) was added a 2.6 M n-BuLi solution in hexane (2.8 mL) at −78° C., followed by stirring for about 2 minutes, and DMF (0.7 mL) was added thereto, followed by warming to −50° C. and stirring for about 1 hour. The reaction mixture was returned to room temperature, an appropriate amount of a saturated aqueous ammonium chloride solution was added thereto, followed by extraction with CH$_3$Cl, and the organic layer was evaporated under reduced pressure. The residue was purified by silica gel column chromatography (hexane:ethyl acetate=4:1) to prepare tert-butyl 1-(4-formylphenyl)cyclopropanecarboxylate (1.41 g) as a colorless oily substance.

Preparation Example 401 tert-Butyl 1-(4-formylphenyl)cyclopropanecarboxylate (1.4 g) was added to EtOH (2 mL), and sodium borohydride (0.25 g) was added thereto at 0° C., followed by stirring at room temperature for 1 hour. To the reaction mixture was added an appropriate amount of purified water, followed by extraction with CHCl$_3$, and the solvent was evaporated. The residue was purified by silica gel column chromatography (hexane:ethyl acetate=2:1) to prepare tert-butyl 1-[4-(hydroxymethyl)phenyl]cyclopropanecarboxylate (1.39 g) as a colorless oily substance.

Preparation Example 402 tert-Butyl 1-[4-(hydroxymethyl)phenyl]cyclopropanecarboxylate (700 mg) was added to DMF (12 mL), and 55% sodium hydride (250 mg) was added thereto under ice-cooling, followed by stirring for 10 minutes. Iodomethane (0.3 mL) was added thereto, followed by returning to room temperature and stirring at room temperature for 1 hour. To the reaction mixture was added an appropriate amount of a saturated aqueous ammonium chloride solution, followed by extraction with CHCl$_3$, and the solvent was evaporated. The residue was purified by silica gel column chromatography (hexane:ethyl acetate=4:1) to prepare tert-butyl 1-[4-(methoxymethyl)phenyl]cyclopropanecarboxylate (580 mg) as a colorless oily substance.

Preparation Example 403

[4-(Methylsulfanyl)phenyl]acetonitrile (2.5 g) and N-benzyl-N,N,N-triethylammonium chloride (0.38 g) was added to bromochloroethane (2.8 mL), and a 50% aqueous sodium hydroxide solution (15 mL) was slowly added thereto under ice-cooling. The reaction mixture was stirred at 40° C. for 18 hours. To the reaction mixture was added an appropriate amount of ice water, followed by extraction with toluene, and the organic layer was washed with brine, dried over Na$_2$SO$_4$, and then evaporated under reduced pressure. The residue was purified by silica gel column chromatography (hexane:ethyl acetate=4:1) to prepare 1-[4-(methylsulfanyl)phenyl]cyclopropanecarbonitrile (2.82 g) as a colorless oily substance.

Next, 1-[4-(methylsulfanyl)phenyl]cyclopropanecarbonitrile (2.82 g) and potassium hydroxide (2.4 g) were added to a mixed solution of purified water (15 mL) and ethylene glycol (15 mL), followed by stirring at 140° C. for 4 hours. The reaction mixture was poured into a mixed solution of ice water (100 mL) and 6 M hydrochloric acid (50 mL), and the precipitated solid was collected by filtration and dried under reduced pressure to prepare 1-[4-(methylsulfanyl)phenyl]cyclopropanecarboxylic acid (1.09 g) as a white solid.

Preparation Example 405

2-Fluoro-4-hydroxybenzaldehyde (5.0 g), triphenylphosphine (14 g), and 2-fluoroethanol (3.43 g) were added to THF (150 mL), and diisopropyl (E)-diazene-1,2-dicarboxylate (10.82 g) was added thereto under ice-cooling, followed by stirring at room temperature for one week. The reaction mixture was evaporated under reduced pressure, and the residue was purified by silica gel column chromatography (hexane to hexane:ethyl acetate=3:1) to prepare 2-fluoro-4-(2-fluoroethoxy)benzaldehyde (4.9 g) as a white solid.

Preparation Example 408

2-Fluoro-4-(2-fluoroethoxy)benzaldehyde (4.9 g), triethylamine (0.73 mL) and trimethylsilanecarbonitrile (4.0 mL) were sequentially added to methylene chloride (50 mL), followed by stirring at room temperature overnight. The reaction mixture was evaporated under reduced pressure, and to the residue were added EtOH (50 mL) and chlorotrimethylsilane (9.8 mL), followed by stirring at 50° C. for 5 hours. Further, an appropriate amount of saturated sodium bicarbonate water was added thereto, followed by stirring at room temperature for 3 hours. The solvent was evaporated under reduced pressure, and the residue was extract with an appropriate amount of ethyl acetate, washed with brine, and then dried over Na$_2$SO$_4$. The residue was purified by silica gel column chromatography (hexane to hexane:ethyl acetate=1:1) to prepare ethyl [2-fluoro-4-(2-fluoroethoxy)phenyl](hydroxy)acetate (4.0 g) as a colorless solid.

Preparation Example 411

Ethyl [2-fluoro-4-(2-fluoroethoxy)phenyl](hydroxy)acetate (4.0 g), [2-(chloromethoxy)ethyl](trimethyl)silane (0.4 mL), a Hunig's base (0.5 mL), and tetra-n-butylammonium iodide (0.78 g) were sequentially added to methylene chloride (5 mL), followed by stirring at room temperature for 5 hours, and then [2-(chloromethoxy)ethyl](trimethyl) silane (0.4 mL), a Hunig's base (0.5 mL), and tetra-n-butylammonium iodide (0.78 g) were added thereto, followed by further stirring for 3 hours. The reaction mixture was evaporated under reduced pressure, and an appropriate amount of purified water was added thereto. The mixture was extracted with ethyl acetate, then washed with brine, and dried over Na$_2$SO$_4$. The solvent was evaporated under reduced pressure and the residue was purified by silica gel column chromatography (hexane to hexane:ethyl acetate=5:1) to prepare ethyl [2-fluoro-4-(2-fluoroethoxy)phenyl]{[2-(trimethylsilyl) ethoxy]methoxy}acetate (0.56 g) as a colorless oily substance.

Preparation Example 420

2-Fluoro-4-hydroxybenzaldehyde (1.5 g), 1-iodopropane (1.26 mL), and potassium carbonate (2.22 g) were sequentially added to acetonitrile (38 mL), followed by stirring at 60° C. for 5 hours. To the reaction mixture was added an appropriate amount of ethyl acetate, followed by stirring for a while. Then, the insoluble material was filtered and the filtrate was concentrated under reduced pressure. The residue was purified by silica gel column chromatography (hexane to hexane:ethyl acetate=5:1) to prepare 2-fluoro-4-propoxybenzaldehyde (1.49 g) as a colorless oily substance.

Preparation Example 421

Ethyl 5-methyl-2-{[(3-phenylpropyl)amino]methyl}-1,3-thiazole-4-carboxylate (0.8 g), a Hunig's base (0.15 mL), (4-ethoxy-2-fluorophenyl) {[2-(trimethylsilyl)ethoxy]methoxy}acetic acid (0.95 g), and HATU (1.1 g) were sequentially added to acetonitrile (53 mL), followed by stirring at room temperature for 3 hours. The reaction mixture was evaporated under reduced pressure, and to the residue were added an appropriate amount of purified water and 1 M hydrochloric acid, followed by extraction with $CHCl_3$. The organic layer was dried over $Na_2SO_4$ and evaporated under reduced pressure. The residue was purified by silica gel column chromatography (hexane to hexane:ethyl acetate=1:1) to prepare ethyl 2-[4-(4-ethoxy-2-fluorophenyl)-10,10-dimethyl-3-oxo-2-(3-phenylpropyl)-5,7-dioxo-2-aza-10-silaneundec-1-yl]-5-methyl-1,3-thiazole-4-carboxylate (1.45 g) as a colorless oily substance.

Next, ethyl 2-[4-(4-ethoxy-2-fluorophenyl)-10,10-dimethyl-3-oxo-2-(3-phenylpropyl)-5,7-dioxo-2-aza-10-silaneundec-1-yl]-5-methyl-1,3-thiazole-4-carboxylate (1.45 g) and a 1 M aqueous sodium hydroxide solution (5 mL) were added to a THF/EtOH (1:1) solution (20 mL), followed by stirring at room temperature overnight. The reaction mixture was evaporated under reduced pressure, and the residue was neutralized by the addition of an appropriate amount of purified water and 1 M hydrochloric acid, and then extracted with ethyl acetate. The organic layer was washed with brine and dried over $Na_2SO_4$, and then the solvent was evaporated under reduced pressure to prepare 2-[4-(4-ethoxy-2-fluorophenyl)-10,10-dimethyl-3-oxo-2-(3-phenylpropyl)-5,7-dioxo-2-aza-10-silaneundec-1-yl]-5-methyl-1,3-thiazole-4-carboxylic acid (1.35 g).

Preparation Example 424

1-(4-Hydroxyphenyl)cyclopropanecarboxylate (4.5 g) and concentrated sulfuric acid (0.2 mL) were added to EtOH (60 mL), followed by stirring at 70° C. for 2 days. The reaction mixture was evaporated under reduced pressure, and to the residue was added an appropriate amount of saturated sodium bicarbonate water, followed by extraction with ethyl acetate. The organic layer was washed with brine and dried over $Na_2SO_4$, and then the solvent was evaporated under reduced pressure. The obtained residue was purified by silica gel column chromatography (hexane to hexane:ethyl acetate=2:1) to prepare ethyl 1-(4-hydroxyphenyl)cyclopropanecarboxylate (5.0 g) as a pale yellow solid.

Preparation Example 425

Ethyl 1-(4-hydroxyphenyl)cyclopropanecarboxylate (0.7 g), potassium carbonate (0.7 g), and iodomethane-$d_2$ were sequentially added to DMF (7 mL), followed by stirring at room temperature overnight. To the reaction mixture was added an appropriate amount of ice water, followed by extraction with ethyl acetate. The organic layer was washed with brine and dried over $Na_2SO_4$, and the solvent was evaporated under reduced pressure. The obtained residue was purified by silica gel column chromatography (hexane to hexane:ethyl acetate=5:1) to prepare ethyl 1-{4-[($^2H_2$)methyloxy]phenyl}cyclopropanecarboxylate (0.705 g) as a colorless oily substance.

Preparation Example 429

A mixture of copper(II) trifluoromethanesulfonate (155 mg) and (4S,4'S)-2,2'-propane-2,2-diylbis(4-benzyl-4,5-dihydro-1,3-oxazole) (155 mg) was dried for 30 minutes under reduced pressure, and then added to methylene chloride (7 mL) under an argon air flow, followed by stirring at room temperature for 1 hour. To this mixture was added a solution containing ethyl {4-[($^2H_2$)methyloxy]phenyl}(oxo)acetate (300 mg) in methylene chloride (3 mL), followed by further stirring at room temperature for 30 minutes. To the reaction mixture was added diethyl 2,6-dimethylpyridine-1,4-dihydropyridine-3,5-dicarboxylate (433 mg) in an ice bath, followed by stirring for 3 hours as it was and subsequently stirring at room temperature overnight. To the reaction mixture was added an appropriate amount of purified water, followed by extraction with $CHCl_3$, the organic layer was dried over $Na_2SO_4$, and then the solvent was evaporated under reduced pressure. The obtained residue was purified by silica gel column chromatography (hexane to hexane:ethyl acetate=1:1) to prepare ethyl (2R)-hydroxy{4-[($^2H_2$)methyloxy]phenyl}acetate (0.25 g) as a colorless oily substance.

Preparation Example 430

N-(2-Hydroxyethyl)-N-methylsulfuric diamide (780 mg), DMAP (309 mg), triethylamine (0.85 mL), and tert-butyl (chloro)dimethylsilane (915 mg) were sequentially added to DMF (8 mL), followed by stirring at room temperature overnight. To the reaction mixture was added an appropriate amount of a saturated aqueous ammonium chloride solution, followed by extraction with $CHCl_3$, and the organic layer was washed with brine and dried over $MgSO_4$. The solvent was evaporated under reduced pressure and the obtained residue was purified by silica gel column chromatography (hexane:ethyl acetate=1:1) to prepare N-(2-{[tert-butyl (dimethyl)silyl]oxy}ethyl)-N-methylsulfuric diamide (801 mg) as a white solid.

Preparation Example 431

Ethyl (2R)-[4-(benzyloxy)phenyl]{[2-(trimethylsilyl)ethoxy]methoxy}acetate (2.65 g), cyclohexene (20 mL), and 10% palladium/carbon (530 mg) were added to EtOH (40 mL), followed by stirring at 100° C. for 2 hours. The insoluble material was filtered through Celite, and the obtained filtrate was evaporated under reduced pressure. The obtained residue was purified by silica gel column chromatography (hexane to hexane:ethyl acetate=2:1) to prepare ethyl (2R)-(4-hydroxyphenyl){[2-(trimethylsilyl)ethoxy]methoxy}acetate (2.0 g) as a colorless oily substance.

Preparation Example 432

[2-(1,3-Dioxo-1,3-dihydro 2H-isoindol-2-yl)ethyl](triphenyl)phosphonium bromide (4.0 g), 3-(difluoromethyl)benzaldehyde (1.1 g), and sodium hydride (0.37 g) were added to DMSO (20 mL), followed by stirring at room temperature for 2 hours under an argon gas atmosphere. An appropriate amount of ice water and a saturated aqueous ammonium chloride solution were poured into the reaction mixture, followed by extraction with ethyl acetate. The obtained organic layer was washed with brine and dried over MgSO$_4$, the solvent was evaporated under reduced pressure, and the obtained yellow oily residue was purified by silica gel column chromatography (hexane:ethyl acetate=3:1) to prepare 2-{3-[3-(difluoromethyl)phenyl]prop-2-en-1-yl}-1H-isoindole-1,3(2H)-dione (1.47 g) as a yellow oily substance.

Preparation Example 437

2-{3-[3-(Difluoromethyl)phenyl]prop-2-en-1-yl}-1H-isoindole-1,3(2H)-dione (1.4 g) and 10% palladium/carbon (0.53 g; 55% wet) were sequentially added to an MeOH/ethyl acetate (3:1) solution (40 mL), followed by stirring at a normal temperature/a normal pressure for about 2 hours under a hydrogen gas atmosphere. The catalyst was filtered through Celite, and the obtained filtrate was evaporated under reduced pressure to prepare, 2-{3-[3-(difluoromethyl)phenyl]propyl}-1H-isoindole-1,3(2H)-dione (1.41 g) as a white solid.

Preparation Example 440

2-{3-[3-(Difluoromethyl)phenyl]propyl}-1H-isoindole-1,3(2H)-dione (1.4 g) and hydrazine hydrate (0.65 mL) were added to EtOH (14 mL), by heating at 90° C. for about 1.5 hours. The reaction mixture was left to be cooled, and the insoluble material was removed by filtration while diluting and washing with an appropriate amount of diethyl ether, and the obtained filtrate was concentrated. The residue was diluted with an appropriate amount of diethyl ether, an appropriate amount of MgSO$_4$ was added thereto, and the precipitated insoluble material was removed by filtration. The obtained filtrate was evaporated under reduced pressure to prepare 3-[3-(difluoromethyl)phenyl]propan-1-amine (0.74 g) as a colorless oily substance.

Preparation Example 443

With reference to the method of Lesac, et al. (Tetrahedron Asymmetry 2003, 14, 2731-2737), 4-methoxy-2-methylbenzaldehyde (10 g), N-benzyl-N,N,N-triethyl ammonium chloride (0.76 g) and a 50% aqueous NaOH solution (40 mL) were sequentially added to CHCl$_3$ (20 mL), followed by stirring at room temperature for 8 hours. The insoluble material was filtered, and the obtained filtrate was diluted with an appropriate amount of purified water and washed with diethyl ether. The aqueous layer was acidified with 1 M hydrochloric acid and then extracted with ethyl acetate. The organic layer was washed with brine and dried over Na$_2$SO$_4$, and then the solvent was evaporated under reduced pressure to prepare hydroxy(4-methoxy-2-methylphenyl)acetic acid (8.0 g) as a pale brown solid.

Preparation Example 445

Hydroxy(4-methoxy-2-methylphenyl)acetic acid (3.05 g) and (1R)-1-(1-naphthyl)ethanamine (0.27 g) were sequentially added to isopropyl alcohol (10 mL), followed by stirring at room temperature for 5 hours. The precipitated solid was collected by filtration and solidified with isopropyl alcohol. To this solid was added an appropriate amount of purified water and adjusted to be weakly acidic with 1 M hydrochloric acid, followed by extraction with ethyl acetate. The organic layer was washed with brine, and subsequently dried over Na$_2$SO$_4$, and the solvent was evaporated under reduced pressure to prepare (2R)-hydroxy(4-methoxy-2-methylphenyl) acetic acid (0.8 g) as a white solid.

Preparation Example 447

(2R)-Hydroxy(4-methoxy-2-methylphenyl)acetic acid (183 mg), potassium carbonate (150 mg), and ethyl iodide (193 mg) were sequentially added to DMF (5 mL), followed by stirring at room temperature for 3 hours. To the reaction mixture was added an appropriate amount of purified water, followed by extraction with ethyl acetate, and the organic layer was washed with brine, and subsequently dried over Na$_2$SO$_4$. The solvent was evaporated under reduced pressure to prepare ethyl (2R)-hydroxy(4-methoxy-2-methylphenyl) acetate (150 mg) as a yellow oily substance.

Preparation Example 448

Ethyl (2R)-hydroxy(4-methoxy-2-methylphenyl)acetate (0.98 g), [2-(chloromethoxy)ethyl](trimethyl) silane (1.54 mL), a Hunig's base (1.5 mL), and tetra-n-butylammonium iodide (1.61 g) were sequentially added to methylene chloride (10 mL), followed by stirring at room temperature overnight. The reaction mixture was evaporated under reduced pressure, and the residue was purified by silica gel column chromatography (hexane to hexane:ethyl acetate=5:1) to prepare ethyl (2R)-(4-methoxy-2-methylphenyl){[2-(trimethylsilyl)ethoxy]methoxy}acetate (934 mg) as a colorless oily substance.

Next, ethyl (2R)-(4-methoxy-2-methylphenyl) {[2-(trimethylsilyl)ethoxy]methoxy}acetate and a 1 M aqueous NaOH solution (5 mL) were sequentially added to an EtOH/THF (1:1) solution (16 mL), followed by stirring at room temperature for 3 hours. The solvent was evaporated under reduced pressure, and the residue was adjusted to a neutral solution by the addition of an appropriate amount of 1 M hydrochloric acid, followed by extraction with ethyl acetate. The organic layer was washed with brine and dried over Na$_2$SO$_4$, and then the solvent was evaporated under reduced pressure to prepare (2R)-(4-m methoxy-2-methylphenyl) {[2-(trimethylsilyl)ethoxy]methoxy}acetic acid (870 mg) as a colorless oily substance.

Preparation Example 449

Hydroxy(6-methoxypyridin-3-yl)acetic acid (1.37 g) was added to EtOH (10 mL), warmed, and dissolved therein, and then (1R)-1-phenethylethylamine (0.95 g) was added thereto, followed by stirring at room temperature for 3 hours. The precipitated solid was collected by filtration and added to an appropriate amount of purified water, followed by adjustment to a weakly acidic solution with 1 M hydrochloric acid and then extraction with ethyl acetate twice. The organic layer was washed with brine and dried over Na$_2$SO$_4$, and then the solvent was evaporated under reduced pressure to prepare (2R)-hydroxy(6-methoxypyridin-3-yl)acetic acid (0.33 g).

Next, (2R)-hydroxy(6-methoxypyridin-3-yl)acetic acid (0.33 g), potassium carbonate (0.5 g), and ethyl iodide (0.56 g) were sequentially added to DMF (5 mL), followed by stirring at room temperature for 5 hours. To the reaction mixture was added an appropriate amount of ice water, followed by extraction with ethyl acetate, and the organic layer was washed with brine and dried over Na$_2$SO$_4$. The solvent was evaporated under reduced pressure, and the obtained residue was purified by silica gel column chromatography (hexane→hexane:ethyl acetate=1:1) to prepare ethyl (2R)-hydroxy(6-methoxypyridin-3-yl)acetate (0.28 g) as a yellow oily substance.

Preparation Example 450

Ethyl 2-[([3-(3-bromophenyl)propyl]{[1-(5-methoxypyridin-2-yl)cyclopropyl]carbonyl}amino)methyl]-5-methyl-1,3-thiazole-4-carboxylate (280 mg), ethynyl(trimethyl) silane (0.17 mL), copper iodide (9.3 mg), and bis(triphenylphosphine) palladium(II) dichloride (34 mg) were sequentially added to triethylamine (2.8 mL), followed by warming at 70° C. for 20 hours under a sealed argon gas. The reaction mixture was diluted with an appropriate amount of ethyl acetate, the black insoluble material was removed by filtration through Celite, and the obtained organic layer was sequentially washed with unsaturated sodium bicarbonate water and brine. The organic layer was dried over MgSO$_4$, and the solvent was evaporated under reduced pressure. The obtained residue was purified by silica gel column chromatography (ethyl acetate: hexane=1:1) to prepare ethyl 2-{[{[1-(5-methoxypyridin-2-yl)cyclopropyl]carbonyl}(3-{3-[(trimethylsilyl)ethynyl]phenyl}propyl)amino]methyl}-5-methyl-1,3-thiazole-4-carboxylate (160 mg).

Preparation Example 451

Ethyl 2-{[{[1-(5-methoxypyridin-2-yl)cyclopropyl]carbonyl}(3-{3-[(trimethylsilyl)ethynyl]phenyl}propyl)amino]methyl}-5-methyl-1,3-thiazole-4-carboxylate (150 mg) and potassium carbonate (42 mg) were added to methanol (2 mL), followed by stirring at room temperature for about 2.5 hours. The reaction mixture was concentrated under reduced pressure, and to the residue was added an appropriate amount of purified water, followed by extraction with ethyl acetate. The organic layer was washed with brine and dried over MgSO$_4$, and then the solvent was evaporated. The resulting residue was purified by silica gel column chromatography (ethyl acetate:hexane=3:2) to prepare methyl 2-[([3-(3-ethynylphenyl)propyl]{[1-(5-methoxypyridin-2-yl)cyclopropyl]carbonyl}amino)methyl]-5-methyl-1,3-thiazole-4-carboxylate (100 mg).

Preparation Example 452

Ethyl 2-[([3-(3-bromophenyl)propyl]{[1-(5-methoxypyridin-2-yl)cyclopropyl]carbonyl}amino)methyl]-5-methyl-1,3-thiazole-4-carboxylate (300 mg), a 2,4,6-trivinylcyclotriboroxane-pyridine complex (133 mg), palladium acetate (24 mg), tricyclohexylphosphine (59 mg), and potassium phosphate (334 mg) were sequentially added to a dioxane/water (10:1) (6.6 mL) solution, followed by heating at 95° C. for 2.5 days. The insoluble material was removed by filtration through Celite while diluting and washing the reaction mixture with an appropriate amount of ethyl acetate and purified water. The filtrate was subjected to liquid-separation, and the obtained organic layer was washed with brine and dried over MgSO$_4$, and then evaporated under reduced pressure. The obtained brown residue was purified by silica gel column chromatography (hexane:ethyl acetate=1:1) to prepare ethyl 2-[({[1-(5-methoxypyridin-2-yl)cyclopropyl]carbonyl}[3-(3-vinylphenyl)propyl]amino)methyl]-5-methyl-1,3-thiazole-4-carboxylate (245 mg) as a colorless oily substance.

Preparation Example 453

(2R)-(2-Fluoro-4-methoxyphenyl)(hydroxy)acetic acid (1.1 g), potassium carbonate (0.9 g), and ethyl iodide (0.6 mL) were sequentially added to DMF (30 mL), followed by stirring at room temperature for 3 hours. To the reaction mixture was added an appropriate amount of purified water, followed by extraction with ethyl acetate. The organic layer was washed with brine and dried over Na$_2$SO$_4$, and then the solvent was evaporated under reduced pressure to prepare ethyl (2R)-(2-fluoro-4-methoxyphenyl)(hydroxy)acetate (1.2 g).

Next, ethyl (2R)-(2-fluoro-4-methoxyphenyl)(hydroxy)acetate (270 mg), [2-(chloromethoxy)ethyl](trimethyl) silane (0.42 mL), a Hunig's base (0.42 mL), and tetra-n-butylammonium iodide (440 mg) were sequentially added to methylene chloride (10 mL), followed by stirring at room temperature overnight. The reaction mixture was concentrated under reduced pressure, and the residue was purified by silica gel column chromatography (hexane to hexane:ethyl acetate=5:1) to prepare ethyl(2R)-(2-fluoro-4-methoxyphenyl){[2-(trimethylsilyl)ethoxy]methoxy}acetate (325 mg) as a colorless oily substance.

Preparation Example 454

Ethyl 5-bromo-2-[(4R)-4-(4-methoxyphenyl)-10,10-dimethyl-3-oxo-2-(3-phenylpropyl)-5,7-dioxo-2-aza-10-silaneundec-1-yl]-1,3-thiazole-4-carboxylate (420 mg), tributyl (vinyl)tin (0.27 mL), (1E,4E)-1,5-diphenylpenta-1,4-dien-3-one palladium (3:2) (60 mg), and tris(2-methylphenyl) phosphine (75 mg) were sequentially added to toluene (10 mL), followed by stirring at 80° C. for 2 hours. The solvent was evaporated under reduced pressure, and the obtained residue was purified by silica gel column chromatography (hexane to hexane:ethyl acetate=1:1) to prepare ethyl 2-[(4R)-4-(4-methoxyphenyl)-10,10-dimethyl-3-oxo-2-(3-phenylpropyl)-5,7-dioxo-2-aza-10-silaneundec-1-yl]-5-vinyl-1,3-thiazole-4-carboxylate (319 mg) as a colorless oily substance.

Preparation Example 455

Using the same condition as the method of Preparation Example 5 as described above, preparation was performed.

Preparation Example 456

N-(2-{[tert-butyl (dimethyl)silyl]oxy}ethyl)-N-ethylsulfamide was prepared from 2-(ethylamino)ethanol by carrying out the reactions successively and sequentially using the same methods of Preparation Example 41, Preparation Example 35, and Preparation Example 430.

The compounds of Preparation Examples shown in Tables below were prepared using the respective corresponding starting materials in the same manner as the methods of Preparation Examples above. The structures, the preparation methods, and the physicochemical data for the compounds of Preparation Examples are shown in Tables below.

TABLE 4

| Rf | Syn | Structure |
|---|---|---|
| 1 | R1 | 4-formyl-3,5-dimethoxybenzoic acid |
| 2 | R2 | 5-(acetoxymethyl)-2-((N-(3,5-dimethoxy-4-methylbenzoyl)-N-(3-phenylpropyl)amino)methyl)thiazole-4-carboxylic acid |
| 3 | R3 | 3,5-dimethoxy-4-vinylbenzoic acid |
| 4 | R4 | 2-((N-(tert-butoxycarbonyl)-N-(3-phenylpropyl)amino)methyl)thiazole-4-carboxylic acid |
| 5 | R5 | 2-((N-(3,5-dimethoxy-4-methylbenzoyl)-N-(3-phenylpropyl)amino)methyl)thiazole-4-carboxylic acid |
| 6 | R6 | N-(2-fluoroethyl)-N-methylsulfamide |
| 7 | R7 | N-methyl-N-(2-(methylthio)ethyl)sulfamide |
| 8 | R8 | 1-(5-methoxypyridin-2-yl)cyclopropanecarboxylic acid |

TABLE 4-continued

| Rf | Syn | Structure |
|---|---|---|
| 9 | R9 | methyl 4-formyl-3,5-dimethoxybenzoate |
| 10 | R10 | tert-butyl 5-(((tert-butyldimethylsilyl)oxy)methyl)-2-((N-(3,5-dimethoxy-4-methylbenzoyl)-N-(3-phenylpropyl)amino)methyl)thiazole-4-carboxylate |
| 11 | R11 | ethyl 3,5-dimethoxy-4-vinylbenzoate |
| 12 | R12 | ethyl 4-cyclopropyl-3,5-dimethoxybenzoate |

TABLE 5

| Rf | Syn | Structure |
|---|---|---|
| 13 | R13 | ethyl 5-cyano-2-((N-(3,5-dimethoxy-4-methylbenzoyl)-N-(3-phenylpropyl)amino)methyl)thiazole-4-carboxylate |

TABLE 5-continued

| Rf | Syn | Structure |
|---|---|---|
| 14 | R14 | 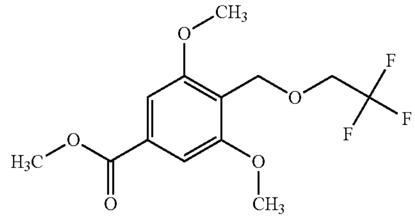 [SMILES: COC(=O)c1cc(OC)c(COCC(F)(F)F)c(OC)c1] |
| 15 | R15 | 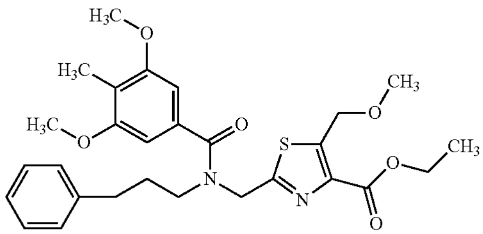 [SMILES: CCOC(=O)c1nc(CN(CCCc2ccccc2)C(=O)c2cc(OC)c(C)c(OC)c2)sc1COC] |
| 16 | R16 | 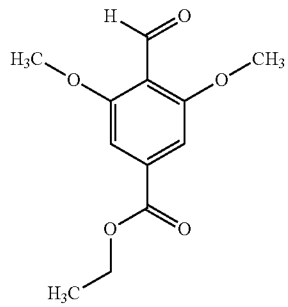 |
| 17 | R17 | 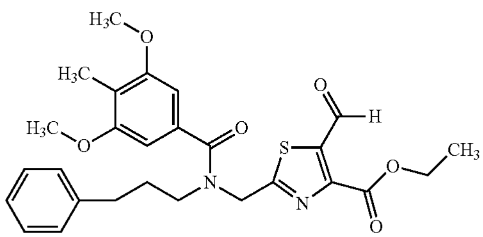 [SMILES: CCOC(=O)c1nc(CN(CCCc2ccccc2)C(=O)c2cc(OC)c(C)c(OC)c2)sc1C=O] |
| 18 | R18 | 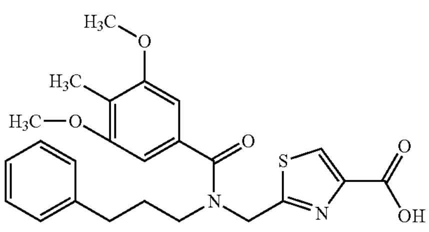 [SMILES: COc1cc(C(=O)N(CCCc2ccccc2)Cc2nc(C(=O)O)cs2)cc(OC)c1C] |
| 19 | R19 | 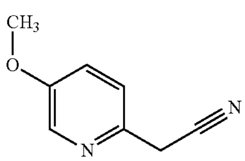 |
| 20 | R20 | 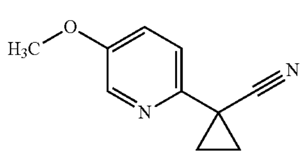 |

TABLE 5-continued

| Rf | Syn | Structure |
|---|---|---|
| 21 | R21 | |
| 22 | R22 | |
| 23 | R23 | |
| 24 | R24 | |

TABLE 6

| Rf | Syn | Structure |
|---|---|---|
| 25 | R25 | 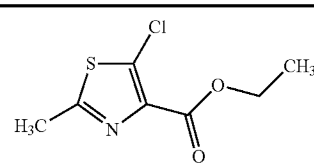 |
| 26 | R26 | 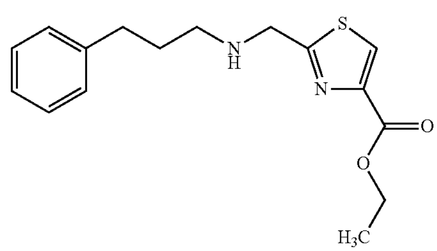 [SMILES: CCOC(=O)c1csc(CNCCCc2ccccc2)n1] |
| 27 | R27 | 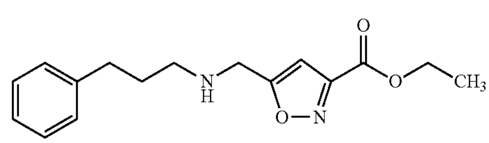 [SMILES: CCOC(=O)c1cc(CNCCCc2ccccc2)on1] |
| 28 | R28 | 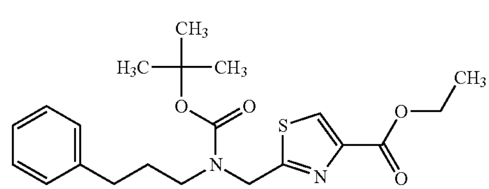 [SMILES: CCOC(=O)c1csc(CN(CCCc2ccccc2)C(=O)OC(C)(C)C)n1] |

TABLE 6-continued
| Rf | Syn | Structure |
|----|-----|-----------|
| 29 | R29 | 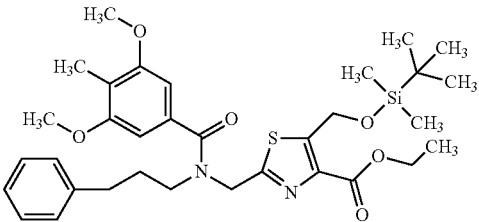 [SMILES: CCOC(=O)c1nc(CN(CCCc2ccccc2)C(=O)c2cc(OC)c(C)c(OC)c2)sc1CO[Si](C)(C)C(C)(C)C] |
| 30 | R30 | 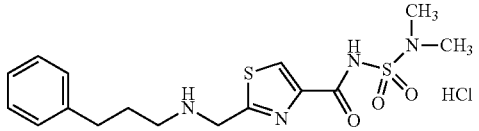 [SMILES: CN(C)S(=O)(=O)NC(=O)c1csc(CNCCCc2ccccc2)n1 ; Cl] |
| 31 | R31 | 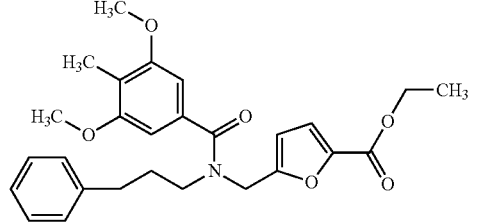 [SMILES: CCOC(=O)c1ccc(CN(CCCc2ccccc2)C(=O)c2cc(OC)c(C)c(OC)c2)o1] |
| 32 | R32 | 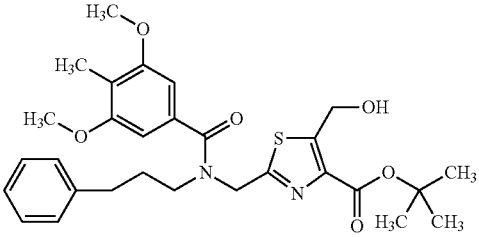 [SMILES: COc1cc(C(=O)N(CCCc2ccccc2)Cc2nc(C(=O)OC(C)(C)C)c(CO)s2)cc(OC)c1C] |
| 33 | R33 | 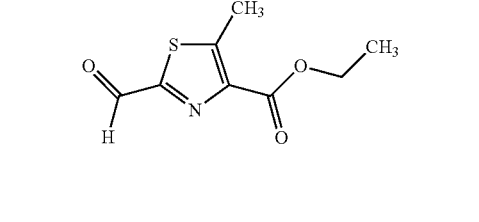 |
| 34 | R34 | 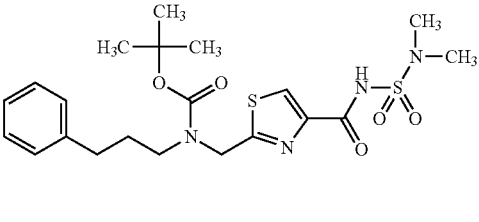 [SMILES: CN(C)S(=O)(=O)NC(=O)c1csc(CN(CCCc2ccccc2)C(=O)OC(C)(C)C)n1] |
TABLE 6-continued
| Rf | Syn | Structure |
|----|-----|-----------|
| 35 | R35 | 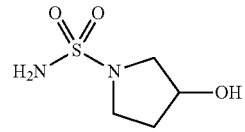 |
| 36 | R36 | 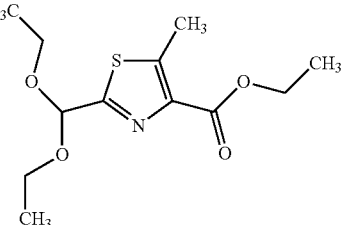 |
TABLE 7
| Rf | Syn | Structure |
|----|-----|-----------|
| 37 | R37 | 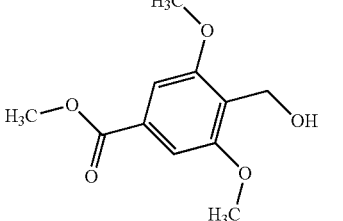 |
| 38 | R38 | 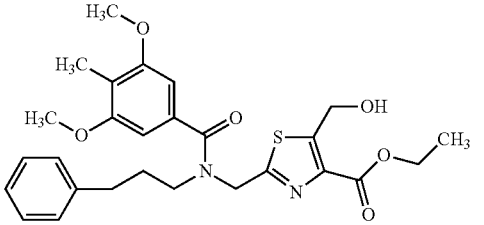 [SMILES: CCOC(=O)c1nc(CN(CCCc2ccccc2)C(=O)c2cc(OC)c(C)c(OC)c2)sc1CO] |
| 39 | R39 | 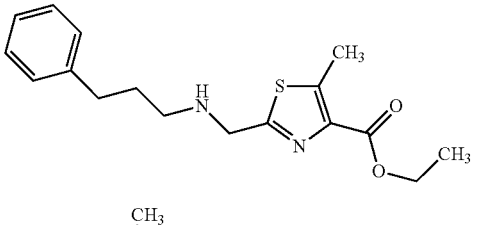 |
| 40 | R40 | 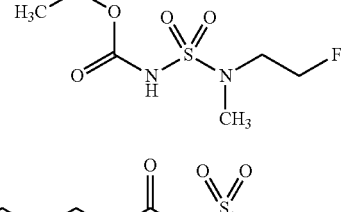 |
| 41 | R41 | 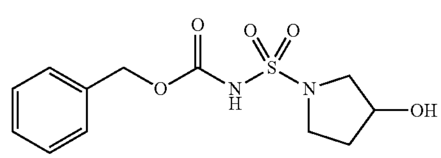 [SMILES: O=C(NS(=O)(=O)N1CCC(O)C1)OCc1ccccc1] |

TABLE 7-continued

| Rf | Syn | Structure |
|----|-----|-----------|
| 42 | R42 | 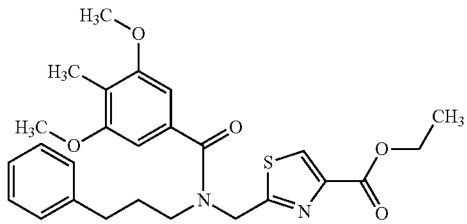 [SMILES: CCOC(=O)c1csc(CN(CCCc2ccccc2)C(=O)c2cc(OC)c(C)c(OC)c2)n1] |
| 43 | R43 | 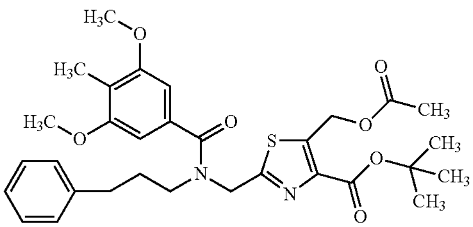 [SMILES: COc1cc(C(=O)N(CCCc2ccccc2)Cc2nc(C(=O)OC(C)(C)C)c(COC(C)=O)s2)cc(OC)c1C] |
| 44 | R44 | 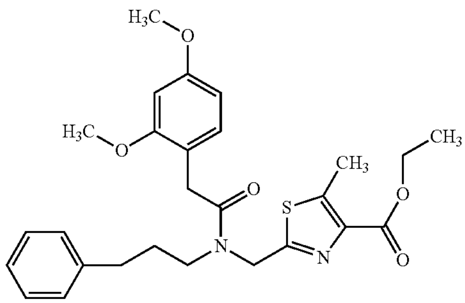 [SMILES: CCOC(=O)c1nc(CN(CCCc2ccccc2)C(=O)Cc2ccc(OC)cc2OC)sc1C] |
| 45 | R45 | 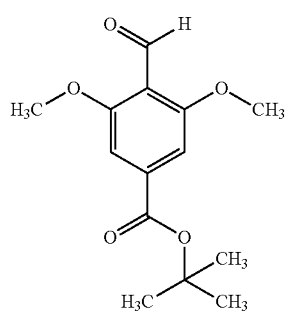 |
| 46 | R46 | 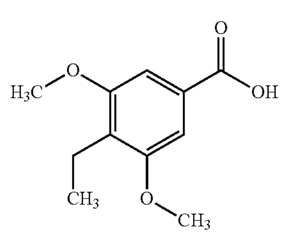 |
| 47 | R47 | 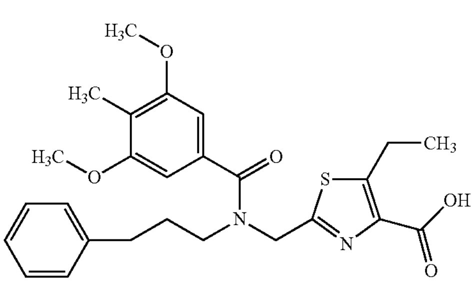 [SMILES: CCc1sc(CN(CCCc2ccccc2)C(=O)c2cc(OC)c(C)c(OC)c2)nc1C(=O)O] |
| 48 | R48 | |

TABLE 8

| Rf | Syn | Structure |
|----|-----|-----------|
| 49 | R49 | 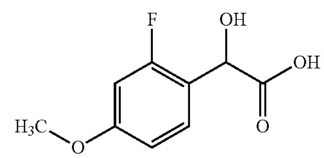 |
| 50 | R50 | 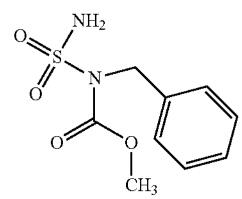 [SMILES: COC(=O)N(Cc1ccccc1)S(N)(=O)=O] |
| 51 | R51 | 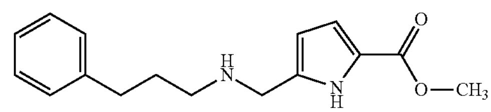 [SMILES: COC(=O)c1ccc(CNCCCc2ccccc2)[nH]1] |
| 52 | R52 | 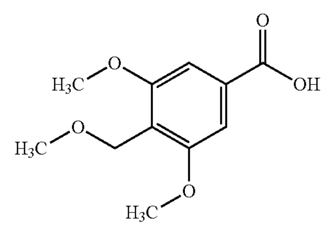 [SMILES: COCc1c(OC)cc(C(=O)O)cc1OC] |
| 53 | R53 | 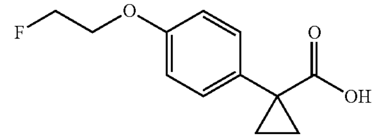 [SMILES: O=C(O)C1(c2ccc(OCCF)cc2)CC1] |
| 54 | R54 | 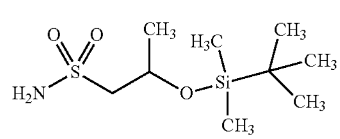 |
| 55 | R35 | 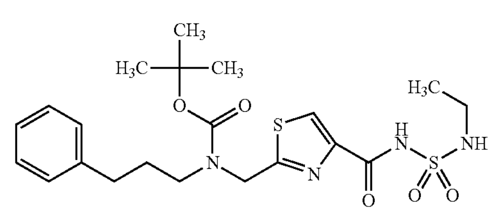 [SMILES: CCNS(=O)(=O)NC(=O)c1csc(CN(CCCc2ccccc2)C(=O)OC(C)(C)C)n1] |

TABLE 8-continued
| Rf | Syn | Structure |
|----|-----|-----------|
| 56 | R30 | 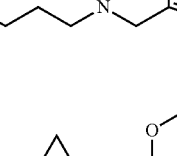 |
| 57 | R3 | 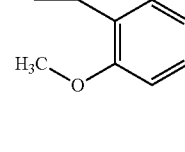 |
| 58 | R3 | 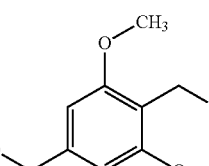 |
| 59 | R5 | 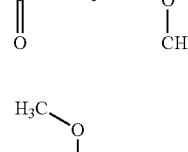 |
| 60 | R5 | 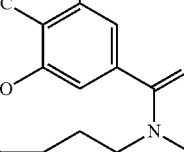 |
| 61 | R5 | 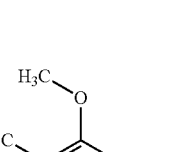 |
| 62 | R5 | 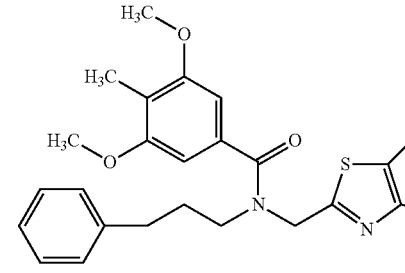 |
TABLE 9
| Rf | Syn | Structure |
|----|-----|-----------|
| 63 | R5 | 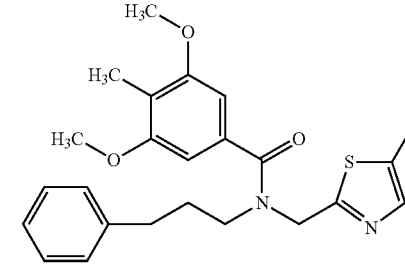 |
| 64 | R5 | 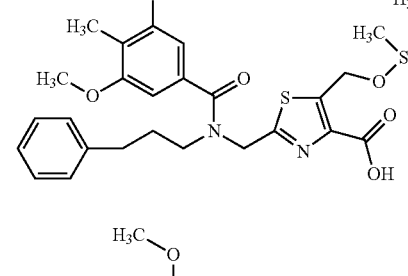 |
| 65 | R5 | 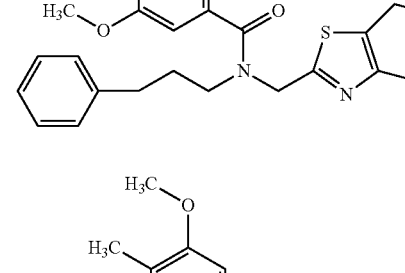 |
| 66 | R5 | 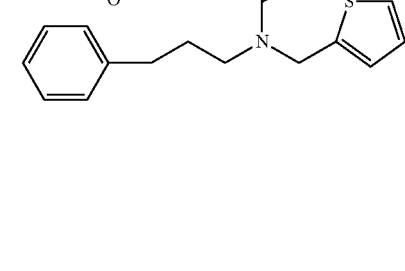 |

TABLE 9-continued

| Rf | Syn | Structure |
|---|---|---|
| 67 | R5 | (structure) |
| 68 | R5 | (structure) |
| 69 | R5 | (structure) |
| 70 | R5 | (structure) |
| 71 | R7 | (structure) |
| 72 | R11 | (structure) |
| 73 | R12 | (structure) |
| 74 | R21 | (structure) |

TABLE 10

| Rf | Syn | Structure |
|---|---|---|
| 75 | R30 | (structure) |
| 76 | R25 | (structure) |
| 77 | R26 | (structure) |
| 78 | R26 | (structure) |
| 79 | R26 | (structure) |
| 80 | R29 | (structure) |

TABLE 10-continued
| Rf | Syn | Structure |
|---|---|---|
| 81 | R29 | 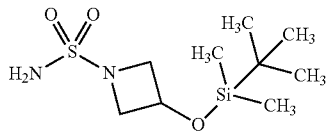 [SMILES: CC(C)(C)[Si](C)(C)OC1CN(S(N)(=O)=O)C1] |
| 82 | R33 | 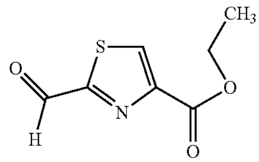 |
| 83 | R35 | 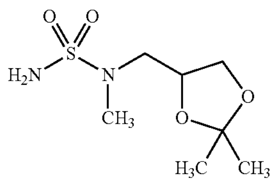 |
| 84 | R35 | 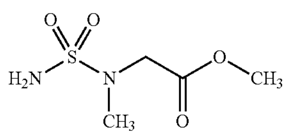 |
| 85 | R35 | 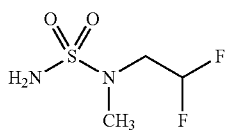 |
| 86 | R35 | 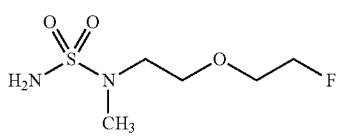 |
| 87 | R35 | 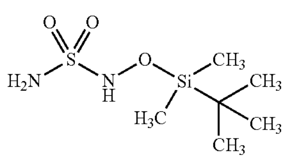 |
| 88 | R35 | 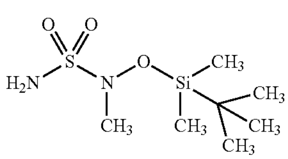 |
TABLE 11
| Rf | Syn | Structure |
|---|---|---|
| 90 | R35 | |
| 91 | R35 | 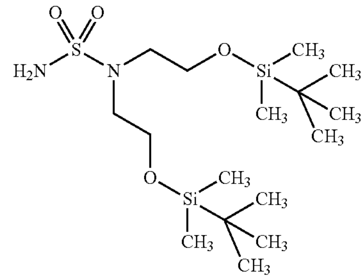 [SMILES: CC(C)(C)[Si](C)(C)OCCN(CCO[Si](C)(C)C(C)(C)C)S(N)(=O)=O] |
| 92 | R35 | 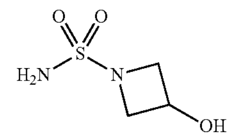 |
| 93 | R93 | 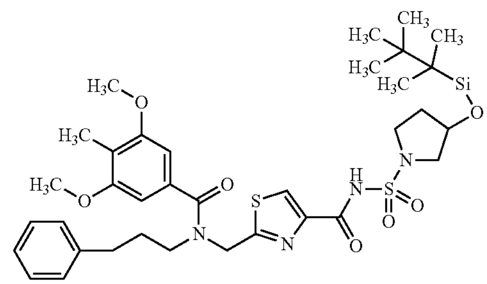 |
| 94 | R36 | 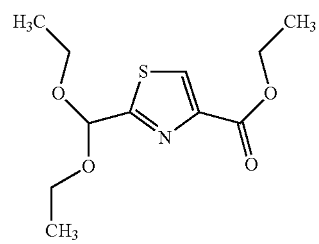 [SMILES: CCOC(=O)c1csc(C(OCC)OCC)n1] |
| 95 | R39 | 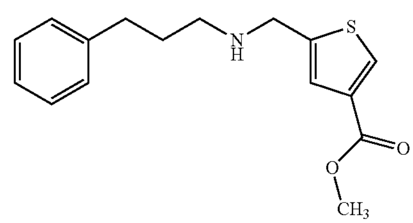 [SMILES: COC(=O)c1csc(CNCCCc2ccccc2)c1] |
| 96 | R39 | 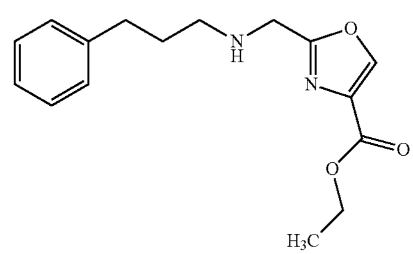 [SMILES: CCOC(=O)c1coc(CNCCCc2ccccc2)n1] |
| 97 | R41 | 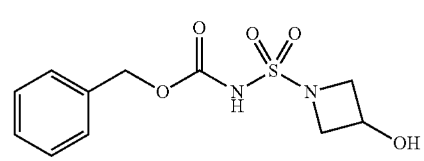 [SMILES: O=C(NS(=O)(=O)N1CC(O)C1)OCc1ccccc1] |
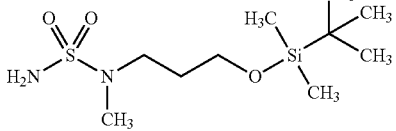
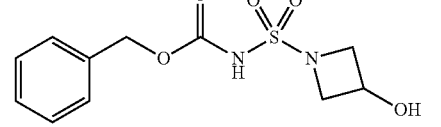

TABLE 11-continued
| Rf | Syn | Structure |
|---|---|---|
| 98 | R42 | 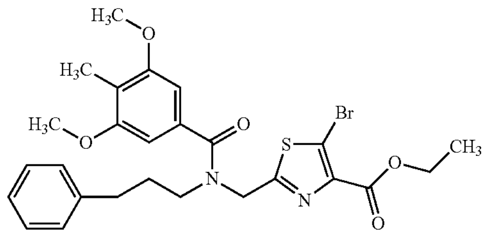 [SMILES: CCOC(=O)c1nc(CN(CCCc2ccccc2)C(=O)c2cc(OC)c(C)c(OC)c2)sc1Br] |
| 99 | R42 | 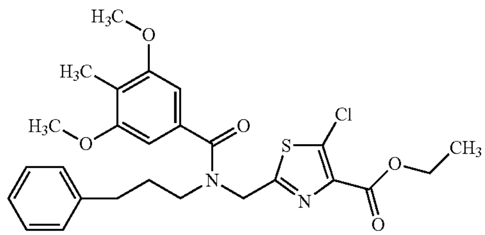 [SMILES: CCOC(=O)c1nc(CN(CCCc2ccccc2)C(=O)c2cc(OC)c(C)c(OC)c2)sc1Cl] |
| 100 | R42 | 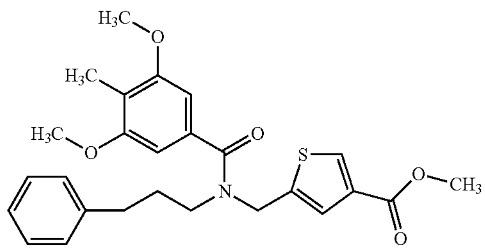 [SMILES: COC(=O)c1csc(CN(CCCc2ccccc2)C(=O)c2cc(OC)c(C)c(OC)c2)c1] |
| 101 | R42 | 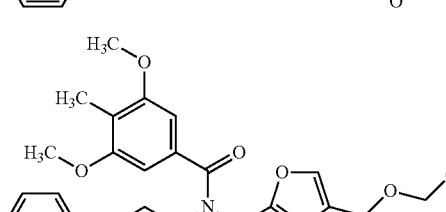 |
TABLE 12
| Rf | Syn | Structure |
|---|---|---|
| 102 | R42 | 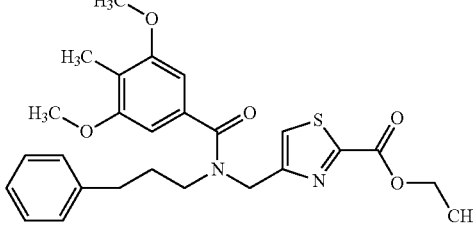 |
| 103 | R42 | 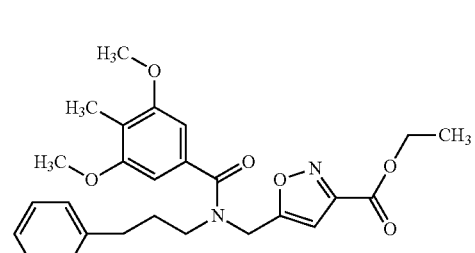 |
TABLE 12-continued
| Rf | Syn | Structure |
|---|---|---|
| 104 | R42 | 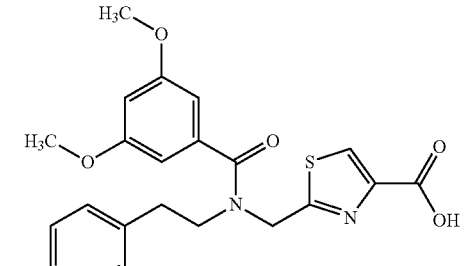 |
| 105 | R42 | 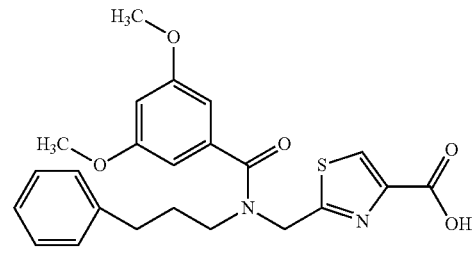 |
| 106 | R106 | 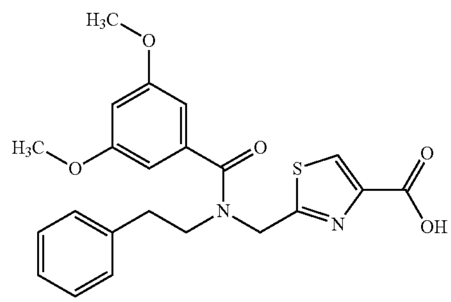 [SMILES: COc1cc(OC)cc(C(=O)N(CCc2ccccc2)Cc2nc(C(=O)O)cs2)c1] |
| 107 | R106 | 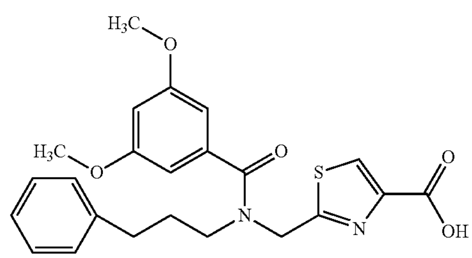 [SMILES: COc1cc(OC)cc(C(=O)N(CCCc2ccccc2)Cc2nc(C(=O)O)cs2)c1] |
| 108 | R106 | 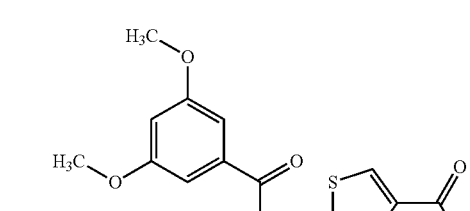 |

TABLE 12-continued

| Rf | Syn | Structure |
|----|-----|-----------|
| 109 | R106 | 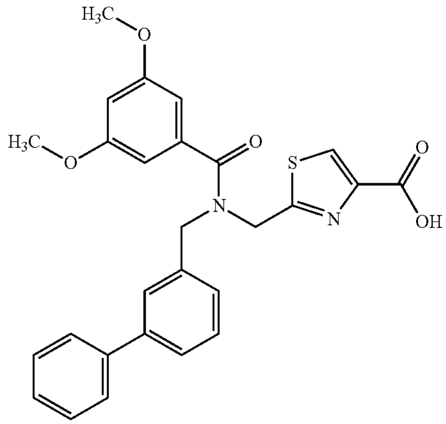 [SMILES: COc1cc(OC)cc(C(=O)N(Cc2cccc(-c3ccccc3)c2)Cc2nc(C(=O)O)cs2)c1] |
| 110 | R106 | 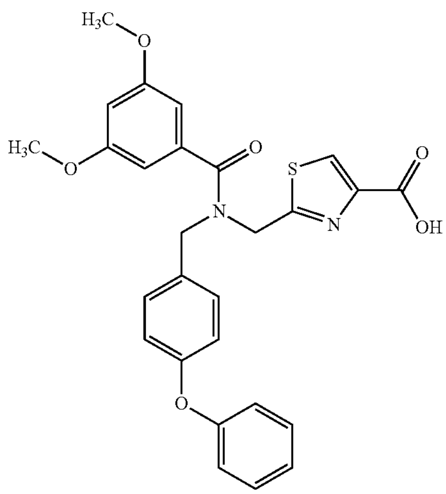 [SMILES: COc1cc(OC)cc(C(=O)N(Cc2ccc(Oc3ccccc3)cc2)Cc2nc(C(=O)O)cs2)c1] |
| 111 | R106 | 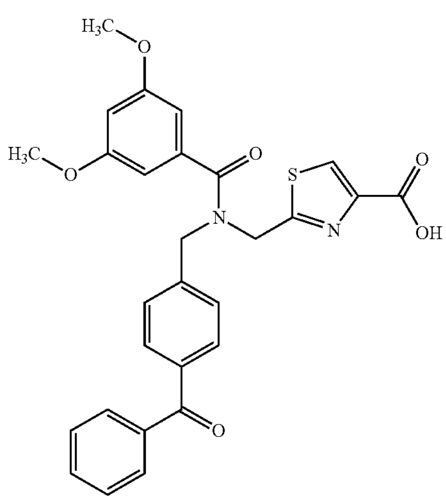 [SMILES: COc1cc(OC)cc(C(=O)N(Cc2ccc(C(=O)c3ccccc3)cc2)Cc2nc(C(=O)O)cs2)c1] |

TABLE 13

| Rf | Syn | Structure |
|----|-----|-----------|
| 112 | R106 | 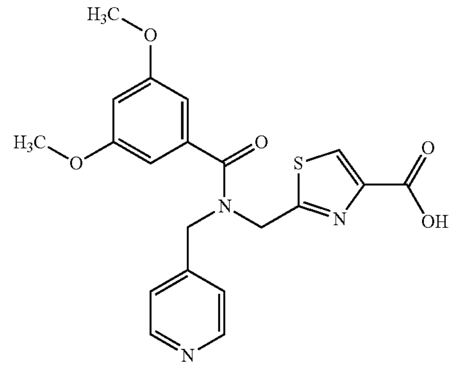 [SMILES: COc1cc(OC)cc(C(=O)N(Cc2ccncc2)Cc2nc(C(=O)O)cs2)c1] |
| 113 | R106 | 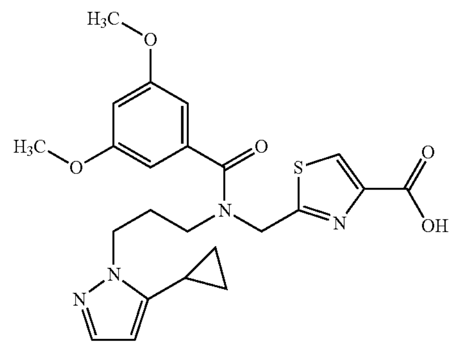 [SMILES: COc1cc(OC)cc(C(=O)N(CCCn2nccc2C2CC2)Cc2nc(C(=O)O)cs2)c1] |
| 114 | R106 | 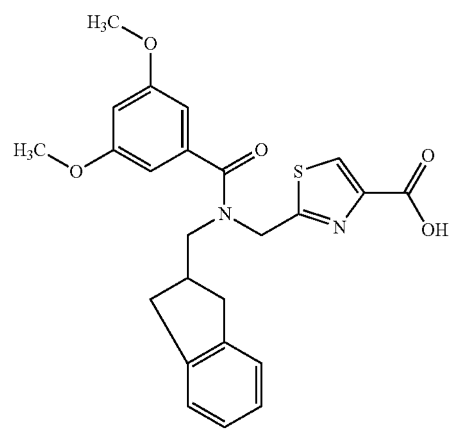 [SMILES: COc1cc(OC)cc(C(=O)N(Cc2nc(C(=O)O)cs2)CC2Cc3ccccc3C2)c1] |
| 115 | R106 | 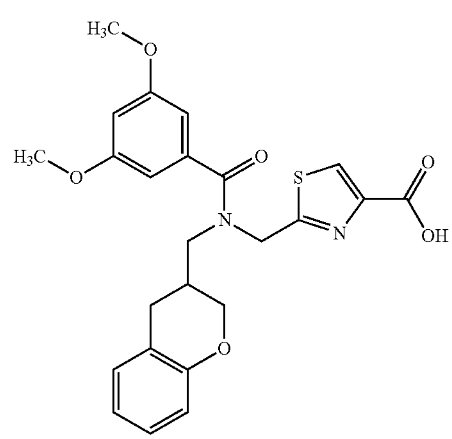 [SMILES: COc1cc(OC)cc(C(=O)N(Cc2nc(C(=O)O)cs2)CC2COc3ccccc3C2)c1] |

TABLE 13-continued
| Rf | Syn | Structure |
|---|---|---|
| 116 | R106 | 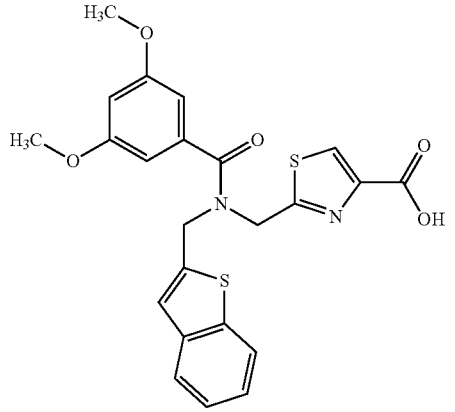 [SMILES: COc1cc(OC)cc(C(=O)N(Cc2cc3ccccc3s2)Cc2nc(C(=O)O)cs2)c1] |
| 117 | R106 | 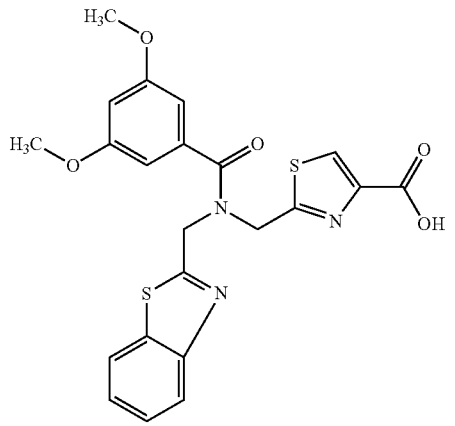 [SMILES: COc1cc(OC)cc(C(=O)N(Cc2nc(C(=O)O)cs2)Cc2nc3ccccc3s2)c1] |
| 118 | R49 | 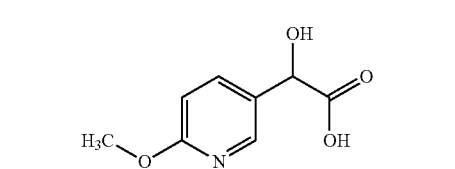 |
| 119 | R50 | 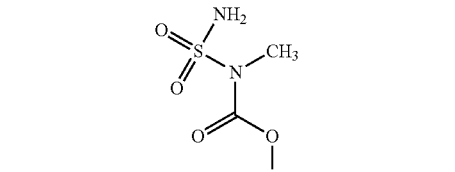 |
| 120 | R50 | 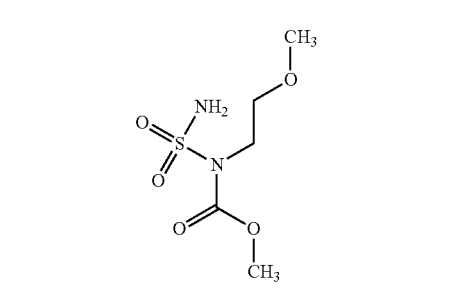 |
| 121 | R50 | 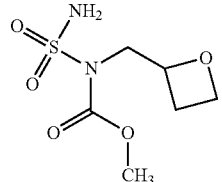 |
TABLE 14
| Rf | Syn | Structure |
|---|---|---|
| 122 | R50 | 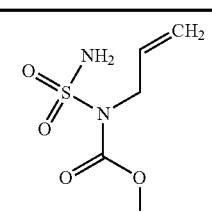 |
| 123 | R34 | 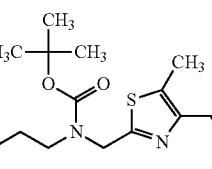 |
| 124 | R4 | 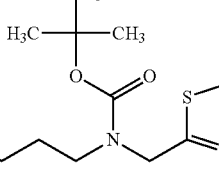 |
| 125 | R28 | 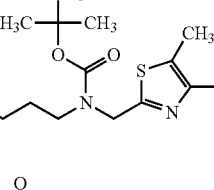 |
| 126 | R7 | 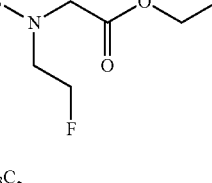 |
| 127 | R42 | 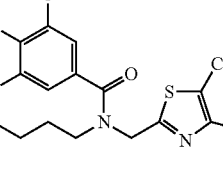 |

TABLE 14-continued

| Rf | Syn | Structure |
|---|---|---|
| 89 | R35 | 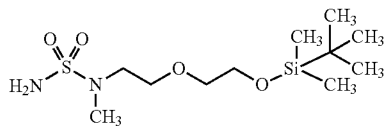 |
| 128 | R5 | 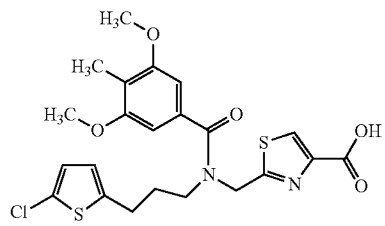 [SMILES: COc1cc(C(=O)N(CCCc2ccc(Cl)s2)Cc2nc(C(=O)O)cs2)cc(OC)c1C] |
| 129 | R5 | 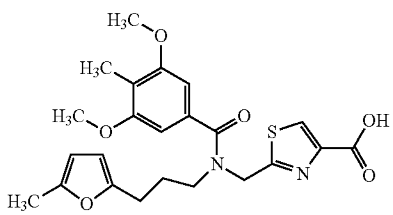 [SMILES: COc1cc(C(=O)N(CCCc2ccc(C)o2)Cc2nc(C(=O)O)cs2)cc(OC)c1C] |
| 130 | R5 | 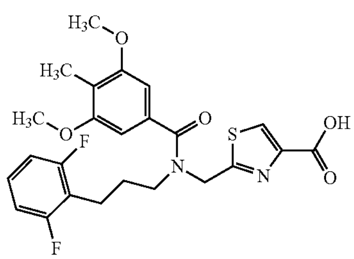 [SMILES: COc1cc(C(=O)N(CCCc2c(F)cccc2F)Cc2nc(C(=O)O)cs2)cc(OC)c1C] |
| 131 | R5 | 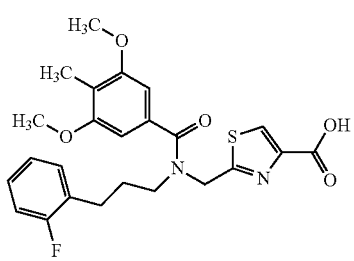 [SMILES: COc1cc(C(=O)N(CCCc2ccccc2F)Cc2nc(C(=O)O)cs2)cc(OC)c1C] |
| 132 | R5 | 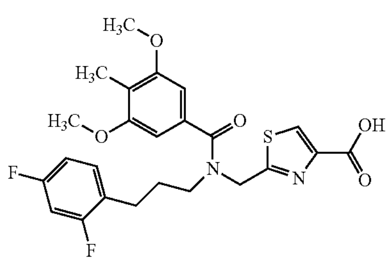 [SMILES: COc1cc(C(=O)N(CCCc2ccc(F)cc2F)Cc2nc(C(=O)O)cs2)cc(OC)c1C] |

TABLE 15

| Rf | Syn | Structure |
|---|---|---|
| 133 | R5 | 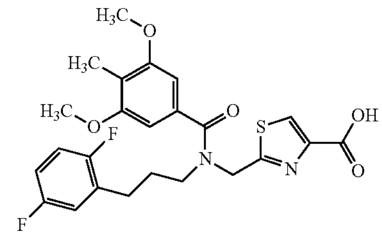 [SMILES: COc1cc(C(=O)N(CCCc2cc(F)ccc2F)Cc2nc(C(=O)O)cs2)cc(OC)c1C] |
| 134 | R5 | 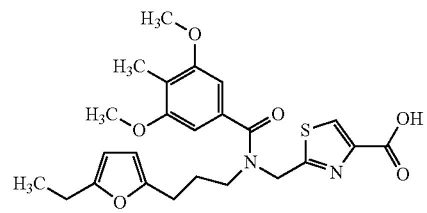 [SMILES: CCc1ccc(CCCN(Cc2nc(C(=O)O)cs2)C(=O)c2cc(OC)c(C)c(OC)c2)o1] |
| 135 | R5 | 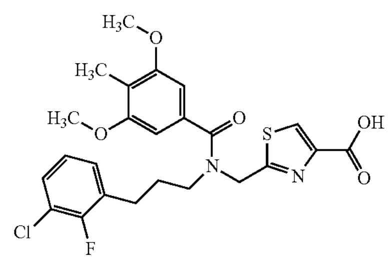 [SMILES: COc1cc(C(=O)N(CCCc2cccc(Cl)c2F)Cc2nc(C(=O)O)cs2)cc(OC)c1C] |
| 136 | R5 | 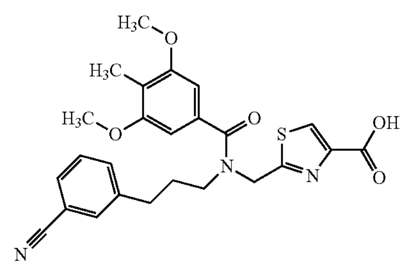 [SMILES: COc1cc(C(=O)N(CCCc2cccc(C#N)c2)Cc2nc(C(=O)O)cs2)cc(OC)c1C] |
| 137 | R5 | 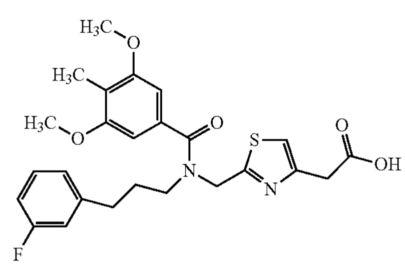 [SMILES: COc1cc(C(=O)N(CCCc2cccc(F)c2)Cc2nc(CC(=O)O)cs2)cc(OC)c1C] |
| 138 | R5 | 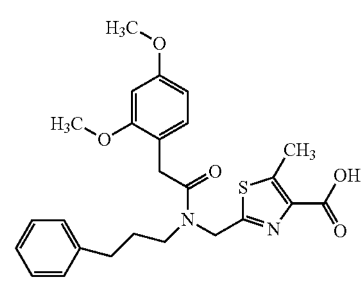 [SMILES: COc1ccc(CC(=O)N(CCCc2ccccc2)Cc2nc(C(=O)O)c(C)s2)c(OC)c1] |

TABLE 15-continued

| Rf | Syn | Structure |
|----|-----|-----------|
| 139 | R5 | 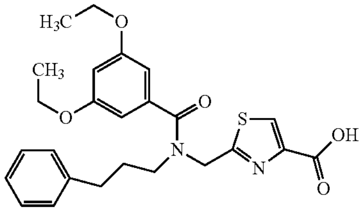 [SMILES: CCOc1cc(OCC)cc(C(=O)N(CCCc2ccccc2)Cc2nc(C(=O)O)cs2)c1] |
| 140 | R5 | 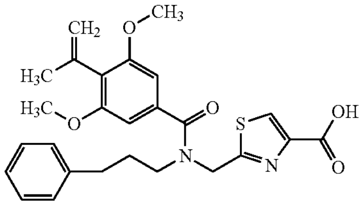 [SMILES: C=C(C)c1c(OC)cc(C(=O)N(CCCc2ccccc2)Cc2nc(C(=O)O)cs2)cc1OC] |
| 141 | R5 | 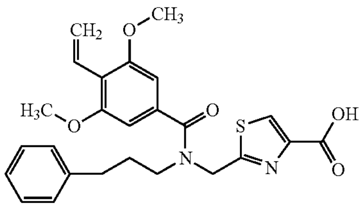 [SMILES: C=Cc1c(OC)cc(C(=O)N(CCCc2ccccc2)Cc2nc(C(=O)O)cs2)cc1OC] |
| 142 | R5 | 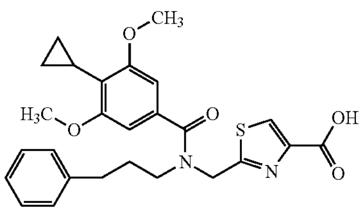 [SMILES: COc1cc(C(=O)N(CCCc2ccccc2)Cc2nc(C(=O)O)cs2)cc(OC)c1C1CC1] |

TABLE 16

| Rf | Syn | Structure |
|----|-----|-----------|
| 143 | R5 | 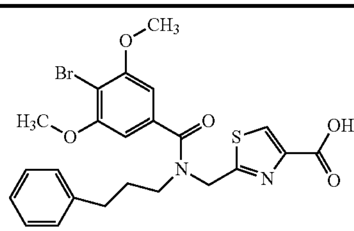 |
| 144 | R5 | 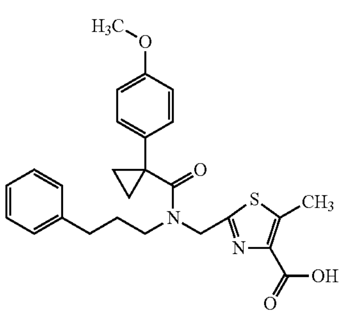 [SMILES: COc1ccc(C2(C(=O)N(CCCc3ccccc3)Cc3nc(C(=O)O)c(C)s3)CC2)cc1] |

TABLE 16-continued

| Rf | Syn | Structure |
|----|-----|-----------|
| 145 | R5 | 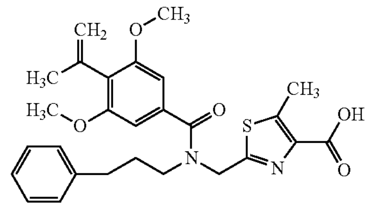 [SMILES: C=C(C)c1c(OC)cc(C(=O)N(CCCc2ccccc2)Cc2nc(C(=O)O)c(C)s2)cc1OC] |
| 146 | R5 | 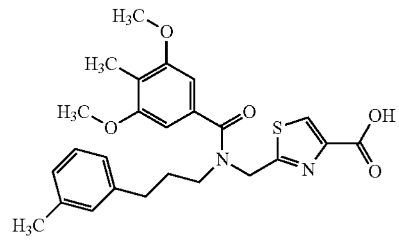 [SMILES: COc1cc(C(=O)N(CCCc2cccc(C)c2)Cc2nc(C(=O)O)cs2)cc(OC)c1C] |
| 147 | R5 | 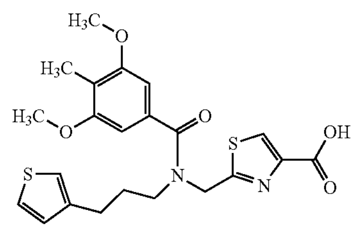 [SMILES: COc1cc(C(=O)N(CCCc2ccsc2)Cc2nc(C(=O)O)cs2)cc(OC)c1C] |
| 148 | R5 | 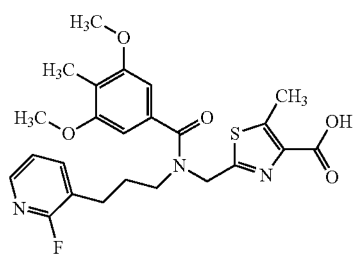 [SMILES: COc1cc(C(=O)N(CCCc2cccnc2F)Cc2nc(C(=O)O)c(C)s2)cc(OC)c1C] |
| 149 | R5 | 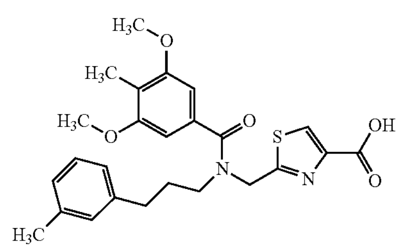 |
| 150 | R5 | 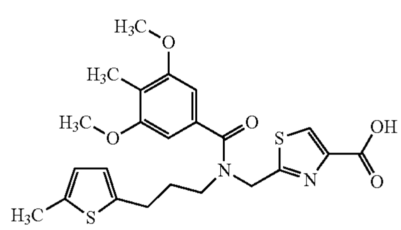 [SMILES: COc1cc(C(=O)N(CCCc2ccc(C)s2)Cc2nc(C(=O)O)cs2)cc(OC)c1C] |

TABLE 16-continued

| Rf | Syn | Structure |
|---|---|---|
| 151 | R5 | (3,5-dimethoxy-4-methylbenzoyl)-N-(2-fluorophenethyl)... 5-methylthiazole-4-carboxylic acid |
| 152 | R5 | 1-(4-methoxyphenyl)cyclopropanecarbonyl-N-(3-(3-chlorophenyl)propyl)... thiazole-4-carboxylic acid |

TABLE 17

| Rf | Syn | Structure |
|---|---|---|
| 153 | R5 | (3,5-dimethoxy-4-methylbenzoyl)-N-(3-phenylpropyl)... 5-chlorothiazole-4-carboxylic acid |
| 154 | R5 | (4-hydroxy-3,5-dimethylbenzoyl)-N-(3-phenylpropyl)... 5-chlorothiazole-4-carboxylic acid |
| 155 | R5 | (4-ethyl-3,5-dimethoxybenzoyl)-N-(3-phenylpropyl)... 5-methylthiazole-4-carboxylic acid |
| 156 | R5 | (3,5-dimethoxybenzoyl)-N-(3-phenylpropyl)... 5-methylthiazole-4-carboxylic acid |
| 157 | R5 | (4-(difluoromethyl)-3,5-dimethoxybenzoyl)-N-(3-phenylpropyl)... 5-methylthiazole-4-carboxylic acid |
| 158 | R5 | (4-cyclopropyl-3,5-dimethoxybenzoyl)-N-(3-phenylpropyl)... 5-methylthiazole-4-carboxylic acid |
| 159 | R5 | (4-chloro-3,5-dimethoxybenzoyl)-N-(3-phenylpropyl)... 5-methylthiazole-4-carboxylic acid |
| 160 | R5 | (3,5-dimethoxy-4-((2,2,2-trifluoroethoxy)methyl)benzoyl)-N-(3-phenylpropyl)... 5-methylthiazole-4-carboxylic acid |

TABLE 17-continued

| Rf | Syn | Structure |
|---|---|---|
| 161 | R5 | 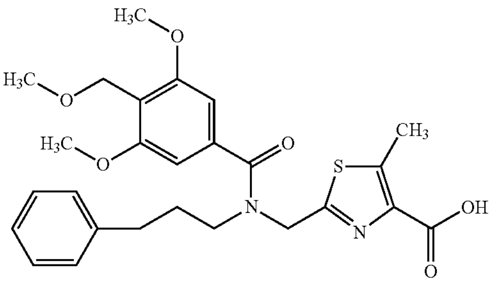 [SMILES: COCc1c(OC)cc(C(=O)N(CCCc2ccccc2)Cc2nc(C(=O)O)c(C)s2)cc1OC] |
| 162 | R5 | 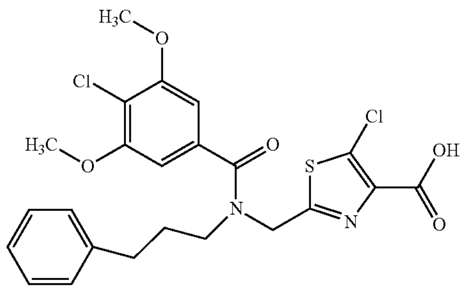 [SMILES: COc1cc(C(=O)N(CCCc2ccccc2)Cc2nc(C(=O)O)c(Cl)s2)cc(OC)c1Cl] |
| 163 | R5 | 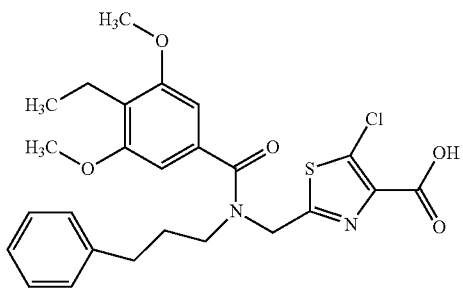 [SMILES: CCc1c(OC)cc(C(=O)N(CCCc2ccccc2)Cc2nc(C(=O)O)c(Cl)s2)cc1OC] |
| 164 | R5 | 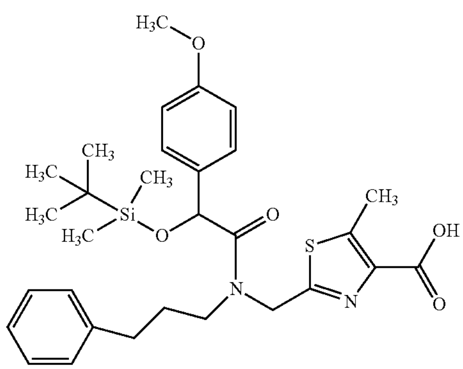 [SMILES: COc1ccc(C(O[Si](C)(C)C(C)(C)C)C(=O)N(CCCc2ccccc2)Cc2nc(C(=O)O)c(C)s2)cc1] |

TABLE 18

| Rf | Syn | Structure |
|---|---|---|
| 165 | R42 | |
| 166 | R42 | 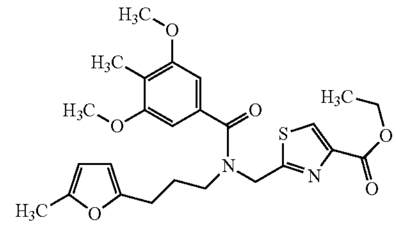 [SMILES: CCOC(=O)c1csc(CN(CCCc2ccc(C)o2)C(=O)c2cc(OC)c(C)c(OC)c2)n1] |
| 167 | R42 | 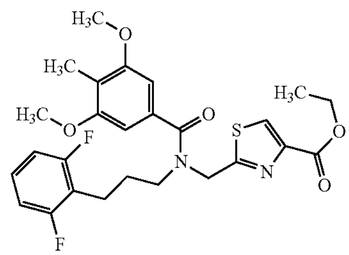 [SMILES: CCOC(=O)c1csc(CN(CCCc2c(F)cccc2F)C(=O)c2cc(OC)c(C)c(OC)c2)n1] |
| 168 | R42 | 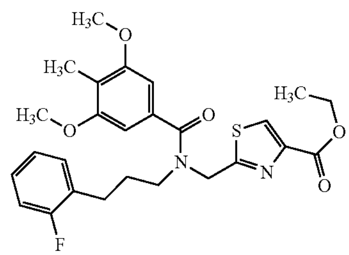 [SMILES: CCOC(=O)c1csc(CN(CCCc2ccccc2F)C(=O)c2cc(OC)c(C)c(OC)c2)n1] |
| 169 | R42 | 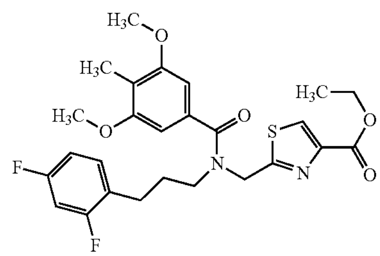 [SMILES: CCOC(=O)c1csc(CN(CCCc2ccc(F)cc2F)C(=O)c2cc(OC)c(C)c(OC)c2)n1] |
| 170 | R42 | 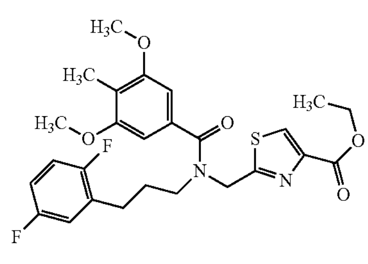 [SMILES: CCOC(=O)c1csc(CN(CCCc2cc(F)ccc2F)C(=O)c2cc(OC)c(C)c(OC)c2)n1] |
| 171 | R42 | 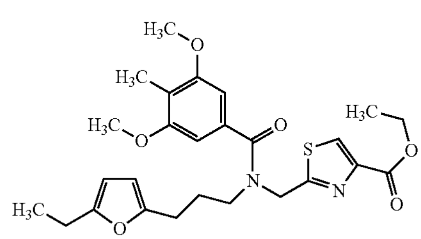 [SMILES: CCOC(=O)c1csc(CN(CCCc2ccc(CC)o2)C(=O)c2cc(OC)c(C)c(OC)c2)n1] |

TABLE 18-continued

| Rf | Syn | Structure |
|---|---|---|
| 172 | R42 | 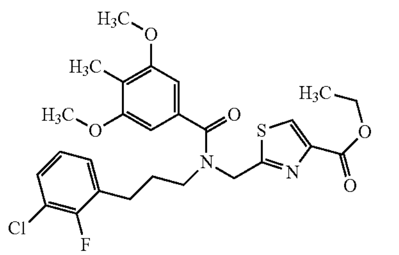 [SMILES: CCOC(=O)c1csc(CN(CCCc2cccc(Cl)c2F)C(=O)c2cc(OC)c(C)c(OC)c2)n1] |
| 173 | R42 | 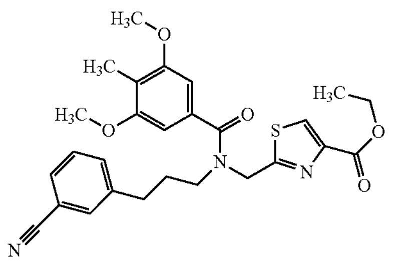 [SMILES: CCOC(=O)c1csc(CN(CCCc2cccc(C#N)c2)C(=O)c2cc(OC)c(C)c(OC)c2)n1] |
| 174 | R42 | 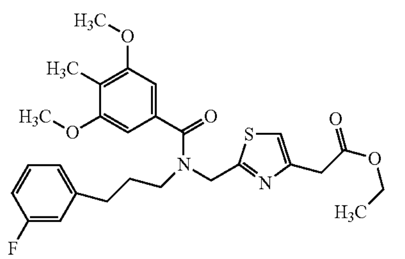 [SMILES: CCOC(=O)Cc1csc(CN(CCCc2cccc(F)c2)C(=O)c2cc(OC)c(C)c(OC)c2)n1] |

TABLE 19

| Rf | Syn | Structure |
|---|---|---|
| 175 | R42 | 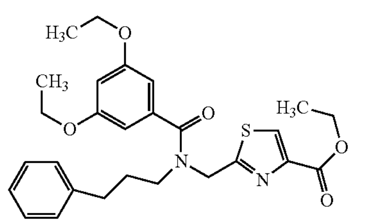 [SMILES: CCOC(=O)c1csc(CN(CCCc2ccccc2)C(=O)c2cc(OCC)cc(OCC)c2)n1] |
| 176 | R42 | 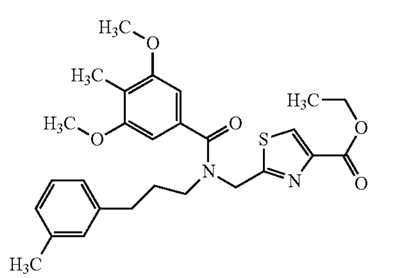 [SMILES: CCOC(=O)c1csc(CN(CCCc2cccc(C)c2)C(=O)c2cc(OC)c(C)c(OC)c2)n1] |

TABLE 19-continued

| Rf | Syn | Structure |
|---|---|---|
| 177 | R42 | 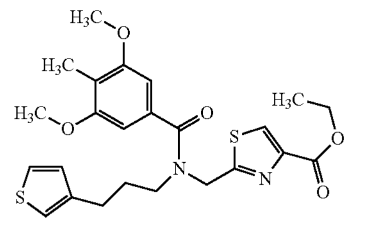 [SMILES: CCOC(=O)c1csc(CN(CCCc2ccsc2)C(=O)c2cc(OC)c(C)c(OC)c2)n1] |
| 178 | R42 | 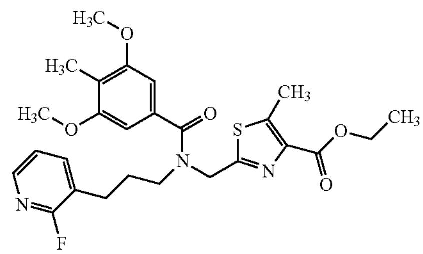 [SMILES: CCOC(=O)c1nc(CN(CCCc2cccnc2F)C(=O)c2cc(OC)c(C)c(OC)c2)sc1C] |
| 179 | R42 | 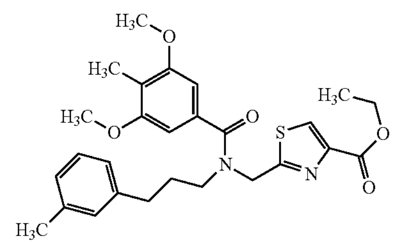 [SMILES: CCOC(=O)c1csc(CN(CCCc2cccc(C)c2)C(=O)c2cc(OC)c(C)c(OC)c2)n1] |
| 180 | R42 | 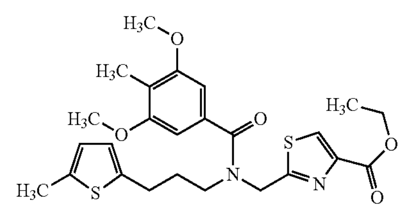 [SMILES: CCOC(=O)c1csc(CN(CCCc2ccc(C)s2)C(=O)c2cc(OC)c(C)c(OC)c2)n1] |
| 181 | R42 | 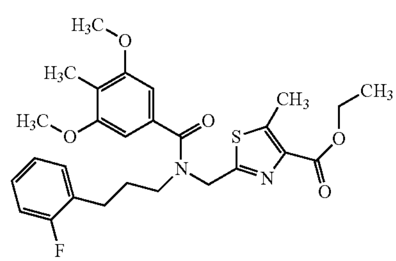 [SMILES: CCOC(=O)c1nc(CN(CCCc2ccccc2F)C(=O)c2cc(OC)c(C)c(OC)c2)sc1C] |
| 182 | R42 | 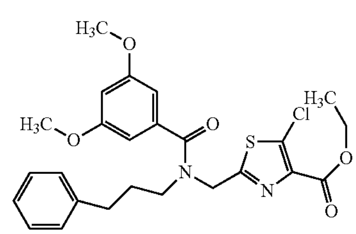 [SMILES: CCOC(=O)c1nc(CN(CCCc2ccccc2)C(=O)c2cc(OC)cc(OC)c2)sc1Cl] |

TABLE 19-continued

| Rf | Syn | Structure |
|---|---|---|
| 183 | R42 | 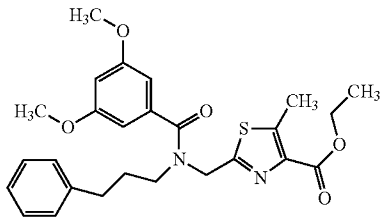 [SMILES: CCOC(=O)c1nc(CN(CCCc2ccccc2)C(=O)c2cc(OC)cc(OC)c2)sc1C] |
| 184 | R26 | 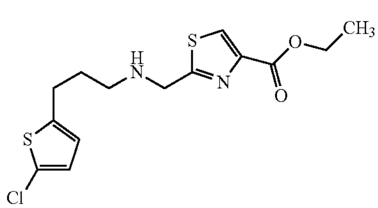 [SMILES: CCOC(=O)c1csc(CNCCCc2ccc(Cl)s2)n1] |
| 185 | R26 | 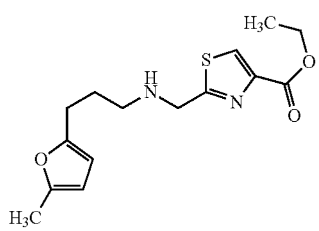 [SMILES: CCOC(=O)c1csc(CNCCCc2ccc(C)o2)n1] |
| 186 | R26 | 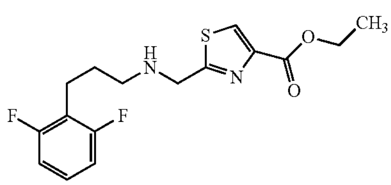 [SMILES: CCOC(=O)c1csc(CNCCCc2c(F)cccc2F)n1] |

TABLE 20

| Rf | Syn | Structure |
|---|---|---|
| 187 | R26 | |
| 188 | R26 | |
| 189 | R26 | 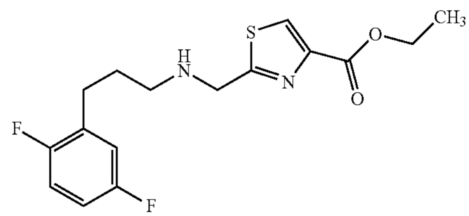 [SMILES: CCOC(=O)c1csc(CNCCCc2cc(F)ccc2F)n1] |
| 190 | R26 | 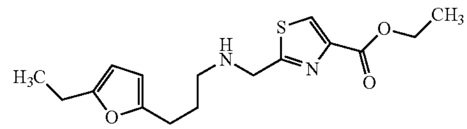 [SMILES: CCOC(=O)c1csc(CNCCCc2ccc(CC)o2)n1] |
| 191 | R26 | 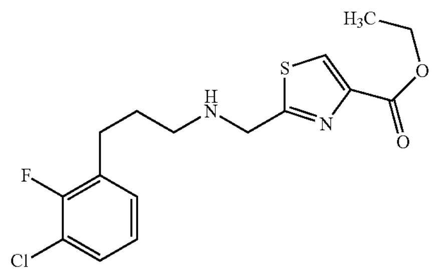 [SMILES: CCOC(=O)c1csc(CNCCCc2cccc(Cl)c2F)n1] |
| 192 | R26 | 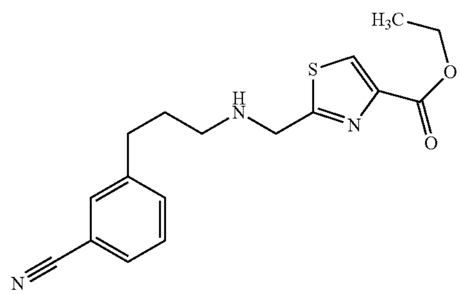 [SMILES: CCOC(=O)c1csc(CNCCCc2cccc(C#N)c2)n1] |
| 193 | R26 | 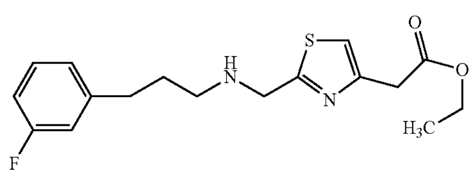 [SMILES: CCOC(=O)Cc1csc(CNCCCc2cccc(F)c2)n1] |
| 194 | R26 | 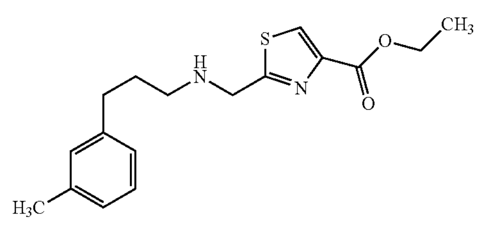 [SMILES: CCOC(=O)c1csc(CNCCCc2cccc(C)c2)n1] |
| 195 | R26 | 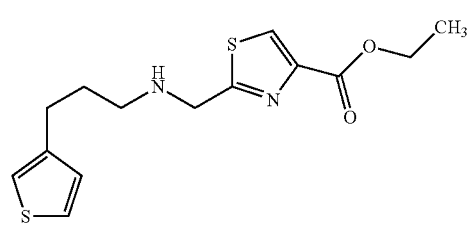 [SMILES: CCOC(=O)c1csc(CNCCCc2ccsc2)n1] |

TABLE 20-continued
| Rf | Syn | Structure |
|---|---|---|
| 196 | R26 | 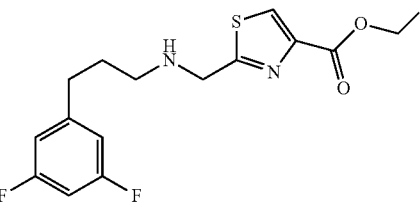 |
| 197 | R26 | 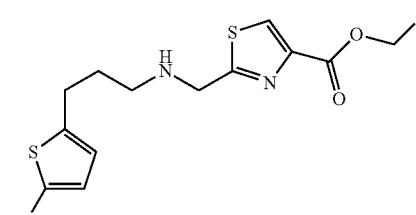 |
| 198 | R26 | 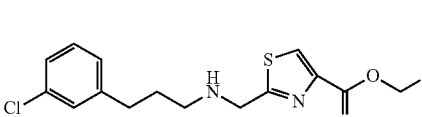 |
TABLE 21
| Rf | Syn | Structure |
|---|---|---|
| 199 | R44 | 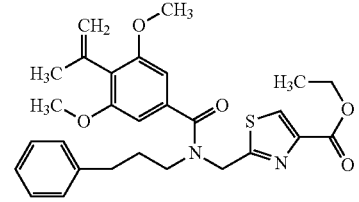 [SMILES: C=C(C)c1c(OC)cc(C(=O)N(CCCc2ccccc2)Cc2nc(C(=O)OCC)cs2)cc1OC] |
| 200 | R44 | 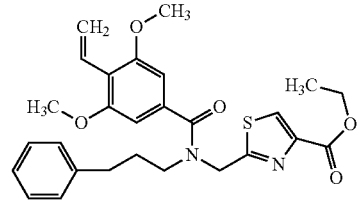 [SMILES: C=Cc1c(OC)cc(C(=O)N(CCCc2ccccc2)Cc2nc(C(=O)OCC)cs2)cc1OC] |
| 201 | R44 | 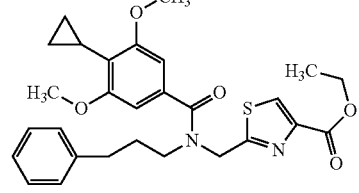 |
| 202 | R44 | 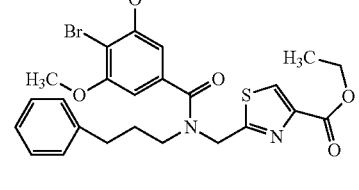 |
TABLE 21-continued
| Rf | Syn | Structure |
|---|---|---|
| 203 | R44 | 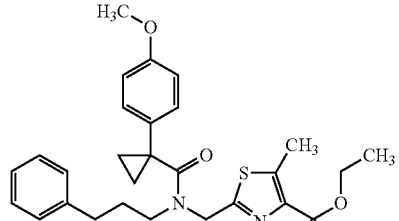 |
| 204 | R44 | 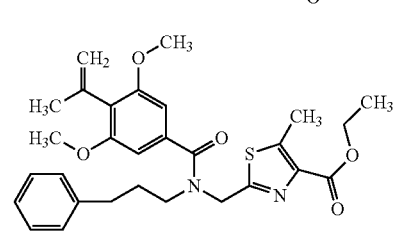 |
| 205 | R44 | 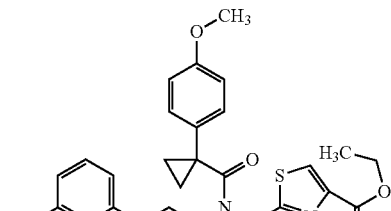 |
| 206 | R44 | 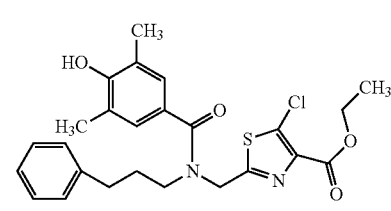 [SMILES: CCOC(=O)c1nc(CN(CCCc2ccccc2)C(=O)c2cc(C)c(O)c(C)c2)sc1Cl] |
| 207 | R44 | 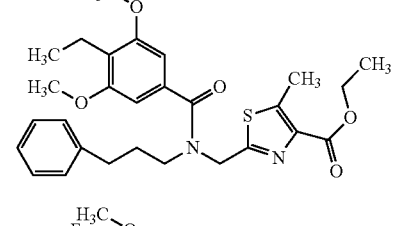 |
| 208 | R44 | 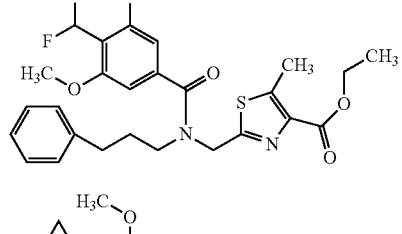 |
| 209 | R44 | 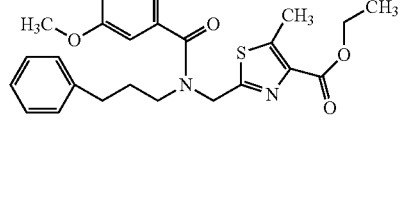 |

TABLE 21-continued
| Rf | Syn | Structure |
|---|---|---|
| 210 | R44 | 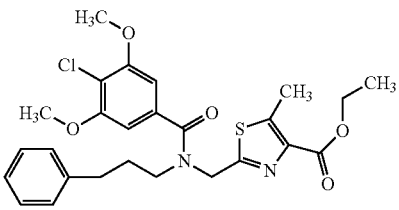 [SMILES: CCOC(=O)c1nc(CN(CCCc2ccccc2)C(=O)c2cc(OC)c(Cl)c(OC)c2)sc1C] |
TABLE 22
| Rf | Syn | Structure |
|---|---|---|
| 211 | R44 | 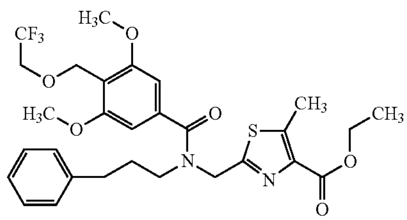 [SMILES: CCOC(=O)c1nc(CN(CCCc2ccccc2)C(=O)c2cc(OC)c(COCC(F)(F)F)c(OC)c2)sc1C] |
| 212 | R44 | 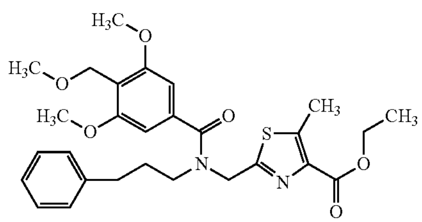 [SMILES: CCOC(=O)c1nc(CN(CCCc2ccccc2)C(=O)c2cc(OC)c(COC)c(OC)c2)sc1C] |
| 213 | R44 | 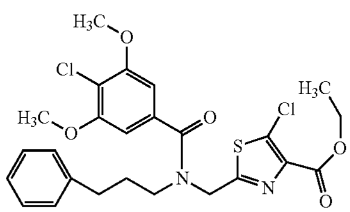 [SMILES: CCOC(=O)c1nc(CN(CCCc2ccccc2)C(=O)c2cc(OC)c(Cl)c(OC)c2)sc1Cl] |
| 214 | R44 | 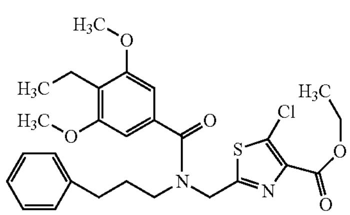 [SMILES: CCOC(=O)c1nc(CN(CCCc2ccccc2)C(=O)c2cc(OC)c(CC)c(OC)c2)sc1Cl] |
| 215 | R44 | 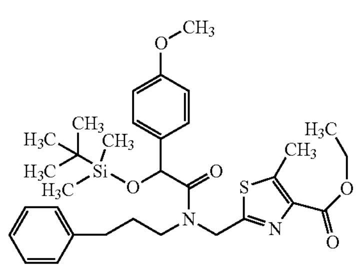 [SMILES: CCOC(=O)c1nc(CN(CCCc2ccccc2)C(=O)C(O[Si](C)(C)C(C)(C)C)c2ccc(OC)cc2)sc1C] |
TABLE 22-continued
| Rf | Syn | Structure |
|---|---|---|
| 216 | R216 | 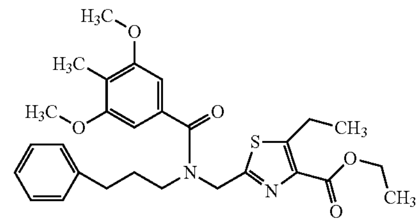 [SMILES: CCOC(=O)c1nc(CN(CCCc2ccccc2)C(=O)c2cc(OC)c(C)c(OC)c2)sc1CC] |
| 217 | R39 | 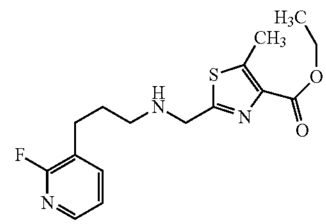 [SMILES: CCOC(=O)c1nc(CNCCCc2cccnc2F)sc1C] |
| 218 | R39 | 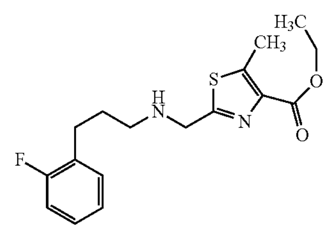 [SMILES: CCOC(=O)c1nc(CNCCCc2ccccc2F)sc1C] |
| 219 | R219 | 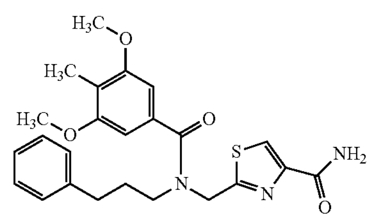 [SMILES: COc1cc(C(=O)N(CCCc2ccccc2)Cc2nc(C(N)=O)cs2)cc(OC)c1C] |
| 220 | R4 | 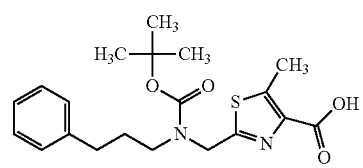 [SMILES: Cc1sc(CN(CCCc2ccccc2)C(=O)OC(C)(C)C)nc1C(=O)O] |
| 222 | R5 | 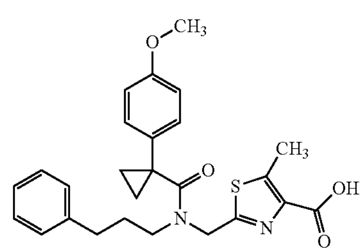 [SMILES: COc1ccc(C2(C(=O)N(CCCc3ccccc3)Cc3nc(C(=O)O)c(C)s3)CC2)nc1] |
| 223 | R5 | 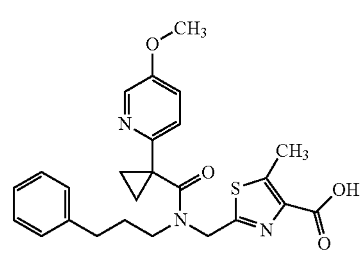 |

TABLE 23

| Rf | Syn | Structure |
|---|---|---|
| 224 | R5 | (structure) |
| 225 | R5 | (structure) |
| 226 | R5 | (structure) |
| 227 | R5 | (structure) |
| 228 | R5 | (structure) |
| 229 | R5 | (structure) |
| 230 | R5 | (structure) |

TABLE 23-continued

| Rf | Syn | Structure |
|---|---|---|
| 231 | R5 | (structure) |
| 232 | R5 | (structure) |
| 233 | R5 | (structure) |

TABLE 24

| Rf | Syn | Structure |
|---|---|---|
| 234 | R5 | (structure) |
| 235 | R5 | (structure) |
| 236 | R5 | (structure) |

TABLE 24-continued
| Rf | Syn | Structure |
|---|---|---|
| 237 | R5 | 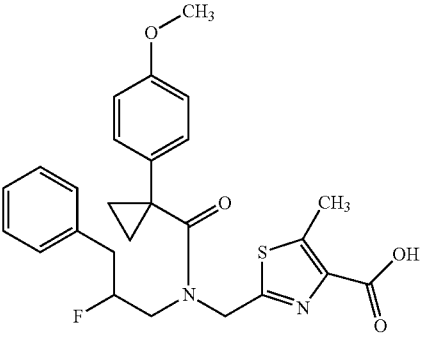 [SMILES: COc1ccc(C2(C(=O)N(Cc3nc(C(=O)O)c(C)s3)CC(F)Cc3ccccc3)CC2)cc1] |
| 238 | R5 | 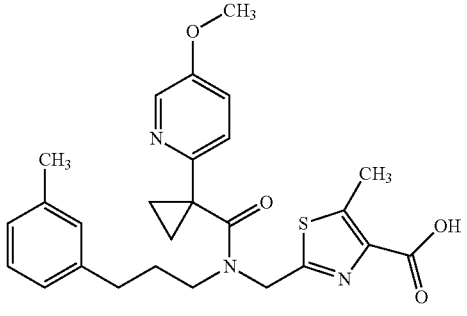 [SMILES: COc1ccc(C2(C(=O)N(CCCc3cccc(C)c3)Cc3nc(C(=O)O)c(C)s3)CC2)nc1] |
| 239 | R5 | 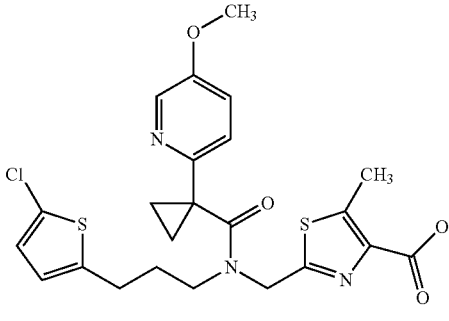 |
| 240 | R5 | 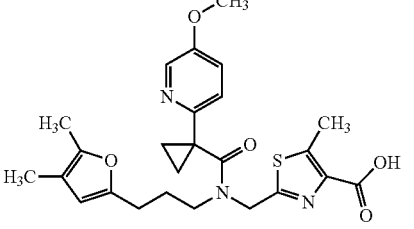 |
| 241 | R5 | 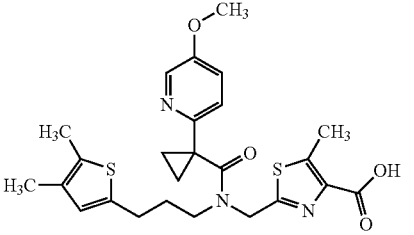 [SMILES: COc1ccc(C2(C(=O)N(CCCc3cc(C)c(C)s3)Cc3nc(C(=O)O)c(C)s3)CC2)nc1] |
TABLE 24-continued
| Rf | Syn | Structure |
|---|---|---|
| 242 | R5 | 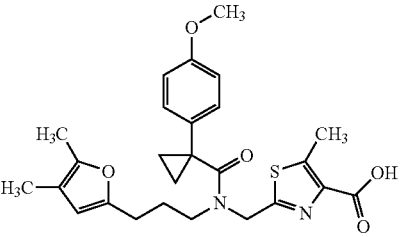 [SMILES: COc1ccc(C2(C(=O)N(CCCc3cc(C)c(C)o3)Cc3nc(C(=O)O)c(C)s3)CC2)cc1] |
| 243 | R5 | 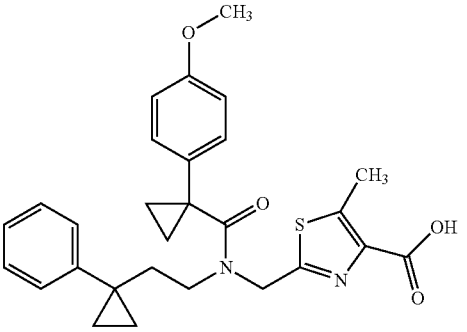 [SMILES: COc1ccc(C2(C(=O)N(CCC3(c4ccccc4)CC3)Cc3nc(C(=O)O)c(C)s3)CC2)cc1] |
TABLE 25
| Rf | Syn | Structure |
|---|---|---|
| 244 | R5 | 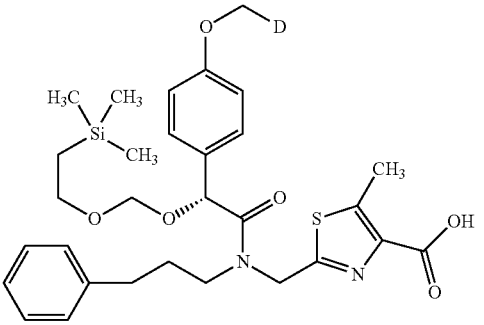 [SMILES: [2H]COc1ccc([C@@H](OCOCC[Si](C)(C)C)C(=O)N(CCCc2ccccc2)Cc2nc(C(=O)O)c(C)s2)cc1] |
| 245 | R5 | 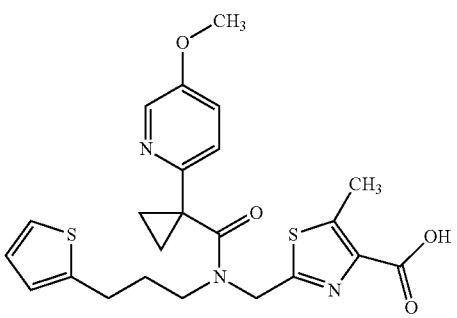 |

TABLE 25-continued
| Rf | Syn | Structure |
|----|-----|-----------|
| 246 | R5 | 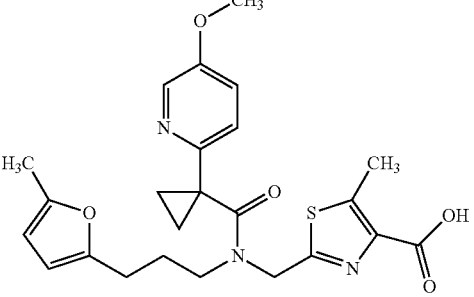 |
| 247 | R5 | 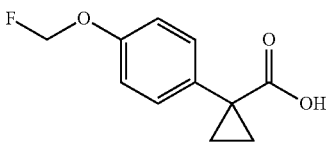 [SMILES: O=C(O)C1(c2ccc(OCF)cc2)CC1] |
| 248 | R5 | 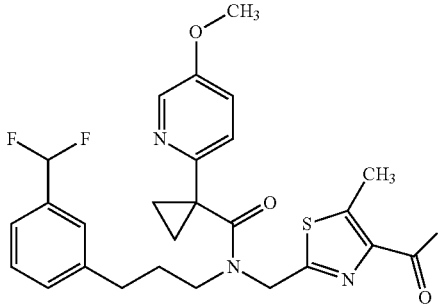 |
| 249 | R5 | 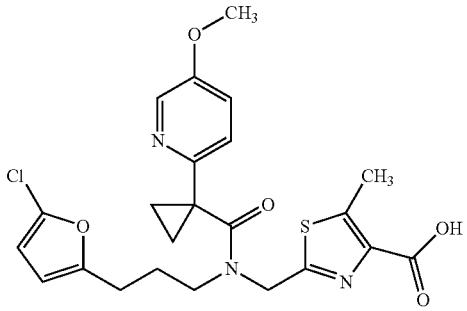 [SMILES: COc1ccc(C2(C(=O)N(CCCc3ccc(Cl)o3)Cc3nc(C(=O)O)c(C)s3)CC2)nc1] |
| 250 | R5 | 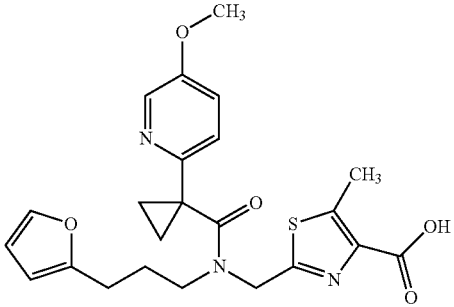 |
| 251 | R5 | 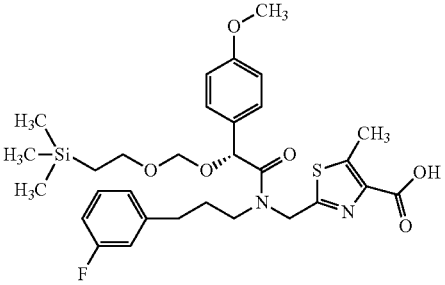 [SMILES: COc1ccc([C@@H](OCOCC[Si](C)(C)C)C(=O)N(CCCc2cccc(F)c2)Cc2nc(C(=O)O)c(C)s2)cc1] |
| 252 | R5 | 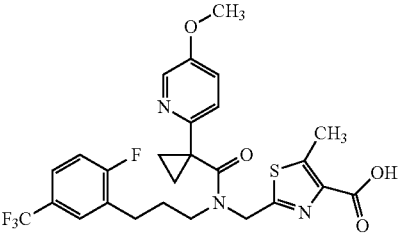 [SMILES: COc1ccc(C2(C(=O)N(CCCc3cc(C(F)(F)F)ccc3F)Cc3nc(C(=O)O)c(C)s3)CC2)nc1] |
| 253 | R5 | 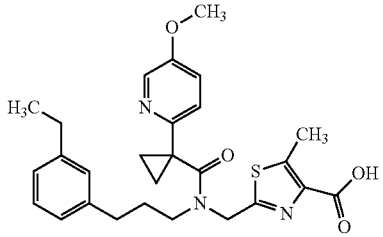 [SMILES: CCc1cccc(CCCN(Cc2nc(C(=O)O)c(C)s2)C(=O)C2(c3ccc(OC)cn3)CC2)c1] |
TABLE 26
| Rf | Syn | Structure |
|----|-----|-----------|
| 254 | R5 | 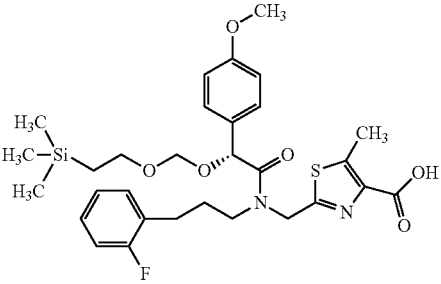 [SMILES: COc1ccc([C@@H](OCOCC[Si](C)(C)C)C(=O)N(CCCc2ccccc2F)Cc2nc(C(=O)O)c(C)s2)cc1] |
| 255 | R5 | 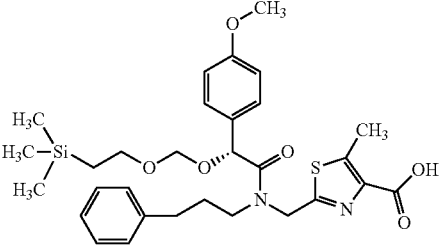 [SMILES: COc1ccc([C@@H](OCOCC[Si](C)(C)C)C(=O)N(CCCc2ccccc2)Cc2nc(C(=O)O)c(C)s2)cc1] |

TABLE 26-continued
| Rf | Syn | Structure |
|---|---|---|
| 256 | R5 | 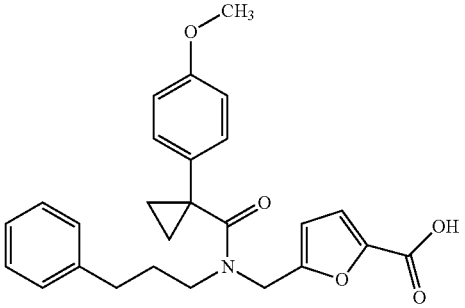 [SMILES: COc1ccc(C2(C(=O)N(CCCc3ccccc3)Cc3ccc(C(=O)O)o3)CC2)cc1] |
| 257 | R5 | 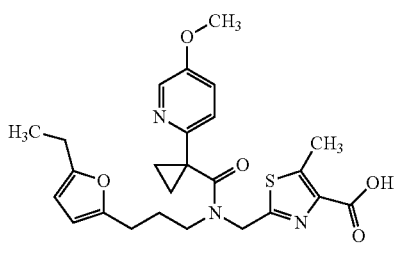 [SMILES: CCc1ccc(CCCN(Cc2nc(C(=O)O)c(C)s2)C(=O)C2(c3ccc(OC)cn3)CC2)o1] |
| 258 | R5 | 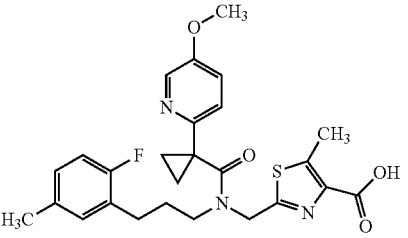 [SMILES: COc1ccc(C2(C(=O)N(CCCc3cc(C)ccc3F)Cc3nc(C(=O)O)c(C)s3)CC2)nc1] |
| 259 | R5 | 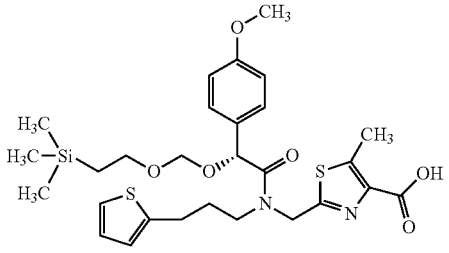 [SMILES: COc1ccc([C@@H](OCOCC[Si](C)(C)C)C(=O)N(CCCc2cccs2)Cc2nc(C(=O)O)c(C)s2)cc1] |
| 260 | R5 | 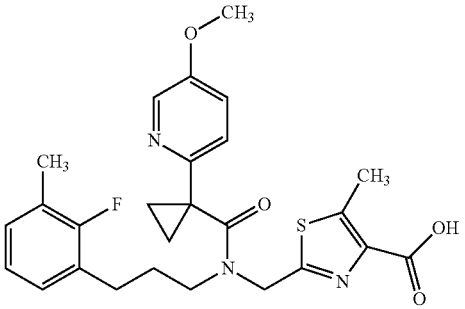 [SMILES: COc1ccc(C2(C(=O)N(CCCc3cccc(C)c3F)Cc3nc(C(=O)O)c(C)s3)CC2)nc1] |
TABLE 26-continued
| Rf | Syn | Structure |
|---|---|---|
| 261 | R5 | 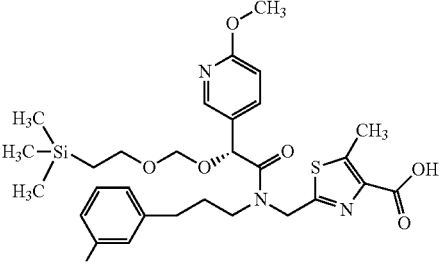 |
| 262 | R5 | 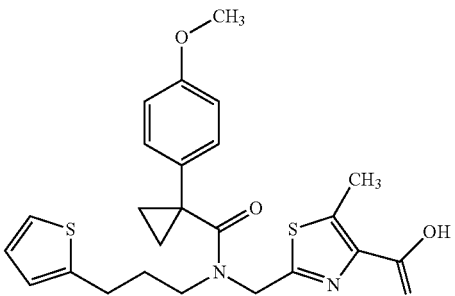 |
| 263 | R5 | 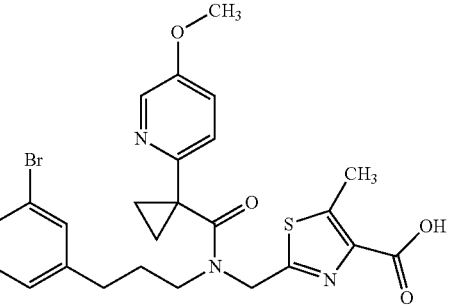 |
| 264 | R5 | 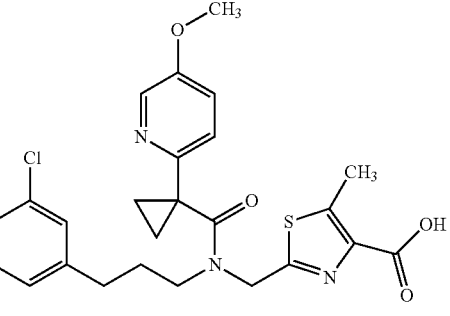 |
| 265 | R5 | 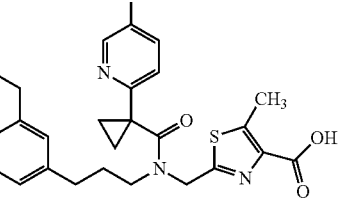 |

TABLE 27
| Rf | Syn | Structure |
|---|---|---|
| 266 | R5 | 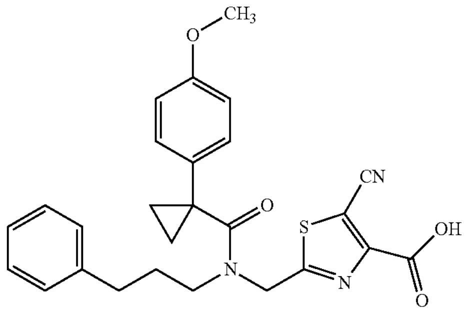 [SMILES: COc1ccc(C2(C(=O)N(CCCc3ccccc3)Cc3nc(C(=O)O)c(C#N)s3)CC2)cc1] |
| 267 | R5 | 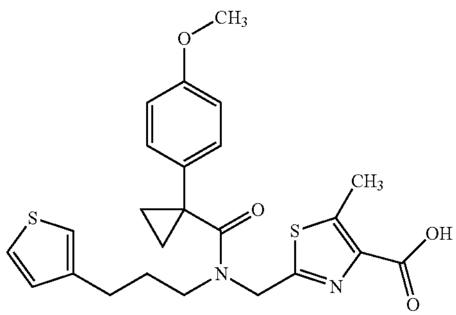 [SMILES: COc1ccc(C2(C(=O)N(CCCc3ccsc3)Cc3nc(C(=O)O)c(C)s3)CC2)cc1] |
| 268 | R5 | 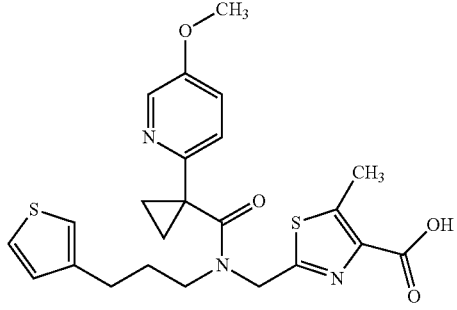 |
| 269 | R5 | 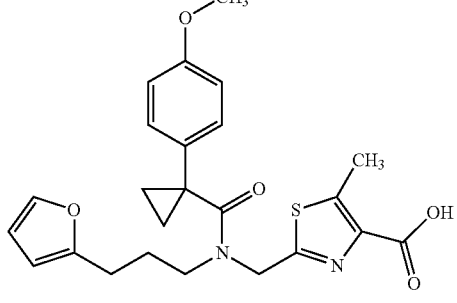 |
| 270 | R5 | 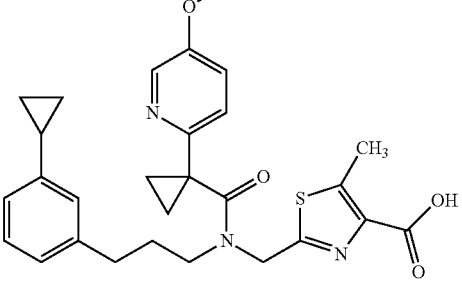 |
| 271 | R5 | 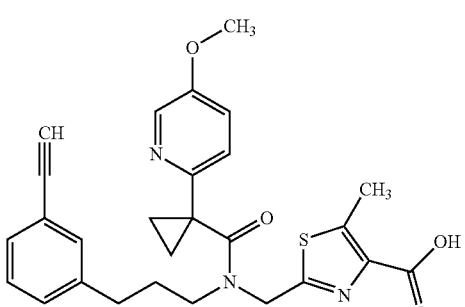 |
| 272 | R5 | 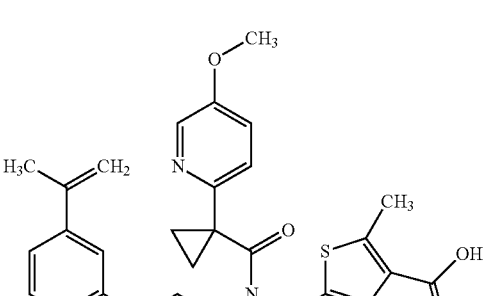 |
| 273 | R5 | 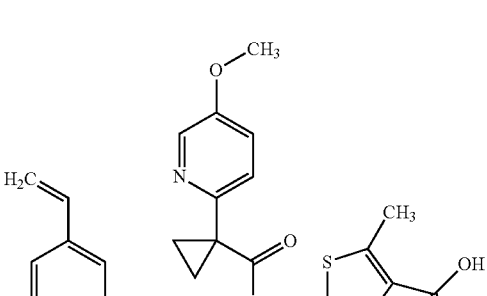 |
| 274 | R5 | 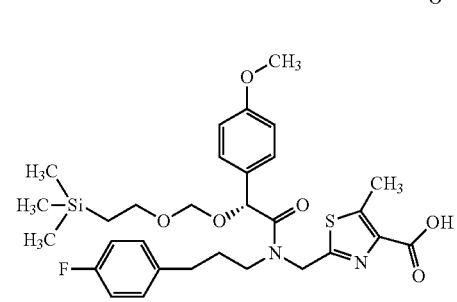 |
| 275 | R5 | 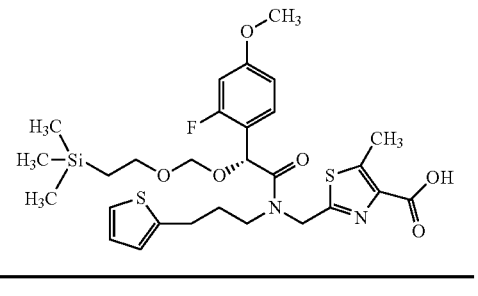 |

TABLE 28
| Rf | Syn | Structure |
|---|---|---|
| 276 | R5 | 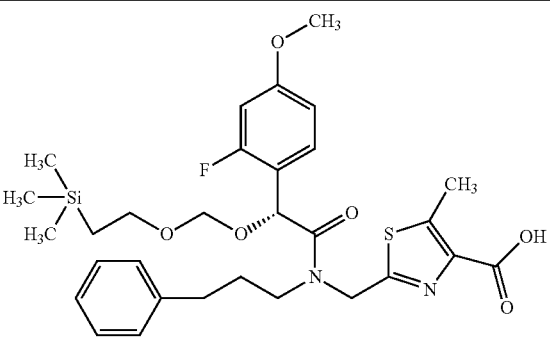 |
| 277 | R5 | 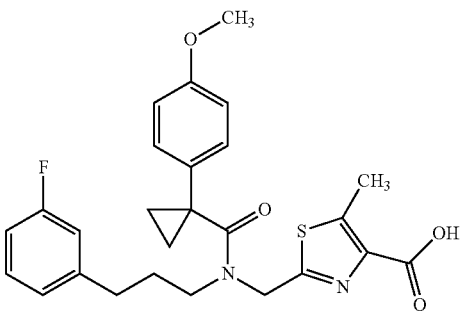 [SMILES: COc1ccc(C2(C(=O)N(CCCc3cccc(F)c3)Cc3nc(C(=O)O)c(C)s3)CC2)cc1] |
| 278 | R5 | 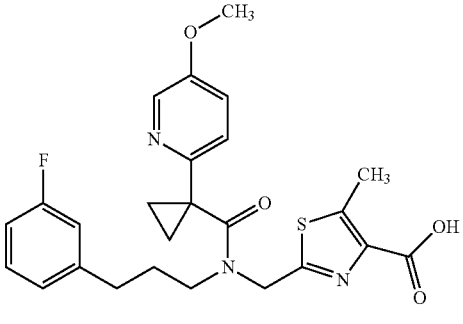 [SMILES: COc1ccc(C2(C(=O)N(CCCc3cccc(F)c3)Cc3nc(C(=O)O)c(C)s3)CC2)nc1] |
| 279 | R5 | 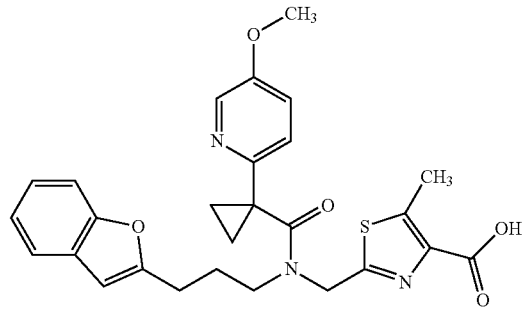 [SMILES: COc1ccc(C2(C(=O)N(CCCc3cc4ccccc4o3)Cc3nc(C(=O)O)c(C)s3)CC2)nc1] |

TABLE 28-continued
| Rf | Syn | Structure |
|---|---|---|
| 280 | R5 | 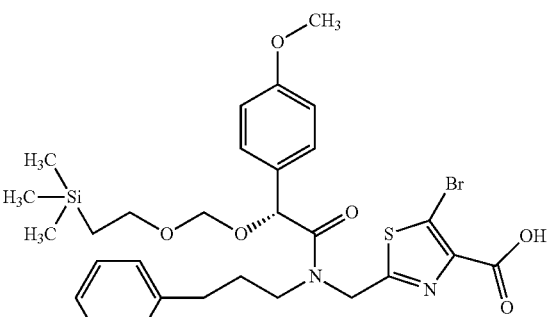 |
| 281 | R5 | 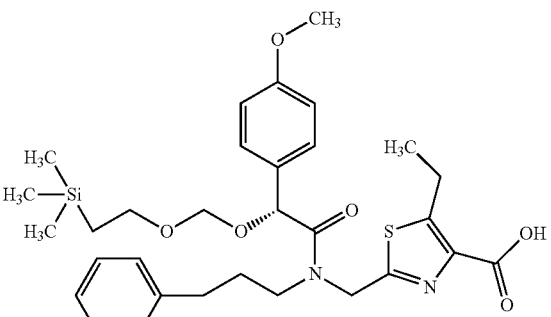 |
| 282 | R4 | 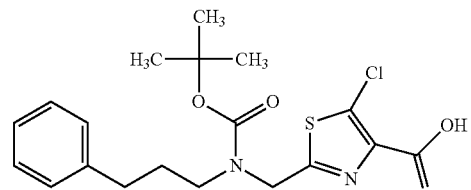 |
| 283 | R5 | 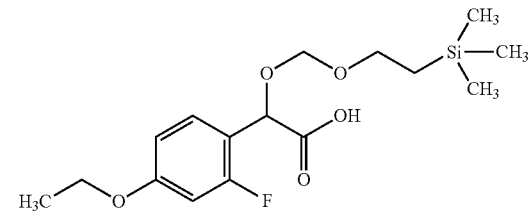 [SMILES: CCOc1ccc(C(OCOCC[Si](C)(C)C)C(=O)O)c(F)c1] |
| 221 | R4 | 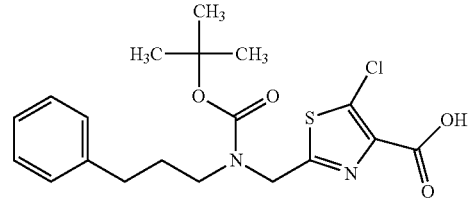 [SMILES: CC(C)(C)OC(=O)N(CCCc1ccccc1)Cc1nc(C(=O)O)c(Cl)s1] |
| 284 | R5 | 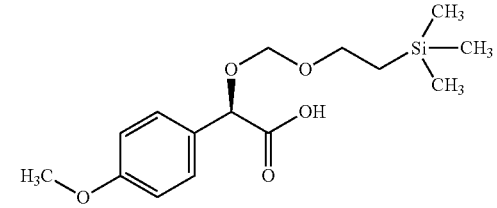 |

TABLE 28-continued
| Rf | Syn | Structure |
|---|---|---|
| 285 | R5 | 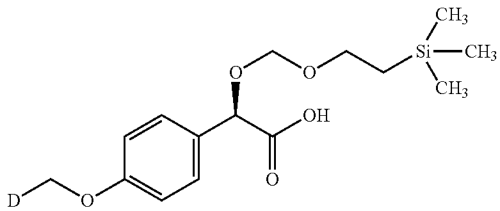 [SMILES: [2H]COc1ccc([C@@H](OCOCC[Si](C)(C)C)C(=O)O)cc1] |
| 286 | R5 | 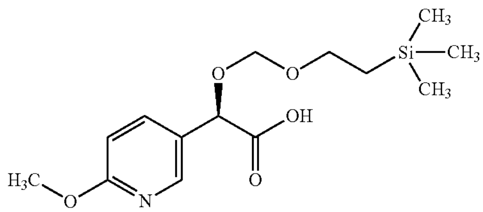 |
| 287 | R5 | 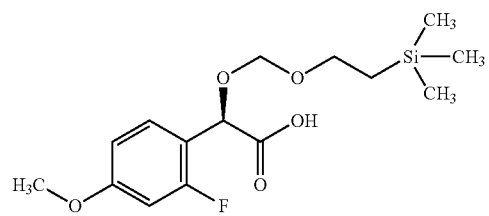 |
| 288 | R6 | 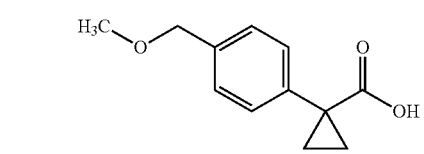 |
TABLE 29
| Rf | Syn | Structure |
|---|---|---|
| 289 | R6 | 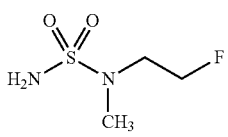 |
| 290 | R6 | 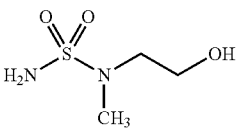 |
| 291 | R8 | 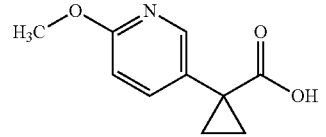 |
| 293 | R8 | 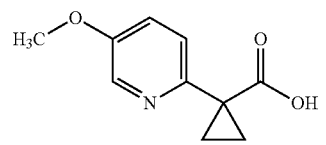 |

TABLE 29-continued
| Rf | Syn | Structure |
|---|---|---|
| 294 | R9 | 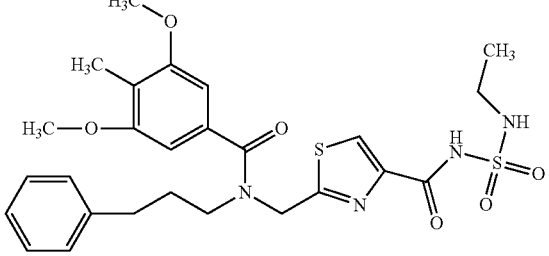 |
| 295 | R9 | 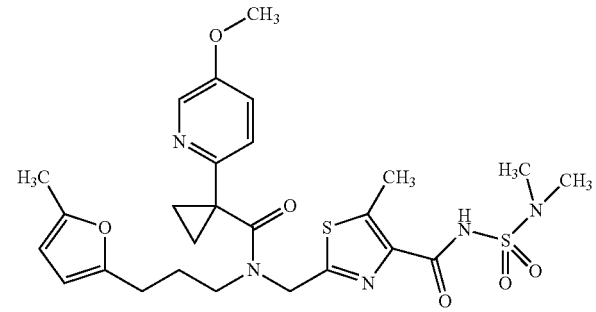 [SMILES: COc1ccc(C2(C(=O)N(CCCc3ccc(C)o3)Cc3nc(C(=O)NS(=O)(=O)N(C)C)c(C)s3)CC2)nc1] |
| 296 | R9 | 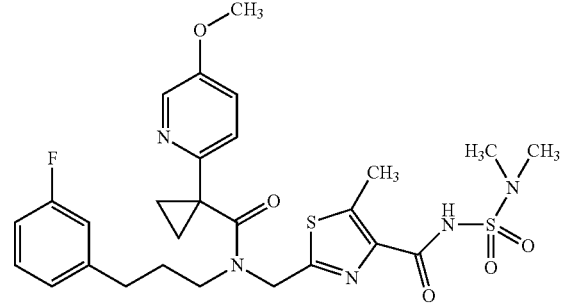 [SMILES: COc1ccc(C2(C(=O)N(CCCc3cccc(F)c3)Cc3nc(C(=O)NS(=O)(=O)N(C)C)c(C)s3)CC2)nc1] |
| 297 | R10 | 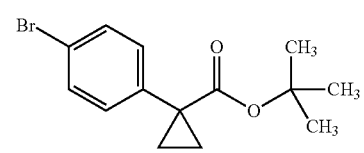 [SMILES: CC(C)(C)OC(=O)C1(c2ccc(Br)cc2)CC1] |
| 298 | R12 | 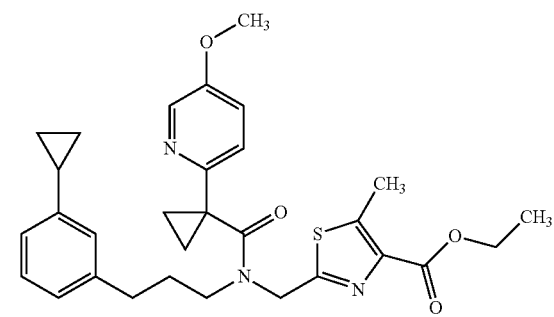 [SMILES: CCOC(=O)c1nc(CN(CCCc2cccc(C3CC3)c2)C(=O)C2(c3ccc(OC)cn3)CC2)sc1C] |

TABLE 29-continued

| Rf | Syn | Structure |
|---|---|---|
| 299 | R12 | 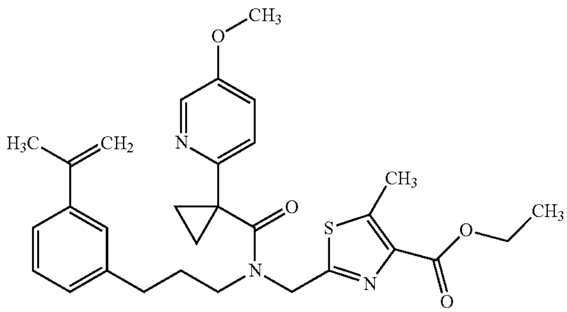 [SMILES: C=C(C)c1cccc(CCCN(Cc2nc(C(=O)OCC)c(C)s2)C(=O)C2(c3ccc(OC)cn3)CC2)c1] |
| 300 | R13 | 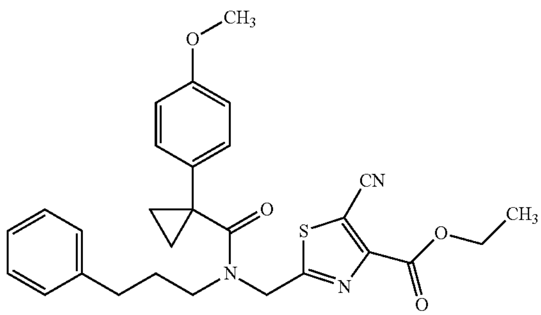 [SMILES: CCOC(=O)c1nc(CN(CCCc2ccccc2)C(=O)C2(c3ccc(OC)cc3)CC2)sc1C#N] |
| 301 | R20 | 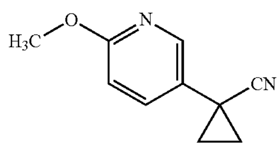 |

TABLE 30

| Rf | Syn | Structure |
|---|---|---|
| 302 | R20 | 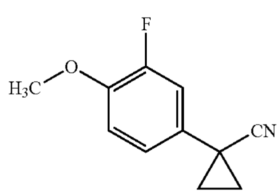 |
| 303 | R26 | 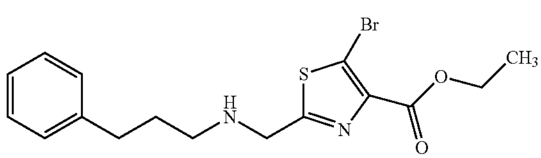 [SMILES: CCOC(=O)c1nc(CNCCCc2ccccc2)sc1Br] |
| 304 | R26 | 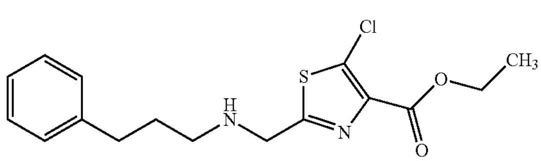 [SMILES: CCOC(=O)c1nc(CNCCCc2ccccc2)sc1Cl] |

TABLE 30-continued

| Rf | Syn | Structure |
|---|---|---|
| 305 | R28 | 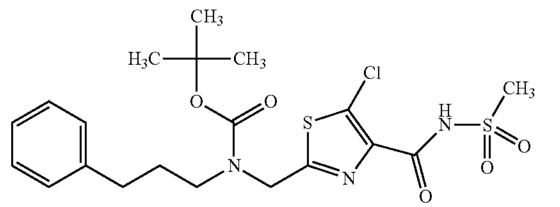 [SMILES: CC(C)(C)OC(=O)N(CCCc1ccccc1)Cc1nc(C(=O)NS(C)(=O)=O)c(Cl)s1] |
| 306 | R28 | 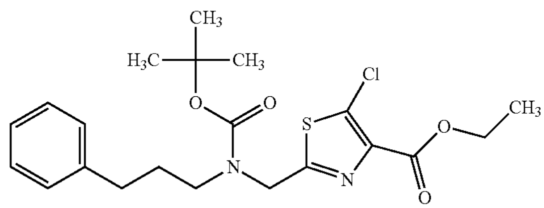 [SMILES: CCOC(=O)c1nc(CN(CCCc2ccccc2)C(=O)OC(C)(C)C)sc1Cl] |
| 307 | R28 | 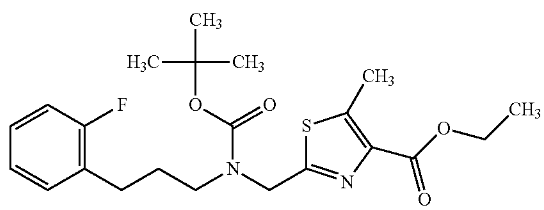 [SMILES: CCOC(=O)c1nc(CN(CCCc2ccccc2F)C(=O)OC(C)(C)C)sc1C] |
| 308 | R30 | 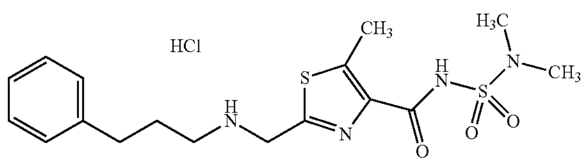 [SMILES: Cc1sc(CNCCCc2ccccc2)nc1C(=O)NS(=O)(=O)N(C)C ; Cl] |
| 309 | R30 | 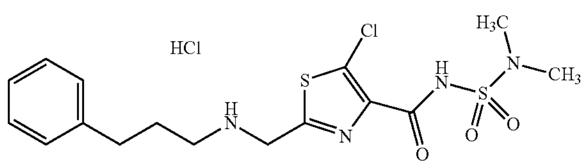 [SMILES: CN(C)S(=O)(=O)NC(=O)c1nc(CNCCCc2ccccc2)sc1Cl ; Cl] |
| 310 | R30 | 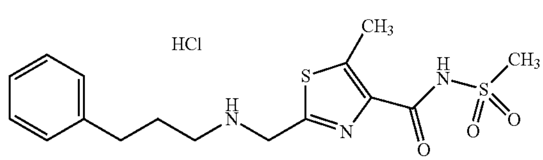 [SMILES: Cc1sc(CNCCCc2ccccc2)nc1C(=O)NS(C)(=O)=O ; Cl] |
| 311 | R30 | 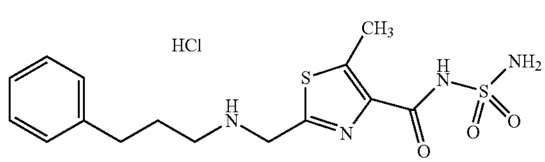 [SMILES: Cc1sc(CNCCCc2ccccc2)nc1C(=O)NS(N)(=O)=O ; Cl] |
| 312 | R30 | 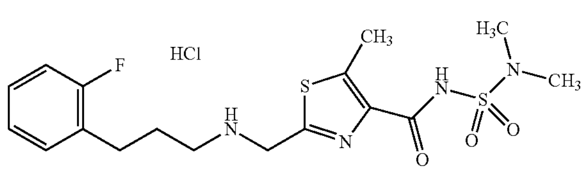 [SMILES: Cc1sc(CNCCCc2ccccc2F)nc1C(=O)NS(=O)(=O)N(C)C ; Cl] |

TABLE 30-continued

| Rf | Syn | Structure |
|---|---|---|
| 313 | R30 | 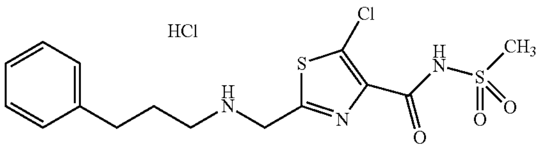 [SMILES: CS(=O)(=O)NC(=O)c1nc(CNCCCc2ccccc2)sc1Cl ; Cl] |
| 314 | R33 | 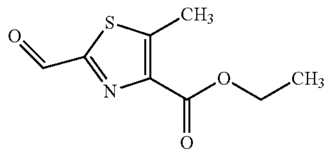 |
| 315 | R34 | 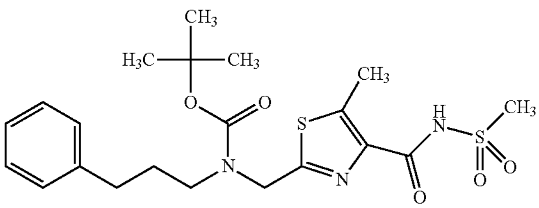 [SMILES: Cc1sc(CN(CCCc2ccccc2)C(=O)OC(C)(C)C)nc1C(=O)NS(C)(=O)=O] |
| 316 | R34 | 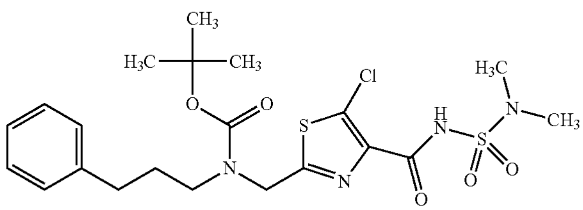 [SMILES: CN(C)S(=O)(=O)NC(=O)c1nc(CN(CCCc2ccccc2)C(=O)OC(C)(C)C)sc1Cl] |
| 317 | R34 | 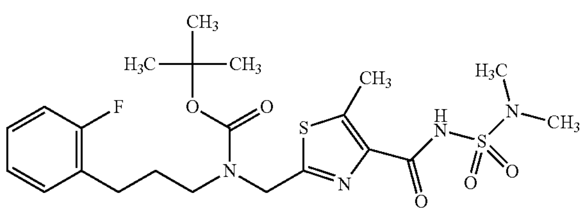 [SMILES: Cc1sc(CN(CCCc2ccccc2F)C(=O)OC(C)(C)C)nc1C(=O)NS(=O)(=O)N(C)C] |
| 318 | R34 | 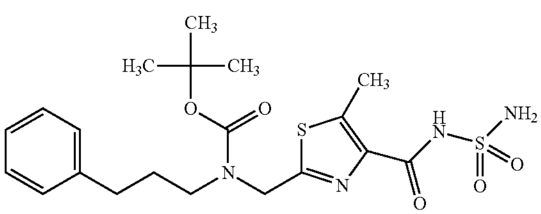 [SMILES: Cc1sc(CN(CCCc2ccccc2)C(=O)OC(C)(C)C)nc1C(=O)NS(N)(=O)=O] |
| 319 | R39 | 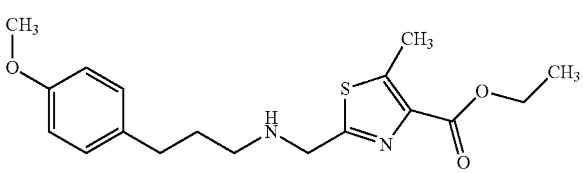 [SMILES: CCOC(=O)c1nc(CNCCCc2ccc(OC)cc2)sc1C] |

TABLE 31

| Rf | Syn | Structure |
|---|---|---|
| 320 | R39 | 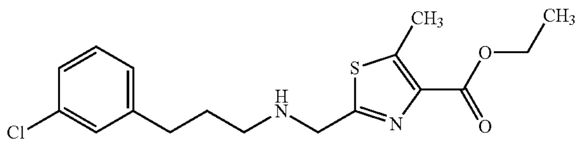 [SMILES: CCOC(=O)c1nc(CNCCCc2cccc(Cl)c2)sc1C] |
| 321 | R39 | 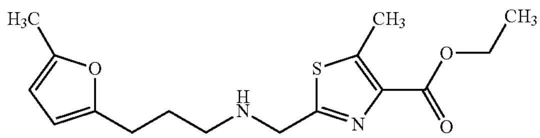 [SMILES: CCOC(=O)c1nc(CNCCCc2ccc(C)o2)sc1C] |
| 322 | R39 | 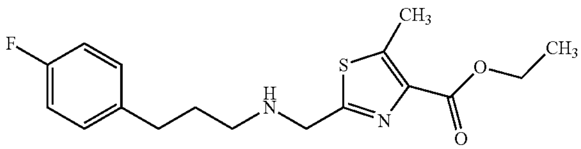 [SMILES: CCOC(=O)c1nc(CNCCCc2ccc(F)cc2)sc1C] |
| 323 | R39 | 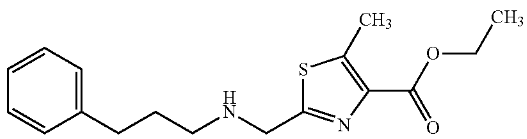 [SMILES: CCOC(=O)c1nc(CNCCCc2ccccc2)sc1C] |
| 324 | R39 | 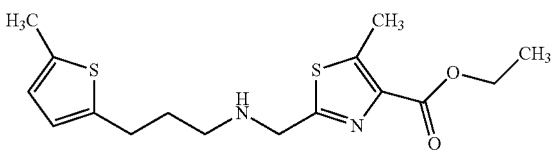 [SMILES: CCOC(=O)c1nc(CNCCCc2ccc(C)s2)sc1C] |
| 325 | R39 | 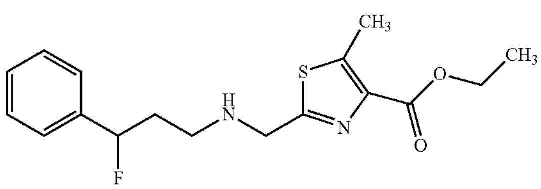 [SMILES: CCOC(=O)c1nc(CNCCC(F)c2ccccc2)sc1C] |
| 326 | R39 | 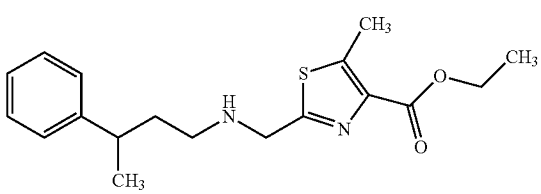 [SMILES: CCOC(=O)c1nc(CNCCC(C)c2ccccc2)sc1C] |
| 327 | R39 | 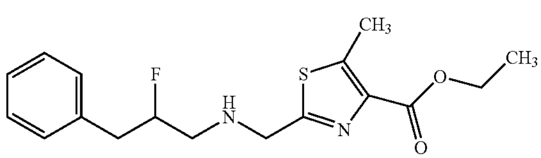 [SMILES: CCOC(=O)c1nc(CNCC(F)Cc2ccccc2)sc1C] |
| 328 | R39 | 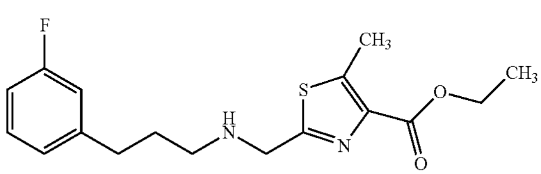 [SMILES: CCOC(=O)c1nc(CNCCCc2cccc(F)c2)sc1C] |

TABLE 31-continued
| Rf | Syn | Structure |
|---|---|---|
| 329 | R39 | 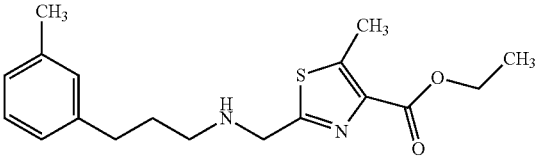 [SMILES: CCOC(=O)c1nc(CNCCCc2cccc(C)c2)sc1C] |
| 330 | R39 | 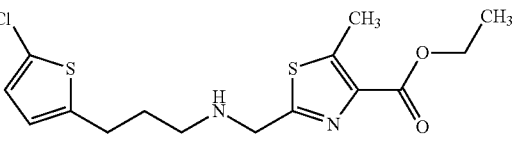 |
| 331 | R39 | 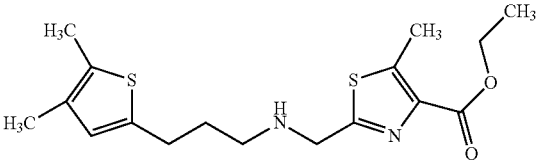 [SMILES: CCOC(=O)c1nc(CNCCCc2cc(C)c(C)s2)sc1C] |
| 332 | R39 | 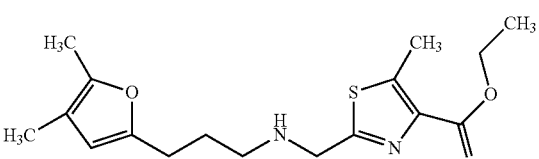 |
| 333 | R39 | 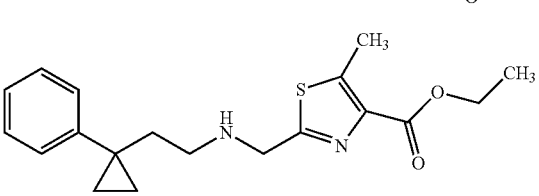 |
| 334 | R39 | 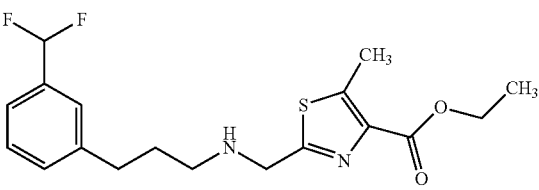 [SMILES: CCOC(=O)c1nc(CNCCCc2cccc(C(F)F)c2)sc1C] |
| 335 | R39 | 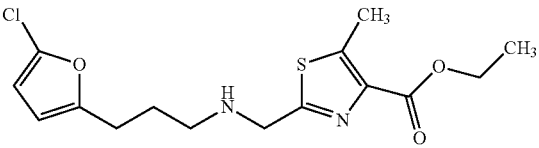 [SMILES: CCOC(=O)c1nc(CNCCCc2ccc(Cl)o2)sc1C] |
| 336 | R39 | 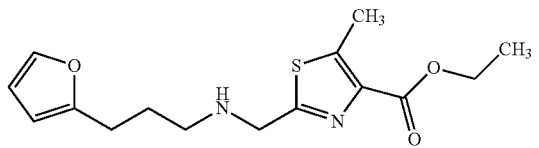 [SMILES: CCOC(=O)c1nc(CNCCCc2ccco2)sc1C] |
| 337 | R39 | 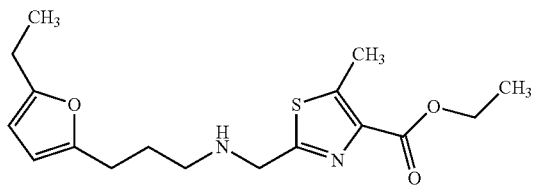 [SMILES: CCOC(=O)c1nc(CNCCCc2ccc(CC)o2)sc1C] |

TABLE 31-continued

| Rf | Syn | Structure |
|---|---|---|
| 338 | R39 | ethyl 2-({[3-(2-fluoro-5-(trifluoromethyl)phenyl)propyl]amino}methyl)-5-methylthiazole-4-carboxylate |
| 339 | R39 | ethyl 2-({[3-(3-methylphenyl)propyl]amino}methyl)-5-methylthiazole-4-carboxylate |

TABLE 32

| Rf | Syn | Structure |
|---|---|---|
| 340 | R39 | ethyl 2-({[3-(2-fluorophenyl)propyl]amino}methyl)-5-methylthiazole-4-carboxylate |
| 341 | R39 | ethyl 5-({[3-phenylpropyl]amino}methyl)furan-2-carboxylate |
| 292 | R8 | 1-(3-fluoro-4-methoxyphenyl)cyclopropanecarboxylic acid |
| 342 | R39 | ethyl 2-({[3-(2-fluoro-5-methylphenyl)propyl]amino}methyl)-5-methylthiazole-4-carboxylate |
| 343 | R39 | ethyl 2-({[3-(2-fluoro-3-methylphenyl)propyl]amino}methyl)-5-methylthiazole-4-carboxylate |
| 344 | R39 | ethyl 2-({[3-(thiophen-2-yl)propyl]amino}methyl)-5-methylthiazole-4-carboxylate |

TABLE 32-continued

| Rf | Syn | Structure |
|---|---|---|
| 345 | R39 | 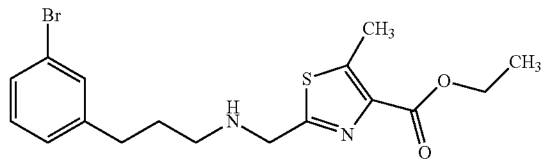 |
| 346 | R39 | 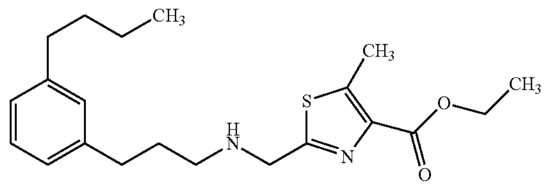 [SMILES: CCCCc1cccc(CCCNCc2nc(C(=O)OCC)c(C)s2)c1] |
| 347 | R39 | 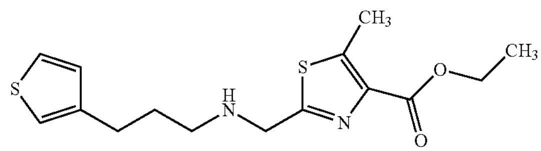 [SMILES: CCOC(=O)c1nc(CNCCCc2ccsc2)sc1C] |
| 348 | R39 | 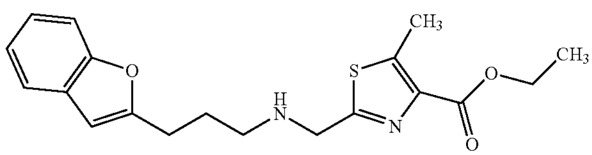 [SMILES: CCOC(=O)c1nc(CNCCCc2cc3ccccc3o2)sc1C] |
| 349 | R40 | 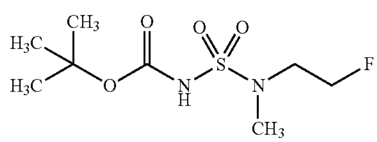 [SMILES: CN(CCF)S(=O)(=O)NC(=O)OC(C)(C)C] |
| 350 | R40 | 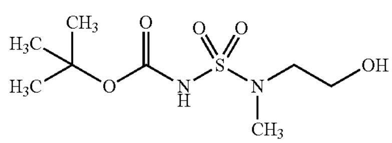 |
| 351 | R44 | 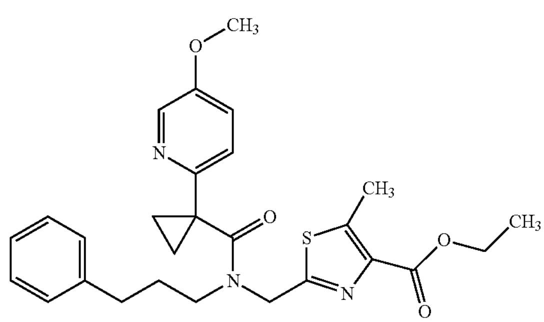 [SMILES: CCOC(=O)c1nc(CN(CCCc2ccccc2)C(=O)C2(c3ccc(OC)cn3)CC2)sc1C] |
| 352 | R44 | 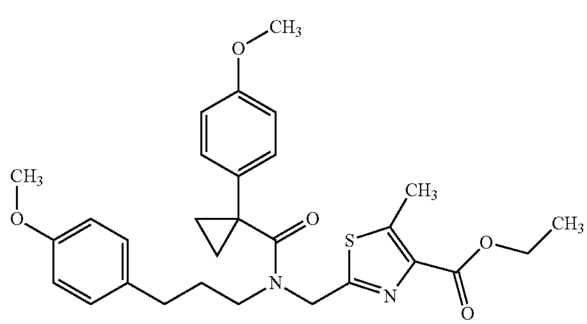 [SMILES: CCOC(=O)c1nc(CN(CCCc2ccc(OC)cc2)C(=O)C2(c3ccc(OC)cc3)CC2)sc1C] |

TABLE 32-continued
| Rf | Syn | Structure |
|---|---|---|
| 353 | R44 | 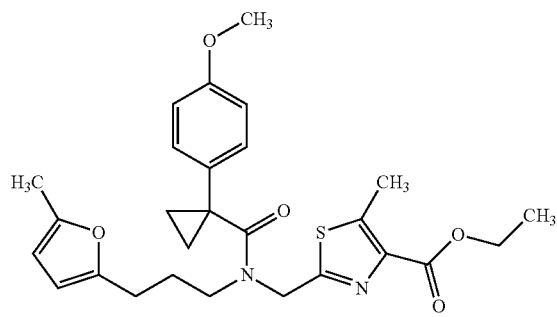 |
| 354 | R44 | 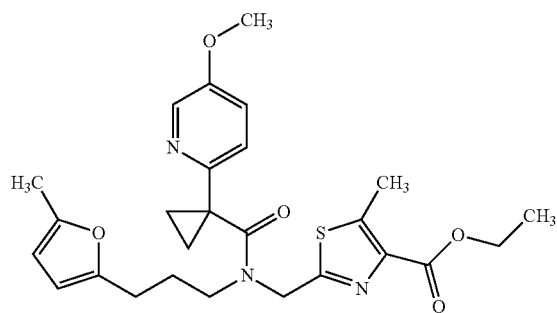 [SMILES: CCOC(=O)c1nc(CN(CCCc2ccc(C)o2)C(=O)C2(c3ccc(OC)cn3)CC2)sc1C] |
TABLE 33
| Rf | Syn | Structure |
|---|---|---|
| 355 | R44 | 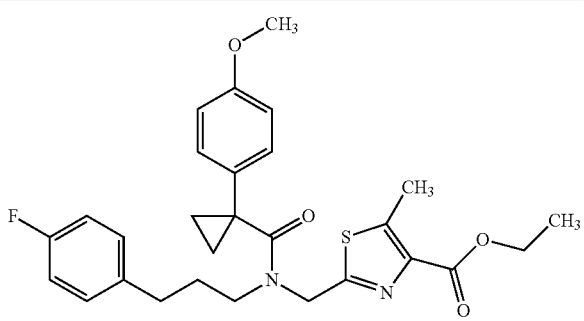 [SMILES: CCOC(=O)c1nc(CN(CCCc2ccc(F)cc2)C(=O)C2(c3ccc(OC)cc3)CC2)sc1C] |
| 356 | R44 | 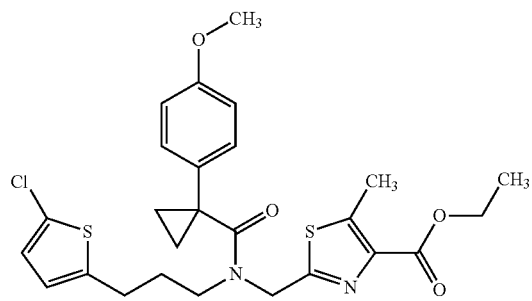 [SMILES: CCOC(=O)c1nc(CN(CCCc2ccc(Cl)s2)C(=O)C2(c3ccc(OC)cc3)CC2)sc1C] |

TABLE 33-continued
| Rf | Syn | Structure |
|---|---|---|
| 357 | R44 | 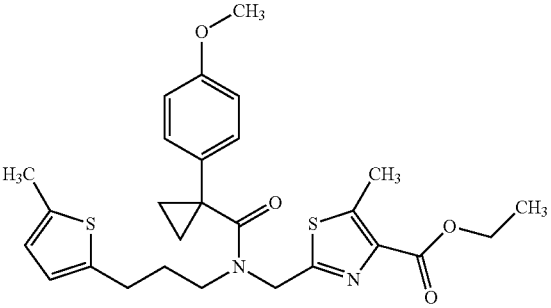 |
| 358 | R44 | 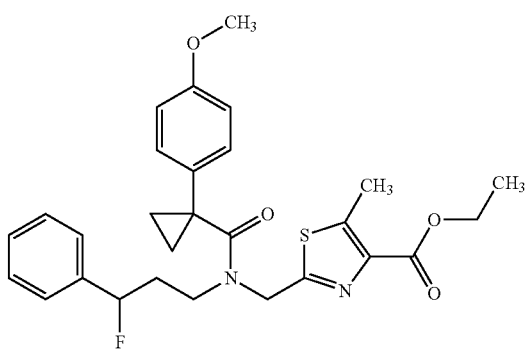 [SMILES: CCOC(=O)c1nc(CN(CCC(F)c2ccccc2)C(=O)C2(c3ccc(OC)cc3)CC2)sc1C] |
| 359 | R44 | 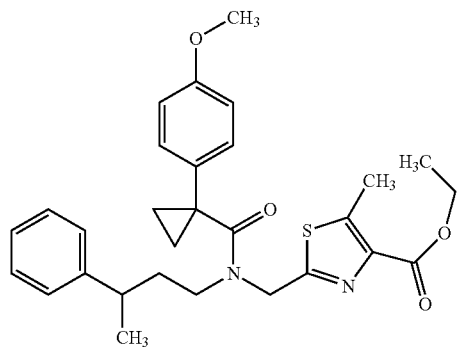 [SMILES: CCOC(=O)c1nc(CN(CCC(C)c2ccccc2)C(=O)C2(c3ccc(OC)cc3)CC2)sc1C] |
| 360 | R44 | 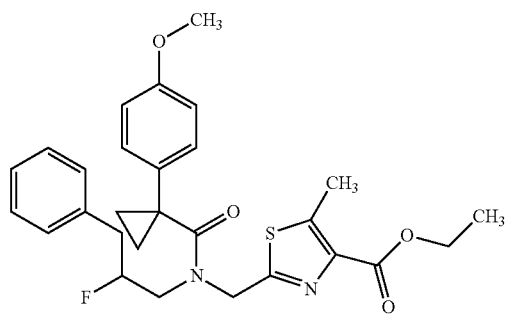 [SMILES: CCOC(=O)c1nc(CN(CC(F)Cc2ccccc2)C(=O)C2(c3ccc(OC)cc3)CC2)sc1C] |

TABLE 33-continued
| Rf | Syn | Structure |
|---|---|---|
| 361 | R44 | 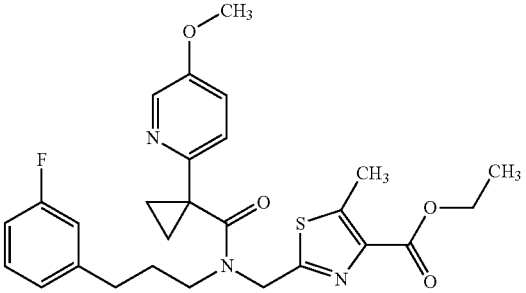 [SMILES: CCOC(=O)c1nc(CN(CCCc2cccc(F)c2)C(=O)C2(c3ccc(OC)cn3)CC2)sc1C] |
| 362 | R44 | 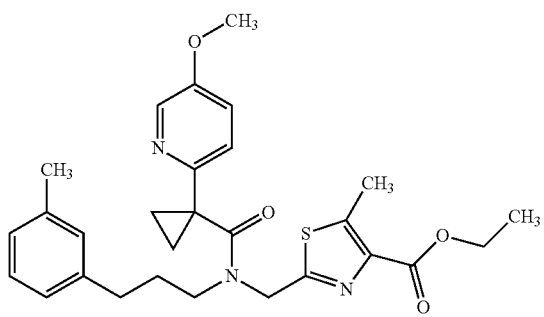 [SMILES: CCOC(=O)c1nc(CN(CCCc2cccc(C)c2)C(=O)C2(c3ccc(OC)cn3)CC2)sc1C] |
| 363 | R44 | 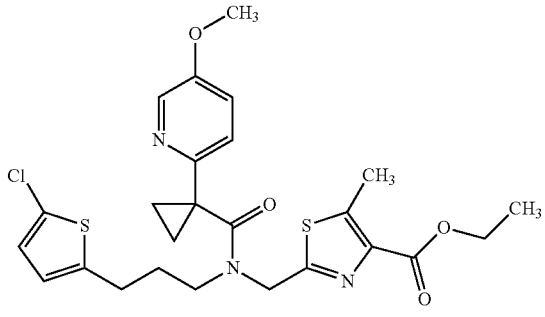 |
| 364 | R44 | 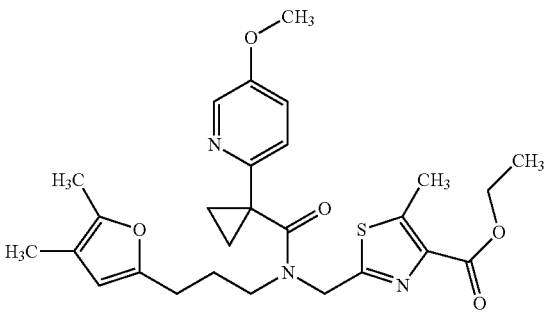 [SMILES: CCOC(=O)c1nc(CN(CCCc2cc(C)c(C)s2)C(=O)C2(c3ccc(OC)cn3)CC2)sc1C] |

TABLE 34
| Rf | Syn | Structure |
|---|---|---|
| 365 | R44 | 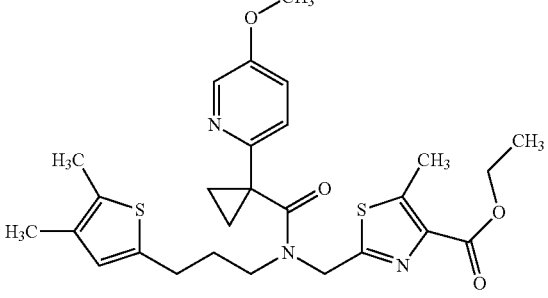 |
| 366 | R44 | 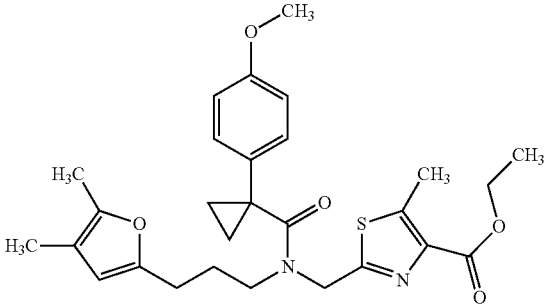 [SMILES: CCOC(=O)c1nc(CN(CCCc2cc(C)c(C)o2)C(=O)C2(c3ccc(OC)cc3)CC2)sc1C] |
| 367 | R44 | 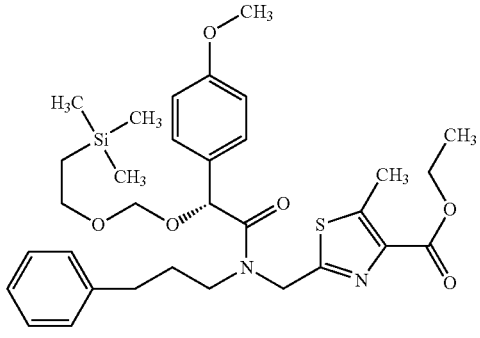 [SMILES: CCOC(=O)c1nc(CN(CCCc2ccccc2)C(=O)[C@H](OCOCC[Si](C)(C)C)c2ccc(OC)cc2)sc1C] |
| 368 | R44 | 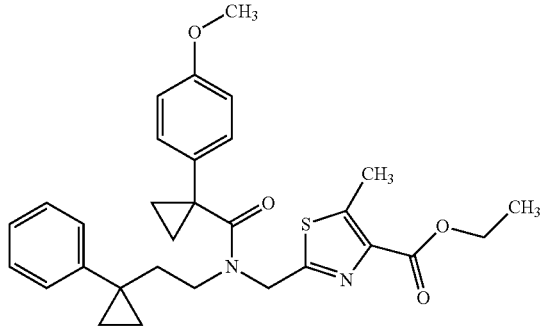 [SMILES: CCOC(=O)c1nc(CN(CCC2(c3ccccc3)CC2)C(=O)C2(c3ccc(OC)cc3)CC2)sc1C] |

TABLE 34-continued
| Rf | Syn | Structure |
|---|---|---|
| 369 | R44 | 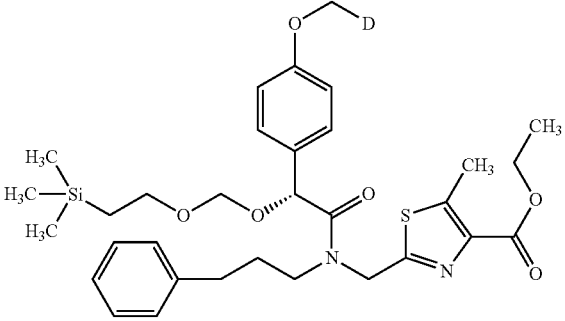 [SMILES: [2H]COc1ccc([C@@H](OCOCC[Si](C)(C)C)C(=O)N(CCCc2ccccc2)Cc2nc(C(=O)OCC)c(C)s2)cc1] |
| 370 | R44 | 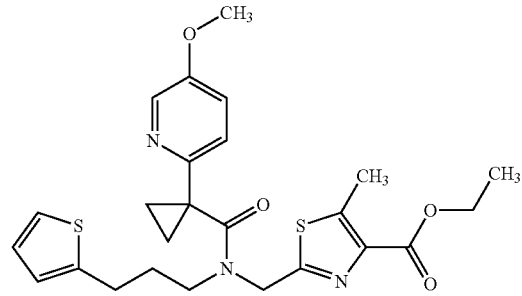 [SMILES: CCOC(=O)c1nc(CN(CCCc2cccs2)C(=O)C2(c3ccc(OC)cn3)CC2)sc1C] |
| 371 | R44 | 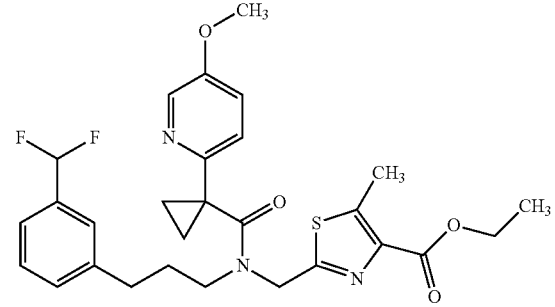 [SMILES: CCOC(=O)c1nc(CN(CCCc2cccc(C(F)F)c2)C(=O)C2(c3ccc(OC)cn3)CC2)sc1C] |
| 372 | R44 | 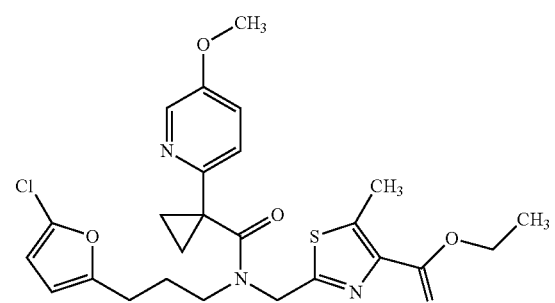 |

TABLE 34-continued
| Rf | Syn | Structure |
|---|---|---|
| 374 | R44 | 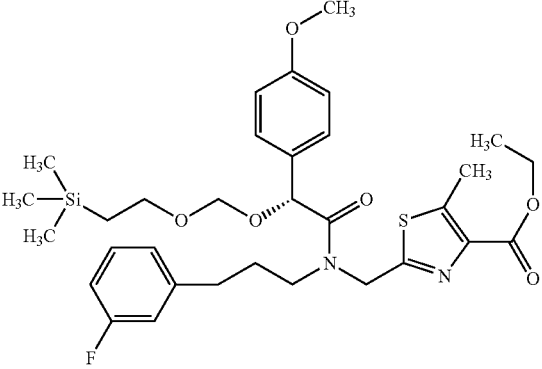 [SMILES: CCOC(=O)c1nc(CN(CCCc2cccc(F)c2)C(=O)[C@H](OCOCC[Si](C)(C)C)c2ccc(OC)cc2)sc1C] |
| 375 | R44 | 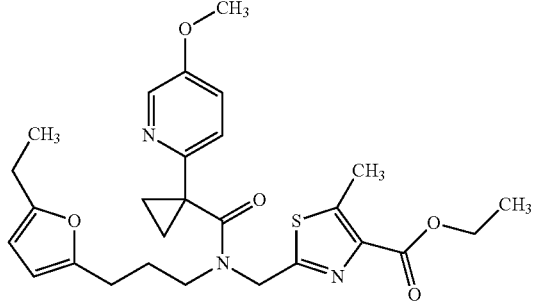 [SMILES: CCOC(=O)c1nc(CN(CCCc2ccc(CC)o2)C(=O)C2(c3ccc(OC)cn3)CC2)sc1C] |
| 376 | R44 | 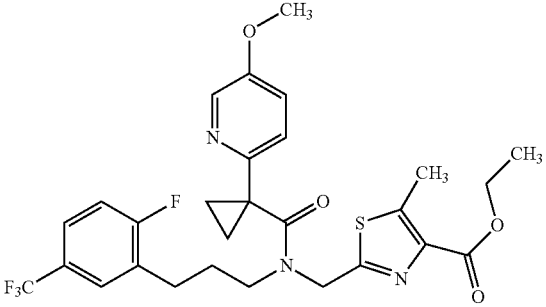 [SMILES: CCOC(=O)c1nc(CN(CCCc2cc(C(F)(F)F)ccc2F)C(=O)C2(c3ccc(OC)cn3)CC2)sc1C] |
| 377 | R44 | 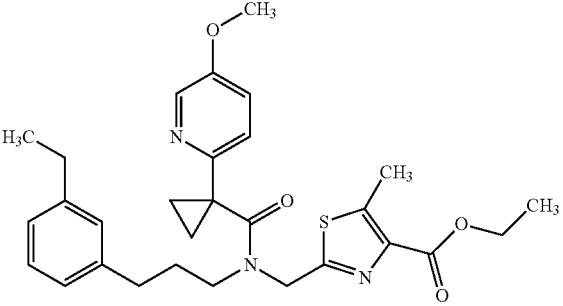 [SMILES: CCOC(=O)c1nc(CN(CCCc2cccc(CC)c2)C(=O)C2(c3ccc(OC)cn3)CC2)sc1C] |

TABLE 35

| Rf | Syn | Structure |
|---|---|---|
| 378 | R44 | 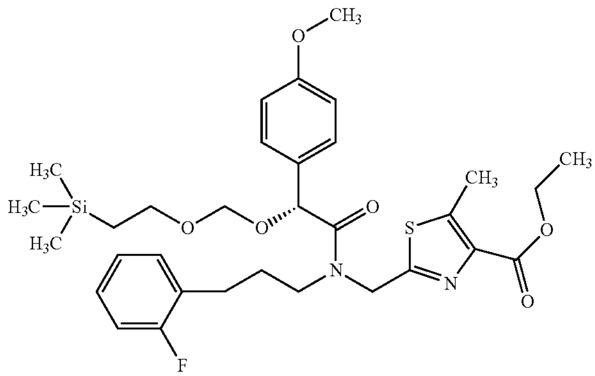 [SMILES: CCOC(=O)c1nc(CN(CCCc2ccccc2F)C(=O)[C@H](OCOCC[Si](C)(C)C)c2ccc(OC)cc2)sc1C] |
| 379 | R44 | 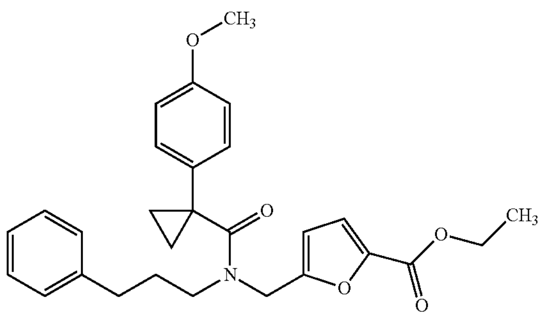 [SMILES: CCOC(=O)c1ccc(CN(CCCc2ccccc2)C(=O)C2(c3ccc(OC)cc3)CC2)o1] |
| 380 | R44 | 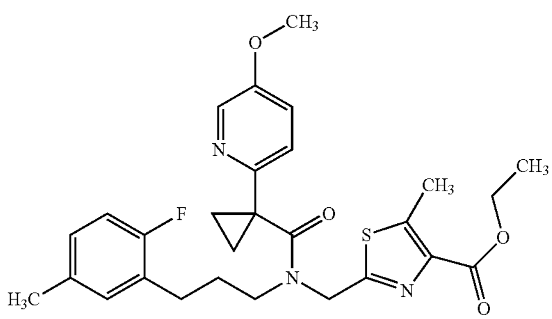 [SMILES: CCOC(=O)c1nc(CN(CCCc2cc(C)ccc2F)C(=O)C2(c3ccc(OC)cn3)CC2)sc1C] |
| 381 | R44 | 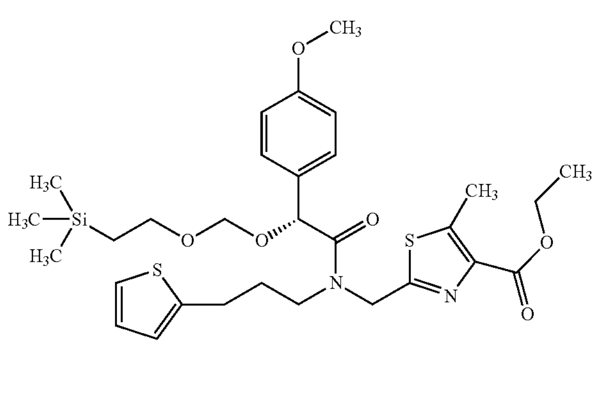 [SMILES: CCOC(=O)c1nc(CN(CCCc2cccs2)C(=O)[C@H](OCOCC[Si](C)(C)C)c2ccc(OC)cc2)sc1C] |

TABLE 35-continued
| Rf | Syn | Structure |
|---|---|---|
| 382 | R44 | 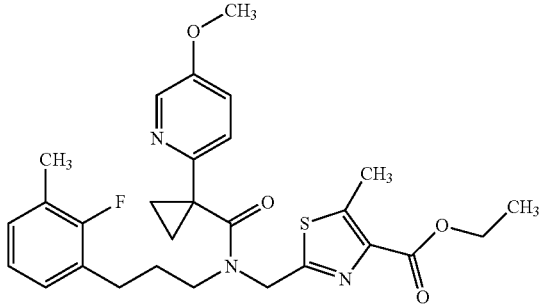 [SMILES: CCOC(=O)c1nc(CN(CCCc2cccc(C)c2F)C(=O)C2(c3ccc(OC)cn3)CC2)sc1C] |
| 383 | R44 | 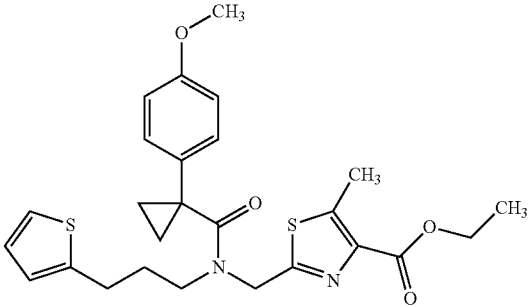 |
| 384 | R44 | 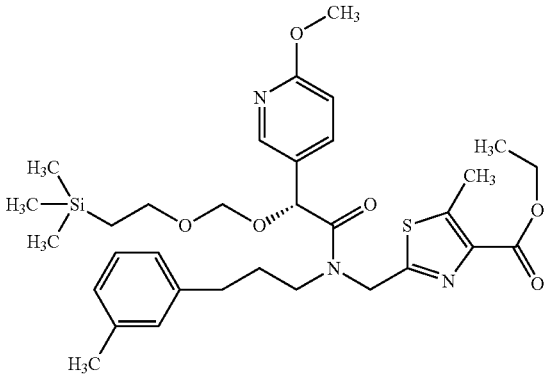 [SMILES: CCOC(=O)c1nc(CN(CCCc2cccc(C)c2)C(=O)[C@H](OCOCC[Si](C)(C)C)c2ccc(OC)nc2)sc1C] |
| 385 | R44 | 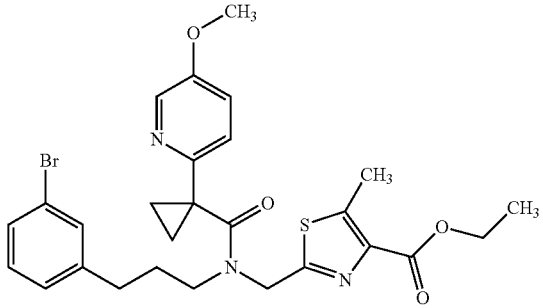 [SMILES: CCOC(=O)c1nc(CN(CCCc2cccc(Br)c2)C(=O)C2(c3ccc(OC)cn3)CC2)sc1C] |

TABLE 35-continued

| Rf | Syn | Structure |
|----|-----|-----------|
| 386 | R44 | 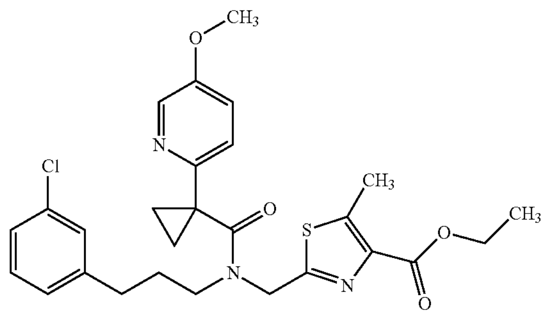 [SMILES: CCOC(=O)c1nc(CN(CCCc2cccc(Cl)c2)C(=O)C2(c3ccc(OC)cn3)CC2)sc1C] |
| 387 | R44 | 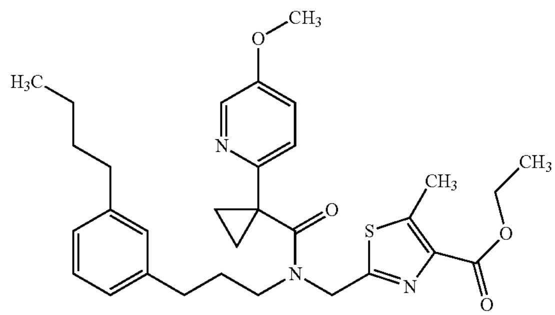 [SMILES: CCCCc1cccc(CCCN(Cc2nc(C(=O)OCC)c(C)s2)C(=O)C2(c3ccc(OC)cn3)CC2)c1] |

TABLE 36

| Rf | Syn | Structure |
|----|-----|-----------|
| 388 | R44 | 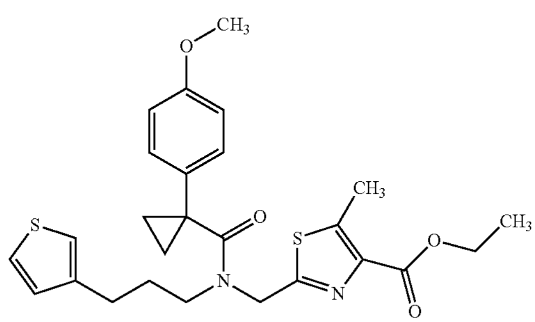 [SMILES: CCOC(=O)c1nc(CN(CCCc2ccsc2)C(=O)C2(c3ccc(OC)cc3)CC2)sc1C] |
| 389 | R44 | 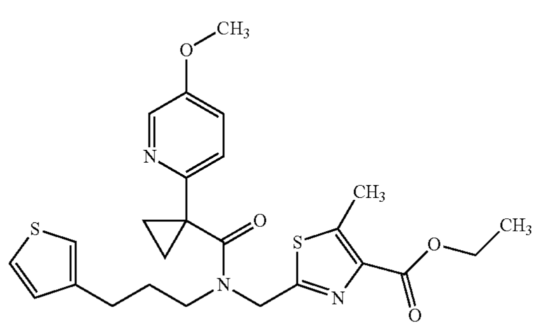 [SMILES: CCOC(=O)c1nc(CN(CCCc2ccsc2)C(=O)C2(c3ccc(OC)cn3)CC2)sc1C] |

TABLE 36-continued
| Rf | Syn | Structure |
|---|---|---|
| 390 | R44 | 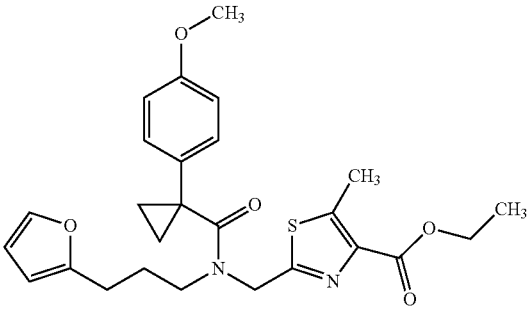 [SMILES: CCOC(=O)c1nc(CN(CCCc2ccco2)C(=O)C2(c3ccc(OC)cc3)CC2)sc1C] |
| 391 | R44 | 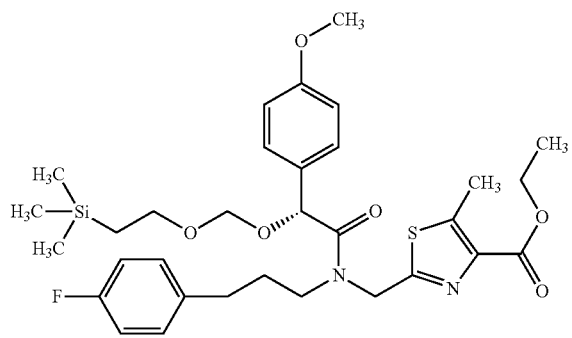 [SMILES: CCOC(=O)c1nc(CN(CCCc2ccc(F)cc2)C(=O)[C@H](OCOCC[Si](C)(C)C)c2ccc(OC)cc2)sc1C] |
| 392 | R44 | 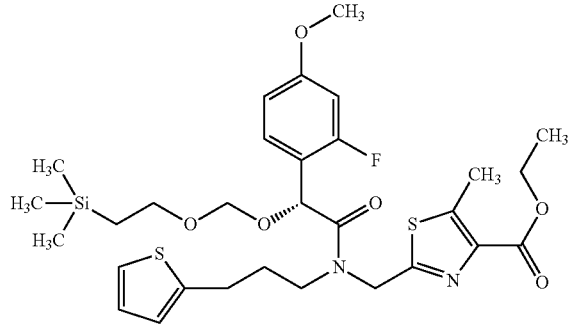 [SMILES: CCOC(=O)c1nc(CN(CCCc2cccs2)C(=O)[C@H](OCOCC[Si](C)(C)C)c2ccc(OC)cc2F)sc1C] |
| 393 | R44 | 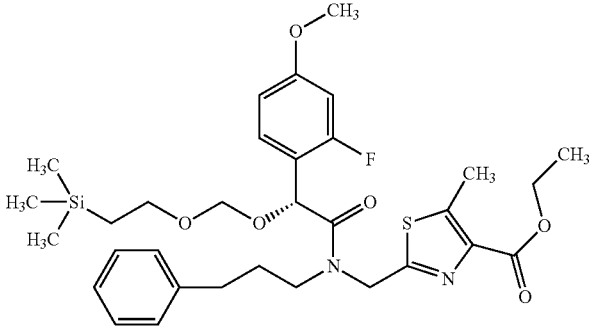 [SMILES: CCOC(=O)c1nc(CN(CCCc2ccccc2)C(=O)[C@H](OCOCC[Si](C)(C)C)c2ccc(OC)cc2F)sc1C] |

TABLE 36-continued
| Rf | Syn | Structure |
|---|---|---|
| 394 | R44 | 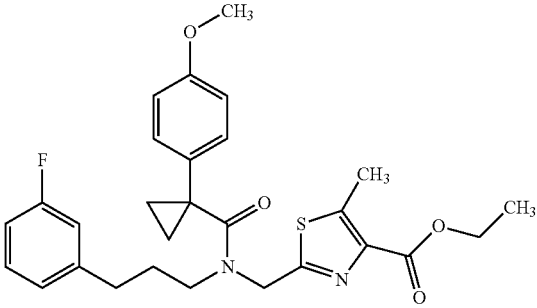 [SMILES: CCOC(=O)c1nc(CN(CCCc2cccc(F)c2)C(=O)C2(c3ccc(OC)cc3)CC2)sc1C] |
| 395 | R44 | 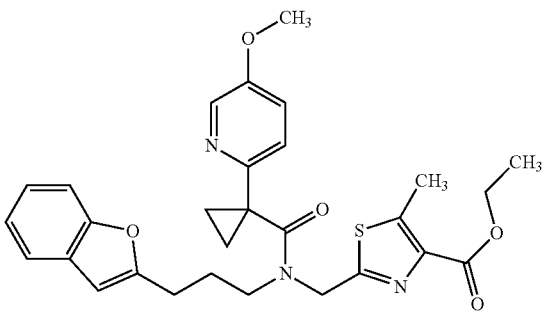 [SMILES: CCOC(=O)c1nc(CN(CCCc2cc3ccccc3o2)C(=O)C2(c3ccc(OC)cn3)CC2)sc1C] |
| 396 | R44 | 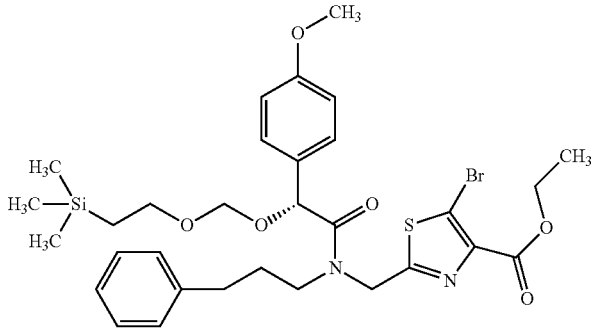 [SMILES: CCOC(=O)c1nc(CN(CCCc2ccccc2)C(=O)[C@H](OCOCC[Si](C)(C)C)c2ccc(OC)cc2)sc1Br] |
| 397 | R44 | 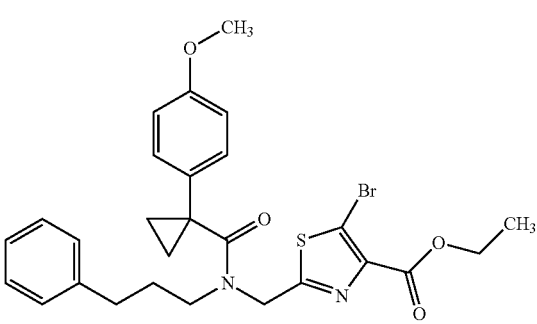 [SMILES: CCOC(=O)c1nc(CN(CCCc2ccccc2)C(=O)C2(c3ccc(OC)cc3)CC2)sc1Br] |
| 398 | R49 | 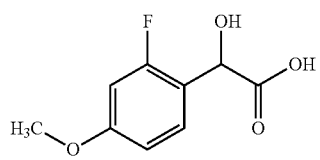 |
| 399 | R53 | 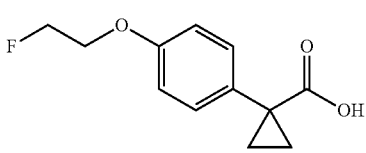 [SMILES: O=C(O)C1(c2ccc(OCCF)cc2)CC1] |

TABLE 36-continued

| Rf | Syn | Structure |
|---|---|---|
| 400 | R400 | 4-formylphenyl cyclopropane-1-carboxylic acid tert-butyl ester |
| 401 | R401 | 4-(hydroxymethyl)phenyl cyclopropane-1-carboxylic acid tert-butyl ester |

TABLE 37

| Rf | Syn | Structure |
|---|---|---|
| 402 | R402 | 1-[4-(methoxymethyl)phenyl]cyclopropane-1-carboxylic acid tert-butyl ester |
| 403 | R403 | 1-[4-(methylthio)phenyl]cyclopropane-1-carboxylic acid |
| 404 | R405 | ethyl 2-{[2-(trimethylsilyl)ethoxy]methoxy}-2-[4-(D-methoxy)phenyl]acetate |
| 405 | R405 | 4-(2-fluoroethoxy)-2-fluorobenzaldehyde |
| 406 | R405 | 4-(2,2-difluoroethoxy)-2-fluorobenzaldehyde |
| 407 | R408 | ethyl 2-(4-ethoxy-2-fluorophenyl)-2-hydroxyacetate |
| 408 | R408 | ethyl 2-[4-(2-fluoroethoxy)-2-fluorophenyl]-2-hydroxyacetate |

TABLE 37-continued

| Rf | Syn | Structure |
|---|---|---|
| 409 | R408 | 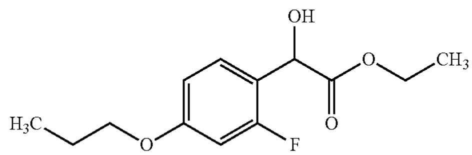 [SMILES: CCCOc1ccc(C(O)C(=O)OCC)c(F)c1] |
| 373 | R44 | 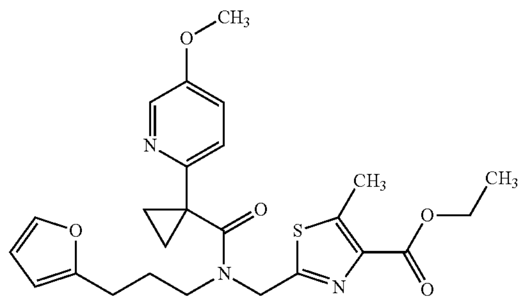 [SMILES: CCOC(=O)c1nc(CN(CCCc2ccco2)C(=O)C2(c3ccc(OC)cn3)CC2)sc1C] |
| 410 | R408 | 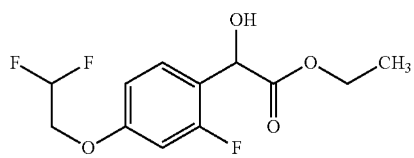 [SMILES: CCOC(=O)C(O)c1ccc(OCC(F)F)cc1F] |
| 411 | R411 | 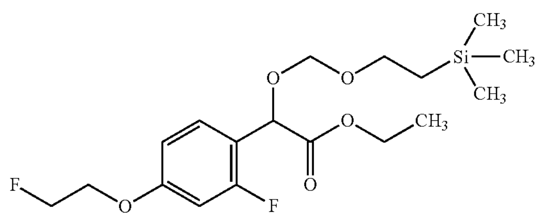 [SMILES: CCOC(=O)C(OCOCC[Si](C)(C)C)c1ccc(OCCF)cc1F] |
| 412 | R411 | 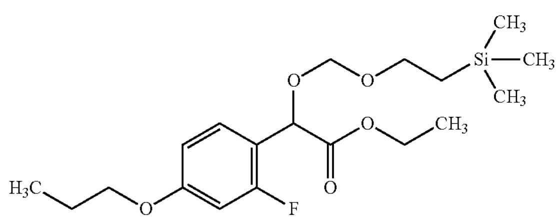 [SMILES: CCCOc1ccc(C(OCOCC[Si](C)(C)C)C(=O)OCC)c(F)c1] |
| 413 | R411 | 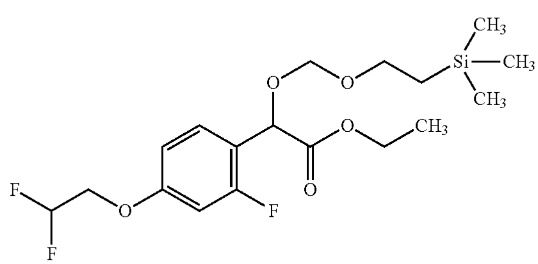 [SMILES: CCOC(=O)C(OCOCC[Si](C)(C)C)c1ccc(OCC(F)F)cc1F] |
| 414 | R411 | 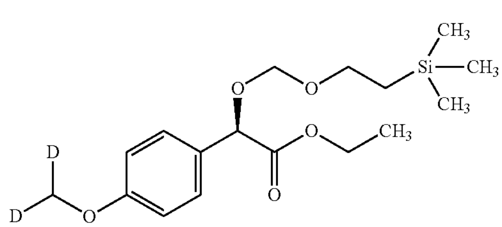 [SMILES: [2H]C([2H])Oc1ccc([C@@H](OCOCC[Si](C)(C)C)C(=O)OCC)cc1] |

TABLE 37-continued

| Rf | Syn | Structure |
|---|---|---|
| 415 | R411 | 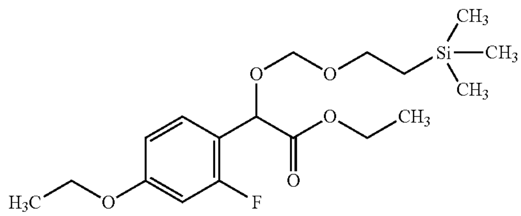 [SMILES: CCOC(=O)C(OCOCC[Si](C)(C)C)c1ccc(OCC)cc1F] |
| 416 | R411 | 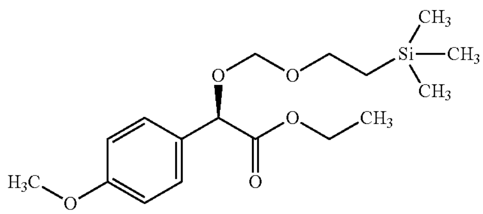 |

TABLE 38

| Rf | Syn | Structure |
|---|---|---|
| 417 | R411 | 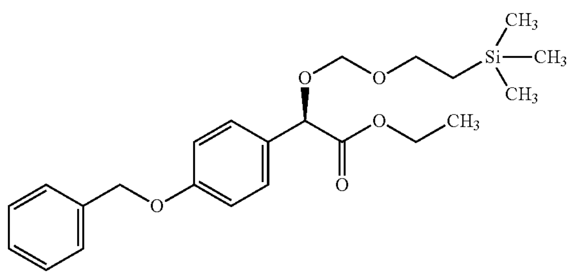 [SMILES: CCOC(=O)[C@H](OCOCC[Si](C)(C)C)c1ccc(OCc2ccccc2)cc1] |
| 418 | R411 | 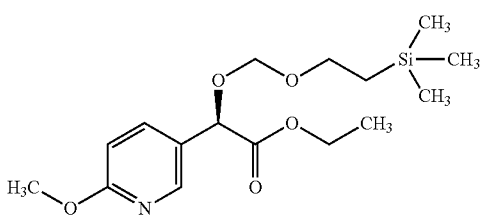 |
| 419 | R411 | 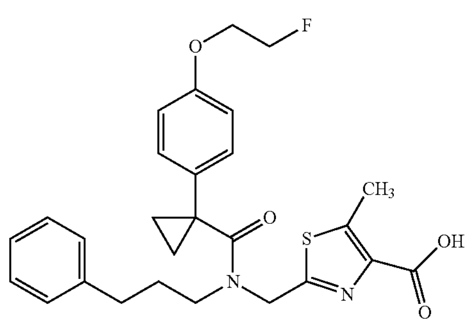 [SMILES: Cc1sc(CN(CCCc2ccccc2)C(=O)C2(c3ccc(OCCF)cc3)CC2)nc1C(=O)O] |
| 420 | R420 | 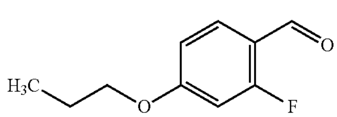 |

TABLE 38-continued
| Rf | Syn | Structure |
|---|---|---|
| 421 | R421 | 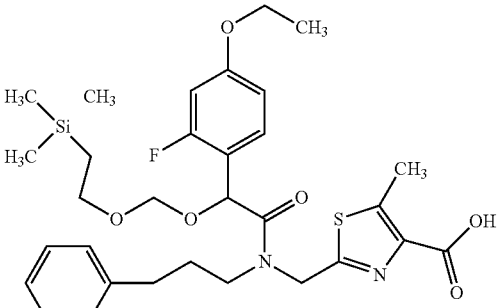 |
| 422 | R421 | 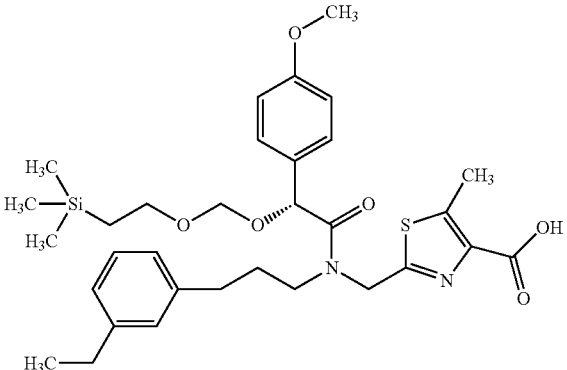 [SMILES: COc1ccc([C@@H](OCOCC[Si](C)(C)C)C(=O)N(CCCc2cccc(Cl)c2)Cc2nc(C(=O)O)c(C)s2)cn1] |
| 423 | R421 | 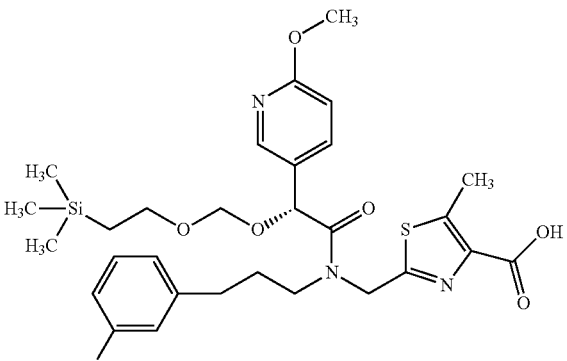 |
| 424 | R424 | 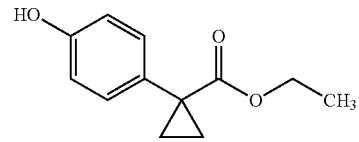 |
| 425 | R425 | 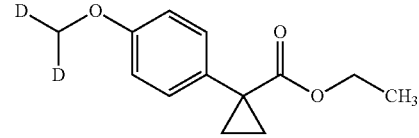 [SMILES: [2H]C([2H])Oc1ccc(C2(C(=O)OCC)CC2)cc1] |
| 426 | R425 | 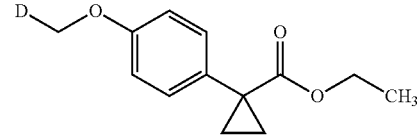 [SMILES: CCOC(=O)C1(c2ccc(OCF)cc2)CC1] |

TABLE 38-continued

| Rf | Syn | Structure |
|---|---|---|
| 427 | R425 | (4-(fluoromethoxy)phenyl)cyclopropane-1-carboxylic acid ethyl ester |
| 428 | R425 | ethyl 2-(4-(dideuteromethoxy)phenyl)-2-oxoacetate |
| 429 | R429 | ethyl (S)-2-(4-(dideuteromethoxy)phenyl)-2-hydroxyacetate |
| 430 | R430 | N-(2-((tert-butyldimethylsilyl)oxy)ethyl)-N-methylsulfamide |

TABLE 39

| Rf | Syn | Structure |
|---|---|---|
| 431 | R431 | ethyl (R)-2-(4-hydroxyphenyl)-2-((2-(trimethylsilyl)ethoxy)methoxy)acetate |
| 432 | R432 | 2-(3-(3-(difluoromethyl)phenyl)allyl)isoindoline-1,3-dione |
| 433 | R432 | 2-(3-(2-fluoro-3-methylphenyl)allyl)isoindoline-1,3-dione |
| 434 | R432 | 2-(3-(3-(but-1-en-1-yl)phenyl)allyl)isoindoline-1,3-dione |

TABLE 39-continued
| Rf | Syn | Structure |
|---|---|---|
| 435 | R432 | 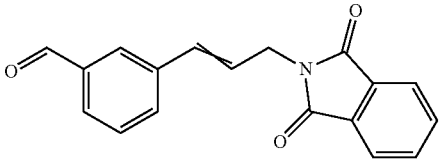 [SMILES: O=Cc1cccc(C=CCN2C(=O)c3ccccc3C2=O)c1] |
| 436 | R437 | 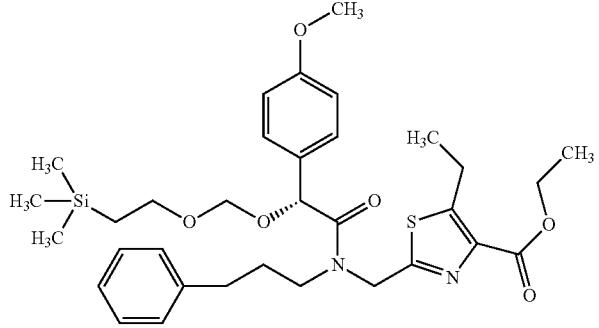 [SMILES: CCOC(=O)c1nc(CN(CCCc2ccccc2)C(=O)[C@H](OCOCC[Si](C)(C)C)c2ccc(OC)cc2)sc1CC] |
| 437 | R437 | 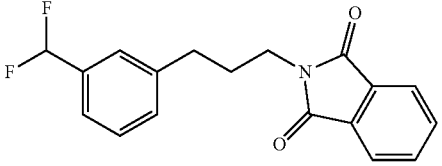 [SMILES: O=C1c2ccccc2C(=O)N1CCCc1cccc(C(F)F)c1] |
| 438 | R437 | 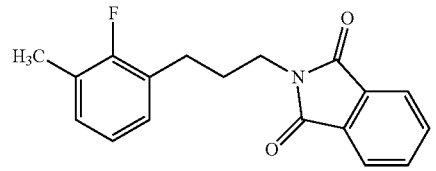 [SMILES: Cc1cccc(CCCN2C(=O)c3ccccc3C2=O)c1F] |
| 439 | R437 | 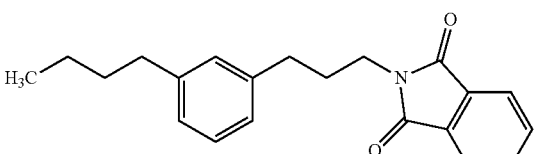 |
| 440 | R440 | 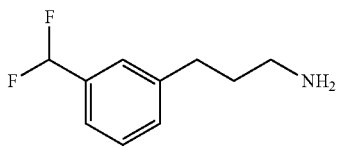 [SMILES: NCCCc1cccc(C(F)F)c1] |
| 441 | R440 | 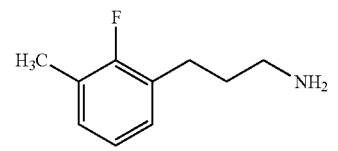 |
| 442 | R440 | 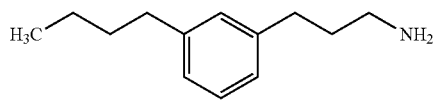 |

//165

TABLE 39-continued

| Rf | Syn | Structure |
|---|---|---|
| 443 | R443 | 2-hydroxy-2-(4-methoxy-2-methylphenyl)acetic acid |
| 444 | R443 | 2-hydroxy-2-(6-methoxypyridin-3-yl)acetic acid |
| 445 | R445 | (R)-2-hydroxy-2-(4-methoxy-2-methylphenyl)acetic acid |
| 446 | R445 | (R)-2-(2-fluoro-4-methoxyphenyl)-2-hydroxyacetic acid |

TABLE 40

| Rf | Syn | Structure |
|---|---|---|
| 447 | R447 | (R)-ethyl 2-hydroxy-2-(4-methoxy-2-methylphenyl)acetate |
| 448 | R448 | (S)-2-(4-methoxy-2-methylphenyl)-2-((2-(trimethylsilyl)ethoxy)methoxy)acetic acid |
| 449 | R449 | (R)-ethyl 2-hydroxy-2-(6-methoxypyridin-3-yl)acetate |

TABLE 40-continued
| Rf | Syn | Structure |
|----|-----|-----------|
| 450 | R450 | 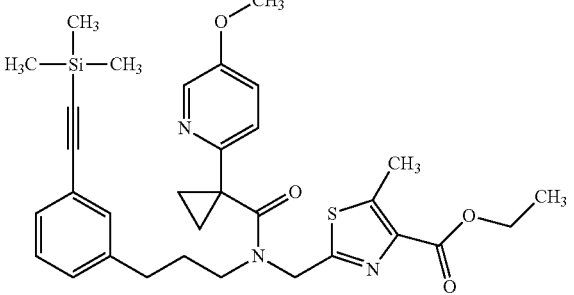 |
| 451 | R451 | 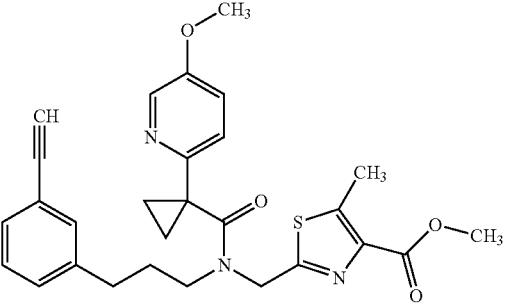 [SMILES: C#Cc1cccc(CCCN(Cc2nc(C(=O)OC)c(C)s2)C(=O)C2(c3ccc(OC)cn3)CC2)c1] |
| 452 | R452 | 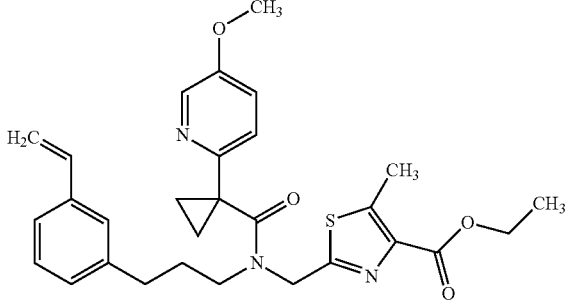 |
| 453 | R453 | 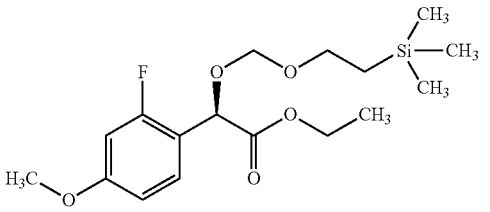 |
| 454 | R454 | 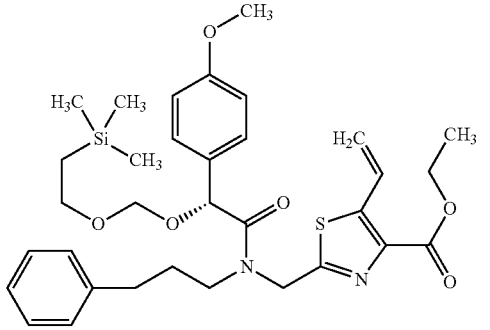 [SMILES: C=Cc1sc(CN(CCCc2ccccc2)C(=O)[C@H](OCOCC[Si](C)(C)C)c2ccc(OC)cc2)nc1C(=O)OCC] |

TABLE 40-continued

| Rf | Syn | Structure |
|---|---|---|
| 455 | R455 | (2-(((3-(2-fluorophenyl)propyl)(tert-butoxycarbonyl)amino)methyl)-5-methylthiazole-4-carboxylic acid) |
| 456 | R456 | (N-ethyl-N-(2-((tert-butyldimethylsilyl)oxy)ethyl)sulfamide) |

TABLE 41

| Rf | Data |
|---|---|
| 1 | [ESI+]: 211 |
| 2 | [ESI+]: 527 |
| 3 | [ESI+]: 209 |
| 4 | [EI+]: 376 |
| 5 | [FAB+]: 441 |
| 6 | [ESI+]: 157 |
| 7 | [EI+]: 184 |
| 8 | [ESI+]: 194 |
| 9 | [ESI+]: 225 |
| 10 | [ESI+]: 655 |
| 11 | [EI+]: 236 |
| 12 | [ESI+]: 251 |
| 13 | [ESI+]: 508 |
| 14 | [EI+]: 308 |
| 15 | [ESI+]: 527 |
| 16 | [ESI+]: 239 |
| 17 | [FAB+]: 511 |
| 18 | [ESI+]: 439 |
| 19 | [ESI+]: 149 |
| 20 | [ESI+]: 175 |
| 21 | [ESI+]: 233 |
| 22 | [ESI+]: 250 |
| 23 | [EI+]: 249, 251 |
| 24 | [ESI+]: 328, 330, 332 |
| 25 | [ESI+]: 206, 208 |
| 26 | [FAB+]: 305 |
| 27 | [ESI+]: 289 |
| 28 | [ESI+]: 405 |
| 29 | [ESI+]: 627 |
| 30 | [ESI+]: 383 |
| 31 | [ESI+]: 466 |
| 32 | [ESI+]: 541 |
| 33 | [EI+]: 199 |

TABLE 42

| Rf | Data |
|---|---|
| 34 | [ESI+]: 483 |
| 35 | [ESI+]: 167 |
| 36 | [FAB+]: 274 |
| 37 | [EI+]: 226 |
| 38 | [ESI+]: 513 |
| 39 | [FAB+]: 319 |
| 40 | [ESI+]: 255 |
| 41 | [ESI+]: 299 |
| 42 | [ESI+]: 483 |
| 43 | [ESI+]: 583 |
| 44 | [ESI+]: 497 |
| 45 | [EI+]: 266 |
| 46 | [ESI+]: 211 |
| 47 | [FAB+]: 483 |
| 48 | NMR-CDCl$_3$: 3.82 (3H, s), 3.84 (3H, s), 6.50 (1H, s), 6.57 (1H, d, J = 8.6 Hz), 7.56 (1H, d, J = 8.6 Hz). |
| 49 | [ESI−]: 199 |
| 50 | NMR-DMSO-d$_6$: 3.73 (3H, s), 4.81 (2H, s), 7.24-7.36 (5H, m), 7.81 (2H, br) |
| 51 | [ESI+]: 273 |
| 52 | [ESI+]: 239 |
| 53 | [ESI+]: 225 |
| 54 | [ESI+]: 254 |
| 55 | [ESI+]: 483 |
| 56 | [ESI+]: 383 |
| 57 | [ESI+]: 223 |
| 58 | [EI+]: 294 |
| 59 | [FAB+]: 469 |
| 60 | [ESI+]: 533, 535 |
| 61 | [ESI+]: 489, 491 |
| 62 | [FAB+]: 481 |
| 63 | [ESI+]: 480 |
| 64 | [ESI+]: 599 |
| 65 | [ESI+]: 499 |

TABLE 43

| Rf | Data |
|---|---|
| 66 | [FAB+]: 454 |
| 67 | [ESI+]: 439 |
| 68 | [ESI+]: 438 |
| 69 | [FAB+]: 437 |
| 70 | [ESI+]: 481 |
| 71 | NMR-DMSO-d$_6$: 3.76-3.86 (2H, m), 3.76-3.86 (2H, m), 3.93-4.02 (2H, m), 5.20-5.37 (1H, m), 7.07 (2H, brs) |
| 72 | [ESI+]: 509 |
| 73 | [ESI+]: 509 |
| 74 | [ESI+]: 533 |
| 75 | [ESI+]: 397 |
| 76 | [FAB+]: 285, 287 |
| 77 | [ESI+]: 383, 385 |
| 78 | [ESI+]: 339 |
| 79 | [ESI+]: 305 |
| 80 | [ESI+]: 281 |
| 81 | [ESI+]: 267 |
| 82 | [APCI+]: 186 |
| 83 | [ESI+]: 225 |
| 84 | [EI+]: 182 |
| 85 | [ESI+]: 173 |
| 86 | [ESI+]: 201 |
| 87 | [ESI+]: 227 |
| 88 | [ESI+]: 241 |
| 89 | [ESI+]: 311 |
| 90 | [FAB+]: 283 |
| 91 | [FAB+]: 413 |

TABLE 43-continued

| Rf | Data |
|---|---|
| 92 | |
| 93 | [ESI+]: 717 |
| 94 | [FAB+]: 260 |
| 95 | [ESI+]: 290 |
| 96 | [ESI+]: 289 |
| 97 | [ESI−]: 285 |

TABLE 44

| Rf | Data |
|---|---|
| 98 | [ESI+]: 561, 563 |
| 99 | [FAB+]: 517 |
| 100 | [FAB+]: 468 |
| 101 | [FAB+]: 467 |
| 102 | [ESI+]: 451 |
| 103 | [ESI+]: 547, 549 |
| 104 | [ESI+]: 483 |
| 105 | [ESI+]: 467 |
| 106 | [ESI+]: 427 |
| 107 | [ESI+]: 441 |
| 108 | [ESI+]: 455 |
| 109 | [ESI+]: 489 |
| 110 | [ESI+]: 505 |
| 111 | [ESI+]: 517 |
| 112 | [ESI+]: 414 |
| 113 | [ESI+]: 471 |
| 114 | [ESI+]: 453 |
| 115 | [ESI+]: 469 |
| 116 | [ESI+]: 469 |
| 117 | [ESI+]: 470 |
| 118 | [ESI+]: 184 |
| 119 | NMR-DMSO-$d_6$: 3.71 (3H, s), 3.74 (3H, s), 7.18 (2H, br) |
| 120 | NMR-CDCl$_3$: 3.39 (3H, s), 3.56 (2H, t, J = 5.2 Hz), 3.88 (3H, s), 4.00 (2H, t, J = 5.2 Hz), 5.49 (2H, br) |
| 121 | NMR-CDCl$_3$: 2.30-2.41 (1H, m), 2.71-2.83 (1H, m), 3.86-3.94 (4H, m), 4.29 (1H, dd, J = 9.0 Hz, 15.0 Hz), 4.67 (2H, t, J = 7.3 Hz), 4.91-5.00 (1H, m), 5.71 (2H, br) |
| 122 | [ESI−]: 193 |
| 123 | [ESI+]: 497 |
| 124 | [ESI+]: 391 |
| 125 | [ESI+]: 419 |
| 126 | [EI+] 290 |
| 127 | [ESI+]: 497 |
| 128 | [ESI+]: 495, 497 |

TABLE 45

| Rf | Data |
|---|---|
| 129 | [ESI+]: 459 |
| 130 | [FAB+]: 491 |
| 131 | [FAB+]: 473 |
| 132 | [FAB+]: 491 |
| 133 | [FAB+]: 491 |
| 134 | [FAB+]: 473 |
| 135 | [ESI+]: 507, 509 |
| 136 | [FAB+]: 480 |
| 137 | [ESI+]: 487 |
| 138 | [ESI+]: 469 |
| 139 | [FAB+]: 469 |
| 140 | [ESI+]: 481 |
| 141 | [ESI+]: 467 |
| 142 | [FAB+]: 481 |
| 143 | [FAB+]: 481 |
| 144 | [ESI+]: 465 |
| 145 | |
| 146 | [ESI+]: 469 |
| 147 | [ESI+]: 461 |
| 148 | [FAB+]: 488 |
| 149 | [ESI+]: 491 |
| 150 | [ESI+]: 475 |
| 151 | [FAB+]: 487 |

TABLE 45-continued

| Rf | Data |
|---|---|
| 152 | [ESI+]: 485, 487 |
| 153 | [ESI+]: 475 |
| 154 | [ESI+]: 459 |
| 155 | [FAB+]: 483 |
| 156 | [FAB+]: 455 |
| 157 | [FAB+]: 505 |
| 158 | [ESI+]: 495 |
| 159 | [ESI+]: 489, 491 |
| 160 | [FAB+]: 567 |
| 161 | [FAB+]: 499 |

TABLE 46

| Rf | Data |
|---|---|
| 162 | [FAB+]: 509 |
| 163 | [FAB+]: 503 |
| 164 | |
| 165 | [ESI+]: 523, 525 |
| 166 | [FAB+]: 487 |
| 167 | [FAB+]: 519 |
| 168 | [FAB+]: 501 |
| 169 | [ESI+]: 519 |
| 170 | [ESI+]: 519 |
| 171 | [ESI+]: 501 |
| 172 | |
| 173 | [FAB+]: 508 |
| 174 | [ESI+]: 515 |
| 175 | [ESI+]: 497 |
| 176 | |
| 177 | |
| 178 | [ESI+]: 516 |
| 179 | |
| 180 | |
| 181 | [ESI+]: 515 |
| 182 | [FAB+]: 503 |
| 183 | [FAB+]: 483 |
| 184 | [ESI+]: 345 |
| 185 | [EI] 308 |
| 186 | [EI] 340 |
| 187 | [CI+]: 323 |
| 188 | [FAB+]: 341 |
| 189 | [ESI+]: 341 |
| 190 | [ESI+]: 323 |
| 191 | |
| 192 | [CI+]: 330 |
| 193 | [ESI+]: 337 |
| 194 | |

TABLE 47

| Rf | Data |
|---|---|
| 195 | |
| 196 | |
| 197 | |
| 198 | [ESI+]: 339, 341 |
| 199 | |
| 200 | NMR-CDCl$_3$: 1.41 (3H, t, J = 7.1 Hz), 1.60 (2H, brs), 1.91 (2H, br), 2.44 (2H, br), 3.44 (2H, br), 3.81 (6H, s), 4.44 (2H, q, J = 7.1 Hz), 5.02 (1H, br), 5.51 (1H, dd, J = 2.5, 12 Hz), 6.22 (1H, d, J = 18 Hz), 6.55 (2H, brs), 6.84-7.03 (2H, m), 7.08-7.25 (3H, m), 8.19 (1H, s). |
| 201 | [ESI+]: 509 |
| 202 | [FAB+]: 547 |
| 203 | |
| 204 | [FAB+]: 537 |
| 205 | [ESI+]: 517, 519 |
| 206 | [ESI+]: 487 |
| 207 | [ESI+]: 511 |
| 208 | [ESI+]: 533 |
| 209 | [ESI+]: 523 |
| 210 | [ESI+]: 517, 519 |

TABLE 47-continued

| Rf | Data |
|---|---|
| 211 | [ESI+]: 595 |
| 212 | [ESI+]: 527 |
| 213 | [ESI+]: 537, 539 |
| 214 | [ESI+]: 531, 533 |
| 215 | |
| 216 | [ESI+]: 511 |
| 217 | [ESI+]: 338 |
| 218 | [ESI+]: 337 |
| 219 | NMR-DMSO-$d_6$: 1.88 (2H, br), 2.01 (3H, s), 2.41-2.60 (2H, m), 3.34-3.42 (2H, m), 3.75 (6H, s), 4.96 (2H, br), 6.61 (2H, br), 7.01-7.16 (5H, m), 7.61-7.66 (2H, m), 8.23 (1H, s). [FAB+]: 454 |
| 220 | [ESI+]: 391 |
| 221 | [ESI+]: 433, 435 (M + 23) |
| 222 | [ESI+]: 465 |

TABLE 48

| Rf | Data |
|---|---|
| 223 | [ESI+]: 466 |
| 224 | [ESI+]: 495 |
| 225 | [ESI+]: 385 (M + 23) |
| 226 | [ESI+]: 469 |
| 227 | [ESI−]: 357 |
| 228 | [ESI+]: 483 |
| 229 | [ESI+]: 505, 507 |
| 230 | [ESI+]: 485 |
| 231 | [ESI+]: 195 |
| 232 | [ESI+]: 194 |
| 233 | [ESI+]: 483 |
| 234 | [ESI+]: 479 |
| 235 | [ESI−]: 379 |
| 236 | [FAB−]: 313 |
| 237 | [ESI+]: 483 |
| 238 | [ESI+]: 480 |
| 239 | [ESI+]: 506, 508 |
| 240 | [ESI+]: 484 |
| 241 | [ESI+]: 500 |
| 242 | [ESI+]: 483 |
| 243 | [ESI+]: 491 |
| 244 | [ESI+]: 586 |
| 245 | [ESI+]: 472 |
| 246 | [ESI+]: 470 |
| 247 | [ESI+]: 211 |
| 248 | [ESI+]: 516 |
| 249 | [ESI+]: 490, 492 |
| 250 | [ESI+]: 456 |
| 251 | [ESI+]: 603 |
| 252 | [ESI+]: 552 |
| 253 | [ESI+]: 494 |
| 254 | [ESI+]: 603 |
| 255 | [ESI+]: 585 |

TABLE 49

| Rf | Data |
|---|---|
| 256 | [ESI+]: 434 |
| 257 | [ESI+]: 484 |
| 258 | [ESI+]: 498 |
| 259 | [ESI+]: 591 |
| 260 | [ESI+]: 498 |
| 261 | [ESI+]: 600 |
| 262 | [ESI+]: 471 |
| 263 | [ESI+]: 544, 546 |
| 264 | [ESI+]: 500, 502 |
| 265 | [ESI+]: 522 |
| 266 | [APCI+]: 476 |
| 267 | [ESI+]: 471 |
| 268 | [ESI+]: 472 |
| 269 | [ESI+]: 455 |
| 270 | [ESI+]: 506 |

TABLE 49-continued

| Rf | Data |
|---|---|
| 271 | [ESI+]: 490 |
| 272 | [ESI+]: 506 |
| 273 | [ESI+]: 492 |
| 274 | [ESI+]: 603 |
| 275 | [ESI+]: 609 |
| 276 | [FAB−]: 601 |
| 277 | [ESI+]: 483 |
| 278 | [ESI+]: 484 |
| 279 | [ESI+]: 506 |
| 280 | [FAB+]: 649, 651 |
| 281 | [ESI+]: 599 |
| 282 | [ESI+]: 433, 435 (M + 23) |
| 283 | [ESI−]: 343 |
| 284 | [FAB−]: 311 |
| 285 | [FAB−]: 312 |
| 286 | [FAB−]: 312 |
| 287 | [ESI+]: 353 (M + 23) |

TABLE 50

| Rf | Data |
|---|---|
| 288 | NMR-CDCl$_3$: 1.24 (2H, m), 1.65 (2H, m), 3.37 (3H, s), 4.43 (2H, s), 7.26 (2H, m), 7.32 (2H, m). |
| 289 | [ESI+]: 157 |
| 290 | [APCI]: 155 |
| 291 | [ESI+]: 194 |
| 292 | [ESI+]: 211 |
| 293 | [ESI+]: 194 |
| 294 | [ESI+]: 561 |
| 295 | [ESI+]: 576 |
| 296 | [ESI+]: 590 |
| 297 | NMR-CDCl$_3$: 1.08 (2H, m), 1.36 (9H, s), 1.52 (2H, m), 7.19 (2H, m), 7.41 (2H, m). |
| 298 | [ESI+]: 534 |
| 299 | [ESI+]: 534 |
| 300 | [APCI+]: 504 |
| 301 | [APCI+]: 175 |
| 302 | [ESI+]: 192 |
| 303 | [ESI+]: 383, 385 |
| 304 | [ESI+]: 339 |
| 305 | [ESI+]: 510, 512 (M + 23) |
| 306 | [ESI+]: 461, 463 (M + 23) |
| 307 | [ESI+]: 437 |
| 308 | [ESI+]: 397 |
| 309 | [ESI+]: 417, 419 |
| 310 | [ESI+]: 368 |
| 311 | [ESI+]: 369 |
| 312 | [ESI+]: 415 |
| 313 | [ESI+]: 388, 390 |
| 314 | [EI]: 199 |
| 315 | [APCI−]: 466 |
| 316 | [ESI+]: 539, 541 (M + 23) |
| 317 | [ESI+]: 515 |
| 318 | [ESI+]: 469 |
| 319 | [ESI+]: 349 |

TABLE 51

| Rf | Data |
|---|---|
| 320 | [ESI+]: 353, 355 |
| 321 | [ESI+]: 323 |
| 322 | [ESI+]: 337 |
| 323 | |
| 324 | [ESI+]: 339 |
| 325 | [ESI+]: 337 |
| 326 | [ESI+]: 333 |
| 327 | [ESI+]: 337 |
| 328 | [ESI+]: 337 |
| 329 | [ESI+]: 333 |
| 330 | [ESI+]: 359, 361 |
| 331 | [ESI+]: 353 |

TABLE 51-continued

| Rf | Data |
|---|---|
| 332 | [ESI+]: 337 |
| 333 | [ESI+]: 345 |
| 334 | [ESI+]: 369 |
| 335 | [ESI+]: 343, 345 |
| 336 | [ESI+]: 309 |
| 337 | [ESI+]: 337 |
| 338 | [ESI+]: 405 |
| 339 | [ESI+]: 347 |
| 340 | [ESI+]: 337 |
| 341 | [ESI+]: 288 |
| 342 | [ESI+]: 351 |
| 343 | [ESI+]: 351 |
| 344 | [ESI+]: 325 |
| 345 | [ESI+]: 397, 399 |
| 346 | [ESI+]: 375 |
| 347 | NMR-CDCl$_3$: 1.41 (3H, t, J = 7.1 Hz), 1.58 (1H, br), 1.84 (2H, m), 3.49 (1H, s), 4.05 (2H, s), 4.41 (2H, q, J = 7.1 Hz), 6.93 (1H, d, J = 4.3 Hz), 7.25 (2H, m). |
| 348 | [ESI+]: 359 |
| 349 | [ESI−]: 255 |
| 350 | [EI]: 254 |
| 351 | [ESI+]: 494 |

TABLE 52

| Rf | Data |
|---|---|
| 352 | [ESI+]: 523 |
| 353 | [ESI+]: 497 |
| 354 | [ESI+]: 498 |
| 355 | [ESI+]: 511 |
| 356 | [ESI+]: 533, 535 |
| 357 | [ESI+]: 512 |
| 358 | [ESI+]: 511 |
| 359 | [ESI+]: 507 |
| 360 | [ESI+]: 511 |
| 361 | [ESI+]: 512 |
| 362 | [ESI+]: 508 |
| 363 | [ESI+]: 534, 536 |
| 364 | [ESI+]: 512 |
| 365 | [ESI+]: 528 |
| 366 | [ESI+]: 511 |
| 367 | [ESI+]: 613 |
| 368 | [ESI+]: 519 |
| 369 | [ESI+]: 614 |
| 370 | [ESI+]: 500 |
| 371 | [ESI+]: 544 |
| 372 | [ESI+]: 518 |
| 373 | [ESI+]: 484 |
| 374 | [ESI+]: 631 |
| 375 | [ESI+]: 512 |
| 376 | [ESI+]: 580 |
| 377 | [ESI+]: 522 |
| 378 | [ESI+]: 631 |
| 379 | [ESI+]: 462 |
| 380 | [ESI+]: 526 |
| 381 | [ESI+]: 619 |
| 382 | [ESI+]: 526 |
| 383 | [ESI+]: 499 |
| 384 | [ESI+]: 628 |

TABLE 53

| Rf | Data |
|---|---|
| 385 | [ESI+]: 572, 574 |
| 386 | [ESI+]: 528, 530 |
| 387 | [ESI+]: 550 |
| 388 | [ESI+]: 499 |
| 389 | [ESI+]: 500 |
| 390 | [ESI+]: 483 |
| 391 | [ESI+]: 631 |
| 392 | [ESI+]: 637 |

TABLE 53-continued

| Rf | Data |
|---|---|
| 393 | [ESI+]: 631 |
| 394 | [ESI+]: 511 |
| 395 | [ESI+]: 534 |
| 396 | [ESI+]: 701, 699 (M + 23) |
| 397 | [ESI+]: 557, 559 |
| 398 | [ESI−]: 199 |
| 399 | [ESI+]: 225 |
| 400 | NMR-CDCl$_3$: 1.15 (2H, m), 1.36 (9H, s), 1.58 (2H, m), 7.49 (2H, m), 7.81 (2H, m), 9.99 (1H, s). |
| 401 | NMR-CDCl$_3$: 1.10 (2H, m), 1.36 (9H, s), 1.52 (2H, m), 2.04 (1H, br), 4.67 (2H, d, J = 5.6 Hz), 7.28-7.34 (4H, m). |
| 402 | NMR-CDCl$_3$: 1.10 (2H, m), 1.36 (9H, s), 1.51 (2H, m), 3.37 (3H, s), 4.43 (2H, s), 7.25 (2H, m), 7.31 (2H, m). |
| 403 | [ESI+]: 209 |
| 404 | [ESI+]: 364 (M + 23) |
| 405 | [ESI+]: 187 |
| 406 | [ESI+]: 205 |
| 407 | [ESI+]: 265 (M + 23) |
| 408 | [ESI+]: 283 (M + 23) |
| 409 | [ESI+]: 279 (M + 23) |
| 410 | [ESI+]: 301 (M + 23) |
| 411 | [ESI+]: 413 (M + 23) |
| 412 | [ESI+]: 409 (M + 23) |
| 413 | [ESI+]: 431 (M + 23) |
| 414 | [ESI+]: 365 (M + 23) |
| 415 | [ESI+]: 395 (M + 23) |

TABLE 54

| Rf | Data |
|---|---|
| 416 | NMR-CDCl$_3$: −0.01 (9H, s), 0.87-0.92 (2H, m), 1.21 (3H, t, J = 7.1 Hz), 3.54-3.73 (2H, m), 3.80 (3H, s), 4.11-4.25 (2H, m), 4.68-4.78 (2H, m), 5.11 (1H, s), 6.88 (2H, d, J = 8.6 Hz), 7.36 (2H, d, J = 8.6 Hz). |
| 417 | ESI+: 439 (M + 23) |
| 418 | [ESI+]: 342 |
| 419 | [ESI+]: 497 |
| 420 | [ESI+]: 183 |
| 421 | [ESI−]: 615 |
| 422 | [ESI+]: 613 |
| 423 | [ESI+]: 620, 622 |
| 424 | [ESI−]: 205 |
| 425 | [ESI+]: 245 (M + 23) |
| 426 | [ESI+]: 244 (M + 23) |
| 427 | [ESI+]: 239 |
| 428 | NMR-CDCl$_3$: 1.42 (3H, t, J = 7.2 Hz), 3.86 (1H, s), 4.43 (2H, q, J = 7.2 Hz), 6.96-6.99 (2H, m), 7.99-8.02 (2H, m). |
| 429 | [ESI+]: 235 (M + 23) |
| 430 | NMR-CDCl$_3$: 0.10 (6H, s), 0.91 (9H, s), 2.92 (3H, s), 3.39 (2H, t, J = 4.8 Hz), 3.80 (2H, t, J = 4.8 Hz), 4.72 (2H, br). |
| 431 | [FAB−]: 325 |
| 432 | [CI+]: 314 |
| 433 | [ESI+]: 296 |
| 434 | [ESI+]: 318 |
| 435 | [ESI+]: 292 |
| 436 | [ESI+]: 627 |
| 437 | EI: 315 |
| 438 | [ESI+]: 298 |
| 439 | [ESI+]: 322 |
| 440 | [ESI+]: 186 |
| 441 | [ESI+]: 168 |
| 442 | [ESI+]: 192 |
| 443 | [ESI−]: 195 |
| 444 | [ESI+]: 184 |
| 445 | [ESI+]: 219 (M + 23) |

TABLE 55

| Rf | Data |
|---|---|
| 446 | [ESI−]: 199 |
| 447 | [EI]: 224 |

TABLE 55-continued

| Rf | Data |
|---|---|
| 448 | [FAB−]: 325 |
| 449 | [ESI+]: 212 |
| 450 | [ESI+]: 590 |
| 451 | [ESI+]: 504 |
| 452 | [ESI+]: 520 |
| 453 | [ESI+]: 381 (M + 23) |
| 454 | [ESI+]: 625 |
| 455 | [ESI+]: 409 |
| 456 | [ESI+]: 283 |

Example 1

N-[(Dimethylamino)sulfonyl]-2-{[(3-phenylpropyl) amino]methyl}-5-methyl-1,3-thiazole-4-carboxamide hydrochloride (100 mg), 1-(4-methoxyphenyl)cyclobutanecarboxylic acid (50 mg), triethylamine (0.15 mL), and HATU (120 mg) were added to acetonitrile (3.5 mL), followed by stirring at room temperature for 5 hours. The reaction mixture was concentrated under reduced pressure, and to the obtained residue were added water and 1 M hydrochloric acid, followed by extraction with CHCl$_3$. The organic layer was dried over Na$_2$SO$_4$, and the solvent was evaporated under reduced pressure. The obtained residue was purified by silica gel column chromatography (hexane:ethyl acetate=1:3) to prepare N-[(dimethylamino)sulfonyl]-2-{[{1-(4-methoxyphenyl)cyclobutyl]carbonyl}(3-phenylpropyl)amino]methyl}-5-methyl-1,3-thiazole-4-carboxamide (47 mg).

Example 2

To a mixture of N-[(dimethylamino)sulfonyl]-2-{[(3-phenylpropyl)amino]methyl}-1,3-thiazole-4-carboxamide hydrochloride (10.5 mg), 3,5-diethoxybenzoic acid (6.3 mg), triethylamine (10.4 µL), and DMF (0.50 mL) was added a HATU (11.4 mg)/DMF (0.10 mL) solution at room temperature, followed by stirring overnight. To the reaction mixture was added an appropriate amount of purified water, followed by extraction with CHCl$_3$. The organic layer was concentrated under reduced pressure, and the obtained residue was purified by preparative high performance liquid chromatography (MeOH/0.1% aqueous formic acid solution) to prepare 2-{[(3,5-diethoxybenzoyl)(3-phenylpropyl)amino]methyl}-N-[(dimethylamino)sulfonyl]-1,3-thiazole-4-carboxamide (9.2 mg).

Example 3

N-({[(2-{[(3,5-Dimethoxy-4-methylbenzoyl)(3-phenylpropyl)amino]methyl}-1,3-thiazol-4-yl)carbonyl]amino}sulfonyl)-N-methylglycine (0.19 g) was prepared from methyl N-({[(2-{[(3,5-dimethoxy-4-methylbenzoyl)(3-phenylpropyl)amino]methyl}-1,3-thiazol-4-yl)carbonyl]amino}sulfonyl)-N-methylglycinate (0.22 g) in the same manner as the method of Preparation Example 5.

Example 4

5-(Difluoromethyl)-2-{[(3,5-dimethoxy-4-methylbenzoyl)(3-phenylpropyl)amino]methyl}-1,3-thiazole-4-carboxylic acid (40 mg) was prepared from ethyl 5-(difluoromethyl)-2-{[(3,5-dimethoxy-4-methylbenzoyl)(3-phenylpropyl)amino]methyl}-1,3-thiazole-4-carboxylate (60 mg) in the same manner as in Preparation Example 5.

Subsequently, 5-(difluoromethyl)-2-{[(3,5-dimethoxy-4-methylbenzoyl)(3-phenylpropyl)amino]methyl}-1,3-thiazole-4-carboxylic acid and CDI (19 mg) was added to anhydrous THF (2 mL), followed by stirring at 80° C. for 1 hour. To the reaction mixture were added sulfamide (23 mg) and DBU (24 mg) under ice-cooling, followed by stirring at room temperature for about 3 hours. The reaction mixture was neutralized by the addition of an appropriate amount of ice water and 1 M hydrochloric acid, and then extracted with CHCl$_3$. The organic layer was washed with brine and dried over MgSO$_4$, and then the solvent was evaporated under reduced pressure. The obtained residue was solidified with diisopropyl ether to prepare N-(aminosulfonyl)-5-(difluoromethyl)-2-{[(3,5-dimethoxy-4-methylbenzoyl)(3-phenylpropyl)amino]methyl}-1,3-thiazole-4-carboxamide (29 mg).

Example 5

2-{[(3,5-Dimethoxy-4-methylbenzoyl)(3-phenylpropyl)amino]methyl}-1,3-thiazole-4-carboxamide (50 mg) and 55% sodium hydride (7.2 mg) was added to THF (2 mL), followed by stirring at room temperature for about 115 minutes. Thereafter, to the reaction mixture was added thiophene-2-sulfonyl chloride (30 mg) under ice-cooling, followed by further stirring at room temperature for about 15 hours. To the reaction mixture was added a saturated aqueous ammonium chloride solution, followed by extraction with an appropriate amount of ethyl acetate. The organic layer was washed with brine and dried over MgSO$_4$, and then the solvent was evaporated under reduced pressure. The obtained residue was purified by silica gel column chromatography (CHCl$_3$:MeOH=50:1) to prepare a colorless viscous substance (55 mg). The substance was crystallized from a small amount of diethyl ether to prepare 2-{[(3,5-dimethoxy-4-methylbenzoyl)(3-phenylpropyl)amino]methyl}-N-(2-thienylsulfonyl)-1,3-thiazole-4-carboxamide (41 mg).

Example 6

(2-{[(3,5-Dimethoxy-4-methylbenzoyl)(3-phenylpropyl)amino]methyl}-4-{[(dimethylamino)sulfonyl]carbamoyl}-1,3-thiazol-5-yl)methyl acetate (95 mg) was added to a THF/EtOH (2:1) solution (1.5 mL), and subsequently, a 1 M aqueous sodium hydroxide solution (0.33 mL) was added dropwise thereto under ice-cooling, followed by stirring at room temperature for about 20 minutes. To the reaction mixture was added an appropriate amount of a mixed solution of a saturated aqueous ammonium chloride solution/ice water, including 1 M hydrochloric acid (1.5 mL), followed by extraction with ethyl acetate twice. The organic layer was washed with brine and dried over MgSO$_4$, and then the solvent was evaporated under reduced pressure to prepare colorless syrup (84 mg). The syrup was crystallized from a small amount of ethyl acetate/hexane (1:1) solution and a diethyl ether/diisopropyl ether (1:1) solution, washed again, and collected by filtration to prepare 2-{[(3,5-dimethoxy-4-methylbenzoyl)(3-phenylpropyl)amino]methyl}-N-[(dimethylamino)sulfonyl]-5-(hydroxymethyl)-1,3-thiazole-4-carboxamide (71 mg).

Example 7

2-{[(3,5-Dimethoxy-4-methylbenzoyl)(3-phenylpropyl)amino]methyl}-5-methyl-1,3-thiazole-4-carboxylic acid (150 mg) and CDI (78 mg) was added to anhydrous THF (5 mL), followed by heating at 60° C. for about 1 hour. To the reaction mixture were added N,N-dimethylsulfamide (60 mg) and DBU (73 mg) under ice-cooling, respectively, followed by stirring at room temperature overnight. The reaction mixture was concentrated under reduced pressure, and neutralized by the addition of an appropriate amount of purified water and 1 M hydrochloric acid, and then extracted from chloroform. The obtained organic layer was dried over MgSO$_4$, and the solvent was evaporated under reduced pressure. The obtained residue was purified by silica gel column chromatography (hexane/ethyl acetate=1:2) to obtain 2-{[(3,5-dimethoxy-4-methylbenzoyl)(3-phenylpropyl)amino]methyl}-N-[(dimethylamino)sulfonyl]-5-methyl-1,3-thiazole-4-carboxamide (111 mg) as a white solid.

Example 8

2-{[(3,5-Dimethoxy-4-methylbenzoyl)(3-phenylpropyl)amino]methyl}-5-methyl-1,3-thiazole-4-carboxylic acid (130 mg), benzene sulfonamide (54 mg), DMAP (42 mg), and WSCD HCl (66 mg) were added to methylene chloride (5.2 mL), followed by stirring at room temperature for about 3 days. To the reaction mixture was added an appropriate amount of CHCl$_3$ and 0.2 M hydrochloric acid, followed by performing liquid-separation. The organic layer was washed and dried, and the solvent was evaporated under reduced pressure. The obtained residue was purified by silica gel column chromatography (CHCl$_3$:MeOH=50:1) to prepare a white foam. This product was crystallized from ethyl acetate/diethyl ether solution to prepare 2-{[(3,5-dimethoxy-4-methylbenzoyl)(3-phenylpropyl)amino]methyl}-N-(phenylsulfonyl)-1,3-thiazole-4-carboxamide (140 mg).

Example 9

N-(Aminosulfonyl)-2-{[(3,5-dimethoxy-4-methylbenzoyl)(3-phenylpropyl)amino]methyl}-1,3-thiazole-4-carboxamide (390 mg) was added to THF (10 mL), followed by cooling to around 0° C. in an ice bath, and subsequently, 55% sodium hydride (38 mg) was added thereto, followed by stirring at room temperature for about 30 minutes. The reaction mixture was cooled to 0° C. again, and methyl iodide (228 mg) was added thereto, followed by stirring at room temperature overnight. To the reaction mixture were added ice water and hydrochloric acid, followed by extraction with ethyl acetate. The organic layer was washed with brine and dried over MgSO$_4$, and then the solvent was evaporated. The obtained residue was purified by (CHCl$_3$:MeOH=20:1) to prepare N-(aminosulfonyl)-2-{[(3,5-dimethoxy-4-methylbenzoyl)(3-phenylpropyl)amino]methyl}-N-methyl-1,3-thiazole-4-carboxamide (181 mg).

Example 10

2-{[(3,5-Dimethoxy-4-methylbenzoyl)(3-phenylpropyl)amino]methyl}-N-{[(2-hydroxyethyl)(methyl)amino]sulfonyl}-1,3-thiazole-4-carboxamide (150 mg), pyridine (0.1 mL), DMAP (31 mg), and acetyl chloride (100 mg) were sequentially added to methylene chloride (10 mL), followed by stirring at room temperature for about 3 hours. To the reaction mixture was added a saturated aqueous ammonium chloride solution, followed by extraction with an appropriate amount of ethyl acetate. The organic layer was washed with brine and dried over MgSO$_4$, and then the solvent was evaporated. The obtained residue was purified by silica gel column chromatography (ethyl acetate), and then solidified with diisopropyl ether to prepare ethyl 2-[({[(2-{[(3,5-dimethoxy-4-methylbenzoyl)(3-phenylpropyl)amino]methyl}-1,3-thiazol-4-yl)carbonyl]amino}sulfonyl)(methyl)amino]acetate (94 mg).

Example 11

N-[(3-{[tert-Butyl (dimethyl)silyl]oxy}pyrrolidin-1-yl)sulfonyl]-2-{[(3,5-dimethoxy-4-methylbenzoyl)(3-phenylpropyl)amino]methyl}-1,3-thiazole-4-carboxamide (580 mg) was added to THF (10 mL), and subsequently, a 1 M TBAF/THF solution (2.02 mL) was added dropwise thereto, followed by stirring at room temperature overnight. The reaction mixture was concentrated under reduced pressure, and the obtained residue was neutralized by the addition of an appropriate amount of 1 M hydrochloric acid, and then extracted with CHCl$_3$ several times. The organic layer was washed with brine and dried over MgSO$_4$, and then the solvent was evaporated under reduced pressure. The obtained residue was purified by silica gel column chromatography (CHCl$_3$:MeOH=20:1) to obtain 2-{[(3,5-dimethoxy-4-methylbenzoyl)(3-phenylpropyl)amino]methyl}-N-[(3-hydroxypyrrolidin-1-yl)sulfonyl]-1,3-thiazole-4-carboxamide (383 mg) as a white solid.

Example 12

Methyl allyl({[(2-{[(3,5-dimethoxy-4-methylbenzoyl)(3-phenylpropyl)amino]methyl}-1,3-thiazol-4-yl)carbonyl]amino}sulfonyl)carbamate (66 mg), tetrakis(triphenylphosphine) palladium (0) (20 mg), and 1,3-pyrimidine-2,4,6(1H,3H,5H)-trione (50 mg) were added to methylene chloride (5 mL), followed by stirring at room temperature for 2 hours. The mixture was acidified by the addition of 1 M hydrochloric acid, and then extracted with CHCl$_3$ several times. The organic layer was washed with brine and dried over MgSO$_4$, and then the solvent was evaporated under reduced pressure. The obtained residue was purified by silica gel column chromatography (CHCl$_3$). The isolated purified product thus obtained was solidified with a hexane/ethyl acetate (2:1) solution to prepare methyl({[(2-{[(3,5-dimethoxy-4-methylbenzoyl)(3-phenylpropyl)amino]methyl}-1,3-thiazol-4-yl)carbonyl]amino}sulfonyl)carbamate (36 mg).

Example 13 tert-Butyl 4-({[(2-{[(3,5-dimethoxy-4-methylbenzoyl)(3-phenylpropyl)amino]methyl}-1,3-thiazol-4-yl)carbonyl]amino}sulfonyl)piperidine-1-carboxylate (235 mg) and a 4 M hydrochloric acid/dioxane solution (5 mL) were added to dioxane (5 mL), followed by stirring at room temperature for 3 hours. The solvent was evaporated under reduced pressure to prepare 2-{[(3,5-dimethoxy-4-methylbenzoyl)(3-phenylpropyl)amino]methyl}-N-(piperazin-1-ylsulfonyl)-1,3-thiazole-4-carboxamide hydrochloride (205 mg).

Example 14

2-{[(3,5-Dimethoxy-4-methylbenzoyl)(3-phenylpropyl)amino]methyl}-N4 {[(2,2-dimethyl-1,3-dioxan-4-yl)methyl](methyl)amino}sulfonyl)-1,3-thiazole-4-carboxamide (260 mg) was added to THF/purified water (10:1) (2.2 mL), and subsequently trifluoroacetic acid (2 mL) was added dropwise thereto under ice-cooling, followed by stirring at room temperature for about 1 hour. To the reaction mixture was added ice water (20 to 30 g), followed by extraction with an appropriate amount of ethyl acetate twice. The organic layer was washed with brine and dried over MgSO$_4$, and then the solvent was evaporated under reduced pressure. The obtained residue was purified by silica gel column chromatography (CHCl₃:MeOH=40:1) to prepare a white foam (210 mg). The obtained white foam was crystallized from a small amount of a hexane/ethyl acetate (1:3) solution, and collected by filtration while diluting and washing with diethyl ether to prepare N-{[(2,3-dihydroxypropyl)(methyl)amino]sulfonyl}-2-{[(3,5-dimethoxy-4-methylbenzoyl)(3-phenylpropyl)amino]methyl}-1,3-thiazole-4-carboxamide (195 mg) as a white powder.

Example 15

Benzyl N-({[(2-{[(3,5-dimethoxy-4-methylbenzoyl)(3-phenylpropyl)amino]methyl}-1,3-thiazol-4-yl)carbonyl]amino}sulfonyl)-N-(2-fluoroethyl)glycinate (1.22 g) and 10% palladium/carbon (50% wet) (240 mg) were added to acetic acid (35 mL), followed by stirring at a normal temperature/a normal pressure overnight. The catalyst was filtered through Celite, and the solvent was evaporated under reduced pressure. To the obtained residue was added an appropriate amount of ethyl acetate/toluene solution, and the solvent was evaporated under reduced pressure. The obtained orange-white foam was purified by silica gel column chromatography (CHCl₃:MeOH-40:1) to obtain a white foam (0.53 g). The obtained white foam was crystallized from a warmed ethyl acetate/hexane (1:1) solution (about 10 mL) to prepare N-({[(2-{[(3,5-dimethoxy-4-methylbenzoyl)(3-phenylpropyl)amino]methyl}-1,3-thiazol-4-yl)carbonyl]amino}sulfonyl)-N-(2-fluoroethyl)glycine (0.4 g).

Example 16

2-{[(3,5-Dimethoxy-4-methylbenzoyl)(3-phenylpropyl)amino]methyl}-N-(piperazin-1-ylsulfonyl)-1,3-thiazole-4-carboxamide hydrochloride (115 mg) was added to acetonitrile (5 mL), and subsequently, triethylamine (0.13 mL) and acetyl chloride (15 mg) were added thereto under ice-cooling, followed by stirring at room temperature for 1 hour. The solvent was evaporated under reduced pressure, and the obtained residue was adjusted to be weakly acidic by the addition of an appropriate amount of purified water and 1 M hydrochloric acid, followed by extraction with an appropriate amount of ethyl acetate. The organic layer was washed with brine and dried over MgSO₄, and then the solvent was evaporated. The obtained residue was purified by silica gel column chromatography (CHCl₃:MeOH=20:1). The isolated product thus obtained was solidified with diisopropyl ether to prepare N-[(4-acetylpiperazin-1-yl)sulfonyl]-2-{[(3,5-dimethoxy-4-methylbenzoyl)(3-phenylpropyl)amino]methyl}-1,3-thiazole-4-carboxamide (116 mg).

Example 17

N-[(2-Acetylhydrazino)sulfonyl]-2-{[(3,5-dimethoxy-4-methylbenzoyl)(3-phenylpropyl)amino]methyl}-1,3-thiazole-4-carboxamide (34 mg) was prepared from tert-butyl 2-({[(2-{[(3,5-dimethoxy-4-methylbenzoyl)(3-phenylpropyl)amino]methyl}-1,3-thiazol-4-yl)carbonyl]amino}sulfonyl)hydrazinecarboxylate (60 mg) by carrying out the same methods as in Example 13 and Example 16, successively.

Example 18

N-({[(2-{[(3,5-Dimethoxy-4-methylbenzoyl)(3-phenylpropyl)amino]methyl}-1,3-thiazol-4-yl)carbonyl]amino}sulfonyl)-N-methylglycine (140 mg), HOBT (38 mg), and WSCD HCl (53 mg) were added to DMF (2 mL), and a 7 M aqueous ammonia/MeOH solution (0.12 mL) was added dropwise thereto, followed by stirring at room temperature for about 13 hours. To the reaction mixture was added 0.2 to 0.3 M aqueous hydrochloric acid (20 to 30 mL), followed by extraction with an appropriate amount of ethyl acetate twice. The organic layer was sequentially washed with a saturated aqueous sodium hydrogen carbonate solution and brine, and dried over MgSO₄, and then the solvent was evaporated under reduced pressure. The obtained residue was purified by silica gel column chromatography (CHCl₃:MeOH=30:1) to prepare colorless oily substance. The obtained oily substance was crystallized from a small amount of ethyl acetate/hexane (2:1) solution, and collected by filtration while diluting and washing with diethyl ether to prepare N-{[(2-amino-2-oxoethyl)(methyl)amino]sulfonyl}-2-{[(3,5-dimethoxy-4-methylbenzoyl)(3-phenylpropyl)amino]methyl}-1,3-thiazole-4-carboxamide (30 mg).

Example 19

2-{[(3,5-Dimethoxy-4-methylbenzoyl)(3-phenylpropyl)amino]methyl}-N-({methyl[2-(methylsulfanyl)ethyl]amino}sulfonyl)-1,3-thiazole-4-carboxamide (90 mg) was added to methylene chloride (3 mL), and subsequently, 3-chloroperbenzoic acid (37 mg) was added thereto while sufficiently cooling in an MeOH/ice bath, followed by stirring for about 40 minutes under cooling. To the reaction mixture was added an aqueous sodium hydrogen carbonate solution, followed by extraction with an appropriate amount of CHCl₃. The organic layer was sequentially washed with a saturated aqueous sodium hydrogen carbonate solution and brine, and dried over MgSO₄, and then the solvent was evaporated under reduced pressure. The obtained residue was purified by silica gel column chromatography (hexane:ethyl acetate=1:2) to prepare 2-{[(3,5-dimethoxy-4-methylbenzoyl)(3-phenylpropyl)amino]methyl}-N-({methyl [2-(methylsulfinyl)ethyl]amino}sulfonyl)-1,3-thiazole-4-carboxamide (71 mg).

Example 20

2-{[(3,5-Dimethoxy-4-methylbenzoyl)(3-phenylpropyl)amino]methyl}-N-({methyl[2-(methylsulfanyl)ethyl]amino}sulfonyl)-1,3-thiazole-4-carboxamide (100 mg) and 3-chloroperbenzoic acid (93 mg) were added to methylene chloride (3 mL), followed by stirring at room temperature for about 3.5 hours. To the reaction mixture was added an aqueous sodium hydrogen carbonate solution, followed by extraction with an appropriate amount of CHCl₃. The organic layer was sequentially washed with a saturated aqueous sodium hydrogen carbonate solution and brine, and dried over MgSO₄, and then the solvent was evaporated under reduced pressure. The obtained residue was purified by silica gel column chromatography (CHCl₃:MeOH=100:1) to prepare 2-{[(3,5-dimethoxy-4-methylbenzoyl)(3-phenylpropyl)amino]methyl}-N-({methyl [2-(methylsulfonyl)ethyl]amino}sulfonyl)-1,3-thiazole-4-carboxamide (86 mg).

Example 21

2-{[(3,5-Dimethoxy-4-methylbenzoyl)(3-phenylpropyl)amino]methyl}-N-[(3-hydroxypyrrolidin-1-yl)sulfonyl]-1,3-thiazole-4-carboxamide (108 mg) and (1,1,1-triacetoxy)-1,1-dihydro-1,2-benziodoxol-3(1H)-one (91 mg) were added to methylene chloride (5 mL), followed by stirring at room temperature for 2 hours. To the reaction mixture was added (1,1,1-triacetoxy)-1,1-dihydro-1,2-benziodoxol-3(1H)-one (100 mg), followed by stirring at room temperature for 1 hour. To the reaction mixture was added an appropriate amount of purified water, followed by extraction with CHCl$_3$. The organic layer was sequentially washed with a saturated aqueous sodium hydrogen carbonate solution and brine, and dried over MgSO$_4$, and then the solvent was evaporated under reduced pressure. The obtained residue was purified by silica gel column chromatography (CHCl$_3$:MeOH=30:1) to prepare 2-{[(3,5-dimethoxy-4-methylbenzoyl)(3-phenylpropyl)amino]methyl}-N-[(3-oxopyrrolidin-1-yl)sulfonyl]-1,3-thiazole-4-carboxamide (117 mg).

Example 22

N-({[(2-{[(3,5-Dimethoxy-4-methylbenzoyl)(3-phenylpropyl)amino]methyl}-1,3-thiazol-4-yl)carbonyl]amino}sulfonyl)-N-(2-fluoroethyl)glycine (160 mg) and 4-methylmorpholine (27 mg) were added to THF (2.5 mL), followed by cooling to −15 to −10° C. in an MeOH/ice bath under an argon atmosphere. To this mixture was added dropwise isobutyl chloroformate (36 mg), followed by stirring at −15 to −10° C. for about 5 minutes. Further, an aqueous solution (30 to 40 μL) of sodium borohydride (29 mg) was added thereto, followed by stirring at −15 to −10° C. for 15 minutes. To the reaction mixture was slowly added an appropriate amount of cooled 0.3 to 0.4 M hydrochloric acid, followed by extraction with ethyl acetate. The organic layer was washed with brine and dried over MgSO$_4$, and then the solvent was evaporated under reduced pressure. The obtained residue was purified by silica gel column chromatography (CHCl$_3$:MeOH=100:1) to prepare colorless oily substance (0.14 g). The obtained colorless oily substance was crystallized from a small amount of an ethyl acetate/hexane (3:2) solution that had been warmed, and the solid was collected by filtration while washing with diethyl ether to prepare white solid 2-{[(3,5-dimethoxy-4-methylbenzoyl)(3-phenylpropyl)amino]methyl}-N-{[(2-fluoroethyl)(2-hydroxyethyl)amino]sulfonyl}-1,3-thiazole-4-carboxamide (0.11 g).

Example 23

2-{[(3,5-Dimethoxy-4-methylbenzoyl)(3-phenylpropyl)amino]methyl}-1,3-thiazole-4-carboxylic acid (200 mg) and CDI (107 mg) were added to THF (10 mL), followed by stirring at room temperature for 2 hours. To the reaction mixture were sequentially added N-(2-{[tert-butyl (dimethyl)silyl]oxy}ethyl) sulfamide (224 mg) and DBU (134 mg), followed by stirring at room temperature overnight. To the reaction mixture were added an appropriate amount of ice water and 1 M hydrochloric acid, followed by extraction with ethyl acetate. The organic layer was washed with brine and dried over MgSO$_4$, and then the solvent was evaporated under reduced pressure. The obtained residue was dissolved in THF to give a solution (10 mL), and a 4 M hydrochloric acid/dioxane solution (5 mL) was added to the solution at 0° C., followed by stirring for 1 hour. The reaction mixture was concentrated under reduced pressure, and the obtained residue was purified by silica gel column chromatography (CHCl$_3$:MeOH=20:1) to prepare purified product. This purified product was solidified with diisopropyl ether to prepare 2-{[(3,5-dimethoxy-4-methylbenzoyl)(3-phenylpropyl)amino]methyl}-N-{[(2-hydroxyethyl)amino]sulfonyl}-1,3-thiazole-4-carboxamide (127 mg).

Example 24

2-{[(3,5-Dimethoxy-4-methylbenzoyl)(3-phenylpropyl)amino]methyl}-1,3-thiazole-4-carboxylic acid (600 mg) and CDI (428 mg) were added to THF (20 mL), followed by stirring at room temperature for 2 hours. To the reaction mixture were sequentially added N-{[tert-butyl (dimethyl)silyl]oxy}sulfamide (747 mg) and DBU (502 mg), followed by stirring at room temperature overnight. To the reaction mixture were added water and 1 M hydrochloric acid, followed by extraction with ethyl acetate. The organic layer was washed with brine and dried over MgSO$_4$, and then the solvent was evaporated. The obtained residue was purified by silica gel column chromatography (ethyl acetate) to prepare N-[({[tert-butyl (dimethyl)silyl]oxy}amino)sulfonyl]-2-{[(3,5-dimethoxy-4-methylbenzoyl)(3-phenylpropyl)amino]methyl}-1,3-thiazole-4-carboxamide (702 mg).

Subsequently, N-[({[tert-butyl (dimethyl)silyl]oxy}amino)sulfonyl]-2-{[(3,5-dimethoxy-4-methylbenzoyl)(3-phenylpropyl)amino]methyl}-1,3-thiazole-4-carboxamide (279 mg) was added to THF (10 mL), and subsequently, 55% sodium hydride (22 mg) was added thereto at 0° C., followed by stirring for 10 minutes. Then, methyl iodide (0.12 g) was added thereto, followed by stirring at room temperature overnight. To the reaction mixture was added diluted hydrochloric acid, followed by extraction with CHCl$_3$. The organic layer was washed with brine and dried over MgSO$_4$, and then the solvent was evaporated. The obtained residue was dissolved in THF (10 mL) to give a solution, a 4 M hydrochloric acid/dioxane solution (5 mL) was added to the solution at 0° C., followed by stirring at 0° C. for 1 hour, and the solvent was evaporated. The obtained residue was purified by silica gel column chromatography (CHCl$_3$:MeOH=20:1), and the purified product was solidified with diisopropyl ether to prepare 2-{[(3,5-dimethoxy-4-methylbenzoyl)(3-phenylpropyl)amino]methyl}-N-[(hydroxyamino)sulfonyl]-N-methyl-1,3-thiazole-4-carboxamide (106 mg).

Example 168

2-{[(3,5-Dimethoxy-4-methylbenzoyl)(3-phenylpropyl)amino]methyl}-N-sulfamoyl-1,3-thiazole-4-carboxamide (100 mg) and acetyl chloride (0.3 mL) were added to acetic acid (3 mL), followed by stirring at about 100° C. for 30 minutes, and acetyl chloride (0.3 mL) was added thereto at the same temperature, followed by heating for 30 minutes. The reaction mixture was evaporated under reduced pressure, and ice water was poured into the residue, followed by extraction with an appropriate amount of ethyl acetate. The organic layer was washed with brine, dried over anhydrous MgSO$_4$, and evaporated under reduced pressure. The resulting residue was purified by silica gel column chromatography (CHCl$_3$:MeOH=−35:1) to prepare N-(acetylsulfamoyl)-2-{[(3,5-dimethoxy-4-methylbenzoyl)(3-phenylpropyl)amino]methyl}-1,3-thiazole-4-carboxamide (77 mg).

Example 286

N-(Dimethylsulfamoyl)-5-methyl-2-{[(3-phenylpropyl)amino]methyl}-1,3-thiazole-4-carboxamide hydrochloride (1:1) (150 mg), a Hunig's base (0.2 mL), (2-fluoro-4-propoxyphenyl){[2-(trimethylsilyl)ethoxy]methoxy}acetic acid (150 mg), and HATU (160 mg) were sequentially added to acetonitrile (10 mL), followed by stirring at room temperature for 3 hours. The reaction mixture was evaporated under reduced pressure, and to the residue were added an appropriate amount of purified water and 1 M hydrochloric acid, followed by extraction with $CHCl_3$. The organic layer was dried and evaporated under reduced pressure, and the residue was purified by silica gel column chromatography (hexane to hexane:ethyl acetate=1:3) to obtain a colorless oily substance (240 mg). This oily substance was dissolved in dioxane (5 mL), and a 4 M hydrogen chloride/dioxane solution (5 mL) was added thereto, followed by stirring at room temperature for 3 hours. The reaction mixture was evaporated under reduced pressure, and the resulting residue was purified by silica gel column chromatography ($CHCl_3$ to $CHCl_3$:MeOH=20:1), and the concentrate was solidified with a hexane-ethyl acetate (5:1) solution to prepare N-(dimethylsulfamoyl)-2-({[(2-fluoro-4-propoxyphenyl)(hydroxy)acetyl](3-phenylpropyl)amino}methyl)-5-methyl-1,3-thiazole-4-carboxamide (172 mg) as a white solid.

Example 296

2-[({[1-(4-Methoxyphenyl)cyclopropyl]carbonyl}[3-(2-thienyl)propyl]amino)methyl]-5-methyl-1,3-thiazole-4-carboxylic acid (150 mg) and CDI (80 mg) were added to THF (6 mL), followed by stirring at 70° C. for 1 hour. The reaction mixture was left to be cooled, and then 3-sulfamoylpropylacetate (116 mg) and DBU (144 mg) were added thereto, followed by stirring at room temperature overnight. The reaction mixture was evaporated under reduced pressure, and the resulting residue was purified by silica gel column chromatography (1% $AcOH/CHCl_3$ to 1% $AcOH/CHCl_3$:MeOH=20:1) to obtain a colorless oily substance. This oily substance was dissolved in a THF/EtOH (1:1) solution (10 mL), and a 1 M aqueous NaOH solution (1 mL) was added thereto, followed by stirring at room temperature for 3 hours. The reaction liquid was evaporated under reduced pressure, adjusted to an acidic solution with an appropriate amount of purified water and 1 M hydrochloric acid, and then extracted with ethyl acetate. The organic layer was washed with brine and dried over $Na_2SO_4$, the solvent was evaporated under reduced pressure, and the residue was purified by silica gel column chromatography ($CHCl_3$ to $CHCl_3$:MeOH=20:1). The obtained concentrate was solidified with a hexane-ethyl acetate (2:1) solution to prepare N-[(3-hydroxypropyl)sulfonyl]-2-[({[1-(4-methoxyphenyl)cyclopropyl]carbonyl}[3-(2-thienyl)propyl]amino)methyl]-5-methyl-1,3-thiazole-4-carboxamide (105 mg) as a white solid.

Example 298

2-[([3-(5-Chloro-2-thienyl)propyl]{[1-(5-methoxypyridin-2-yl)cyclopropyl]carbonyl}amino)methyl]-5-methyl-1,3-thiazole-4-carboxylic acid (156 mg) and CDI (80 mg) were added to anhydrous THF (10 mL), followed by stirring at 50° C. for 3 hours. The reaction mixture was left to be cooled, and then N,N-dimethylsulfamide (80 mg) and DBU (97 mg) were sequentially added thereto, followed by stirring at room temperature overnight. To the reaction mixture was added an appropriate amount of diluted hydrochloric acid, followed by extraction with chloroform, the aqueous layer was removed, and the solvent was evaporated. The residue was purified by silica gel column chromatography ($CHCl_3$:MeOH=20:1), and the obtained colorless oily substance was dissolved in ethyl acetate (5 mL). A 4 M hydrogen chloride/ethyl acetate (5 mL) was added thereto, followed by stirring for 30 minutes. The solvent was evaporated, and to the resulting residue was added an appropriate amount of diisopropyl ether, followed by further stirring. The resulting solid was collected by filtration to prepare 2-[([3-(5-chloro-2-thienyl)propyl]{[1-(5-methoxypyridin-2-yl)cyclopropyl]carbonyl}amino)methyl]-N-(dimethylsulfamoyl)-5-methyl-1,3-thiazole-4-carboxamide hydrochloride (140 mg) as a white solid.

Example 305

2-[([3-(1-Benzofuran-2-yl)propyl]{[1-(5-methoxypyridin-2-yl)cyclopropyl]carbonyl}amino)methyl]-5-methyl-1,3-thiazole-4-carboxylic acid (150 mg) and CDI (72 mg) were added to anhydrous THF (5 mL), followed by heating at about 60° C. for 1 hour under an argon gas atmosphere. To the ice-cooled reaction mixture were sequentially added N,N-dimethylsulfamide (74 mg) and DBU (54 mg), followed by stirring at room temperature for 3 days. Ice water (about 10 g) including 1 M hydrochloric acid (0.5 mL) was poured into the reaction solution, followed by extraction with an appropriate amount of ethyl acetate several times. The obtained organic layer was washed with brine and dried over anhydrous magnesium sulfate. The solvent was evaporated under reduced pressure, and the resulting residue was purified by silica gel column chromatography ($CHCl_3$:MeOH=200:1) to obtain a colorless syrup (140 mg). This product was dissolved in ethanol (2.5 mL), and a 8 M aqueous potassium hydroxide solution (32 μL) was added dropwise thereto, followed by stirring at room temperature for about 1 hour. The resulting precipitate was collected by filtration while diluting/washing with a small amount of ethanol:diethyl ether:diisopropyl ether(1:1:1) solution to prepare 1-({2-[([3-(1-benzo furan-2-yl)propyl]{[1-(5-methoxypyridin-2-yl)cyclopropyl]carbonyl}amino)methyl]-5-methyl-1,3-thiazol-4-yl}carbonyl)-3,3-dimethyldiazathian-1-iodo-2,2-dioxide potassium salt (93 mg).

Example 308

N-(Dimethylsulfamoyl)-2-[([3-(3-fluorophenyl)propyl]{[1-(5-methoxypyridin-2-yl)cyclopropyl]carbonyl}amino)methyl]-5-methyl-1,3-thiazole-4-carboxamide (100 mg) was dissolved in methylene chloride (3 mL), followed by evaporation under reduced pressure, to give an amorphous substance. Ethanol (1 mL) including a 8 M aqueous potassium hydroxide solution (21 μL) was poured thereinto, followed by stirring at room temperature for about 4 hours as it was. The resulting white precipitate was collected by filtration while washing with a cooled 90% aqueous EtOH solution (2 mL) to prepare 1-({2-[([3-(3-fluorophenyl)propyl]{[1-(5-methoxypyridin-2-yl)cyclopropyl]carbonyl}amino)methyl]-5-methyl-1,3-thiazol-4-yl}carbonyl)-3,3-dimethyldiazathian-1-iodo-2,2-dioxide potassium salt (33 mg) as a white solid.

The compounds of Examples shown in Tables below were prepared using the respective corresponding starting materials in the same manner as the methods of Examples above. The structures, the preparation methods, and the physico- chemical data for the compounds of Examples are shown in Tables below.

TABLE 56

| Ex | Syn | Structure |
|----|-----|-----------|
| 1 | 1 | 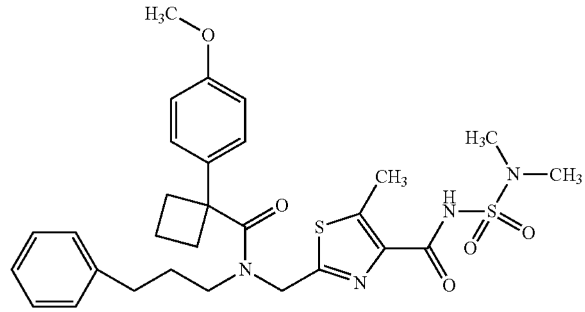 [SMILES: COc1ccc(C2(C(=O)N(CCCc3ccccc3)Cc3nc(C(=O)NS(=O)(=O)N(C)C)c(C)s3)CCC2)cc1] |
| 2 | 2 | 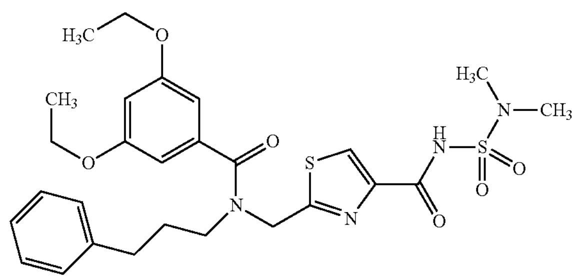 [SMILES: CCOc1cc(OCC)cc(C(=O)N(CCCc2ccccc2)Cc2nc(C(=O)NS(=O)(=O)N(C)C)cs2)c1] |
| 3 | 3 | 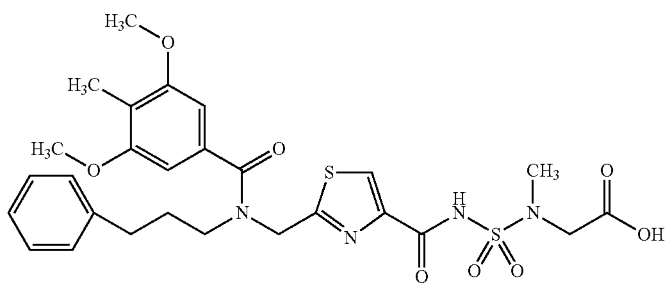 [SMILES: COc1cc(C(=O)N(CCCc2ccccc2)Cc2nc(C(=O)NS(=O)(=O)N(C)CC(=O)O)cs2)cc(OC)c1C] |
| 4 | 4 | 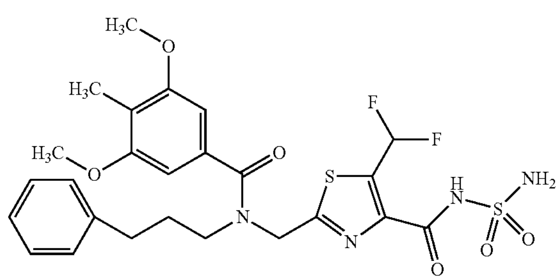 [SMILES: COc1cc(C(=O)N(CCCc2ccccc2)Cc2nc(C(=O)NS(N)(=O)=O)c(C(F)F)s2)cc(OC)c1C] |
| 5 | 5 | 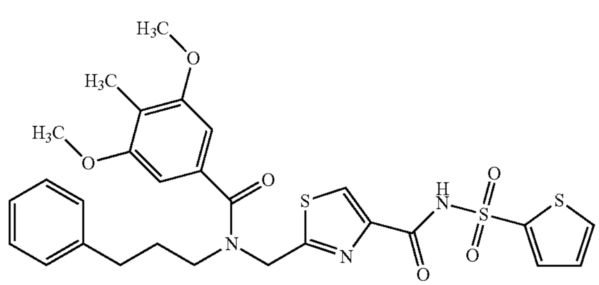 [SMILES: COc1cc(C(=O)N(CCCc2ccccc2)Cc2nc(C(=O)NS(=O)(=O)c3cccs3)cs2)cc(OC)c1C] |

TABLE 57
| Ex | Syn | Structure |
|---|---|---|
| 6 | 6 | 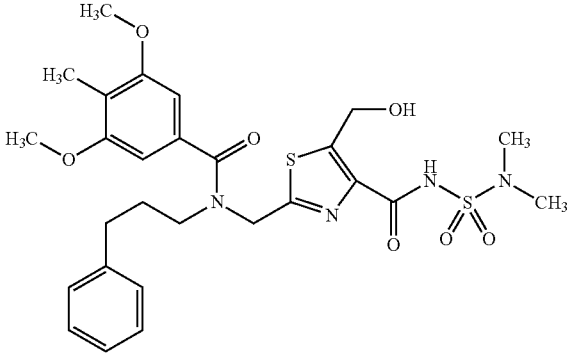 |
| 7 | 7 | 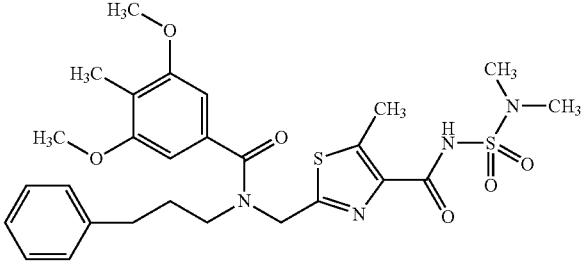 [SMILES: COc1cc(C(=O)N(CCCc2ccccc2)Cc2nc(C(=O)NS(=O)(=O)N(C)C)c(C)s2)cc(OC)c1C] |
| 8 | 8 | 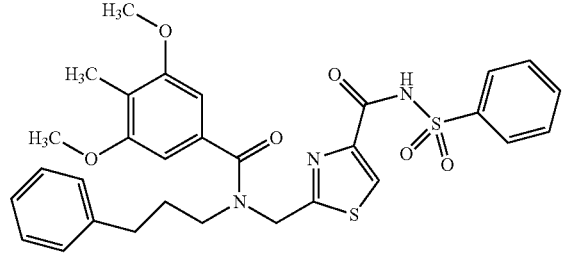 [SMILES: COc1cc(C(=O)N(CCCc2ccccc2)Cc2nc(C(=O)NS(=O)(=O)c3ccccc3)cs2)cc(OC)c1C] |
| 9 | 9 | 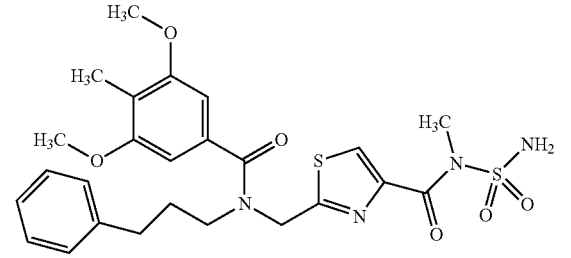 [SMILES: COc1cc(C(=O)N(CCCc2ccccc2)Cc2nc(C(=O)N(C)S(N)(=O)=O)cs2)cc(OC)c1C] |
| 10 | 10 | 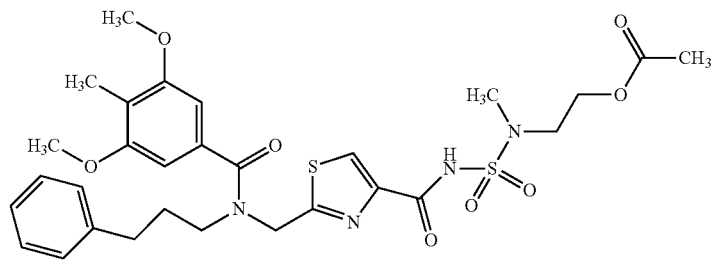 [SMILES: COc1cc(C(=O)N(CCCc2ccccc2)Cc2nc(C(=O)NS(=O)(=O)N(C)CCOC(C)=O)cs2)cc(OC)c1C] |

TABLE 58

| Ex | Syn | Structure |
|---|---|---|
| 11 | 11 | 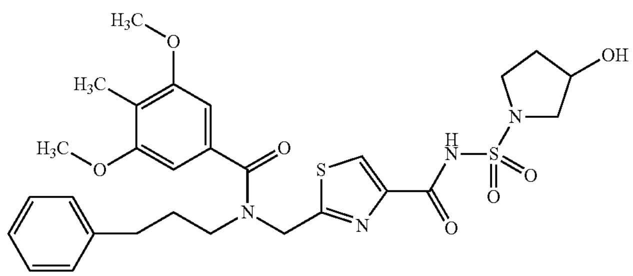 [SMILES: COc1cc(C(=O)N(CCCc2ccccc2)Cc2nc(C(=O)NS(=O)(=O)N3CCC(O)C3)cs2)cc(OC)c1C] |
| 12 | 12 | 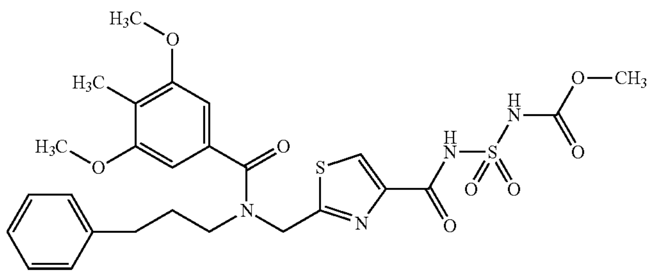 [SMILES: COC(=O)NS(=O)(=O)NC(=O)c1csc(CN(CCCc2ccccc2)C(=O)c2cc(OC)c(C)c(OC)c2)n1] |
| 13 | 13 | 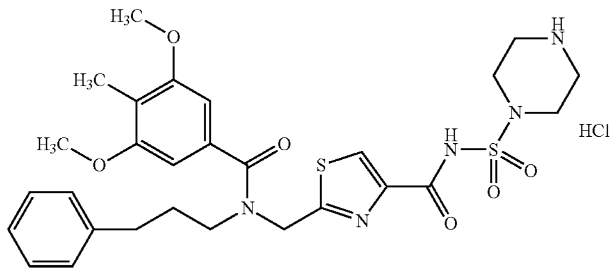 [SMILES: COc1cc(C(=O)N(CCCc2ccccc2)Cc2nc(C(=O)NS(=O)(=O)N3CCNCC3)cs2)cc(OC)c1C ; Cl] |
| 14 | 14 | 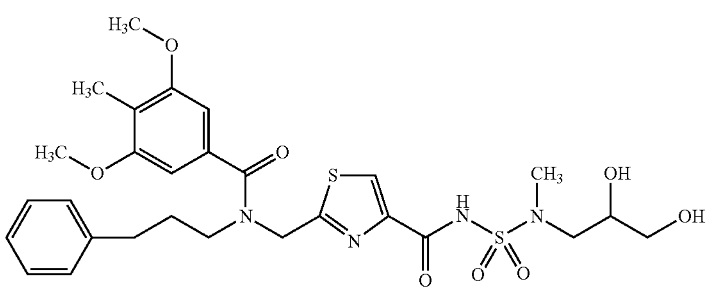 [SMILES: COc1cc(C(=O)N(CCCc2ccccc2)Cc2nc(C(=O)NS(=O)(=O)N(C)CC(O)CO)cs2)cc(OC)c1C] |
| 15 | 15 | 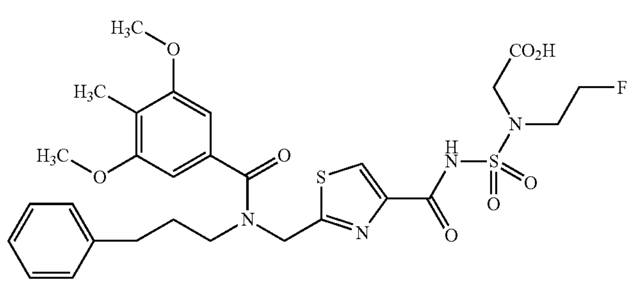 [SMILES: COc1cc(C(=O)N(CCCc2ccccc2)Cc2nc(C(=O)NS(=O)(=O)N(CCF)CC(=O)O)cs2)cc(OC)c1C] |

TABLE 59

| Ex | Syn | Structure |
|----|-----|-----------|
| 16 | 16 | 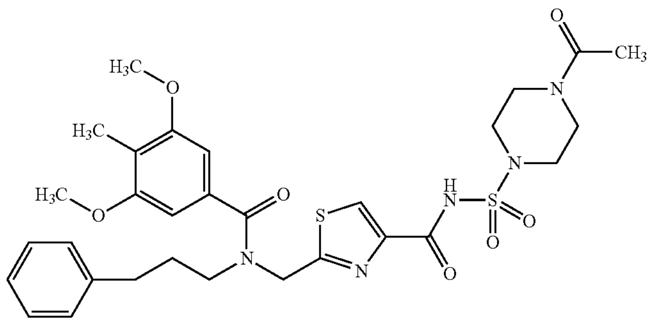 [SMILES: COc1cc(C(=O)N(CCCc2ccccc2)Cc2nc(C(=O)NS(=O)(=O)N3CCN(C(C)=O)CC3)cs2)cc(OC)c1C] |
| 17 | 17 | 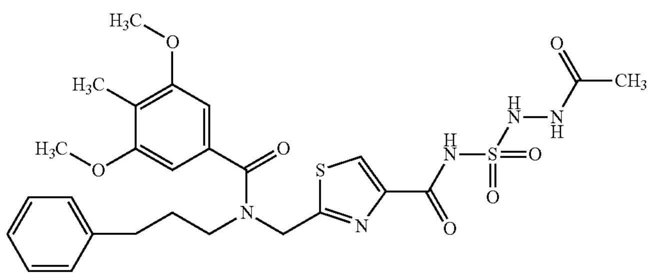 [SMILES: COc1cc(C(=O)N(CCCc2ccccc2)Cc2nc(C(=O)NS(=O)(=O)NNC(C)=O)cs2)cc(OC)c1C] |
| 18 | 18 | 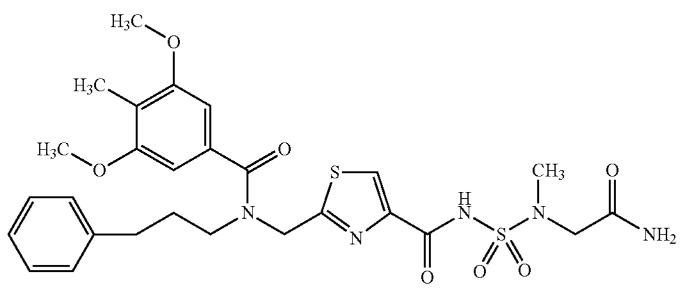 [SMILES: COc1cc(C(=O)N(CCCc2ccccc2)Cc2nc(C(=O)NS(=O)(=O)N(C)CC(N)=O)cs2)cc(OC)c1C] |
| 19 | 19 | 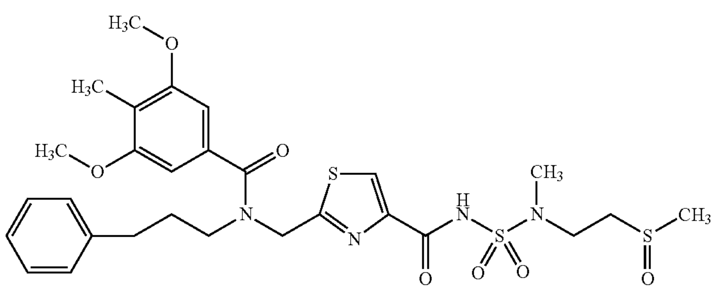 [SMILES: COc1cc(C(=O)N(CCCc2ccccc2)Cc2nc(C(=O)NS(=O)(=O)N(C)CCS(C)=O)cs2)cc(OC)c1C] |
| 20 | 20 | 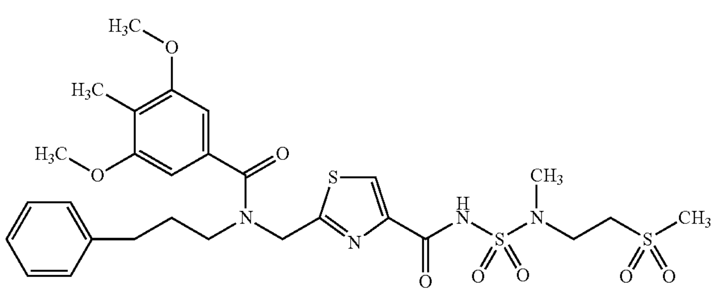 [SMILES: COc1cc(C(=O)N(CCCc2ccccc2)Cc2nc(C(=O)NS(=O)(=O)N(C)CCS(C)(=O)=O)cs2)cc(OC)c1C] |

TABLE 60
| Ex | Syn | Structure |
|----|-----|-----------|
| 21 | 21 | 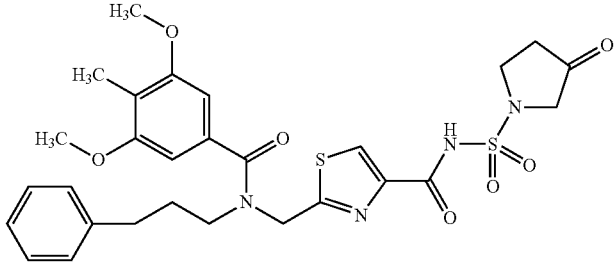 [SMILES: COc1cc(C(=O)N(CCCc2ccccc2)Cc2nc(C(=O)NS(=O)(=O)N3CCC(=O)C3)cs2)cc(OC)c1C] |
| 22 | 22 | 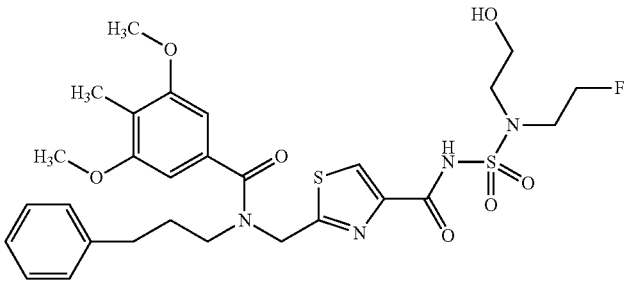 [SMILES: COc1cc(C(=O)N(CCCc2ccccc2)Cc2nc(C(=O)NS(=O)(=O)N(CCO)CCF)cs2)cc(OC)c1C] |
| 23 | 23 | 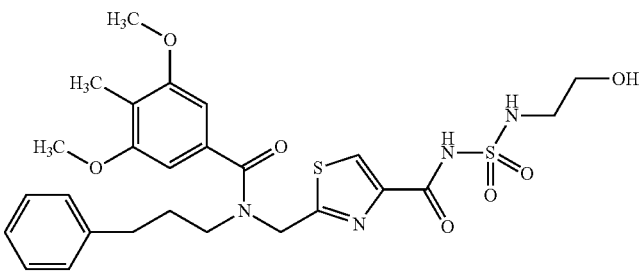 [SMILES: COc1cc(C(=O)N(CCCc2ccccc2)Cc2nc(C(=O)NS(=O)(=O)NCCO)cs2)cc(OC)c1C] |
| 24 | 24 | 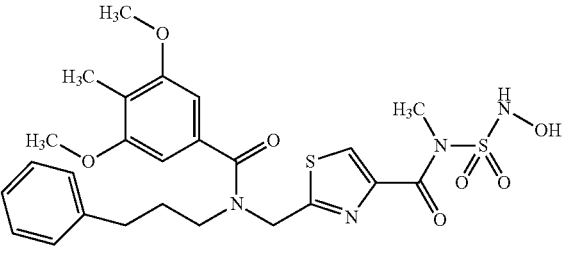 [SMILES: COc1cc(C(=O)N(CCCc2ccccc2)Cc2nc(C(=O)N(C)S(=O)(=O)NO)cs2)cc(OC)c1C] |
| 25 | 1  | 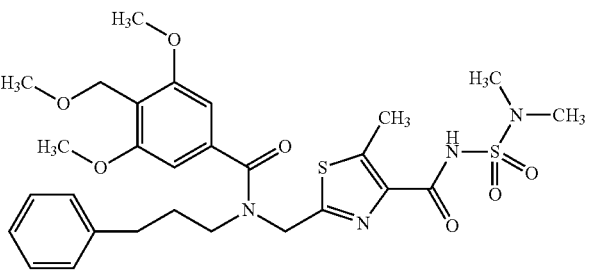 [SMILES: COCc1c(OC)cc(C(=O)N(CCCc2ccccc2)Cc2nc(C(=O)NS(=O)(=O)N(C)C)c(C)s2)cc1OC] |

TABLE 61

| Ex | Syn | Structure |
|----|-----|-----------|
| 26 | 1 | 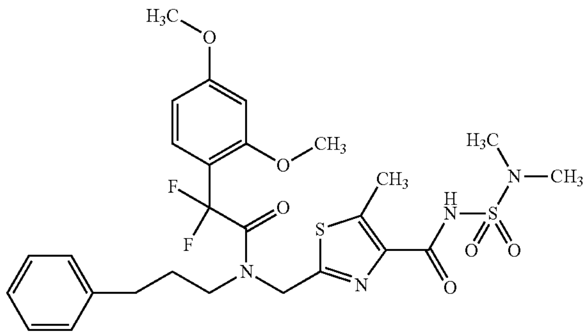 [SMILES: COc1ccc(C(F)(F)C(=O)N(CCCc2ccccc2)Cc2nc(C(=O)NS(=O)(=O)N(C)C)c(C)s2)c(OC)c1] |
| 27 | 1 | 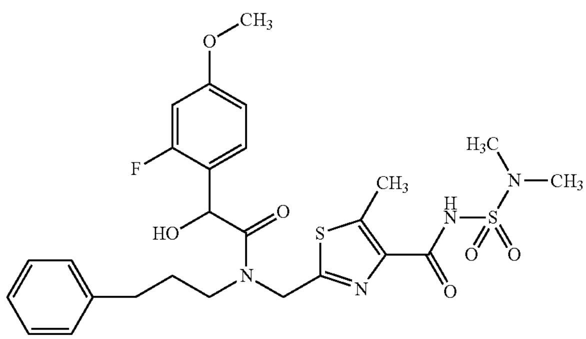 [SMILES: COc1ccc(C(O)C(=O)N(CCCc2ccccc2)Cc2nc(C(=O)NS(=O)(=O)N(C)C)c(C)s2)c(F)c1] |
| 28 | 1 | 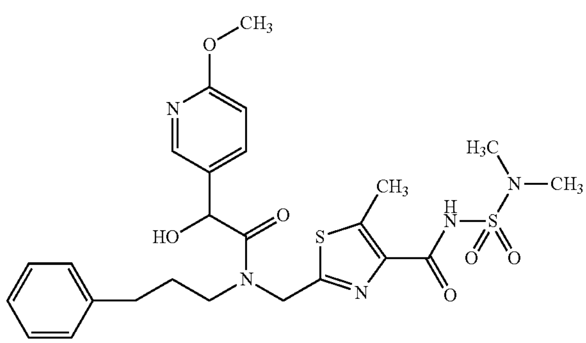 [SMILES: COc1ccc(C(O)C(=O)N(CCCc2ccccc2)Cc2nc(C(=O)NS(=O)(=O)N(C)C)c(C)s2)cn1] |
| 29 | 1 | 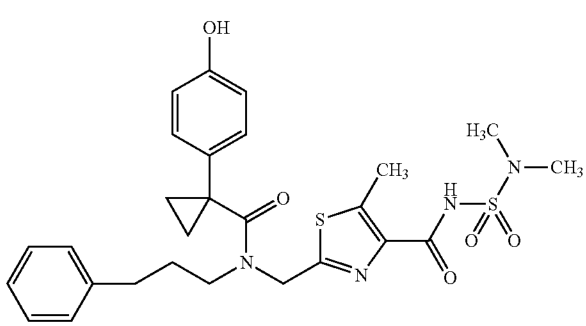 [SMILES: Cc1sc(CN(CCCc2ccccc2)C(=O)C2(c3ccc(O)cc3)CC2)nc1C(=O)NS(=O)(=O)N(C)C] |

TABLE 61-continued
| Ex | Syn | Structure |
|---|---|---|
| 30 | 1 | 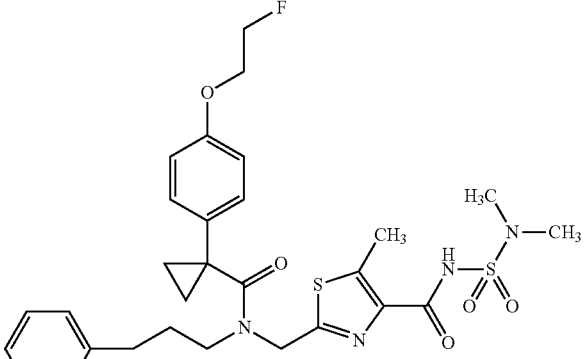 |
TABLE 62
| Ex | Syn | Structure |
|---|---|---|
| 31 | 1 | 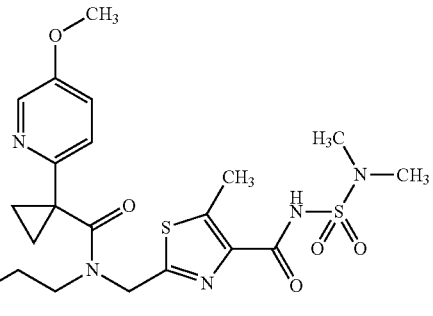 |
| 32 | 2 | 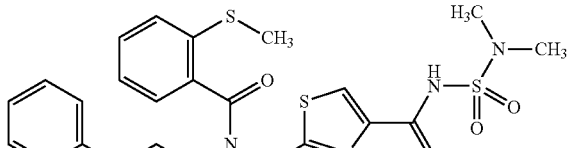 |
| 33 | 2 | 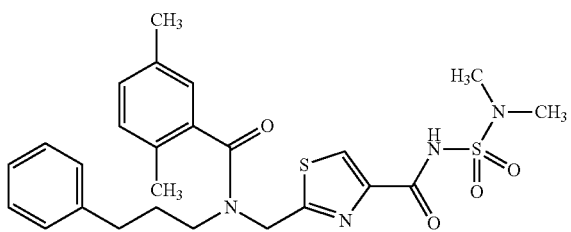 [SMILES: Cc1ccc(C)c(C(=O)N(CCCc2ccccc2)Cc2nc(C(=O)NS(=O)(=O)N(C)C)cs2)c1] |
| 34 | 2 | 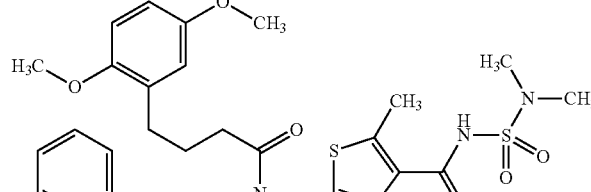 |

TABLE 62-continued

| Ex | Syn | Structure |
|----|-----|-----------|
| 35 | 2 | 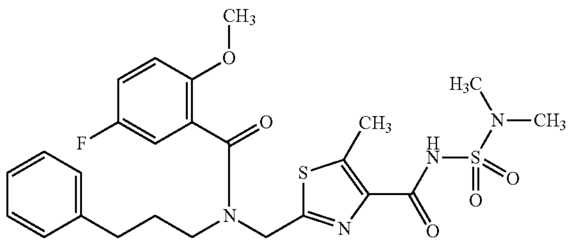 [SMILES: COc1ccc(F)cc1C(=O)N(CCCc1ccccc1)Cc1nc(C(=O)NS(=O)(=O)N(C)C)c(C)s1] |

TABLE 63

| Ex | Syn | Structure |
|----|-----|-----------|
| 36 | 2 | 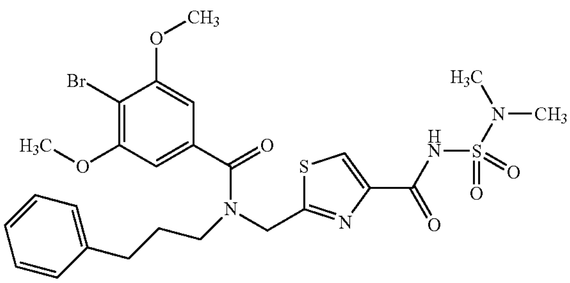 [SMILES: COc1cc(C(=O)N(CCCc2ccccc2)Cc2nc(C(=O)NS(=O)(=O)N(C)C)cs2)cc(OC)c1Br] |
| 37 | 2 | 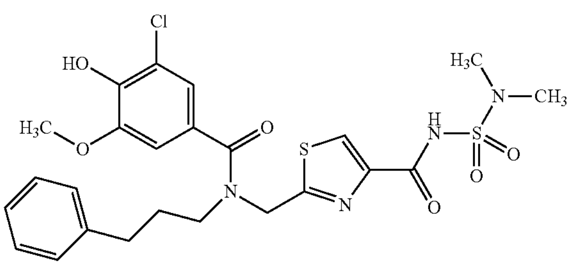 [SMILES: COc1cc(C(=O)N(CCCc2ccccc2)Cc2nc(C(=O)NS(=O)(=O)N(C)C)cs2)cc(Cl)c1O] |
| 38 | 2 | 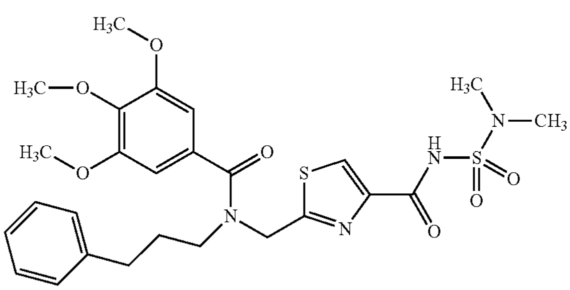 [SMILES: COc1cc(C(=O)N(CCCc2ccccc2)Cc2nc(C(=O)NS(=O)(=O)N(C)C)cs2)cc(OC)c1OC] |
| 39 | 2 | 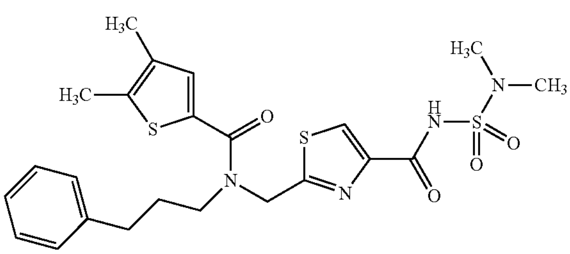 [SMILES: Cc1cc(C(=O)N(CCCc2ccccc2)Cc2nc(C(=O)NS(=O)(=O)N(C)C)cs2)sc1C] |

TABLE 63-continued

| Ex | Syn | Structure |
|----|-----|-----------|
| 40 | 2 | 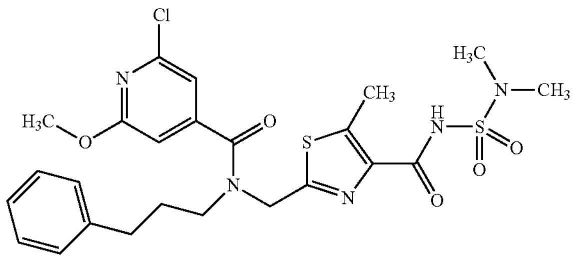 [SMILES: COc1cc(C(=O)N(CCCc2ccccc2)Cc2nc(C(=O)NS(=O)(=O)N(C)C)c(C)s2)cc(Cl)n1] |

TABLE 64

| Ex | Syn | Structure |
|----|-----|-----------|
| 41 | 2 | 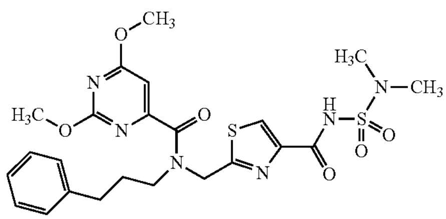 [SMILES: COc1cc(C(=O)N(CCCc2ccccc2)Cc2nc(C(=O)NS(=O)(=O)N(C)C)cs2)nc(OC)n1] |
| 42 | 2 | 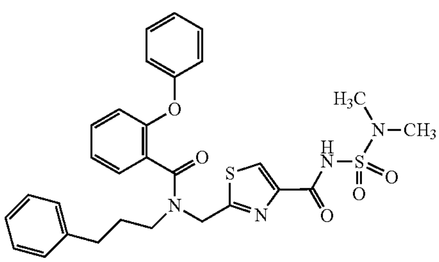 [SMILES: CN(C)S(=O)(=O)NC(=O)c1csc(CN(CCCc2ccccc2)C(=O)c2ccccc2Oc2ccccc2)n1] |
| 43 | 2 | 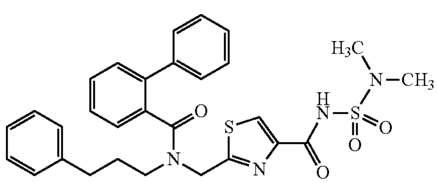 [SMILES: CN(C)S(=O)(=O)NC(=O)c1csc(CN(CCCc2ccccc2)C(=O)c2ccccc2-c2ccccc2)n1] |
| 44 | 2 | 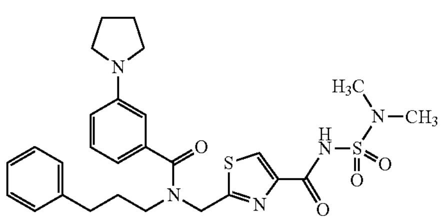 [SMILES: CN(C)S(=O)(=O)NC(=O)c1csc(CN(CCCc2ccccc2)C(=O)c2cccc(N3CCCC3)c2)n1] |
| 45 | 2 | 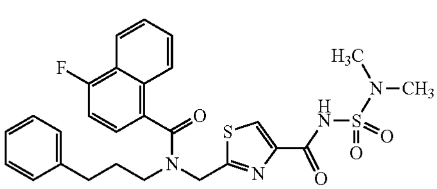 [SMILES: CN(C)S(=O)(=O)NC(=O)c1csc(CN(CCCc2ccccc2)C(=O)c2ccc(F)c3ccccc23)n1] |

TABLE 65

| Ex | Syn | Structure |
|----|-----|-----------|
| 46 | 2 | 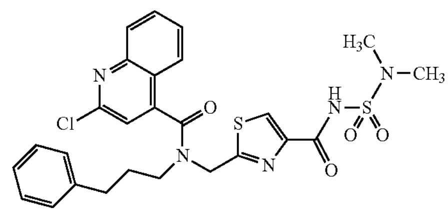 [SMILES: CN(C)S(=O)(=O)NC(=O)c1csc(CN(CCCc2ccccc2)C(=O)c2cc(Cl)nc3ccccc23)n1] |
| 47 | 2 | 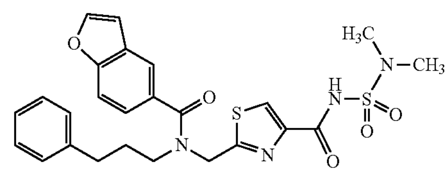 [SMILES: CN(C)S(=O)(=O)NC(=O)c1csc(CN(CCCc2ccccc2)C(=O)c2ccc3occc3c2)n1] |
| 48 | 2 | 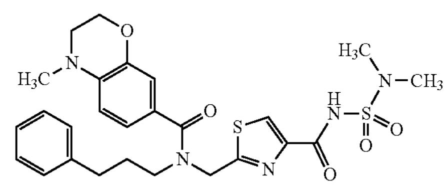 [SMILES: CN1CCOc2cc(C(=O)N(CCCc3ccccc3)Cc3nc(C(=O)NS(=O)(=O)N(C)C)cs3)ccc21] |
| 49 | 2 | 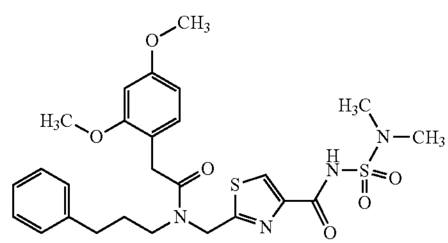 [SMILES: COc1ccc(CC(=O)N(CCCc2ccccc2)Cc2nc(C(=O)NS(=O)(=O)N(C)C)cs2)c(OC)c1] |
| 50 | 2 | 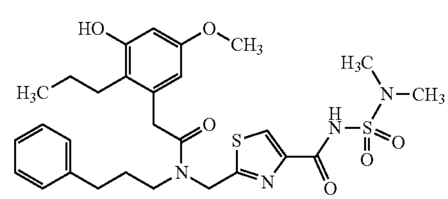 [SMILES: CCCc1c(O)cc(OC)cc1CC(=O)N(CCCc1ccccc1)Cc1nc(C(=O)NS(=O)(=O)N(C)C)cs1] |

TABLE 66

| Ex | Syn | Structure |
|---|---|---|
| 51 | 2 | (structure) |
| 52 | 2 | (structure) |
| 53 | 2 | (structure) |

TABLE 66-continued

| Ex | Syn | Structure |
|---|---|---|
| 54 | 2 | (structure) |
| 55 | 2 | (structure) |

TABLE 67

| Ex | Syn | Structure |
|---|---|---|
| 56 | 2 | (structure) |
| 57 | 2 | (structure) |

TABLE 67-continued

| Ex | Syn | Structure |
|---|---|---|
| 58 | 2 | 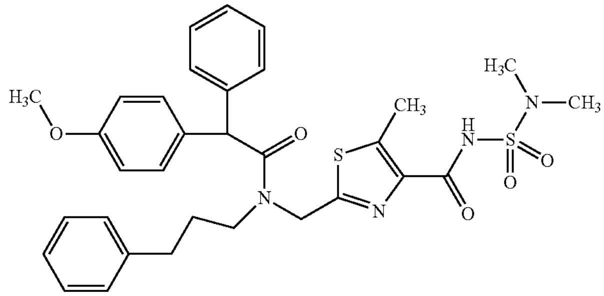 |
| 59 | 2 | 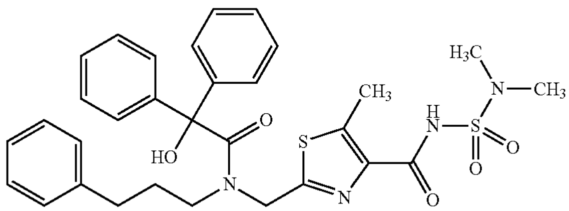 [SMILES: Cc1sc(CN(CCCc2ccccc2)C(=O)C(O)(c2ccccc2)c2ccccc2)nc1C(=O)NS(=O)(=O)N(C)C] |
| 60 | 2 | 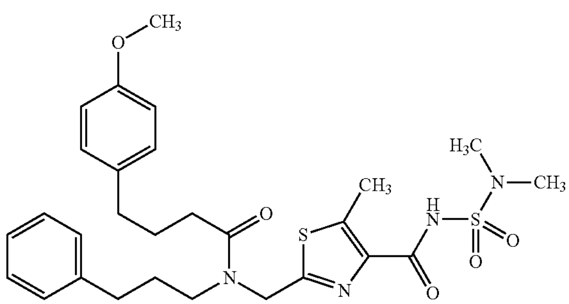 [SMILES: COc1ccc(CCCC(=O)N(CCCc2ccccc2)Cc2nc(C(=O)NS(=O)(=O)N(C)C)c(C)s2)cc1] |

TABLE 68

| Ex | Syn | Structure |
|---|---|---|
| 61 | 2 | 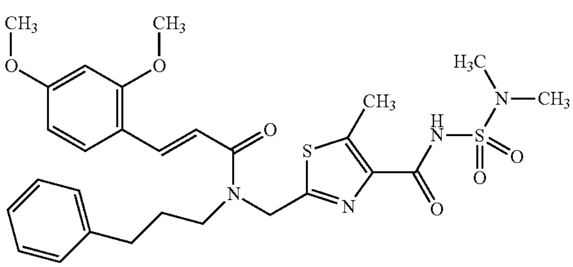 [SMILES: COc1ccc(/C=C/C(=O)N(CCCc2ccccc2)Cc2nc(C(=O)NS(=O)(=O)N(C)C)c(C)s2)c(OC)c1] |
| 62 | 4 | 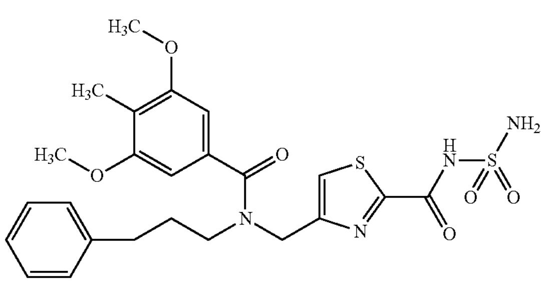 [SMILES: COc1cc(C(=O)N(CCCc2ccccc2)Cc2csc(C(=O)NS(N)(=O)=O)n2)cc(OC)c1C] |

TABLE 68-continued
| Ex | Syn | Structure |
|---|---|---|
| 63 | 4 | 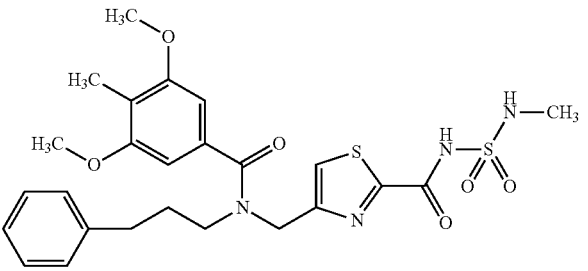 [SMILES: CNS(=O)(=O)NC(=O)c1nc(CN(CCCc2ccccc2)C(=O)c2cc(OC)c(C)c(OC)c2)cs1] |
| 64 | 4 | 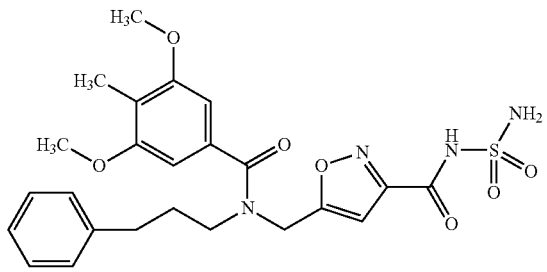 |
| 65 | 5 | 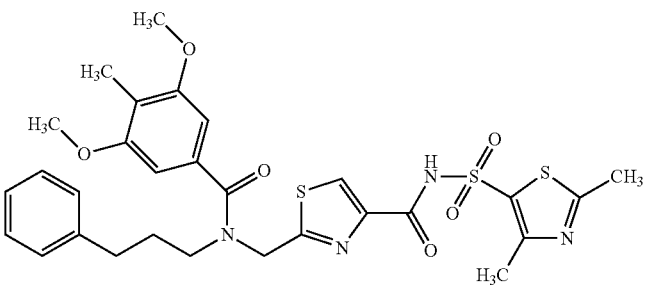 [SMILES: COc1cc(C(=O)N(CCCc2ccccc2)Cc2nc(C(=O)NS(=O)(=O)c3sc(C)nc3C)cs2)cc(OC)c1C] |
TABLE 69
| Ex | Syn | Structure |
|---|---|---|
| 66 | 5 | 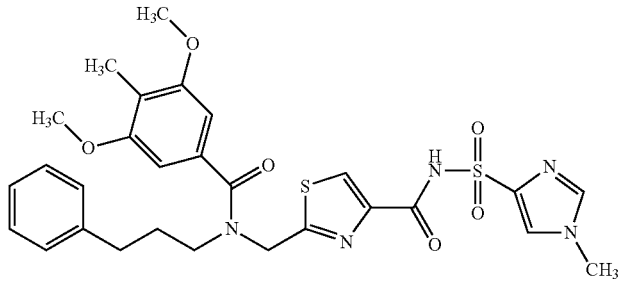 [SMILES: COc1cc(C(=O)N(CCCc2ccccc2)Cc2nc(C(=O)NS(=O)(=O)c3cn(C)cn3)cs2)cc(OC)c1C] |
| 67 | 5 | 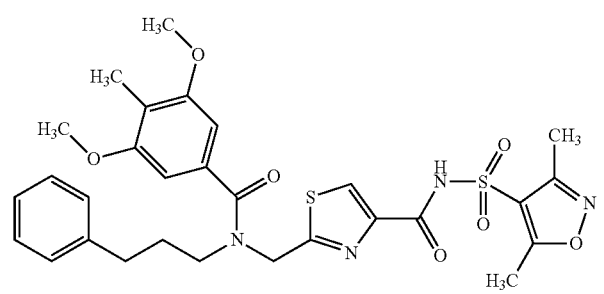 [SMILES: COc1cc(C(=O)N(CCCc2ccccc2)Cc2nc(C(=O)NS(=O)(=O)c3c(C)noc3C)cs2)cc(OC)c1C] |

TABLE 69-continued

| Ex | Syn | Structure |
|---|---|---|
| 68 | 7 | 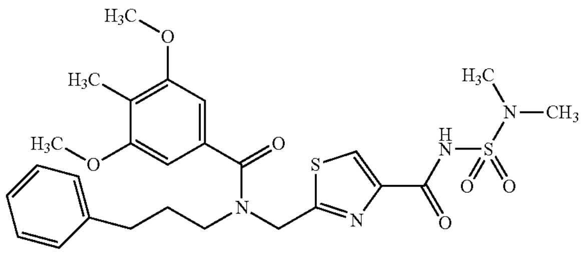 [SMILES: COc1cc(C(=O)N(CCCc2ccccc2)Cc2nc(C(=O)NS(=O)(=O)N(C)C)cs2)cc(OC)c1C] |
| 69 | 7 | 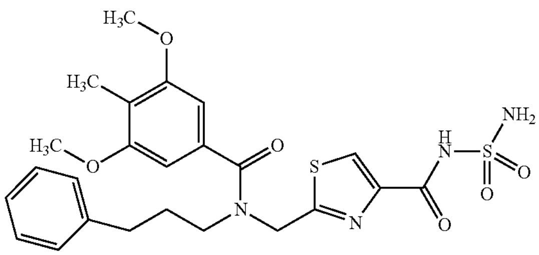 [SMILES: COc1cc(C(=O)N(CCCc2ccccc2)Cc2nc(C(=O)NS(N)(=O)=O)cs2)cc(OC)c1C] |
| 70 | 7 | 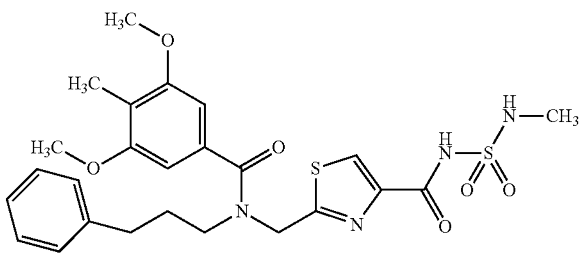 [SMILES: CNS(=O)(=O)NC(=O)c1csc(CN(CCCc2ccccc2)C(=O)c2cc(OC)c(C)c(OC)c2)n1] |

TABLE 70

| Ex | Syn | Structure |
|---|---|---|
| 71 | 7 | 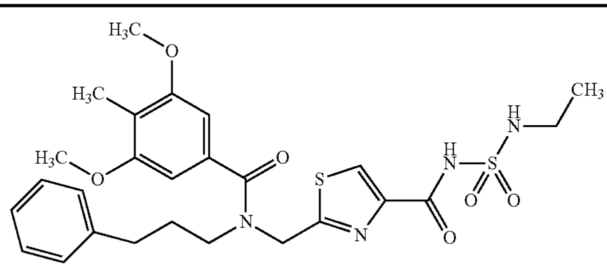 |
| 72 | 7 | 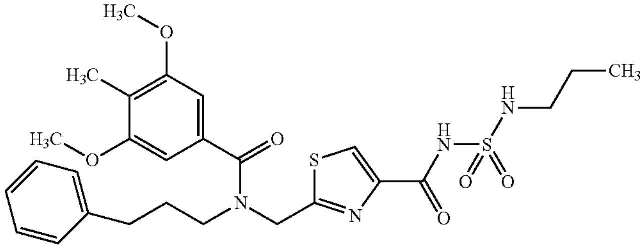 [SMILES: CCCNS(=O)(=O)NC(=O)c1csc(CN(CCCc2ccccc2)C(=O)c2cc(OC)c(C)c(OC)c2)n1] |

TABLE 70-continued
| Ex | Syn | Structure |
|---|---|---|
| 73 | 7 | 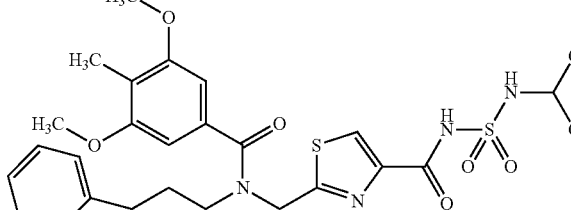 |
| 74 | 7 | 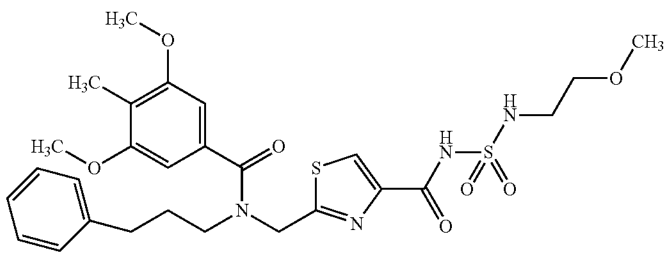 [SMILES: COCCNS(=O)(=O)NC(=O)c1csc(CN(CCCc2ccccc2)C(=O)c2cc(OC)c(C)c(OC)c2)n1] |
| 75 | 7 | 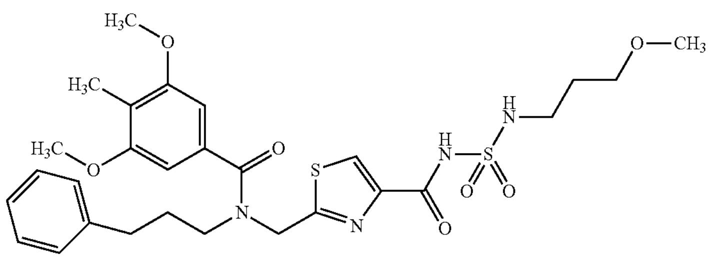 [SMILES: COCCCNS(=O)(=O)NC(=O)c1csc(CN(CCCc2ccccc2)C(=O)c2cc(OC)c(C)c(OC)c2)n1] |
TABLE 71
| Ex | Syn | Structure |
|---|---|---|
| 76 | 7 | 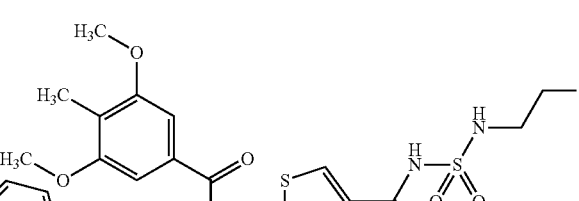 |
| 77 | 7 | 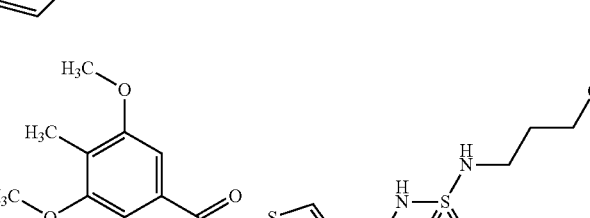 |

TABLE 71-continued
| Ex | Syn | Structure |
|---|---|---|
| 78 | 7 | 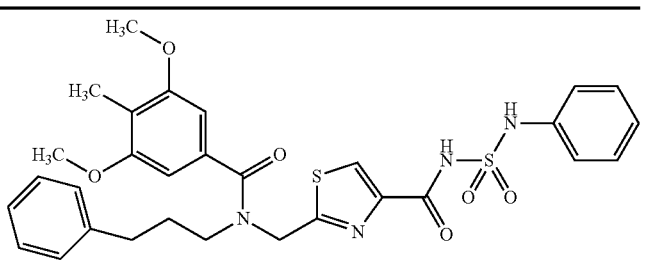 |
| 79 | 7 | 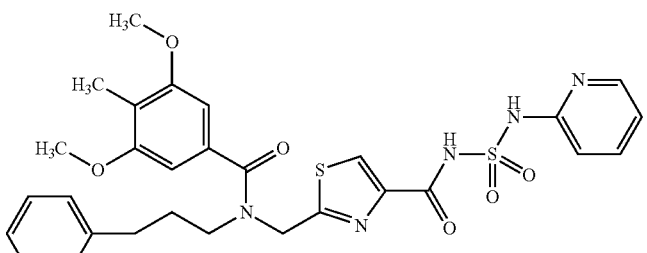 |
| 80 | 7 | 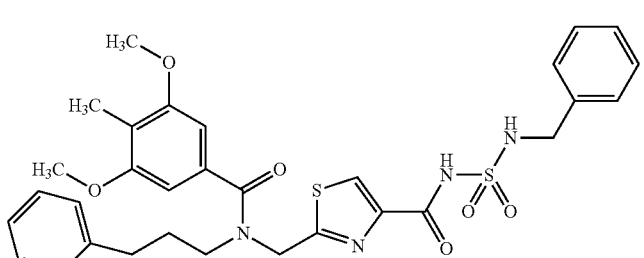 |
TABLE 72
| Ex | Syn | Structure |
|---|---|---|
| 81 | 7 | 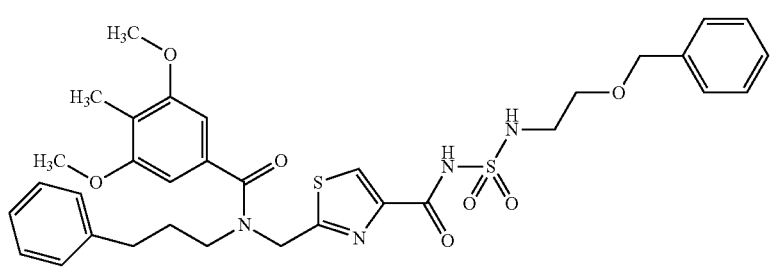 [SMILES: COc1cc(C(=O)N(CCCc2ccccc2)Cc2nc(C(=O)NS(=O)(=O)NCCOCc3ccccc3)cs2)cc(OC)c1C] |
| 82 | 7 | 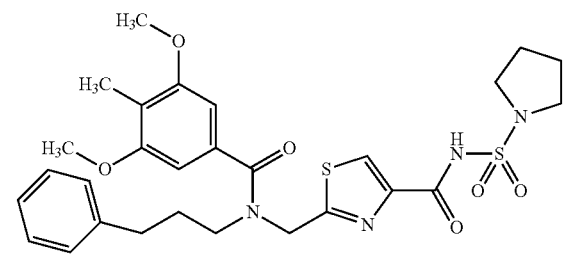 [SMILES: COc1cc(C(=O)N(CCCc2ccccc2)Cc2nc(C(=O)NS(=O)(=O)N3CCCC3)cs2)cc(OC)c1C] |

TABLE 72-continued
| Ex | Syn | Structure |
|---|---|---|
| 83 | 7 | 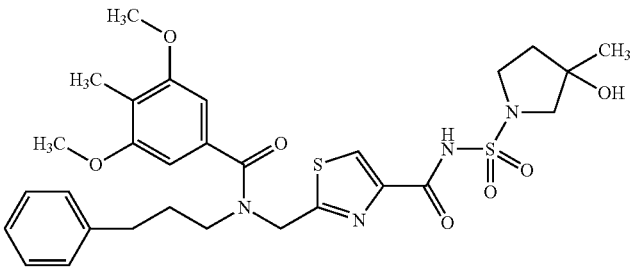 [SMILES: COc1cc(C(=O)N(CCCc2ccccc2)Cc2nc(C(=O)NS(=O)(=O)N3CCC(C)(O)C3)cs2)cc(OC)c1C] |
| 84 | 7 | 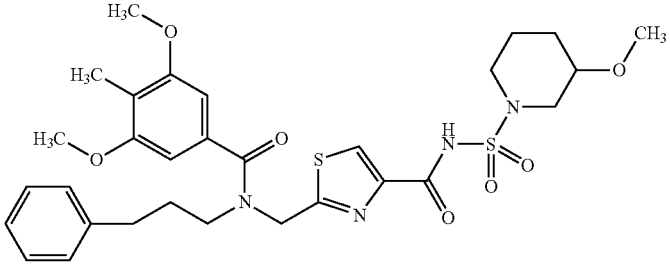 [SMILES: COc1cc(C(=O)N(CCCc2ccccc2)Cc2nc(C(=O)NS(=O)(=O)N3CCCC(OC)C3)cs2)cc(OC)c1C] |
| 85 | 7 | 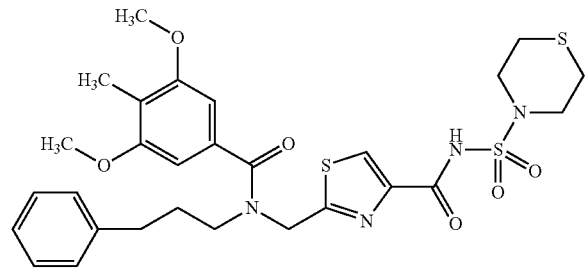 [SMILES: COc1cc(C(=O)N(CCCc2ccccc2)Cc2nc(C(=O)NS(=O)(=O)N3CCSCC3)cs2)cc(OC)c1C] |
TABLE 73
| Ex | Syn | Structure |
|---|---|---|
| 86 | 7 | 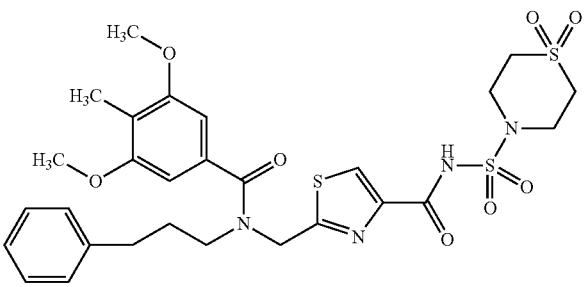 [SMILES: COc1cc(C(=O)N(CCCc2ccccc2)Cc2nc(C(=O)NS(=O)(=O)N3CCS(=O)(=O)CC3)cs2)cc(OC)c1C] |
| 87 | 7 | 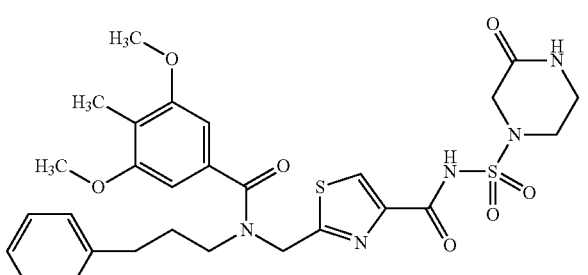 |

TABLE 73-continued

| Ex | Syn | Structure |
|---|---|---|
| 88 | 7 | 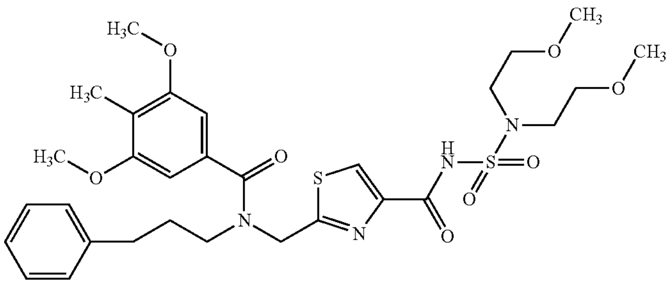 [SMILES: COCCN(CCOC)S(=O)(=O)NC(=O)c1csc(CN(CCCc2ccccc2)C(=O)c2cc(OC)c(C)c(OC)c2)n1] |
| 89 | 7 | 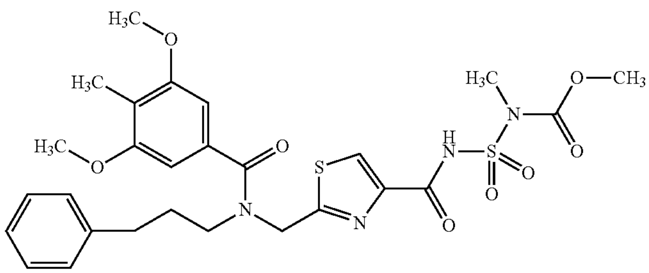 [SMILES: COC(=O)N(C)S(=O)(=O)NC(=O)c1csc(CN(CCCc2ccccc2)C(=O)c2cc(OC)c(C)c(OC)c2)n1] |
| 90 | 7 | 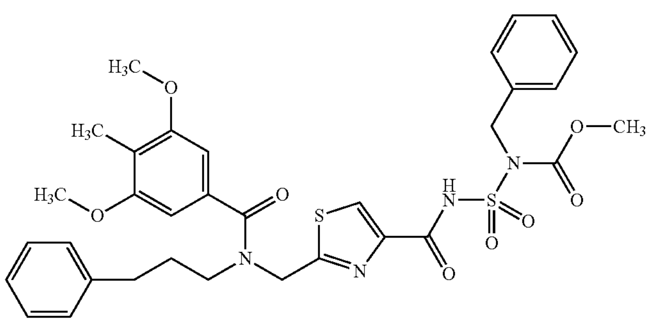 [SMILES: COC(=O)N(Cc1ccccc1)S(=O)(=O)NC(=O)c1csc(CN(CCCc2ccccc2)C(=O)c2cc(OC)c(C)c(OC)c2)n1] |

TABLE 74

| Ex | Syn | Structure |
|---|---|---|
| 91 | 7 | 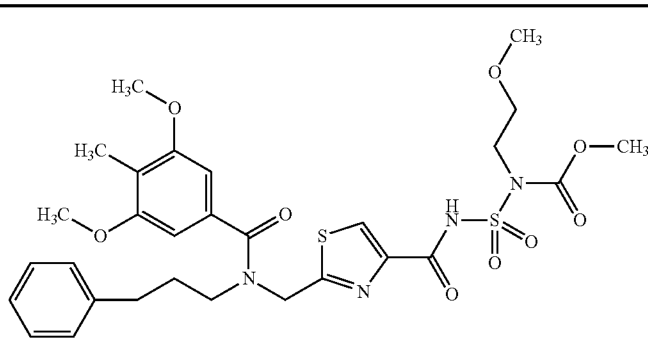 |

TABLE 74-continued
| Ex | Syn | Structure |
|----|-----|-----------|
| 92 | 7 | 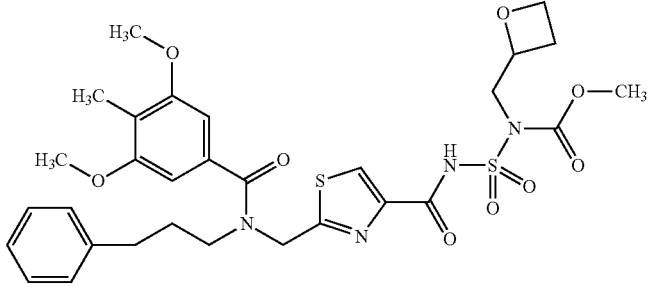 [SMILES: COC(=O)N(CC1CCO1)S(=O)(=O)NC(=O)c1csc(CN(CCCc2ccccc2)C(=O)c2cc(OC)c(C)c(OC)c2)n1] |
| 93 | 7 | 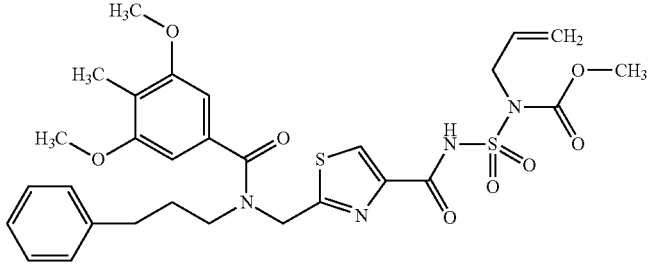 [SMILES: C=CCN(C(=O)OC)S(=O)(=O)NC(=O)c1csc(CN(CCCc2ccccc2)C(=O)c2cc(OC)c(C)c(OC)c2)n1] |
| 94 | 7 | 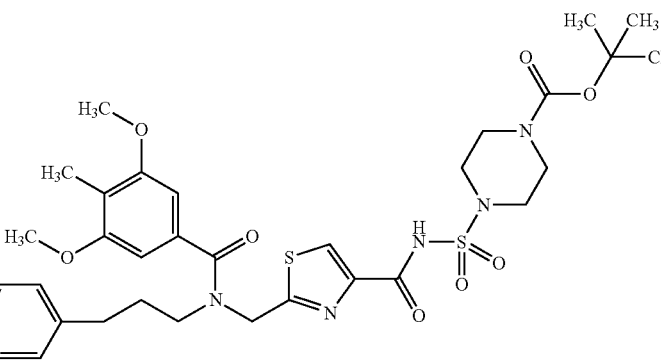 |
| 95 | 7 | 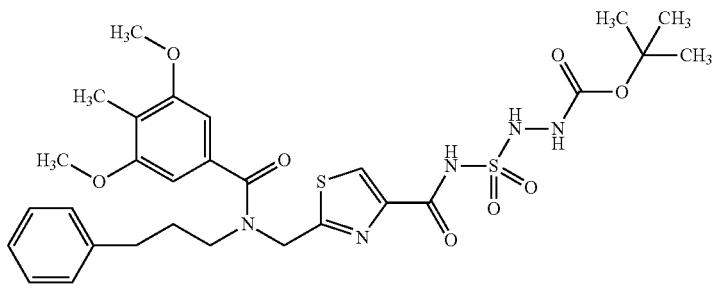 [SMILES: COc1cc(C(=O)N(CCCc2ccccc2)Cc2nc(C(=O)NS(=O)(=O)NNC(=O)OC(C)(C)C)cs2)cc(OC)c1C] |

TABLE 75

| Ex | Syn | Structure |
|---|---|---|
| 96 | 7 | 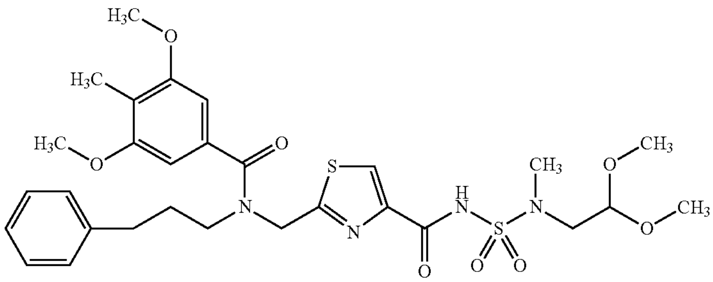 [SMILES: COc1cc(C(=O)N(CCCc2ccccc2)Cc2nc(C(=O)NS(=O)(=O)N(C)CC(OC)OC)cs2)cc(OC)c1C] |
| 97 | 7 | 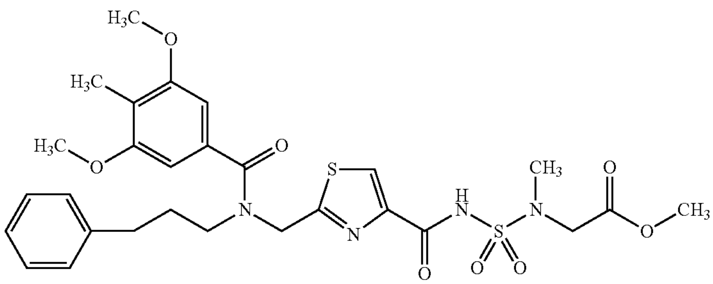 [SMILES: COC(=O)CN(C)S(=O)(=O)NC(=O)c1csc(CN(CCCc2ccccc2)C(=O)c2cc(OC)c(C)c(OC)c2)n1] |
| 98 | 7 | 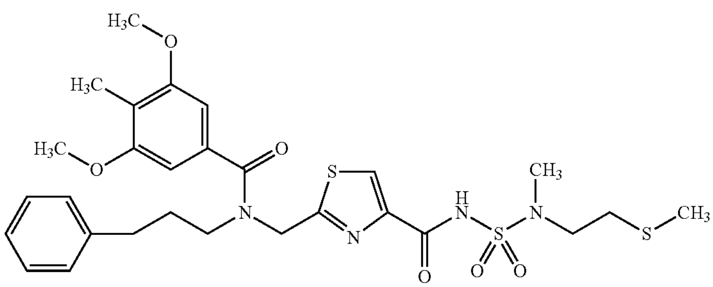 [SMILES: COc1cc(C(=O)N(CCCc2ccccc2)Cc2nc(C(=O)NS(=O)(=O)N(C)CCSC)cs2)cc(OC)c1C] |
| 99 | 7 | 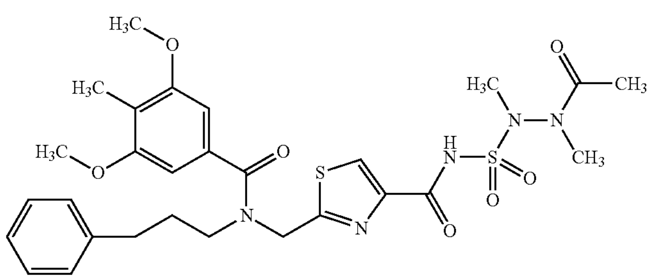 [SMILES: COc1cc(C(=O)N(CCCc2ccccc2)Cc2nc(C(=O)NS(=O)(=O)N(C)N(C)C(C)=O)cs2)cc(OC)c1C] |
| 100 | 7 | 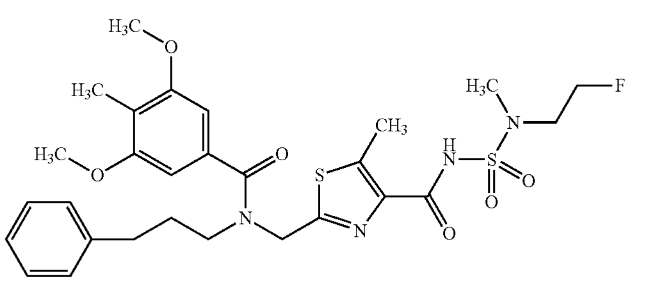 [SMILES: COc1cc(C(=O)N(CCCc2ccccc2)Cc2nc(C(=O)NS(=O)(=O)N(C)CCF)c(C)s2)cc(OC)c1C] |

TABLE 76
| Ex | Syn | Structure |
|---|---|---|
| 101 | 7 | 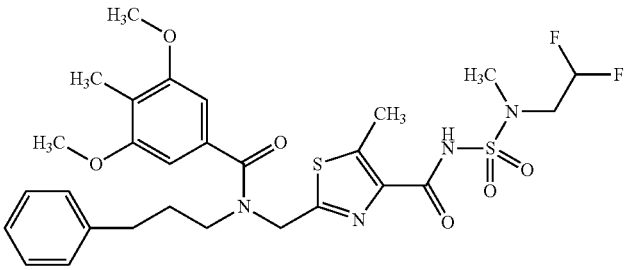 [SMILES: COc1cc(C(=O)N(CCCc2ccccc2)Cc2nc(C(=O)NS(=O)(=O)N(C)CC(F)F)c(C)s2)cc(OC)c1C] |
| 102 | 7 | 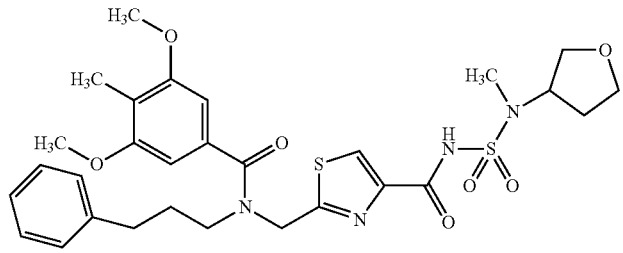 [SMILES: COc1cc(C(=O)N(CCCc2ccccc2)Cc2nc(C(=O)NS(=O)(=O)N(C)C3CCOC3)cs2)cc(OC)c1C] |
| 103 | 7 | 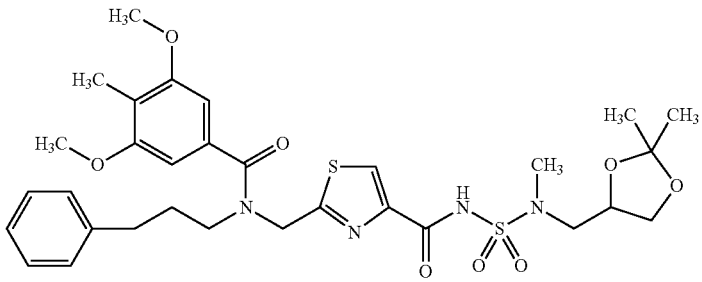 [SMILES: COc1cc(C(=O)N(CCCc2ccccc2)Cc2nc(C(=O)NS(=O)(=O)N(C)CC3COC(C)(C)O3)cs2)cc(OC)c1C] |
| 104 | 7 | 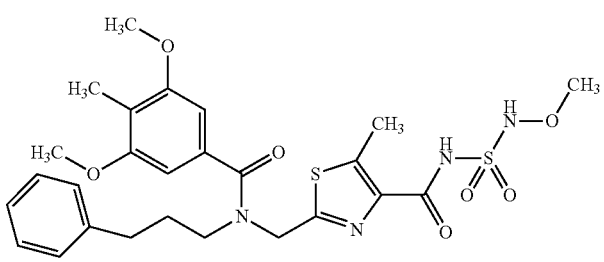 [SMILES: CONS(=O)(=O)NC(=O)c1nc(CN(CCCc2ccccc2)C(=O)c2cc(OC)c(C)c(OC)c2)sc1C] |
| 105 | 7 | 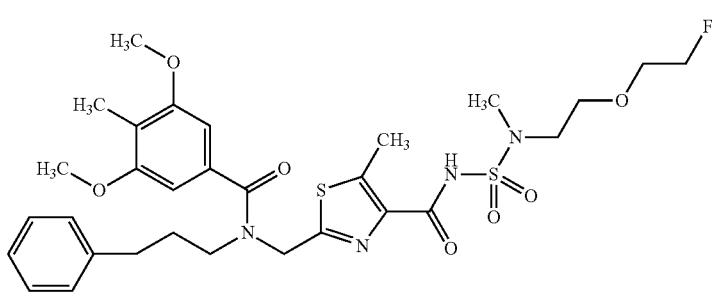 [SMILES: COc1cc(C(=O)N(CCCc2ccccc2)Cc2nc(C(=O)NS(=O)(=O)N(C)CCOCCF)c(C)s2)cc(OC)c1C] |

TABLE 77

| Ex | Syn | Structure |
|---|---|---|
| 106 | 7 | 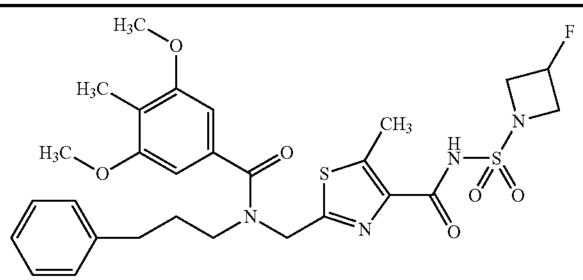 |
| 107 | 7 | 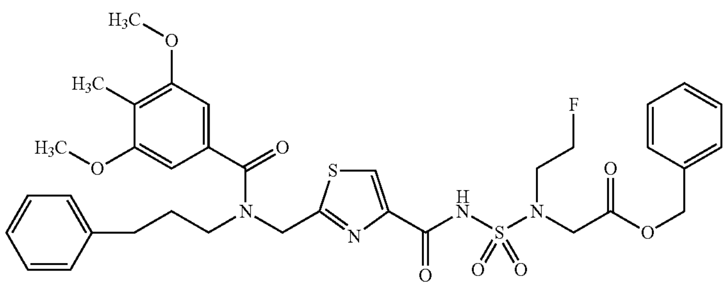 [SMILES: COc1cc(C(=O)N(CCCc2ccccc2)Cc2nc(C(=O)NS(=O)(=O)N(CCF)CC(=O)OCc3ccccc3)cs2)cc(OC)c1C] |
| 108 | 7 | 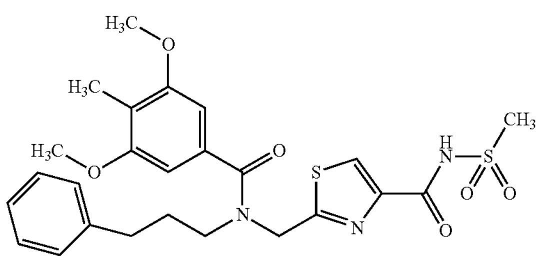 [SMILES: COc1cc(C(=O)N(CCCc2ccccc2)Cc2nc(C(=O)NS(C)(=O)=O)cs2)cc(OC)c1C] |
| 109 | 7 | 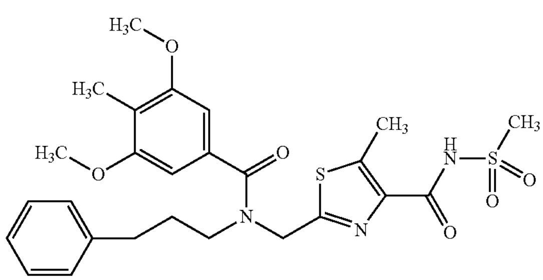 [SMILES: COc1cc(C(=O)N(CCCc2ccccc2)Cc2nc(C(=O)NS(C)(=O)=O)c(C)s2)cc(OC)c1C] |
| 110 | 7 | 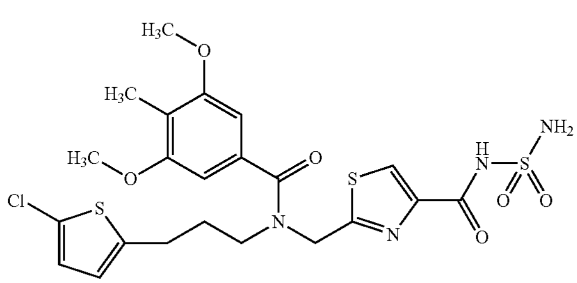 [SMILES: COc1cc(C(=O)N(CCCc2ccc(Cl)s2)Cc2nc(C(=O)NS(N)(=O)=O)cs2)cc(OC)c1C] |

TABLE 78

| Ex | Syn | Structure |
|---|---|---|
| 111 | 7 | 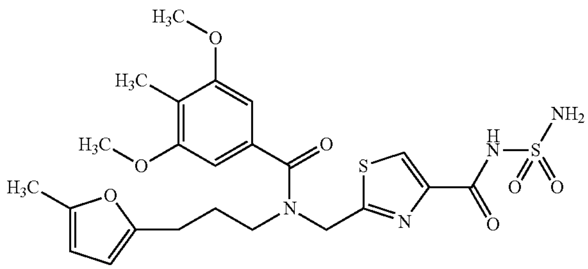 [SMILES: COc1cc(C(=O)N(CCCc2ccc(C)o2)Cc2nc(C(=O)NS(N)(=O)=O)cs2)cc(OC)c1C] |
| 112 | 7 | 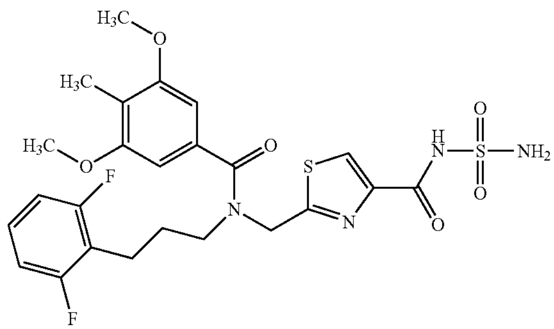 [SMILES: COc1cc(C(=O)N(CCCc2c(F)cccc2F)Cc2nc(C(=O)NS(N)(=O)=O)cs2)cc(OC)c1C] |
| 113 | 7 | 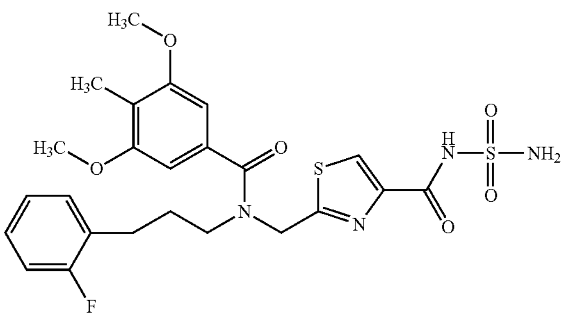 [SMILES: COc1cc(C(=O)N(CCCc2ccccc2F)Cc2nc(C(=O)NS(N)(=O)=O)cs2)cc(OC)c1C] |
| 114 | 7 | 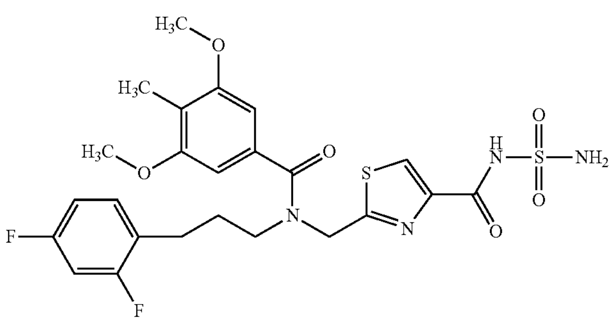 [SMILES: COc1cc(C(=O)N(CCCc2ccc(F)cc2F)Cc2nc(C(=O)NS(N)(=O)=O)cs2)cc(OC)c1C] |
| 115 | 7 | 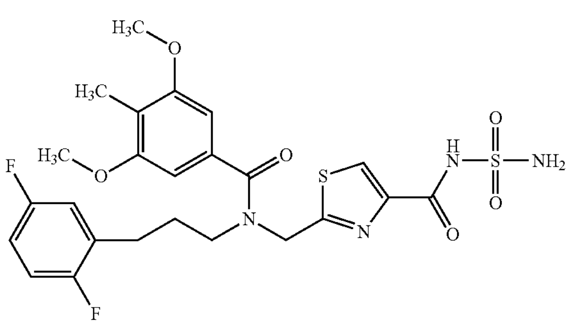 [SMILES: COc1cc(C(=O)N(CCCc2cc(F)ccc2F)Cc2nc(C(=O)NS(N)(=O)=O)cs2)cc(OC)c1C] |

TABLE 79

| Ex | Syn | Structure |
|---|---|---|
| 116 | 7 | 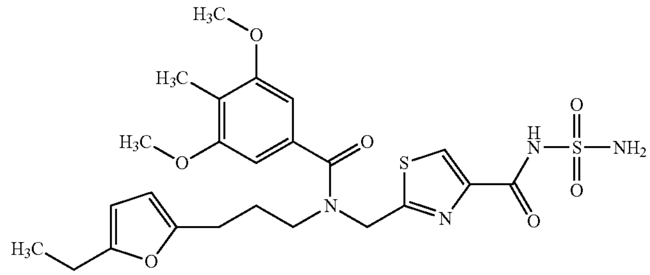 [SMILES: CCc1ccc(CCCN(Cc2nc(C(=O)NS(N)(=O)=O)cs2)C(=O)c2cc(OC)c(C)c(OC)c2)o1] |
| 117 | 7 | 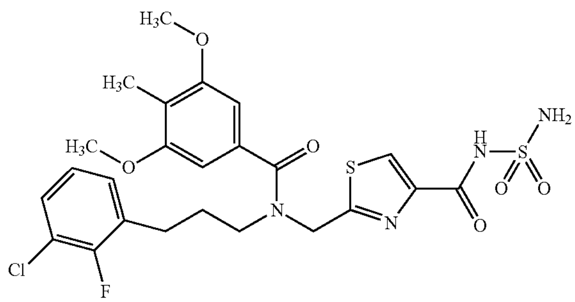 [SMILES: COc1cc(C(=O)N(CCCc2cccc(Cl)c2F)Cc2nc(C(=O)NS(N)(=O)=O)cs2)cc(OC)c1C] |
| 118 | 7 | 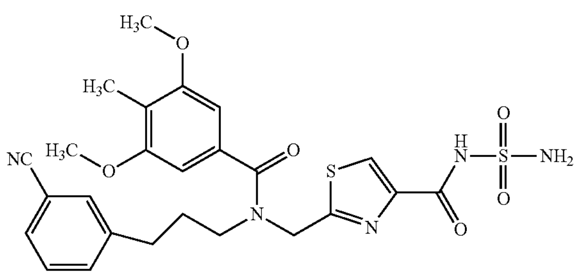 [SMILES: COc1cc(C(=O)N(CCCc2cccc(C#N)c2)Cc2nc(C(=O)NS(N)(=O)=O)cs2)cc(OC)c1C] |
| 119 | 7 | 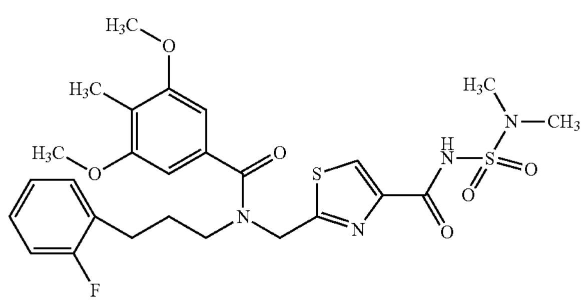 [SMILES: COc1cc(C(=O)N(CCCc2ccccc2F)Cc2nc(C(=O)NS(=O)(=O)N(C)C)cs2)cc(OC)c1C] |
| 120 | 7 | 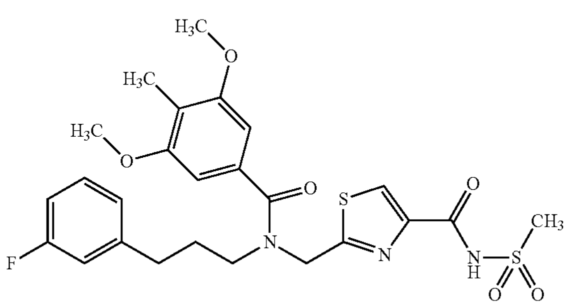 [SMILES: COc1cc(C(=O)N(CCCc2cccc(F)c2)Cc2nc(C(=O)NS(C)(=O)=O)cs2)cc(OC)c1C] |

TABLE 80

| Ex | Syn | Structure |
|---|---|---|
| 121 | 7 | 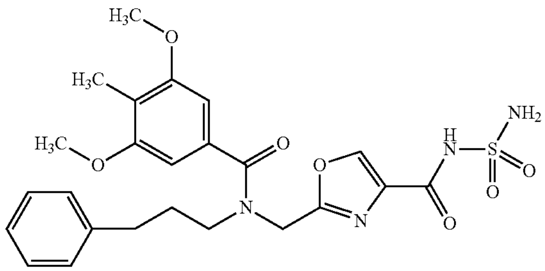 [SMILES: COc1cc(C(=O)N(CCCc2ccccc2)Cc2nc(C(=O)NS(N)(=O)=O)co2)cc(OC)c1C] |
| 122 | 7 | 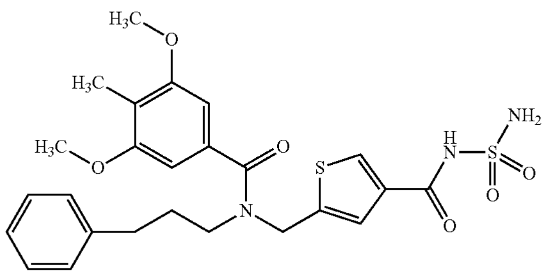 |
| 123 | 7 | 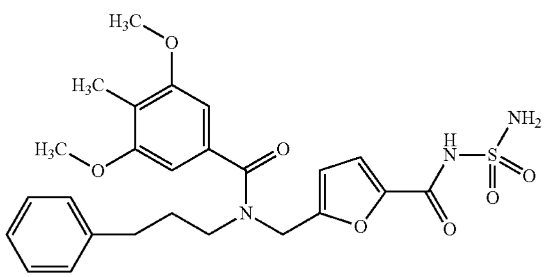 [SMILES: COc1cc(C(=O)N(CCCc2ccccc2)Cc2ccc(C(=O)NS(N)(=O)=O)o2)cc(OC)c1C] |
| 124 | 7 | 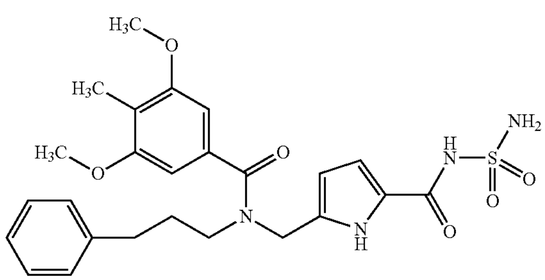 [SMILES: COc1cc(C(=O)N(CCCc2ccccc2)Cc2ccc(C(=O)NS(N)(=O)=O)[nH]2)cc(OC)c1C] |
| 125 | 7 | 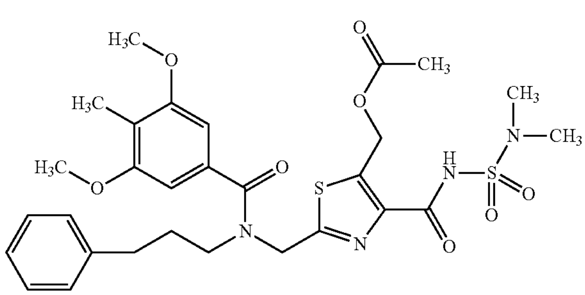 [SMILES: COc1cc(C(=O)N(CCCc2ccccc2)Cc2nc(C(=O)NS(=O)(=O)N(C)C)c(COC(C)=O)s2)cc(OC)c1C] |

TABLE 81
| Ex | Syn | Structure |
|---|---|---|
| 126 | 7 | 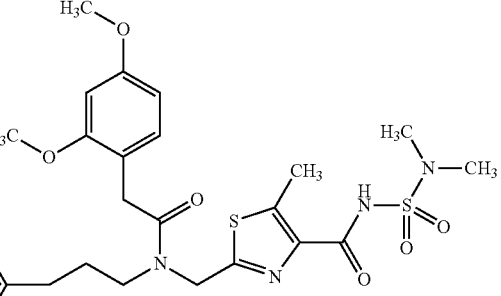 |
| 127 | 7 | 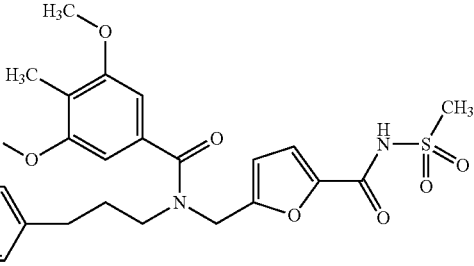 |
| 128 | 7 | 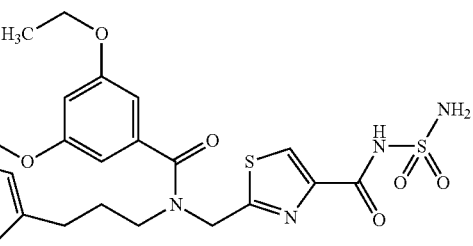 |
| 129 | 7 | 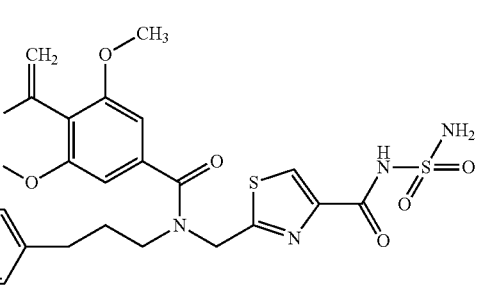 |
| 130 | 7 | 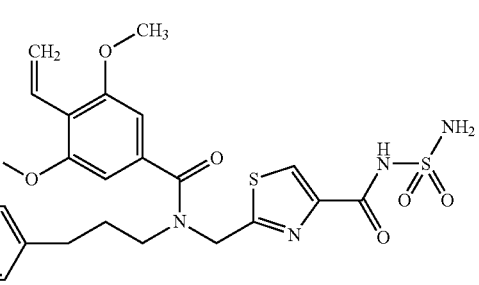 |

TABLE 82

| Ex | Syn | Structure |
|---|---|---|
| 131 | 7 | 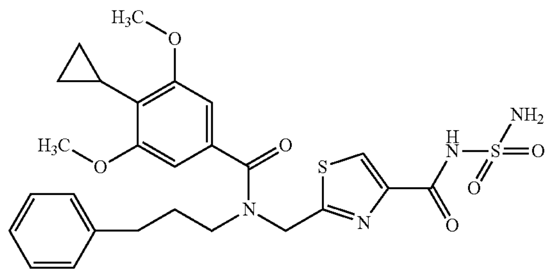 [SMILES: COc1cc(C(=O)N(CCCc2ccccc2)Cc2nc(C(=O)NS(N)(=O)=O)cs2)cc(OC)c1C1CC1] |
| 132 | 7 | 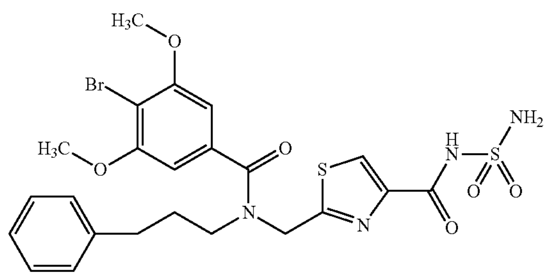 [SMILES: COc1cc(C(=O)N(CCCc2ccccc2)Cc2nc(C(=O)NS(N)(=O)=O)cs2)cc(OC)c1Br] |
| 133 | 7 | 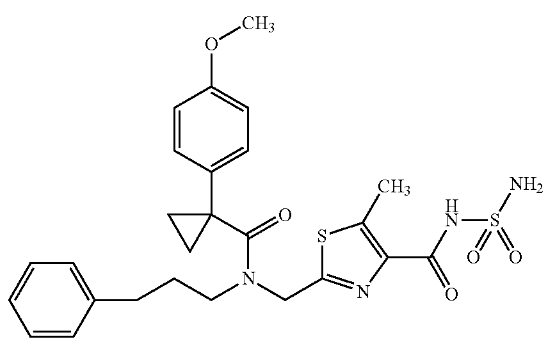 [SMILES: COc1ccc(C2(C(=O)N(CCCc3ccccc3)Cc3nc(C(=O)NS(N)(=O)=O)c(C)s3)CC2)cc1] |
| 134 | 7 | 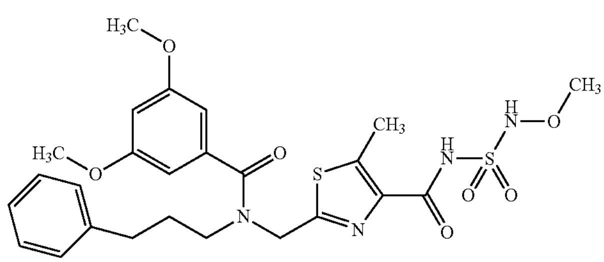 [SMILES: CONS(=O)(=O)NC(=O)c1nc(CN(CCCc2ccccc2)C(=O)c2cc(OC)cc(OC)c2)sc1C] |
| 135 | 7 | 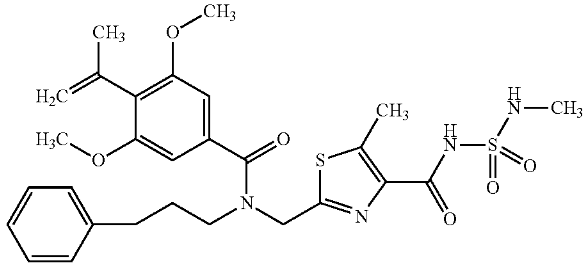 [SMILES: C=C(C)c1c(OC)cc(C(=O)N(CCCc2ccccc2)Cc2nc(C(=O)NS(=O)(=O)NC)c(C)s2)cc1OC] |

TABLE 83

| Ex | Syn | Structure |
|----|-----|-----------|
| 136 | 7 | 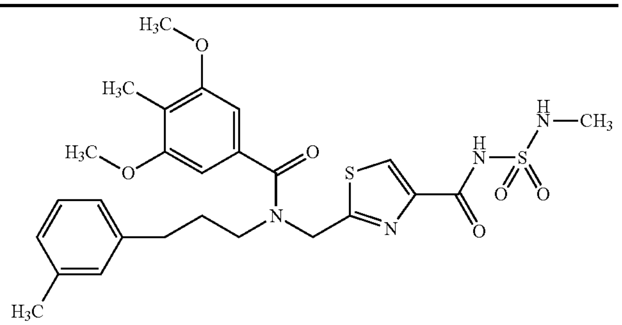 |
| 137 | 7 | 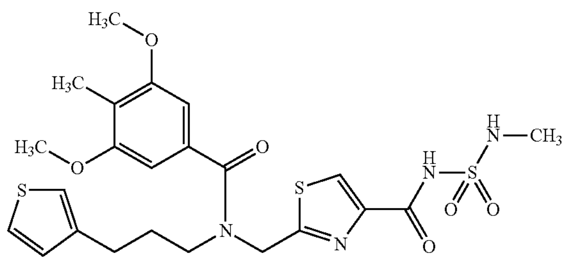 [SMILES: CNS(=O)(=O)NC(=O)c1csc(CN(CCCc2ccsc2)C(=O)c2cc(OC)c(C)c(OC)c2)n1] |
| 138 | 7 | 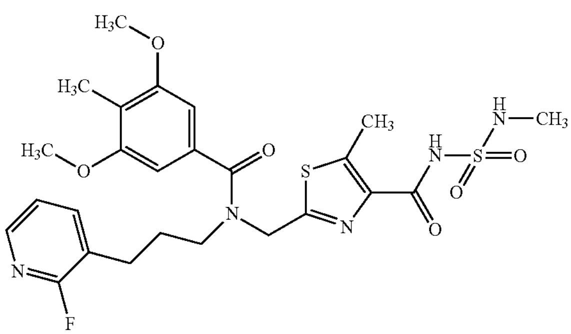 [SMILES: CNS(=O)(=O)NC(=O)c1nc(CN(CCCc2cccnc2F)C(=O)c2cc(OC)c(C)c(OC)c2)sc1C] |
| 139 | 7 | 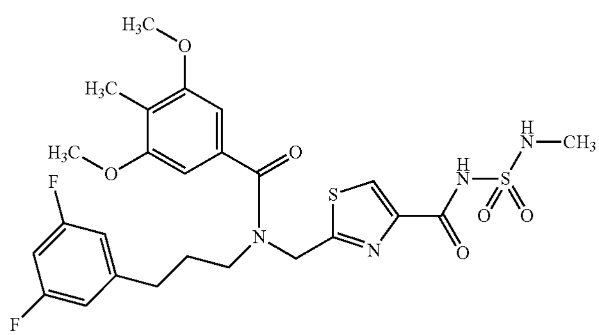 [SMILES: CNS(=O)(=O)NC(=O)c1csc(CN(CCCc2cc(F)cc(F)c2)C(=O)c2cc(OC)c(C)c(OC)c2)n1] |
| 140 | 7 | 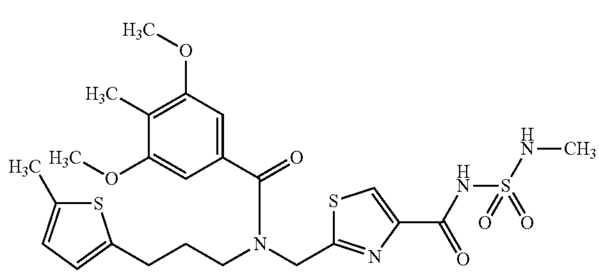 |

TABLE 84

| Ex | Syn | Structure |
|---|---|---|
| 141 | 7 | 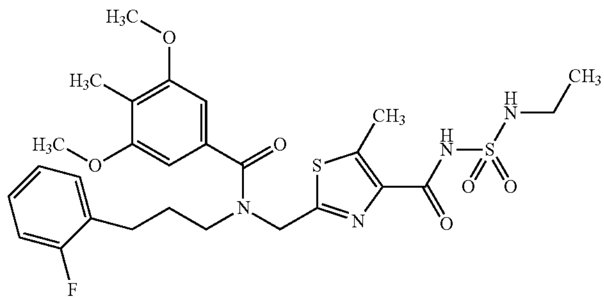 [SMILES: CCNS(=O)(=O)NC(=O)c1nc(CN(CCCc2ccccc2F)C(=O)c2cc(OC)c(C)c(OC)c2)sc1C] |
| 142 | 7 | 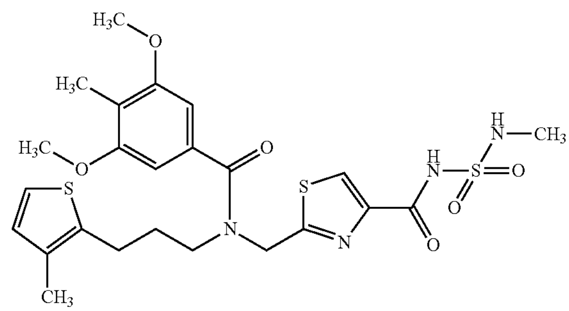 [SMILES: CNS(=O)(=O)NC(=O)c1csc(CN(CCCc2sccc2C)C(=O)c2cc(OC)c(C)c(OC)c2)n1] |
| 143 | 7 | 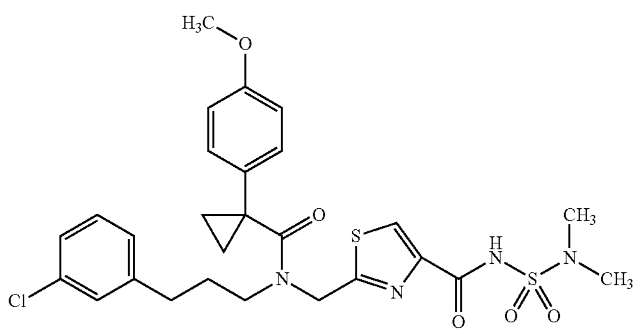 [SMILES: COc1ccc(C2(C(=O)N(CCCc3cccc(Cl)c3)Cc3nc(C(=O)NS(=O)(=O)N(C)C)cs3)CC2)cc1] |
| 144 | 7 | 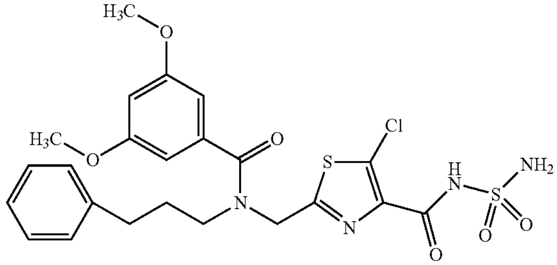 [SMILES: COc1cc(OC)cc(C(=O)N(CCCc2ccccc2)Cc2nc(C(=O)NS(N)(=O)=O)c(Cl)s2)c1] |
| 145 | 7 | 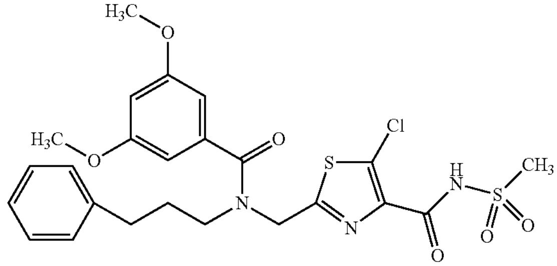 [SMILES: COc1cc(OC)cc(C(=O)N(CCCc2ccccc2)Cc2nc(C(=O)NS(C)(=O)=O)c(Cl)s2)c1] |

TABLE 85

| Ex | Syn | Structure |
|---|---|---|
| 146 | 7 | 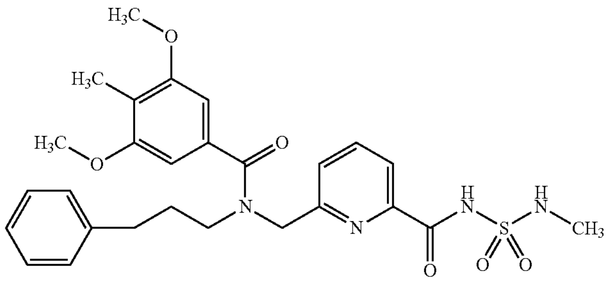 [SMILES: CNS(=O)(=O)NC(=O)c1cccc(CN(CCCc2ccccc2)C(=O)c2cc(OC)c(C)c(OC)c2)n1] |
| 147 | 7 | 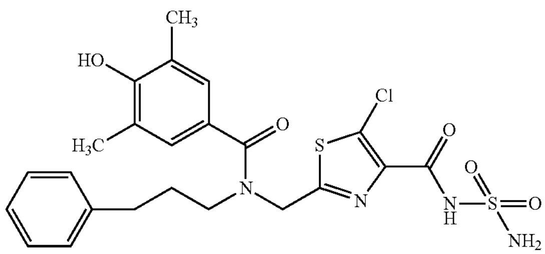 [SMILES: Cc1cc(C(=O)N(CCCc2ccccc2)Cc2nc(C(=O)NS(N)(=O)=O)c(Cl)s2)cc(C)c1O] |
| 148 | 7 | 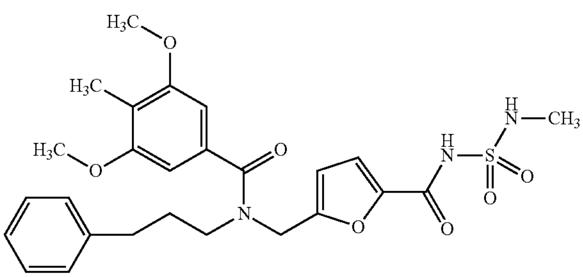 [SMILES: CNS(=O)(=O)NC(=O)c1ccc(CN(CCCc2ccccc2)C(=O)c2cc(OC)c(C)c(OC)c2)o1] |
| 149 | 7 | 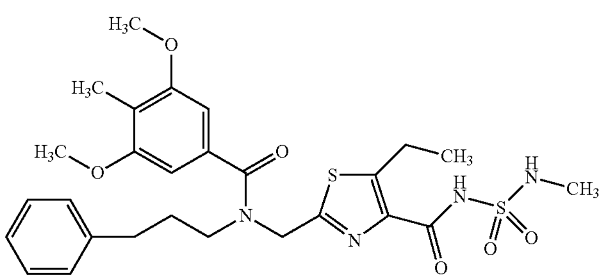 [SMILES: CCc1sc(CN(CCCc2ccccc2)C(=O)c2cc(OC)c(C)c(OC)c2)nc1C(=O)NS(=O)(=O)NC] |
| 150 | 7 | 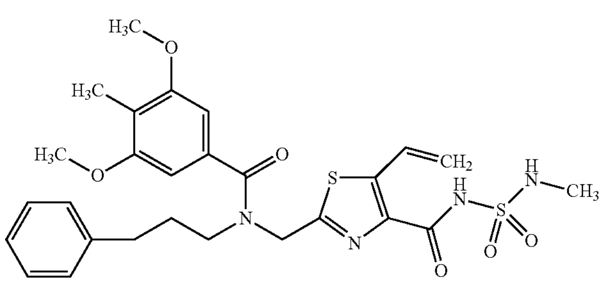 [SMILES: C=Cc1sc(CN(CCCc2ccccc2)C(=O)c2cc(OC)c(C)c(OC)c2)nc1C(=O)NS(=O)(=O)NC] |

TABLE 86
| Ex | Syn | Structure |
|---|---|---|
| 151 | 7 | 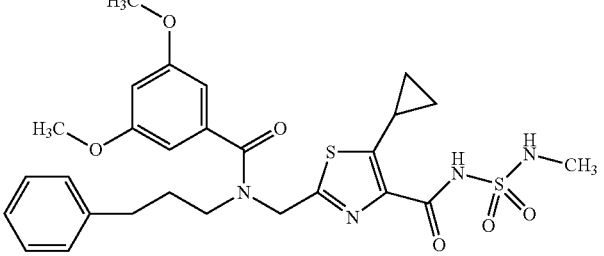 |
| 152 | 7 | 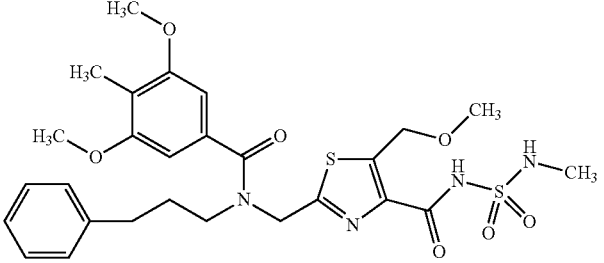 [SMILES: CNS(=O)(=O)NC(=O)c1nc(CN(CCCc2ccccc2)C(=O)c2cc(OC)c(C)c(OC)c2)sc1COC] |
| 153 | 7 | 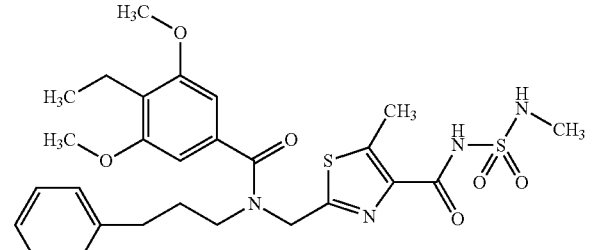 |
| 154 | 7 | 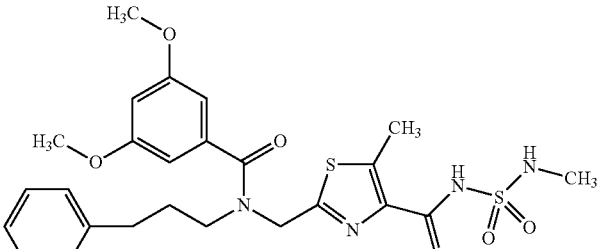 |
| 155 | 7 | 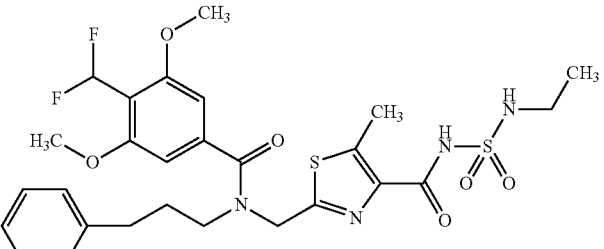 |

TABLE 87
| Ex | Syn | Structure |
|---|---|---|
| 156 | 7 | 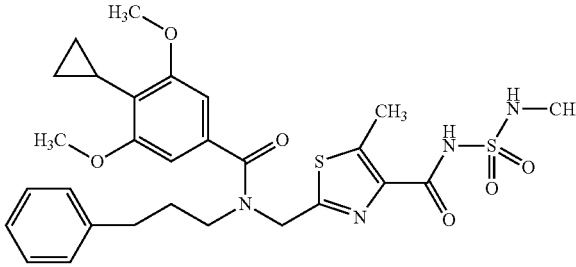 |
| 157 | 7 | 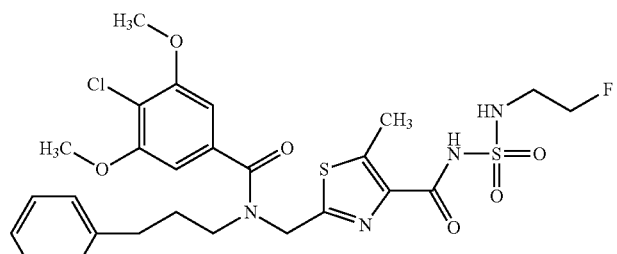 |
| 158 | 7 | 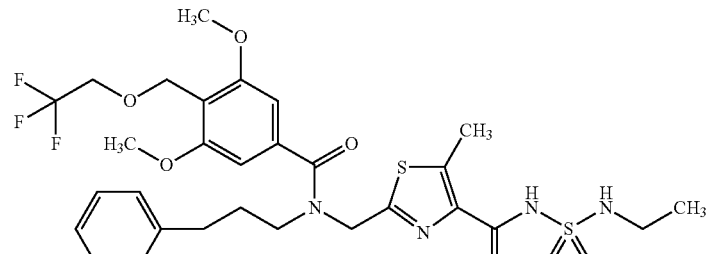 |
| 159 | 7 | 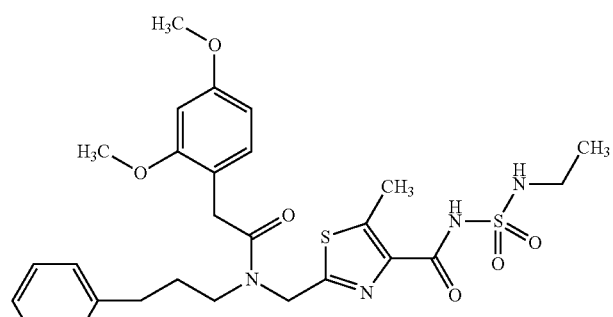 |
| 160 | 7 | 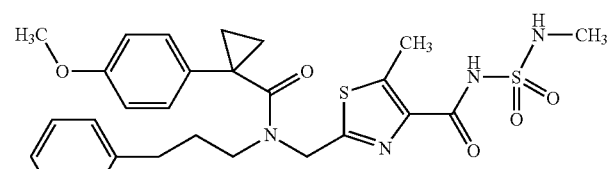 |

TABLE 88

| Ex | Syn | Structure |
|---|---|---|
| 161 | 7 | 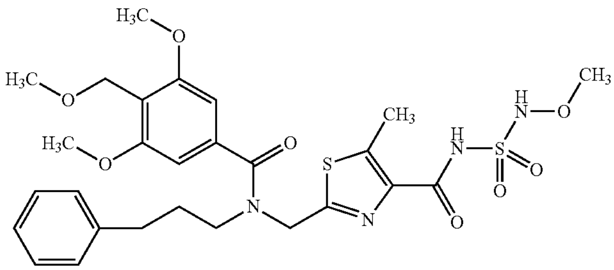 [SMILES: COCc1c(OC)cc(C(=O)N(CCCc2ccccc2)Cc2nc(C(=O)NS(=O)(=O)NOC)c(C)s2)cc1OC] |
| 162 | 7 | 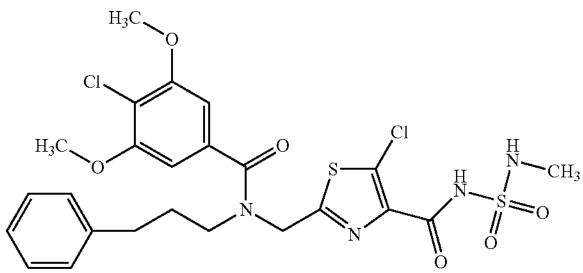 [SMILES: CNS(=O)(=O)NC(=O)c1nc(CN(CCCc2ccccc2)C(=O)c2cc(OC)c(Cl)c(OC)c2)sc1Cl] |
| 163 | 7 | 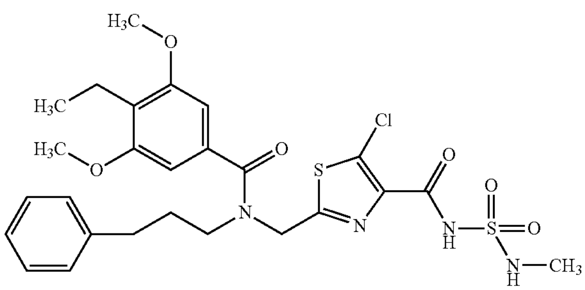 [SMILES: CCc1c(OC)cc(C(=O)N(CCCc2ccccc2)Cc2nc(C(=O)NS(=O)(=O)NC)c(Cl)s2)cc1OC] |
| 164 | 10 | 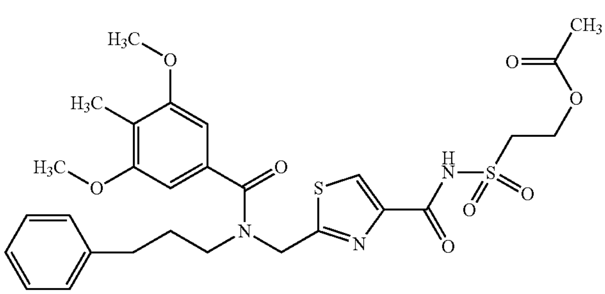 [SMILES: COc1cc(C(=O)N(CCCc2ccccc2)Cc2nc(C(=O)NS(=O)(=O)CCOC(C)=O)cs2)cc(OC)c1C] |
| 165 | 11 | 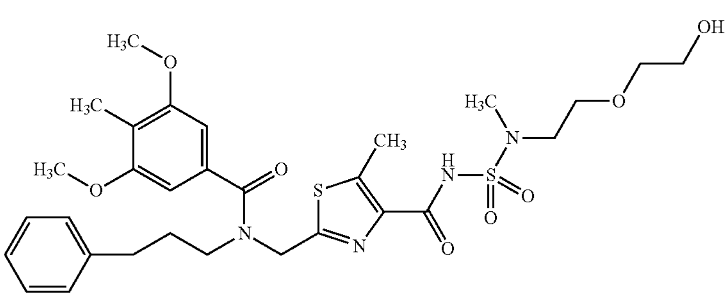 [SMILES: COc1cc(C(=O)N(CCCc2ccccc2)Cc2nc(C(=O)NS(=O)(=O)N(C)CCOCCO)c(C)s2)cc(OC)c1C] |

TABLE 89
| Ex | Syn | Structure |
|---|---|---|
| 166 | 11 | 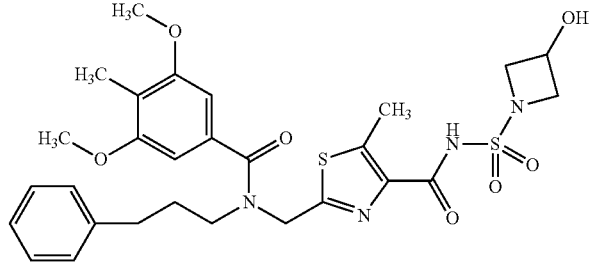 [SMILES: COc1cc(C(=O)N(CCCc2ccccc2)Cc2nc(C(=O)NS(=O)(=O)N3CC(O)C3)c(C)s2)cc(OC)c1C] |
| 167 | 11 | 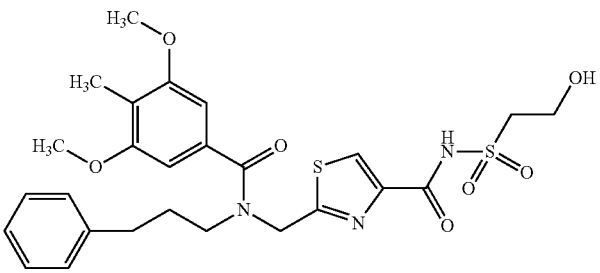 [SMILES: COc1cc(C(=O)N(CCCc2ccccc2)Cc2nc(C(=O)NS(=O)(=O)CCO)cs2)cc(OC)c1C] |
| 168 | 168 | 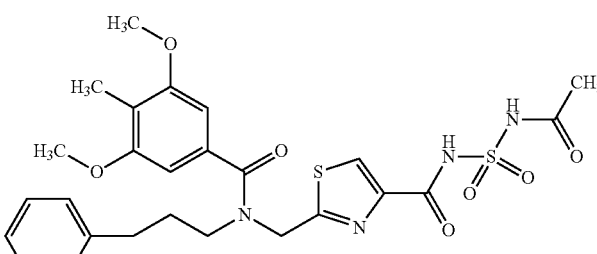 |
| 169 | 23 | 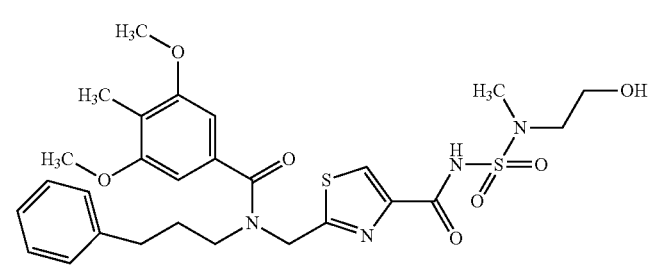 [SMILES: COc1cc(C(=O)N(CCCc2ccccc2)Cc2nc(C(=O)NS(=O)(=O)N(C)CCO)cs2)cc(OC)c1C] |
| 170 | 23 | 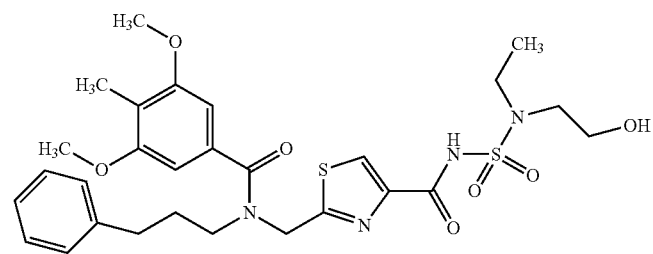 [SMILES: CCN(CCO)S(=O)(=O)NC(=O)c1csc(CN(CCCc2ccccc2)C(=O)c2cc(OC)c(C)c(OC)c2)n1] |

TABLE 90

| Ex | Syn | Structure |
|---|---|---|
| 171 | 23 | 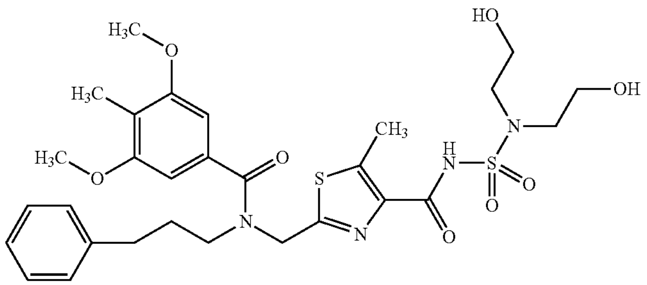 [SMILES: COc1cc(C(=O)N(CCCc2ccccc2)Cc2nc(C(=O)NS(=O)(=O)N(CCO)CCO)c(C)s2)cc(OC)c1C] |
| 172 | 23 | 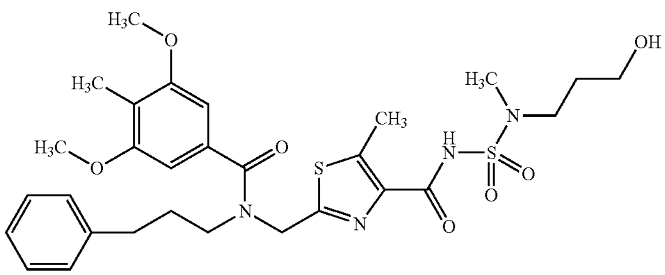 [SMILES: COc1cc(C(=O)N(CCCc2ccccc2)Cc2nc(C(=O)NS(=O)(=O)N(C)CCCO)c(C)s2)cc(OC)c1C] |
| 173 | 23 | 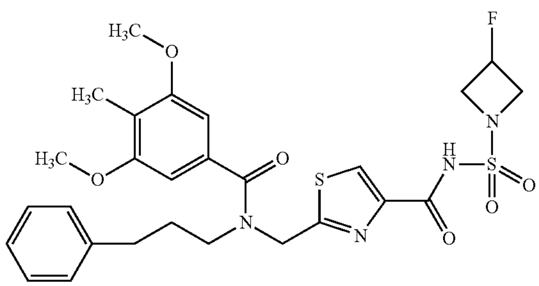 [SMILES: COc1cc(C(=O)N(CCCc2ccccc2)Cc2nc(C(=O)NS(=O)(=O)N3CC(F)C3)cs2)cc(OC)c1C] |
| 174 | 23 | 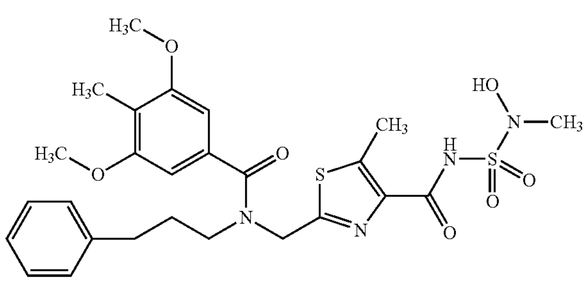 [SMILES: COc1cc(C(=O)N(CCCc2ccccc2)Cc2nc(C(=O)NS(=O)(=O)N(C)O)c(C)s2)cc(OC)c1C] |
| 175 | 23 | 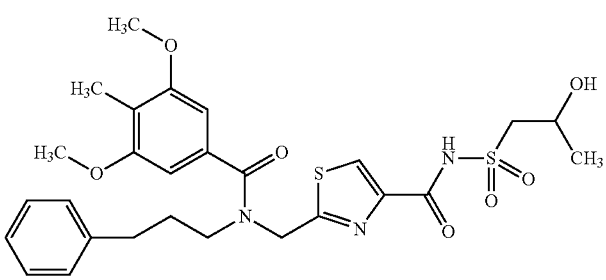 [SMILES: COc1cc(C(=O)N(CCCc2ccccc2)Cc2nc(C(=O)NS(=O)(=O)CC(C)O)cs2)cc(OC)c1C] |

TABLE 91
| Ex | Syn | Structure |
|---|---|---|
| 176 | 23 | 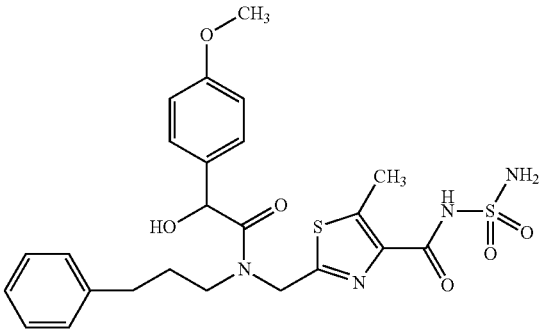 [SMILES: COc1ccc(C(O)C(=O)N(CCCc2ccccc2)Cc2nc(C(=O)NS(N)(=O)=O)c(C)s2)cc1] |
| 177 | 23 | 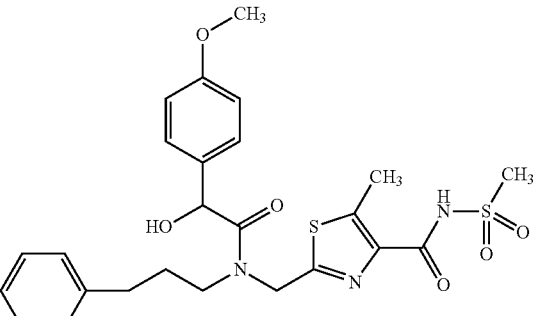 |
| 178 | 23 | 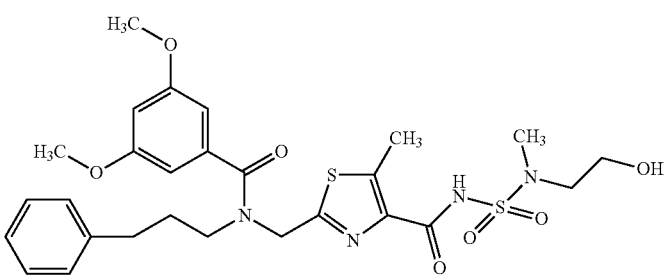 [SMILES: COc1cc(OC)cc(C(=O)N(CCCc2ccccc2)Cc2nc(C(=O)NS(=O)(=O)N(C)CCO)c(C)s2)c1] |
| 179 | 1 | 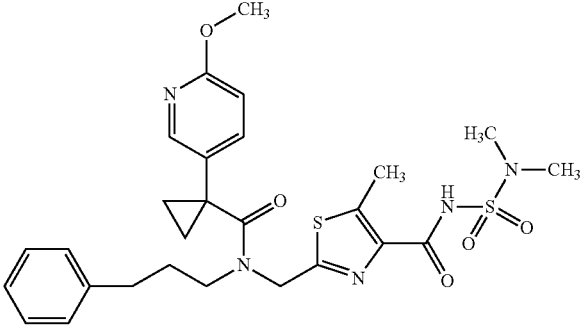 [SMILES: COc1ccc(C2(C(=O)N(CCCc3ccccc3)Cc3nc(C(=O)NS(=O)(=O)N(C)C)c(C)s3)CC2)cn1] |

TABLE 91-continued
| Ex | Syn | Structure |
|---|---|---|
| 180 | 1 | 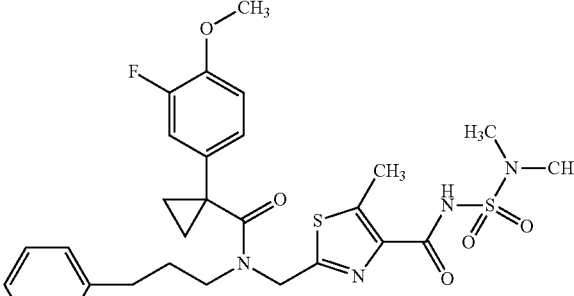 |
TABLE 92
| Ex | Syn | Structure |
|---|---|---|
| 181 | 1 | 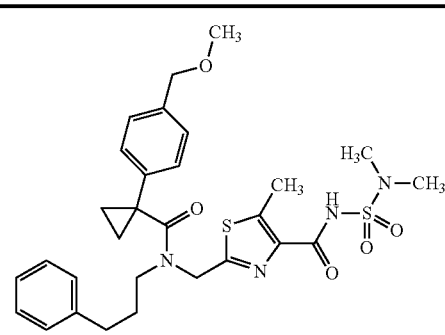 |
| 182 | 1 | 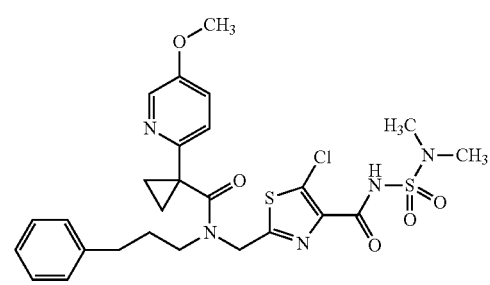 [SMILES: COc1ccc(C2(C(=O)N(CCCc3ccccc3)Cc3nc(C(=O)NS(=O)(=O)N(C)C)c(Cl)s3)CC2)nc1] |
| 183 | 1 | 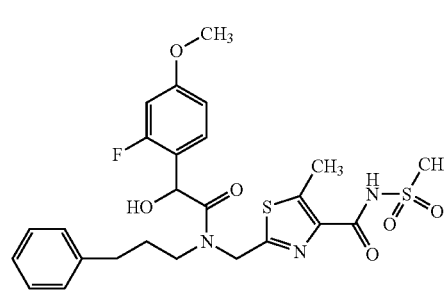 |
TABLE 92-continued
| Ex | Syn | Structure |
|---|---|---|
| 184 | 1 | 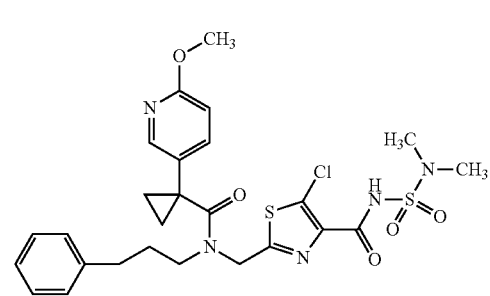 [SMILES: COc1ccc(C2(C(=O)N(CCCc3ccccc3)Cc3nc(C(=O)NS(=O)(=O)N(C)C)c(Cl)s3)CC2)cn1] |
| 185 | 1 | 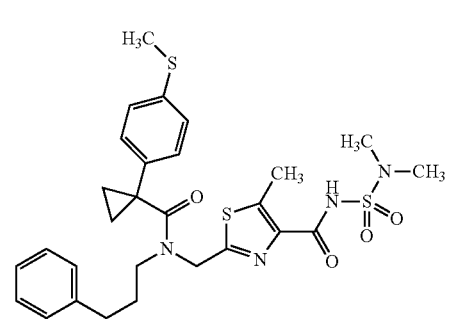 |
TABLE 93
| Ex | Syn | Structure |
|---|---|---|
| 186 | 1 | 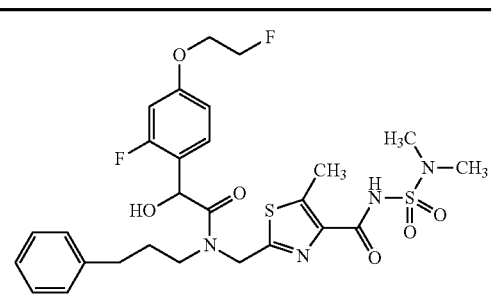 |

TABLE 93-continued
| Ex | Syn | Structure |
|---|---|---|
| 187 | 1 | 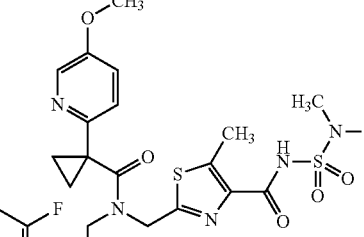 |
| 188 | 1 | 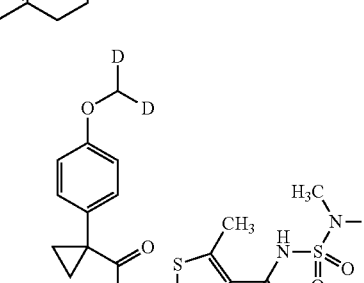 |
| 189 | 1 | 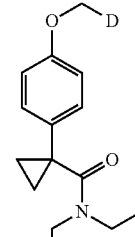 |
| 190 | 1 | 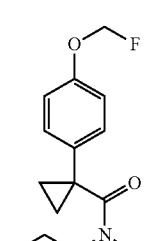 |
TABLE 94
| Ex | Syn | Structure |
|---|---|---|
| 191 | 1 | 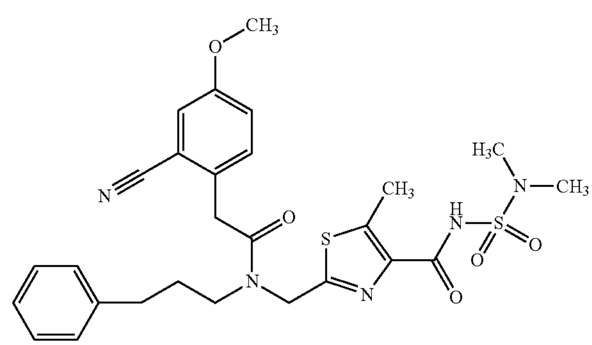 [SMILES: COc1ccc(CC(=O)N(CCCc2ccccc2)Cc2nc(C(=O)NS(=O)(=O)N(C)C)c(C)s2)c(C#N)c1] |
| 192 | 1 | 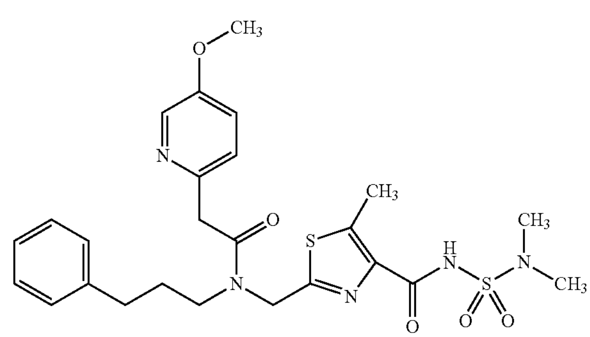 [SMILES: COc1ccc(CC(=O)N(CCCc2ccccc2)Cc2nc(C(=O)NS(=O)(=O)N(C)C)c(C)s2)nc1] |

TABLE 94-continued
| Ex | Syn | Structure |
|---|---|---|
| 193 | 7 | 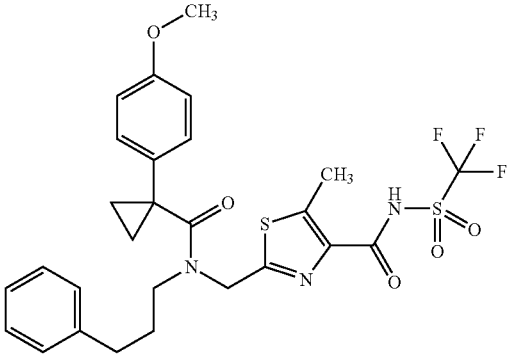 [SMILES: COc1ccc(C2(C(=O)N(CCCc3ccccc3)Cc3nc(C(=O)NS(=O)(=O)C(F)(F)F)c(C)s3)CC2)cc1] |
| 194 | 7 | 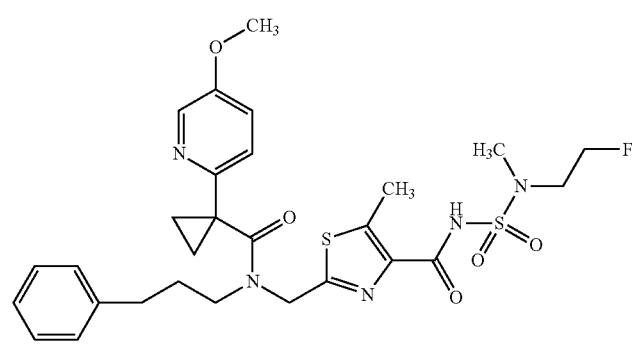 [SMILES: COc1ccc(C2(C(=O)N(CCCc3ccccc3)Cc3nc(C(=O)NS(=O)(=O)N(C)CCF)c(C)s3)CC2)nc1] |
| 195 | 7 | 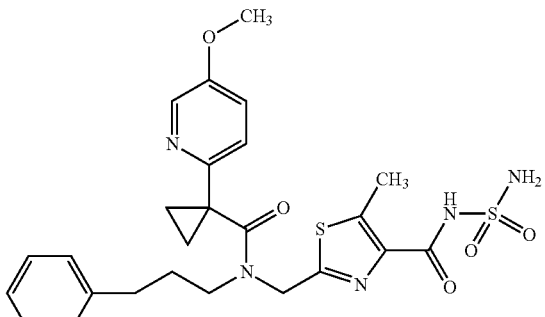 |
TABLE 95
| Ex | Syn | Structure |
|---|---|---|
| 196 | 7 | 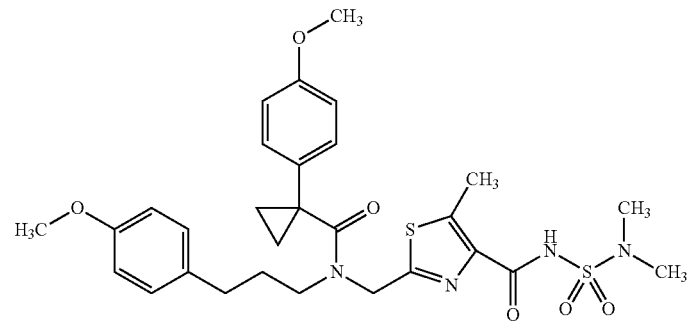 |

TABLE 95-continued
| Ex | Syn | Structure |
|---|---|---|
| 197 | 7 | 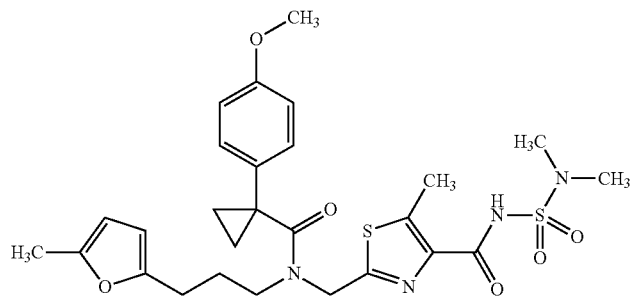 |
| 198 | 7 | 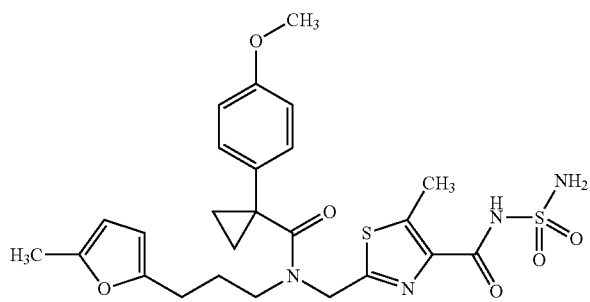 [SMILES: COc1ccc(C2(C(=O)N(CCCc3ccc(C)o3)Cc3nc(C(=O)NS(N)(=O)=O)c(C)s3)CC2)cc1] |
| 199 | 7 | 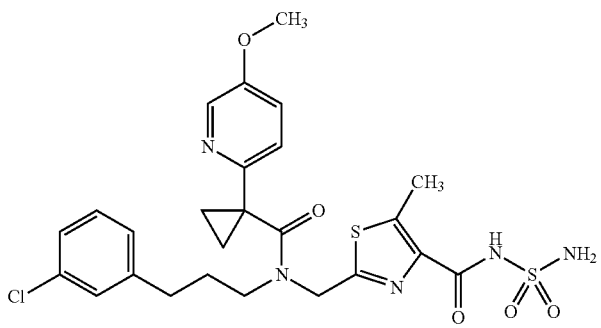 [SMILES: COc1ccc(C2(C(=O)N(CCCc3cccc(Cl)c3)Cc3nc(C(=O)NS(N)(=O)=O)c(C)s3)CC2)nc1] |
| 200 | 7 | 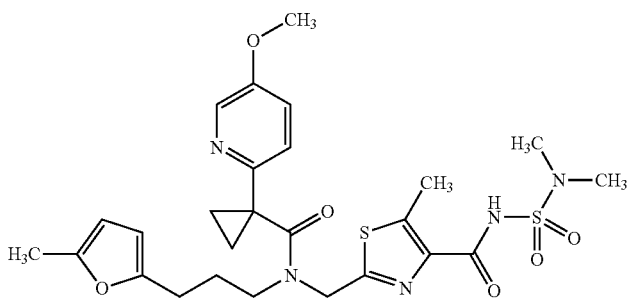 |

TABLE 96

| Ex | Syn | Structure |
|---|---|---|
| 201 | 7 | 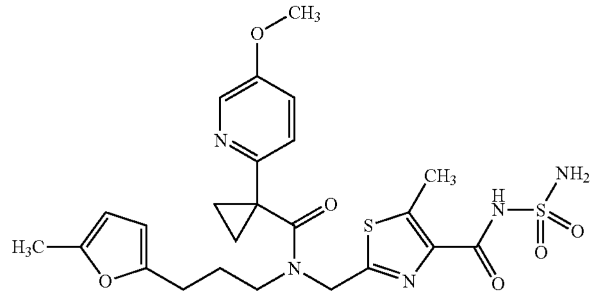 [SMILES: COc1ccc(C2(C(=O)N(CCCc3ccc(C)o3)Cc3nc(C(=O)NS(N)(=O)=O)c(C)s3)CC2)nc1] |
| 202 | 7 | 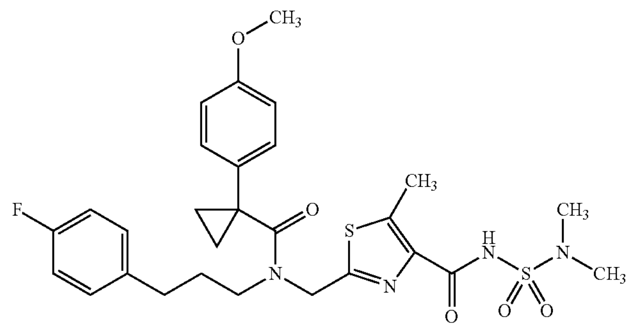 [SMILES: COc1ccc(C2(C(=O)N(CCCc3ccc(F)cc3)Cc3nc(C(=O)NS(=O)(=O)N(C)C)c(C)s3)CC2)cc1] |
| 203 | 7 | 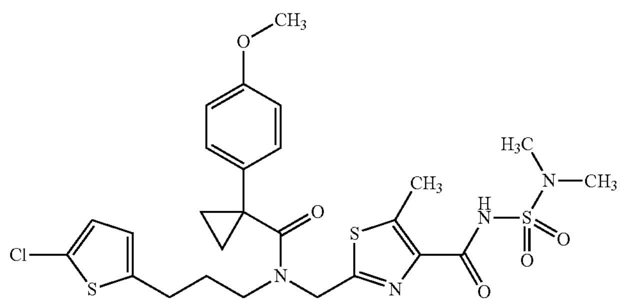 |
| 204 | 7 | 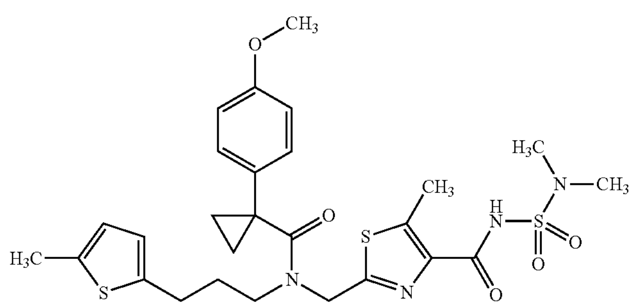 |
| 205 | 7 | 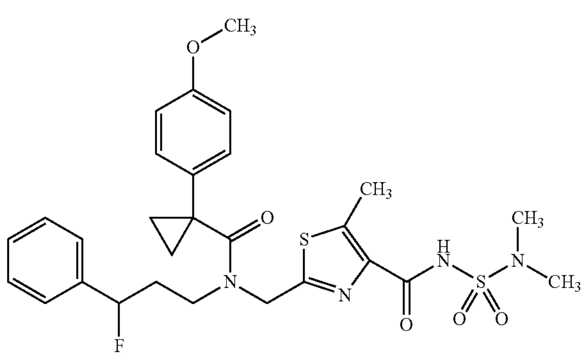 [SMILES: COc1ccc(C2(C(=O)N(CCC(F)c3ccccc3)Cc3nc(C(=O)NS(=O)(=O)N(C)C)c(C)s3)CC2)cc1] |

TABLE 97
| Ex | Syn | Structure |
|---|---|---|
| 206 | 7 | 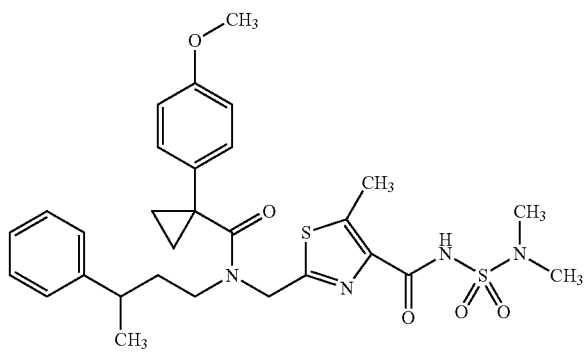 [SMILES: COc1ccc(C2(C(=O)N(CCC(C)c3ccccc3)Cc3nc(C(=O)NS(=O)(=O)N(C)C)c(C)s3)CC2)cc1] |
| 207 | 7 | 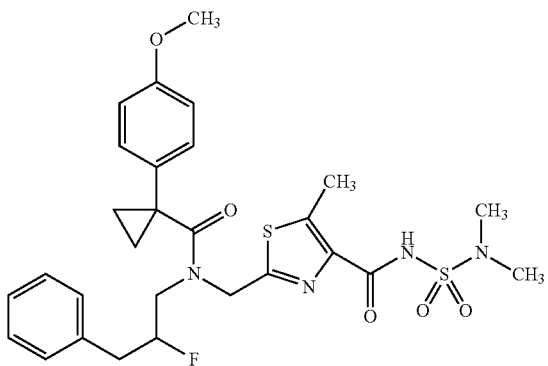 [SMILES: COc1ccc(C2(C(=O)N(Cc3nc(C(=O)NS(=O)(=O)N(C)C)c(C)s3)CC(F)Cc3ccccc3)CC2)cc1] |
| 208 | 7 | 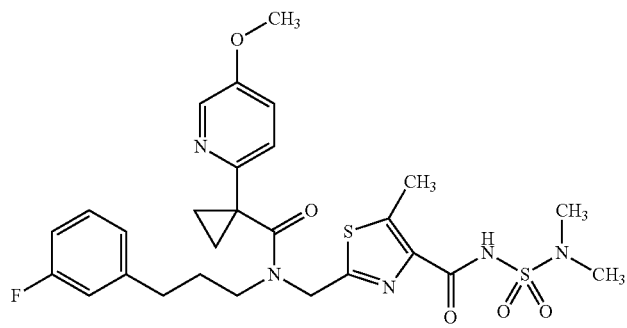 [SMILES: COc1ccc(C2(C(=O)N(CCCc3cccc(F)c3)Cc3nc(C(=O)NS(=O)(=O)N(C)C)c(C)s3)CC2)nc1] |
| 209 | 7 | 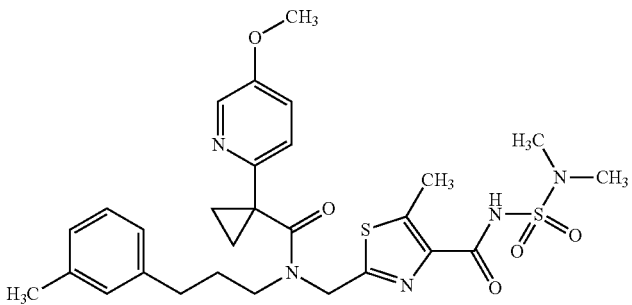 |

TABLE 97-continued
| Ex | Syn | Structure |
|---|---|---|
| 210 | 7 | 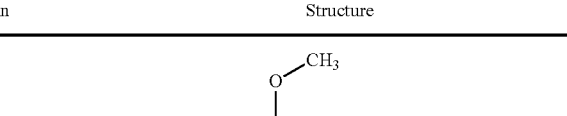 |
TABLE 98
| Ex | Syn | Structure |
|---|---|---|
| 211 | 7 | 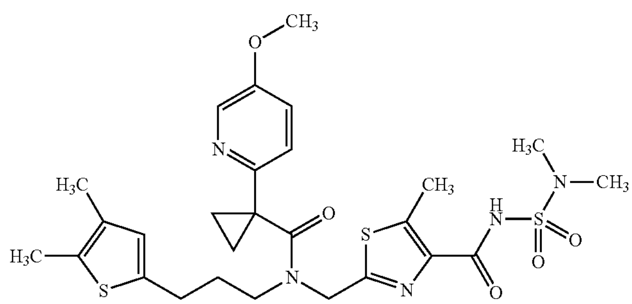 |
| 212 | 7 | 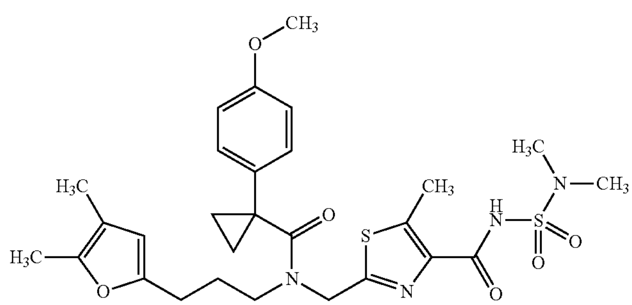 |
| 213 | 7 | 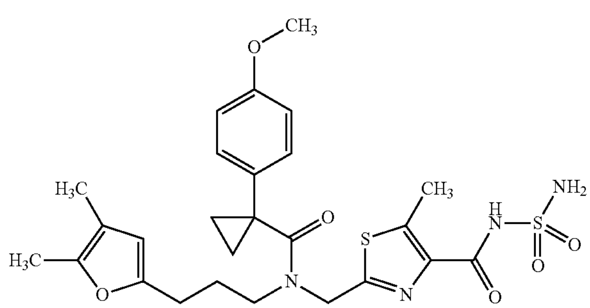 [SMILES: COc1ccc(C2(C(=O)N(CCCc3cc(C)c(C)o3)Cc3nc(C(=O)NS(N)(=O)=O)c(C)s3)CC2)cc1] |

TABLE 98-continued

| Ex | Syn | Structure |
|---|---|---|
| 214 | 7 | 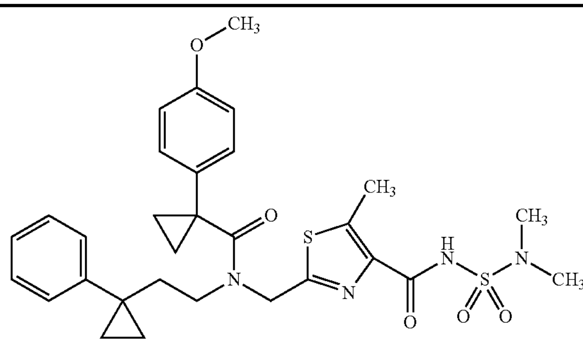 |
| 215 | 7 | 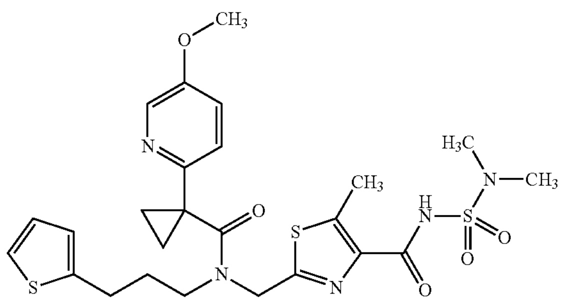 |

TABLE 99

| Ex | Syn | Structure |
|---|---|---|
| 216 | 7 | 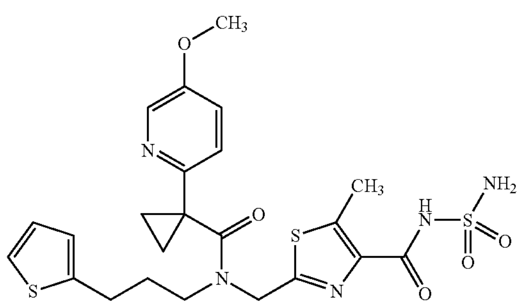 [SMILES: COc1ccc(C2(C(=O)N(CCCc3cccs3)Cc3nc(C(=O)NS(N)(=O)=O)c(C)s3)CC2)nc1] |
| 217 | 7 | 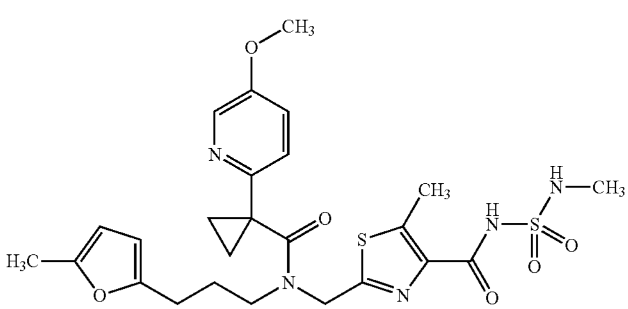 |

TABLE 99-continued
| Ex | Syn | Structure |
|---|---|---|
| 218 | 7 | 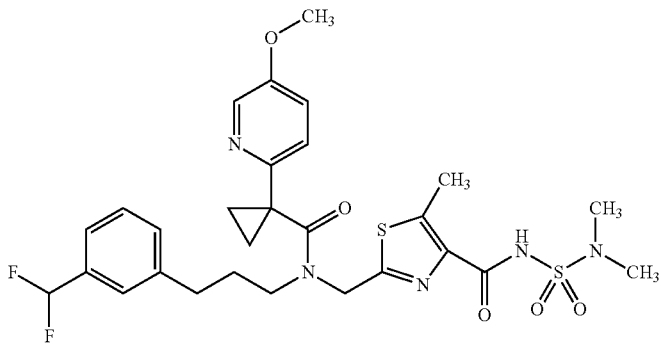 [SMILES: COc1ccc(C2(C(=O)N(CCCc3cccc(C(F)F)c3)Cc3nc(C(=O)NS(=O)(=O)N(C)C)c(C)s3)CC2)nc1] |
| 219 | 7 | 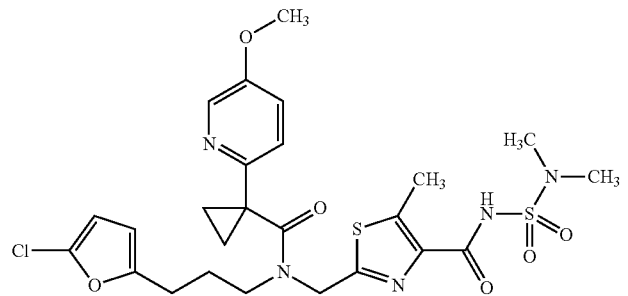 [SMILES: COc1ccc(C2(C(=O)N(CCCc3ccc(Cl)o3)Cc3nc(C(=O)NS(=O)(=O)N(C)C)c(C)s3)CC2)nc1] |
| 220 | 7 | 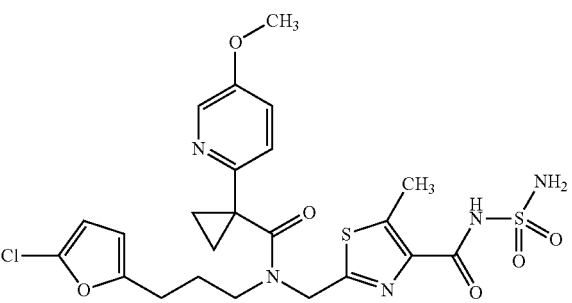 [SMILES: COc1ccc(C2(C(=O)N(CCCc3ccc(Cl)o3)Cc3nc(C(=O)NS(N)(=O)=O)c(C)s3)CC2)nc1] |
TABLE 100
| Ex | Syn | Structure |
|---|---|---|
| 221 | 7 | 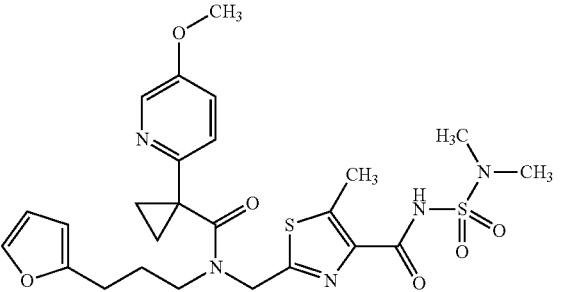 [SMILES: COc1ccc(C2(C(=O)N(CCCc3ccco3)Cc3nc(C(=O)NS(=O)(=O)N(C)C)c(C)s3)CC2)nc1] |

TABLE 100-continued
| Ex | Syn | Structure |
|----|-----|-----------|
| 222 | 7 | 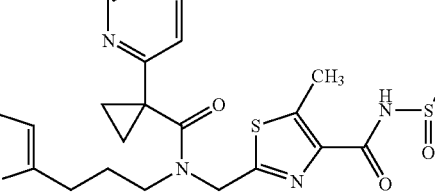 |
| 223 | 7 | 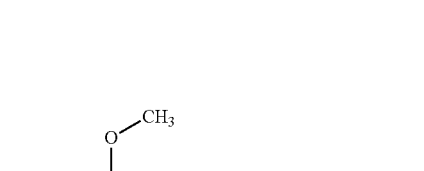 |
| 224 | 7 | 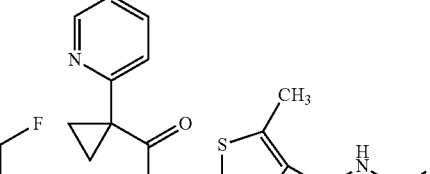 |
| 225 | 7 | 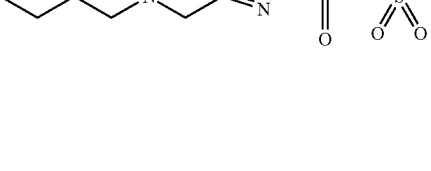 |

TABLE 101
| Ex | Syn | Structure |
|---|---|---|
| 226 | 7 | 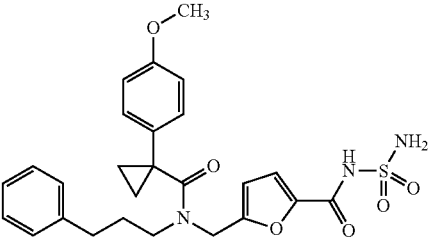 [SMILES: COc1ccc(C2(C(=O)N(CCCc3ccccc3)Cc3ccc(C(=O)NS(N)(=O)=O)o3)CC2)cc1] |
| 227 | 7 | 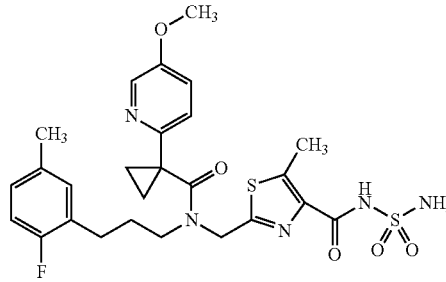 |
| 228 | 7 | 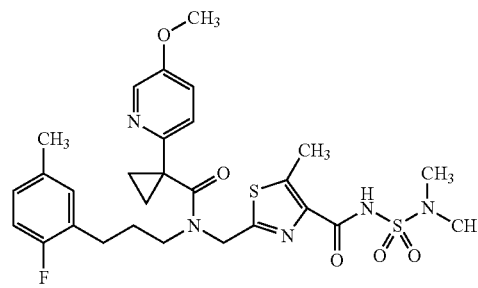 |
TABLE 101-continued
| Ex | Syn | Structure |
|---|---|---|
| 229 | 7 | 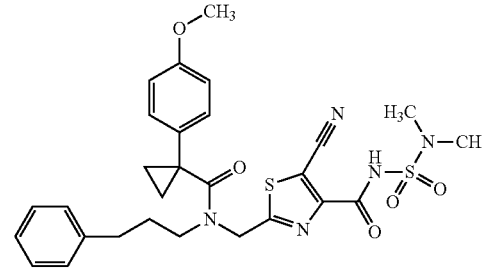 |
| 230 | 7 | 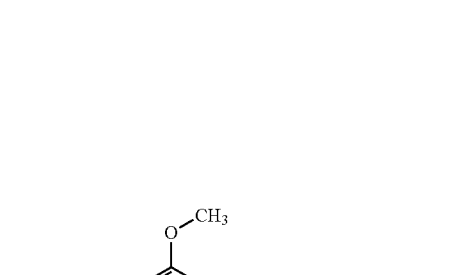 |
TABLE 102
| Ex | Syn | Structure |
|---|---|---|
| 231 | 7 | 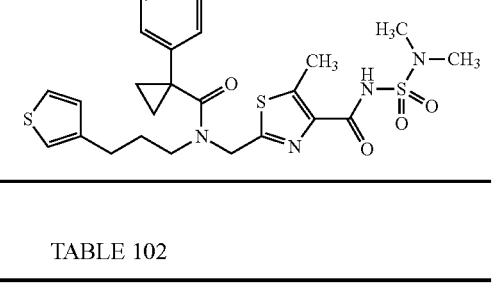 |
| 232 | 7 | 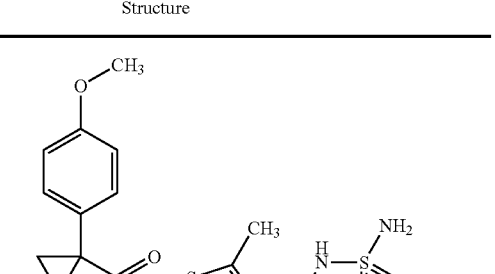 |

TABLE 102-continued

| Ex | Syn | Structure |
|---|---|---|
| 233 | 7 | 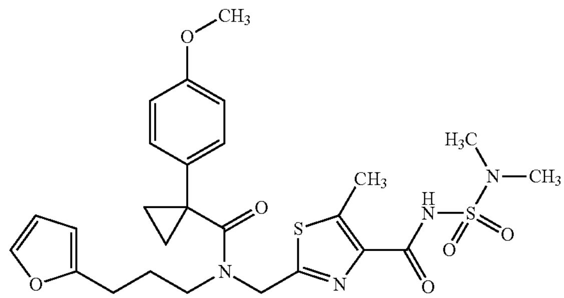 [SMILES: COc1ccc(C2(C(=O)N(CCCc3ccco3)Cc3nc(C(=O)NS(=O)(=O)N(C)C)c(C)s3)CC2)cc1] |
| 234 | 7 | 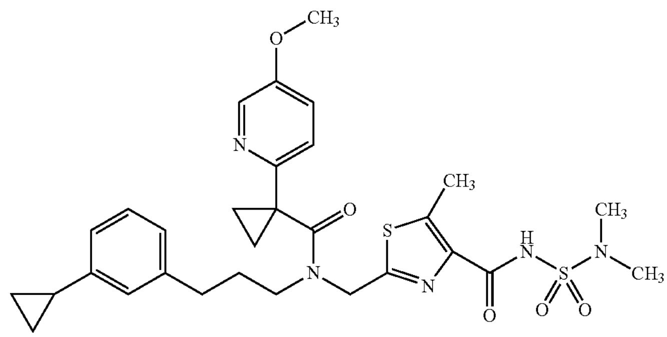 [SMILES: COc1ccc(C2(C(=O)N(CCCc3cccc(C4CC4)c3)Cc3nc(C(=O)NS(=O)(=O)N(C)C)c(C)s3)CC2)nc1] |
| 235 | 7 | 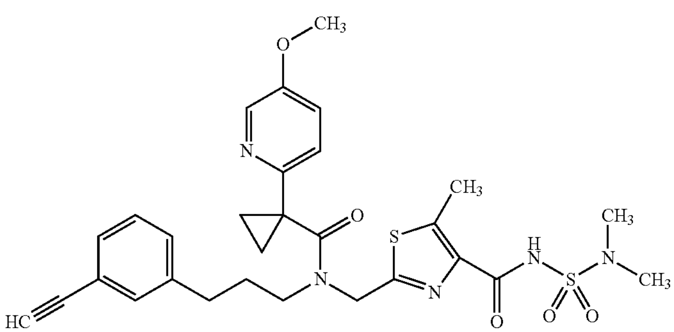 [SMILES: C#Cc1cccc(CCCN(Cc2nc(C(=O)NS(=O)(=O)N(C)C)c(C)s2)C(=O)C2(c3ccc(OC)cn3)CC2)c1] |

TABLE 103

| Ex | Syn | Structure |
|---|---|---|
| 236 | 7 | 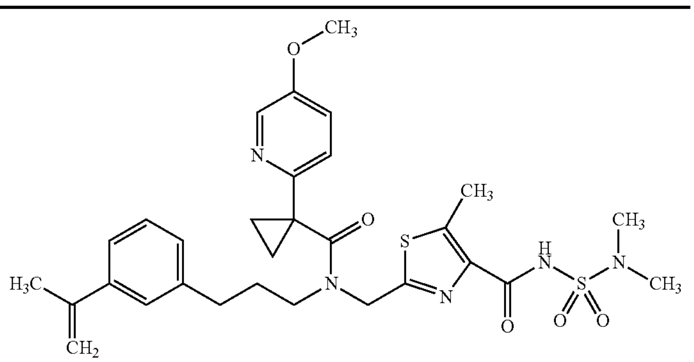 |

TABLE 103-continued
| Ex | Syn | Structure |
|---|---|---|
| 237 | 7 | 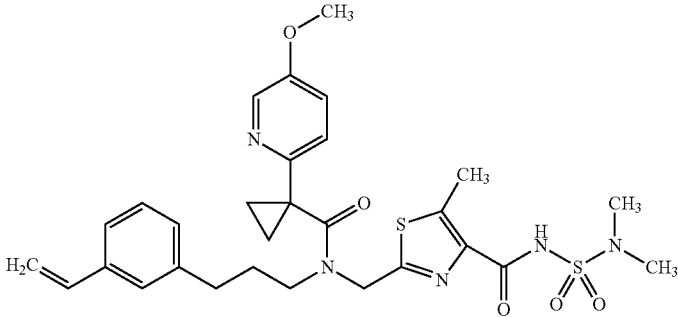 [SMILES: C=Cc1cccc(CCCN(Cc2nc(C(=O)NS(=O)(=O)N(C)C)c(C)s2)C(=O)C2(c3ccc(OC)cn3)CC2)c1] |
| 238 | 7 | 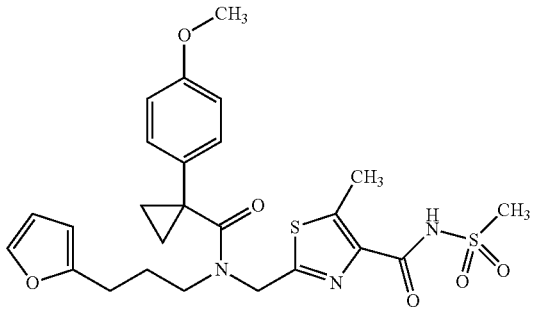 [SMILES: COc1ccc(C2(C(=O)N(CCCc3ccco3)Cc3nc(C(=O)NS(C)(=O)=O)c(C)s3)CC2)cc1] |
| 239 | 7 | 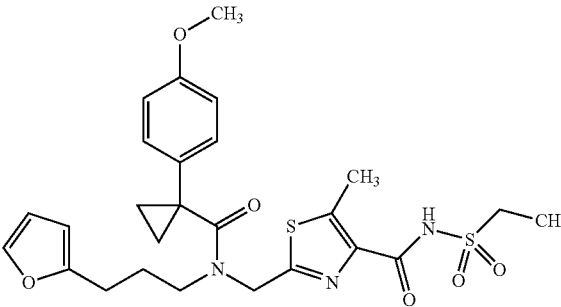 [SMILES: CCS(=O)(=O)NC(=O)c1nc(CN(CCCc2ccco2)C(=O)C2(c3ccc(OC)cc3)CC2)sc1C] |
| 240 | 23 | 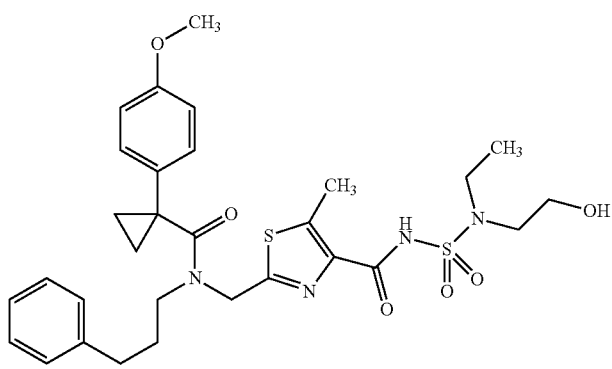 [SMILES: CCN(CCO)S(=O)(=O)NC(=O)c1nc(CN(CCCc2ccccc2)C(=O)C2(c3ccc(OC)cc3)CC2)sc1C] |

TABLE 104

| Ex | Syn | Structure |
|---|---|---|
| 241 | 23 | 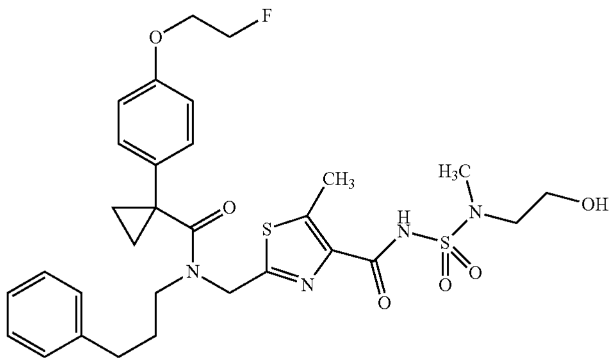 [SMILES: Cc1sc(CN(CCCc2ccccc2)C(=O)C2(c3ccc(OCCF)cc3)CC2)nc1C(=O)NS(=O)(=O)N(C)CCO] |
| 242 | 23 | 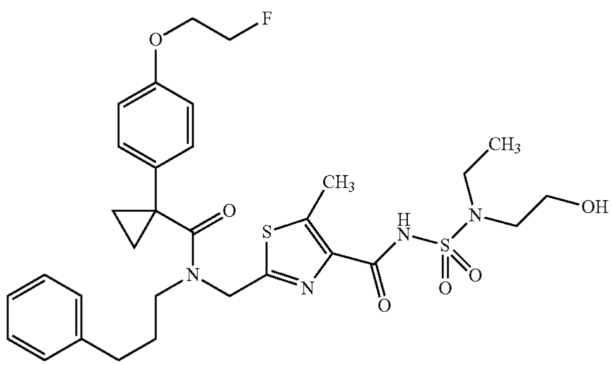 [SMILES: CCN(CCO)S(=O)(=O)NC(=O)c1nc(CN(CCCc2ccccc2)C(=O)C2(c3ccc(OCCF)cc3)CC2)sc1C] |
| 243 | 23 | 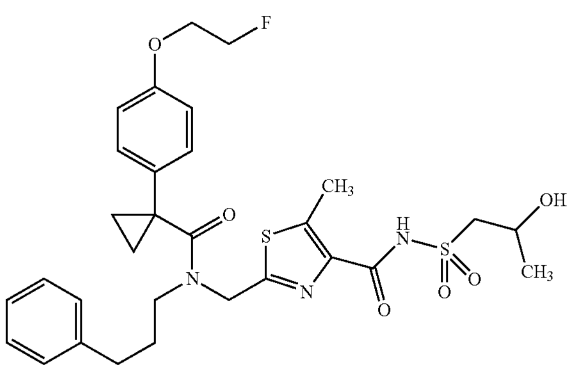 [SMILES: Cc1sc(CN(CCCc2ccccc2)C(=O)C2(c3ccc(OCCF)cc3)CC2)nc1C(=O)NS(=O)(=O)CC(C)O] |
| 244 | 23 | 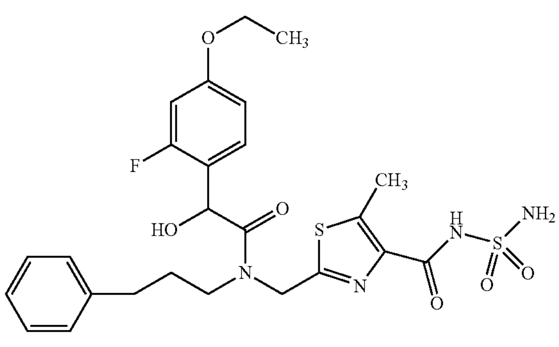 [SMILES: CCOc1ccc(C(O)C(=O)N(CCCc2ccccc2)Cc2nc(C(=O)NS(N)(=O)=O)c(C)s2)c(F)c1] |

TABLE 104-continued
| Ex | Syn | Structure |
|---|---|---|
| 245 | 23 | 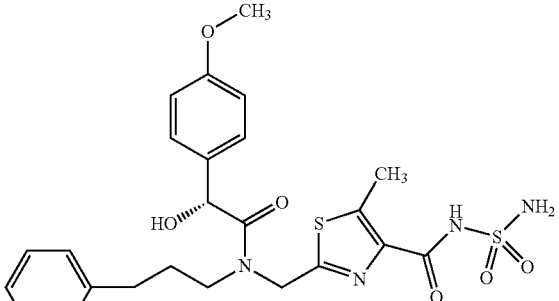 |
TABLE 105
| Ex | Syn | Structure |
|---|---|---|
| 246 | 23 | 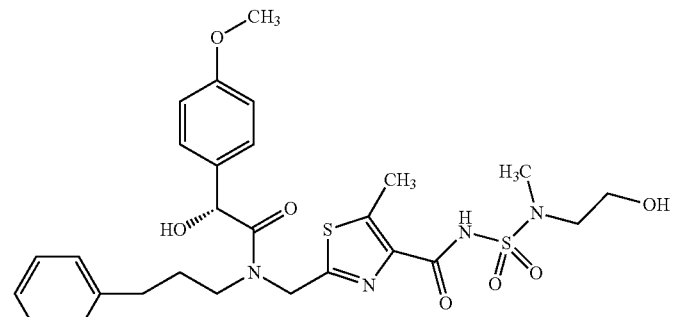 |
| 247 | 23 | 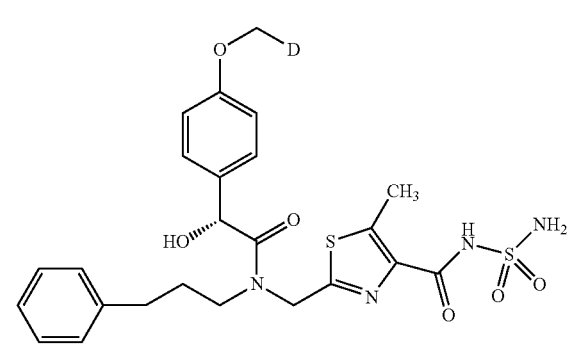 [SMILES: [2H]COc1ccc([C@@H](O)C(=O)N(CCCc2ccccc2)Cc2nc(C(=O)NS(N)(=O)=O)c(C)s2)cc1] |
| 248 | 23 | 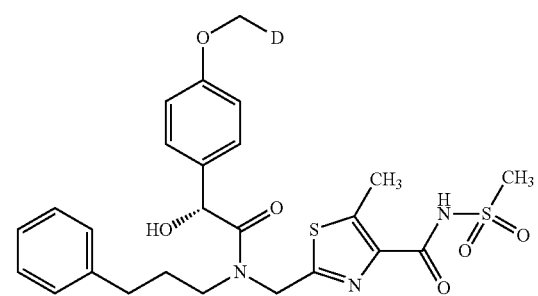 [SMILES: [2H]COc1ccc([C@@H](O)C(=O)N(CCCc2ccccc2)Cc2nc(C(=O)NS(C)(=O)=O)c(C)s2)cc1] |

TABLE 105-continued

| Ex | Syn | Structure |
|---|---|---|
| 249 | 23 | 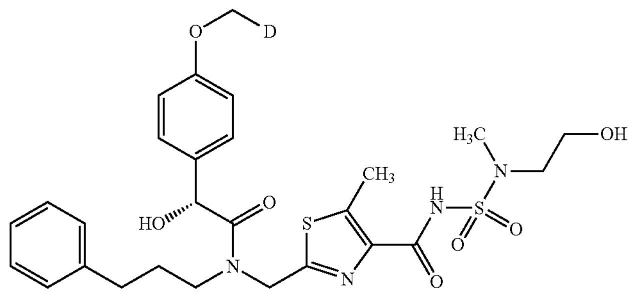 [SMILES: [2H]COc1ccc([C@@H](O)C(=O)N(CCCc2ccccc2)Cc2nc(C(=O)NS(=O)(=O)N(C)CCO)c(C)s2)cc1] |
| 250 | 23 | 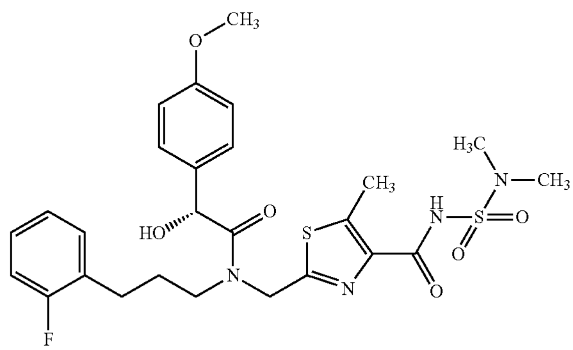 [SMILES: COc1ccc([C@@H](O)C(=O)N(CCCc2ccccc2F)Cc2nc(C(=O)NS(=O)(=O)N(C)C)c(C)s2)cc1] |

TABLE 106

| Ex | Syn | Structure |
|---|---|---|
| 251 | 23 | 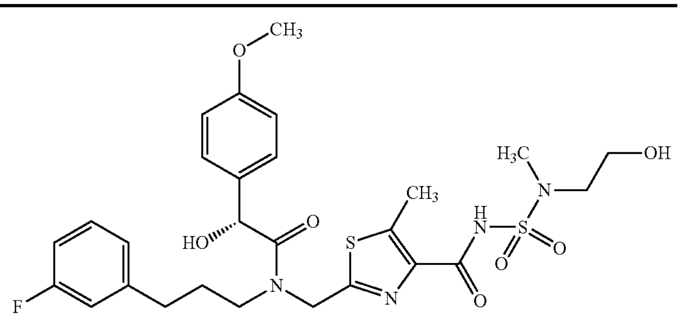 |
| 252 | 23 | 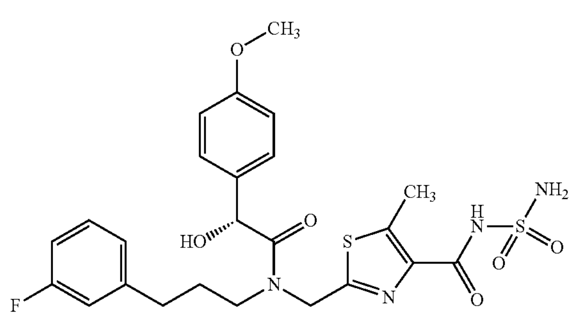 [SMILES: COc1ccc([C@@H](O)C(=O)N(CCCc2cccc(F)c2)Cc2nc(C(=O)NS(N)(=O)=O)c(C)s2)cc1] |

TABLE 106-continued

| Ex | Syn | Structure |
|---|---|---|
| 253 | 23 | 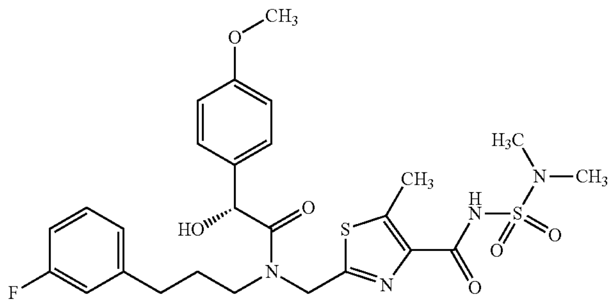 [SMILES: COc1ccc([C@@H](O)C(=O)N(CCCc2cccc(F)c2)Cc2nc(C(=O)NS(=O)(=O)N(C)C)c(C)s2)cc1] |
| 254 | 23 | 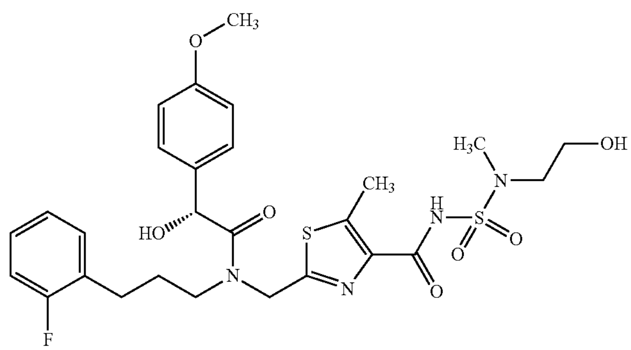 [SMILES: COc1ccc([C@@H](O)C(=O)N(CCCc2ccccc2F)Cc2nc(C(=O)NS(=O)(=O)N(C)CCO)c(C)s2)cc1] |
| 255 | 23 | 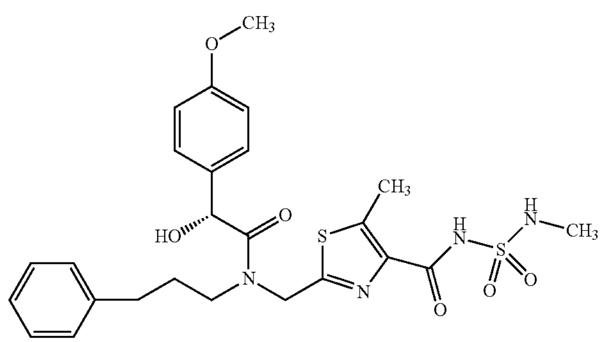 [SMILES: CNS(=O)(=O)NC(=O)c1nc(CN(CCCc2ccccc2)C(=O)[C@H](O)c2ccc(OC)cc2)sc1C] |

TABLE 107

| Ex | Syn | Structure |
|---|---|---|
| 256 | 23 | 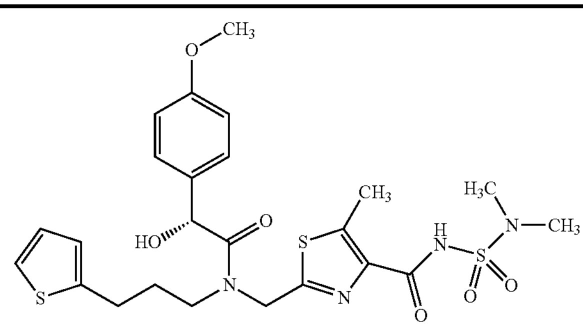 |

TABLE 107-continued
| Ex | Syn | Structure |
|---|---|---|
| 257 | 23 | 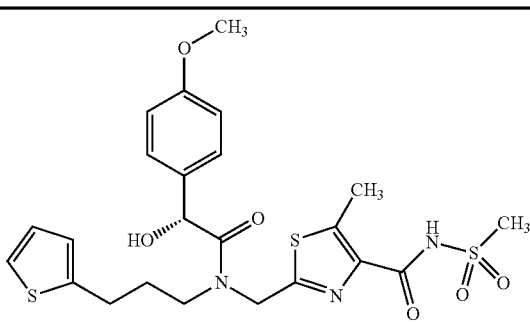 |
| 258 | 23 | 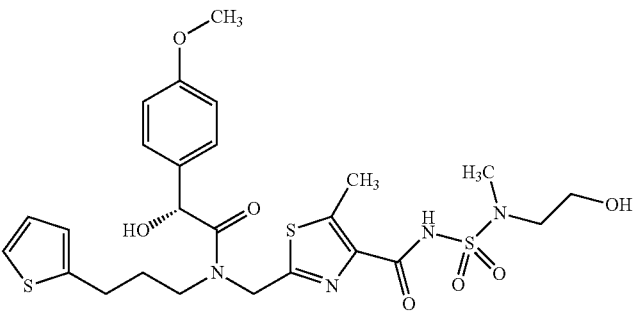 [SMILES: COc1ccc([C@@H](O)C(=O)N(CCCc2cccs2)Cc2nc(C(=O)NS(=O)(=O)N(C)CCO)c(C)s2)cc1] |
| 259 | 23 | 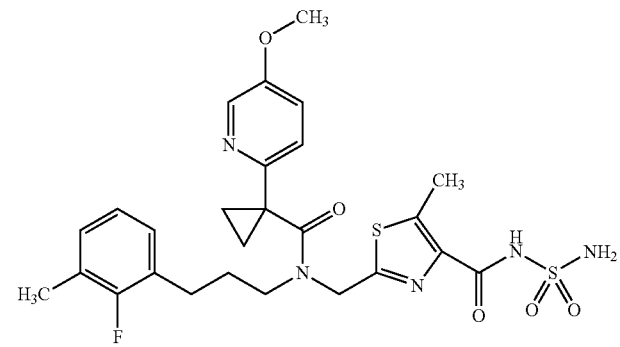 [SMILES: COc1ccc(C2(C(=O)N(CCCc3cccc(C)c3F)Cc3nc(C(=O)NS(N)(=O)=O)c(C)s3)CC2)nc1] |
| 260 | 23 | 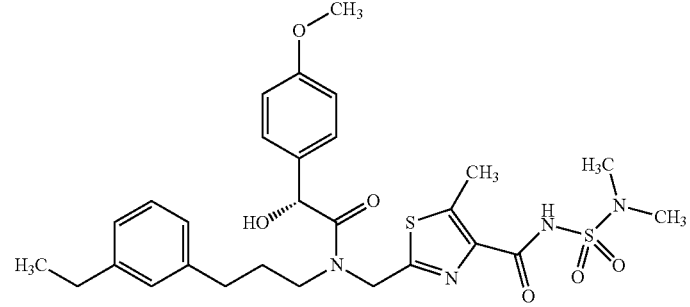 [SMILES: CCc1cccc(CCCN(Cc2nc(C(=O)NS(=O)(=O)N(C)C)c(C)s2)C(=O)[C@H](O)c2ccc(OC)cc2)c1] |

TABLE 108

| Ex | Syn | Structure |
|---|---|---|
| 261 | 23 | 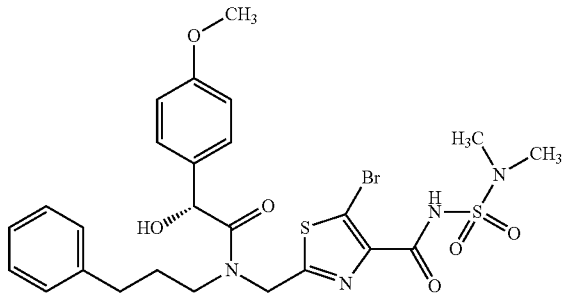 [SMILES: COc1ccc([C@@H](O)C(=O)N(CCCc2ccccc2)Cc2nc(C(=O)NS(=O)(=O)N(C)C)c(Br)s2)cc1] |
| 262 | 23 | 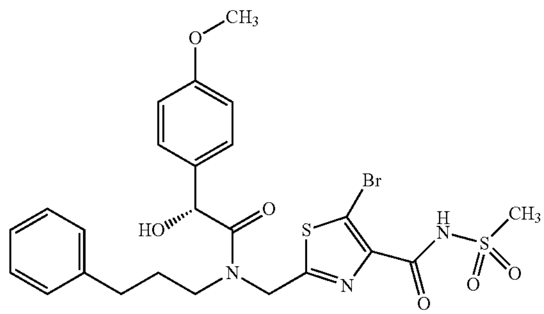 [SMILES: COc1ccc([C@@H](O)C(=O)N(CCCc2ccccc2)Cc2nc(C(=O)NS(C)(=O)=O)c(Br)s2)cc1] |
| 263 | 23 | 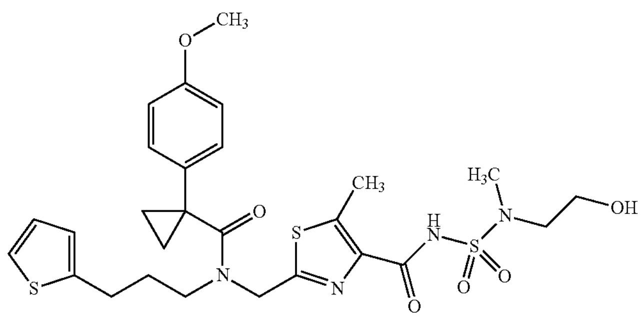 |
| 264 | 23 | 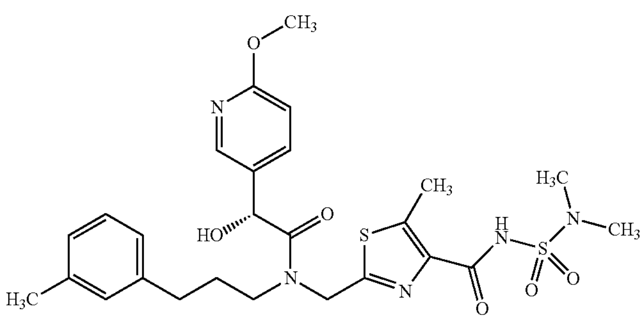 |
| 265 | 23 | 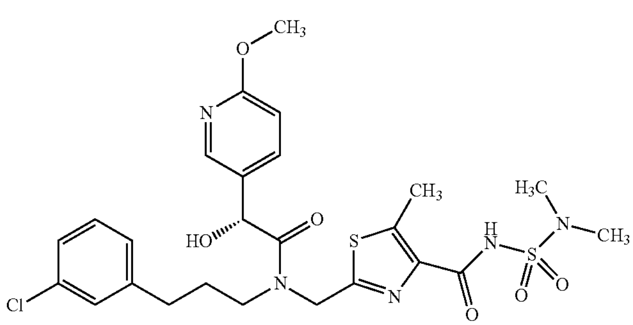 [SMILES: COc1ccc([C@@H](O)C(=O)N(CCCc2cccc(Cl)c2)Cc2nc(C(=O)NS(=O)(=O)N(C)C)c(C)s2)cn1] |

TABLE 109
| Ex | Syn | Structure |
|---|---|---|
| 266 | 23 | 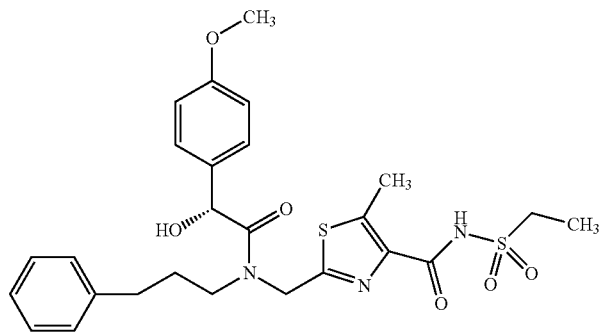 [SMILES: CCS(=O)(=O)NC(=O)c1nc(CN(CCCc2ccccc2)C(=O)[C@H](O)c2ccc(OC)cc2)sc1C] |
| 267 | 23 | 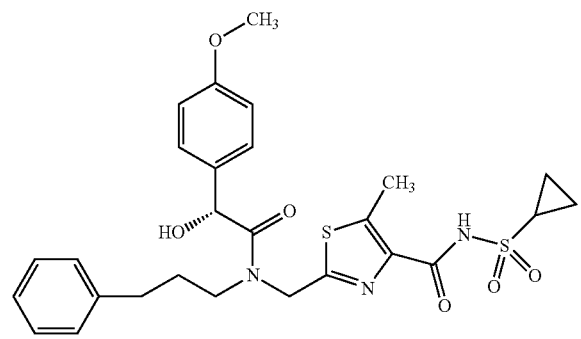 [SMILES: COc1ccc([C@@H](O)C(=O)N(CCCc2ccccc2)Cc2nc(C(=O)NS(=O)(=O)C3CC3)c(C)s2)cc1] |
| 268 | 23 | 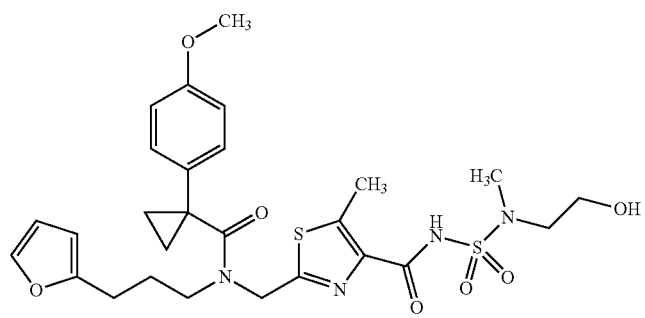 [SMILES: COc1ccc(C2(C(=O)N(CCCc3ccco3)Cc3nc(C(=O)NS(=O)(=O)N(C)CCO)c(C)s3)CC2)cc1] |
| 269 | 23 | 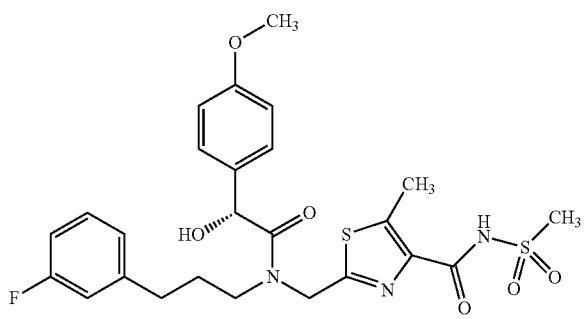 [SMILES: COc1ccc([C@@H](O)C(=O)N(CCCc2cccc(F)c2)Cc2nc(C(=O)NS(C)(=O)=O)c(C)s2)cc1] |

TABLE 109-continued

| Ex | Syn | Structure |
|---|---|---|
| 270 | 23 | (structure) |

TABLE 110

| Ex | Syn | Structure |
|---|---|---|
| 271 | 23 | (structure) |
| 272 | 23 | (structure) |
| 273 | 23 | (structure) |

TABLE 110-continued

| Ex | Syn | Structure |
|---|---|---|
| 274 | 23 | (structure) |
| 275 | 23 | (structure) |

TABLE 111

| Ex | Syn | Structure |
|---|---|---|
| 276 | 23 | (structure) |

TABLE 111-continued
| Ex | Syn | Structure |
|---|---|---|
| 277 | 23 | 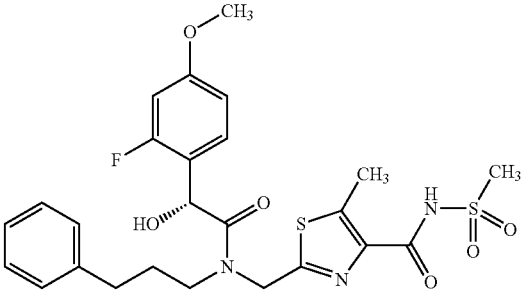 [SMILES: COc1ccc([C@@H](O)C(=O)N(CCCc2ccccc2)Cc2nc(C(=O)NS(C)(=O)=O)c(C)s2)c(F)c1] |
| 278 | 23 | 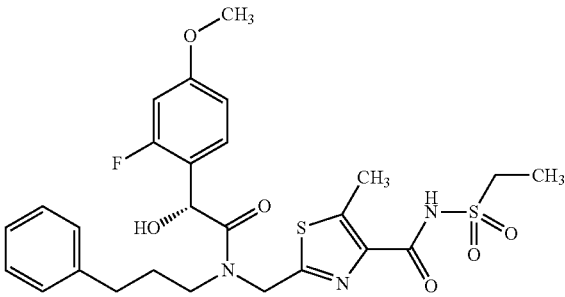 [SMILES: CCS(=O)(=O)NC(=O)c1nc(CN(CCCc2ccccc2)C(=O)[C@H](O)c2ccc(OC)cc2F)sc1C] |
| 279 | 23 | 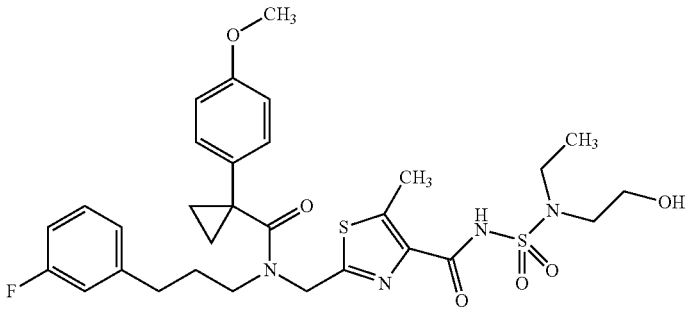 [SMILES: CCN(CCO)S(=O)(=O)NC(=O)c1nc(CN(CCCc2cccc(F)c2)C(=O)C2(c3ccc(OC)cc3)CC2)sc1C] |
| 280 | 23 | 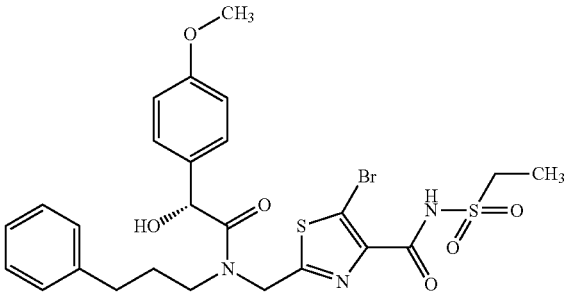 [SMILES: CCS(=O)(=O)NC(=O)c1nc(CN(CCCc2ccccc2)C(=O)[C@H](O)c2ccc(OC)cc2)sc1Br] |

TABLE 112

| Ex | Syn | Structure |
|---|---|---|
| 281 | 23 | 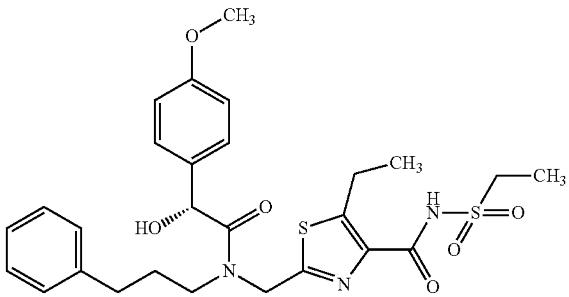 [SMILES: CCc1sc(CN(CCCc2ccccc2)C(=O)[C@H](O)c2ccc(OC)cc2)nc1C(=O)NS(=O)(=O)CC] |
| 282 | 23 | 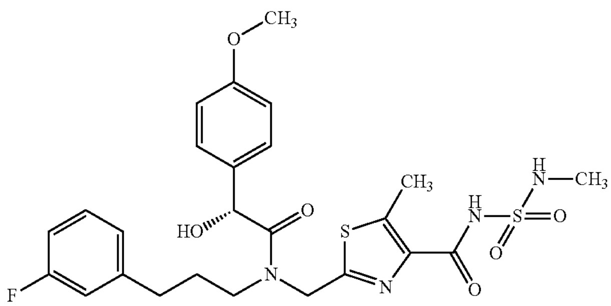 [SMILES: CNS(=O)(=O)NC(=O)c1nc(CN(CCCc2cccc(F)c2)C(=O)[C@H](O)c2ccc(OC)cc2)sc1C] |
| 283 | 23 | 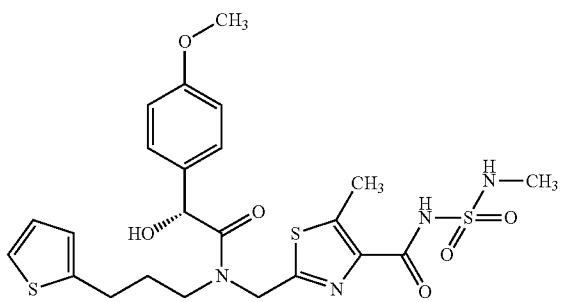 [SMILES: CNS(=O)(=O)NC(=O)c1nc(CN(CCCc2cccs2)C(=O)[C@H](O)c2ccc(OC)cc2)sc1C] |
| 284 | 23 | 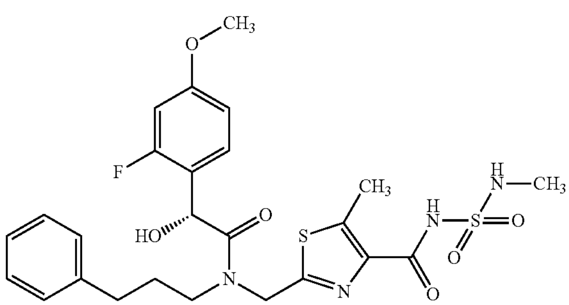 [SMILES: CNS(=O)(=O)NC(=O)c1nc(CN(CCCc2ccccc2)C(=O)[C@H](O)c2ccc(OC)cc2F)sc1C] |
| 285 | 23 | 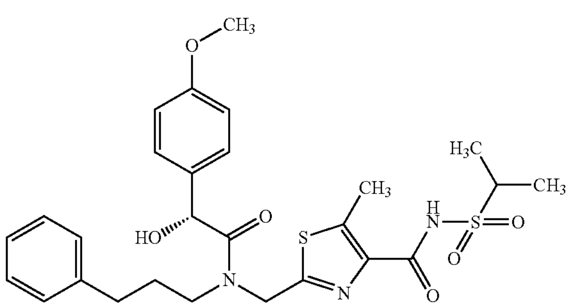 [SMILES: COc1ccc([C@@H](O)C(=O)N(CCCc2ccccc2)Cc2nc(C(=O)NS(=O)(=O)C(C)C)c(C)s2)cc1] |

TABLE 113
| Ex | Syn | Structure |
|----|-----|-----------|
| 286 | 286 | 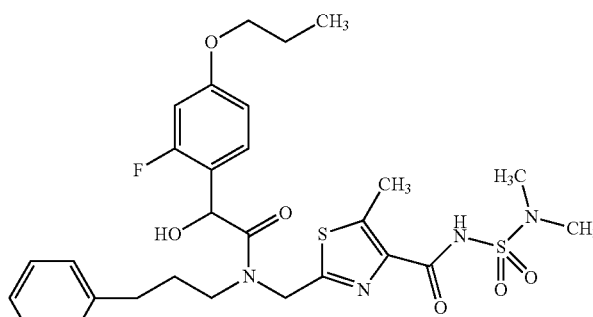 |
| 287 | 286 | 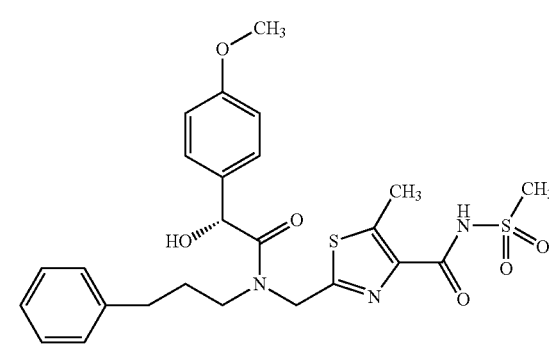 |
| 288 | 286 | 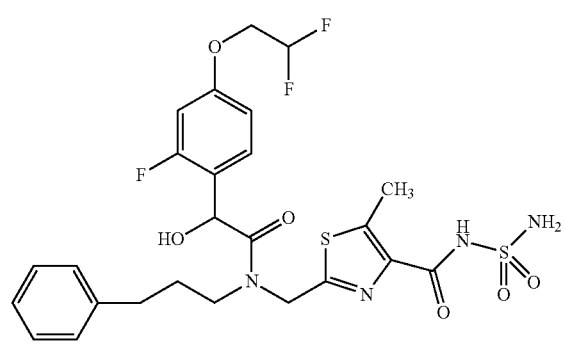 [SMILES: Cc1sc(CN(CCCc2ccccc2)C(=O)C(O)c2ccc(OCC(F)F)cc2F)nc1C(=O)NS(N)(=O)=O] |
| 289 | 286 | 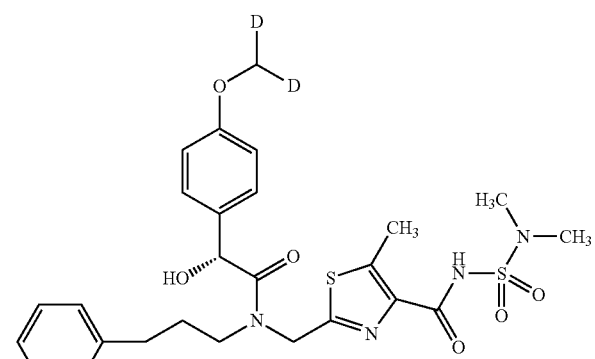 |

TABLE 113-continued
| Ex | Syn | Structure |
|---|---|---|
| 290 | 286 | 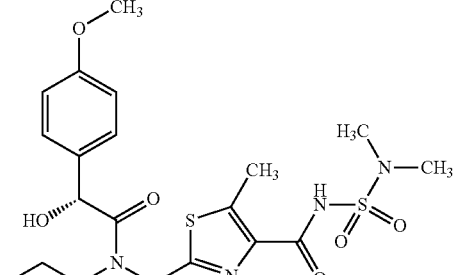 |
TABLE 114
| Ex | Syn | Structure |
|---|---|---|
| 291 | 286 | 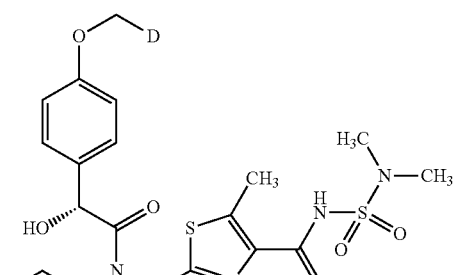 |
| 292 | 286 | 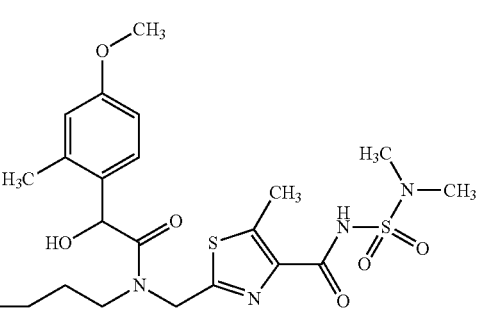 |
| 293 | 286 | 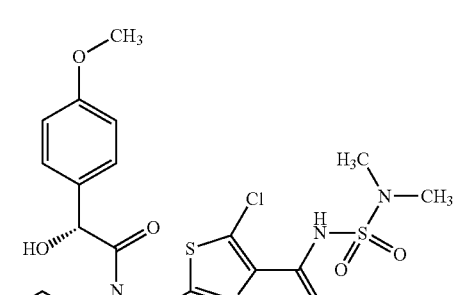 |

TABLE 114-continued
| Ex | Syn | Structure |
|---|---|---|
| 294 | 286 | 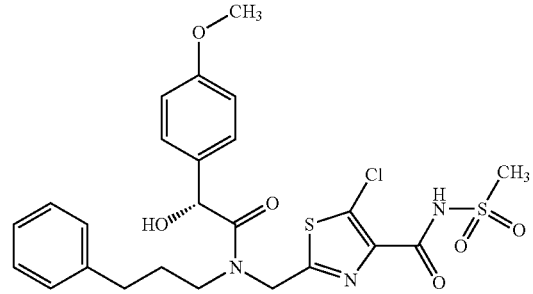 [SMILES: COc1ccc([C@@H](O)C(=O)N(CCCc2ccccc2)Cc2nc(C(=O)NS(C)(=O)=O)c(Cl)s2)cc1] |
| 295 | 286 | 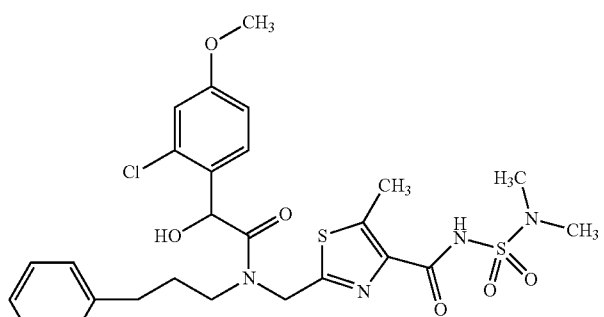 |
TABLE 115
| Ex | Syn | Structure |
|---|---|---|
| 296 | 296 | 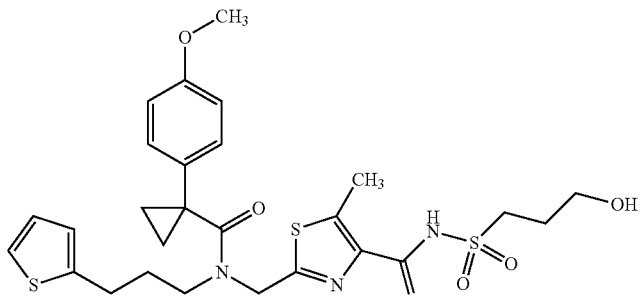 |
| 297 | 296 | 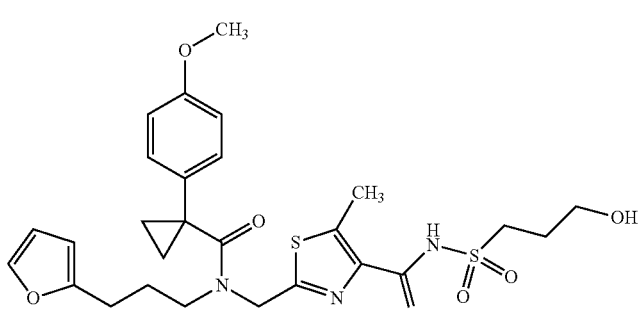 |

TABLE 115-continued
| Ex | Syn | Structure |
|---|---|---|
| 298 | 298 | 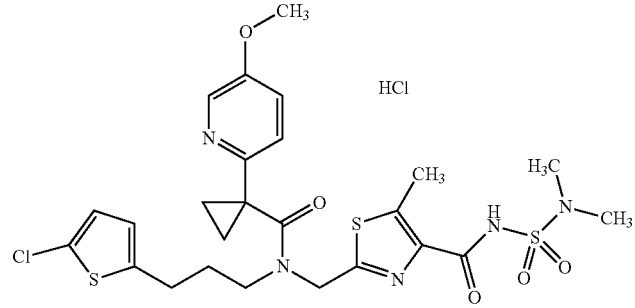 [SMILES: COc1ccc(C2(C(=O)N(CCCc3ccc(Cl)s3)Cc3nc(C(=O)NS(=O)(=O)N(C)C)c(C)s3)CC2)nc1 ; Cl] |
| 299 | 298 | 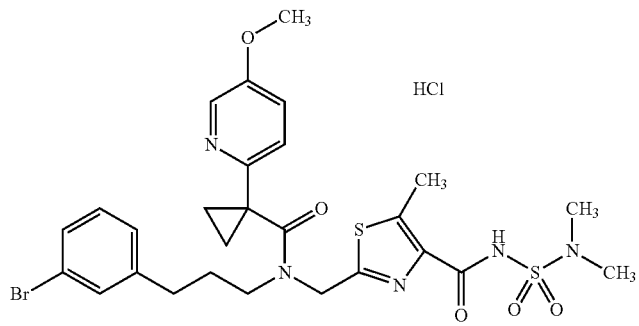 |
| 300 | 298 | 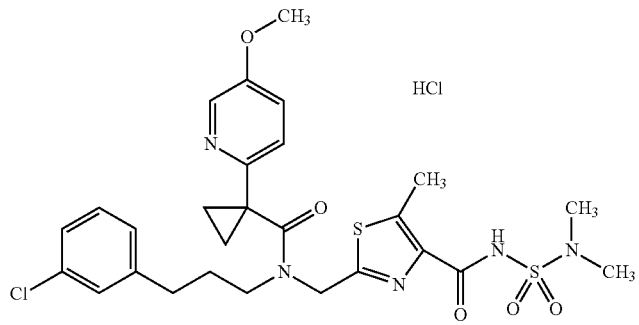 [SMILES: COc1ccc(C2(C(=O)N(CCCc3cccc(Cl)c3)Cc3nc(C(=O)NS(=O)(=O)N(C)C)c(C)s3)CC2)nc1 ; Cl] |
TABLE 116
| Ex | Syn | Structure |
|---|---|---|
| 301 | 298 | 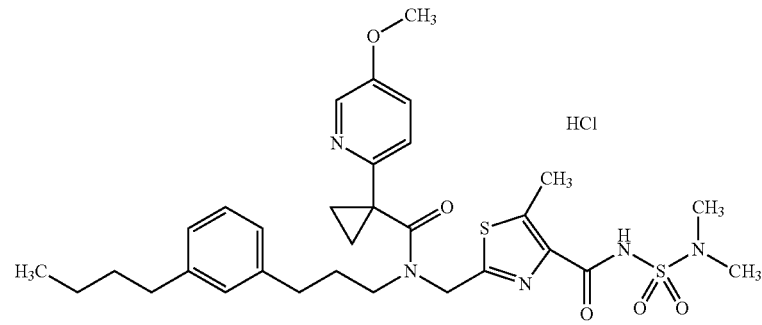 [SMILES: CCCCc1cccc(CCCN(Cc2nc(C(=O)NS(=O)(=O)N(C)C)c(C)s2)C(=O)C2(c3ccc(OC)cn3)CC2)c1 ; Cl] |

TABLE 116-continued
| Ex | Syn | Structure |
|---|---|---|
| 302 | 298 | 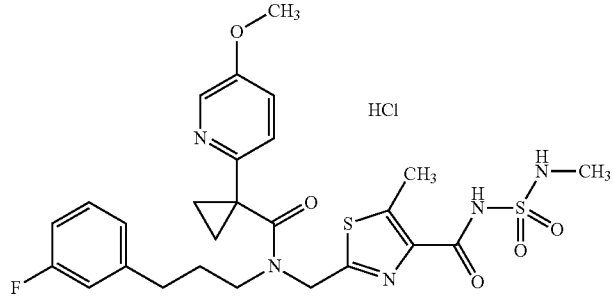 [SMILES: CNS(=O)(=O)NC(=O)c1nc(CN(CCCc2cccc(F)c2)C(=O)C2(c3ccc(OC)cn3)CC2)sc1C ; Cl] |
| 303 | 298 | 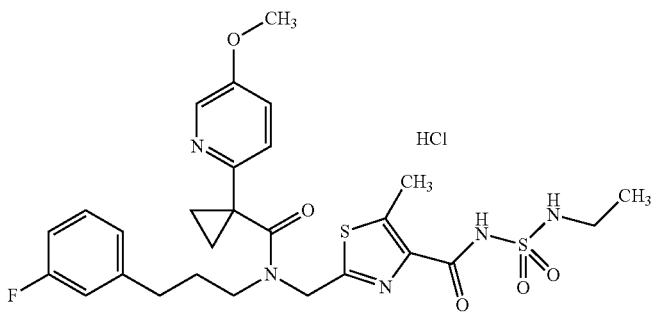 [SMILES: CCNS(=O)(=O)NC(=O)c1nc(CN(CCCc2cccc(F)c2)C(=O)C2(c3ccc(OC)cn3)CC2)sc1C ; Cl] |
| 304 | 305 | 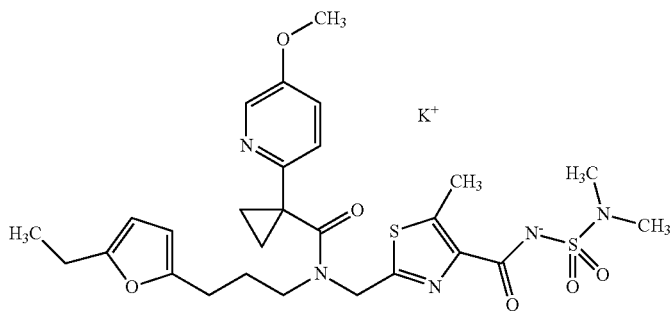 [SMILES: CCc1ccc(CCCN(Cc2nc(C(=O)[N-]S(=O)(=O)N(C)C)c(C)s2)C(=O)C2(c3ccc(OC)cn3)CC2)o1 ; [K+]] |
| 305 | 305 | 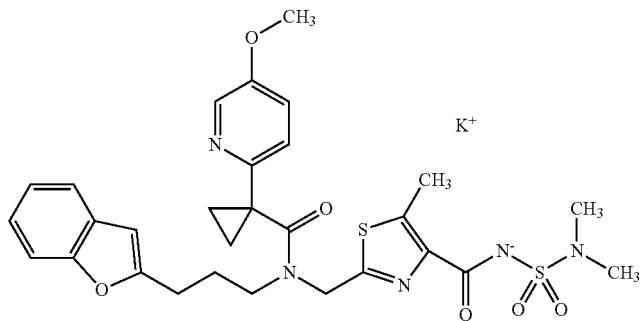 [SMILES: COc1ccc(C2(C(=O)N(CCCc3cc4ccccc4o3)Cc3nc(C(=O)[N-]S(=O)(=O)N(C)C)c(C)s3)CC2)nc1 ; [K+]] |

TABLE 117
| Ex | Syn | Structure |
|---|---|---|
| 306 | 308 | 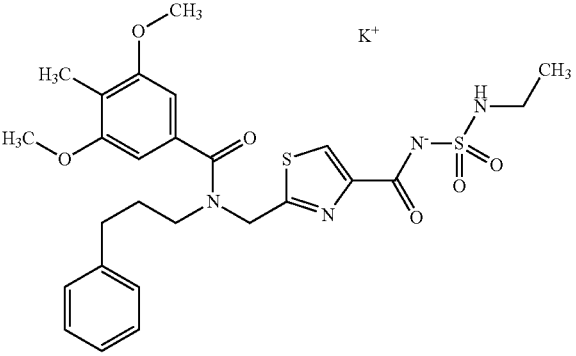 [SMILES: CCNS(=O)(=O)[N-]C(=O)c1csc(CN(CCCc2ccccc2)C(=O)c2cc(OC)c(C)c(OC)c2)n1 ; [K+]] |
| 307 | 308 | 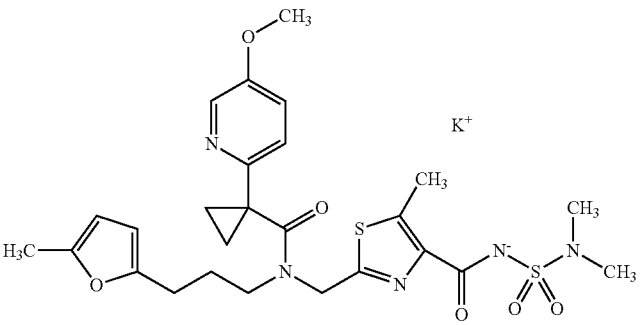 |
| 308 | 308 | 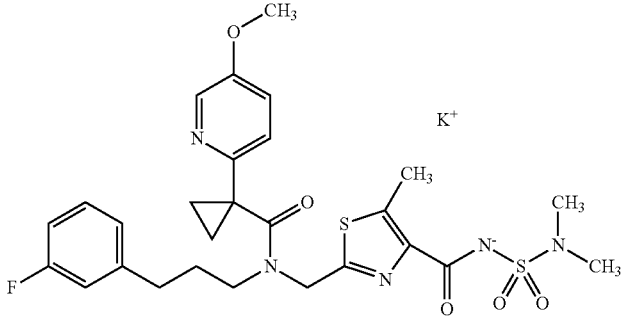 [SMILES: COc1ccc(C2(C(=O)N(CCCc3cccc(F)c3)Cc3nc(C(=O)[N-]S(=O)(=O)N(C)C)c(C)s3)CC2)nc1 ; [K+]] |
TABLE 118
| Ex | Data |
|---|---|
| 1 | NMR-DMSO-d$_6$: 1.76-1.83 (2H, m), 2.49-2.57 (2H, m), 2.12-2.24 (4H, m), 2.62-2.71 (5H, m), 2.86 (6H, s), 2.95-2.99 (2H, m), 3.71-3.74 (3H, m), 4.39-4.64 (2H, m), 6.86-6.95 (4H, m), 7.14-7.25 (5H, m), 10.75 (1H, br).<br>[ESI+]: 585 |
| 2 | [ESI+]: 575 |
| 3 | [EI+]: 604 |
| 4 | [FAB+]: 583 |
| 5 | [FAB+]: 600 |
| 6 | [ESI+]: 591 |
| 7 | NMR-DMSO-d$_6$: 1.87 (2H, br), 2.00 (3H, s), 2.30-2.50 (2H, m), 2.69 (3H, s), 2.87 (6H, s), 3.31-3.50 (2H, m), 3.75 (6H, s), 4.60-4.90 (2H, m), 6.55-7.30 (7H, m), 10.90 (1H, s).<br>[ESI+]: 575 |
| 8 | [ESI+]: 594 |
| 9 | [ESI+]: 547 |
| 10 | [ESI+]: 632 |
| 11 | NMR-DMSO-d$_6$: 1.80-2.05 (7H, m), 2.30-2.65 (2H, m), 3.16-3.60 (7H, m), 3.75 (6H, s), 4.29 (1H, s), 4.70-5.20 (2H, m), 6.45-7.45 (7H, m), 8.55 (1H, s), 11.40 (1H, s).<br>[ESI+]: 603 |
| 12 | NMR-DMSO-d$_6$: 1.77-2.05 (5H, m), 2.30-2.62 (2H, m), 3.20-3.60 (5H, m), 3.74 (6H, s), 4.61-4.99 (2H, m), 6.48-6.80 (2H, m), 6.95-7.72 (6H, m), 7.95 (1H, s).<br>[ESI+]: 591 |
| 13 | NMR-DMSO-d$_6$: 1.81-2.03 (5H, m), 2.30-2.68 (2H, m), 3.15-3.60 (10H, m), 3.75 (6H, s), 4.74-5.02 (2H, m), 6.51-6.76 (2H, m), 6.92-7.31 (5H, m), 8.61 (1H, s), 9.04-9.34 (2H, m), 11.94 (1H, brs).<br>[ESI+]: 602 |
| 14 | [EI+]: 620 |
| 15 | [FAB+]: 637 |
| 16 | [ESI+]: 644 |
| 17 | [ESI+]: 590 |
| 18 | [FAB+]: 604 |

TABLE 119

| Ex | Data |
|---|---|
| 19 | [FAB+]: 637 |
| 20 | [FAB+]: 653 |
| 21 | NMR-DMSO-$d_6$: 1.80-2.05 (5H, m), 2.30-2.70 (4H, m), 3.20-4.00 (12H, m), 4.71-5.03 (2H, m), 6.45-7.40 (7H, m), 8.62 (1H, s), 11.83 (1H, brs).<br>[ESI+]: 601 |
| 22 | [FAB+]: 623 |
| 23 | NMR-DMSO-$d_6$: 1.87 (2H, br), 2.00 (3H, s), 2.31 (2H, br), 3.02 (2H, br), 3.38-3.53 (4H, m), 3.75 (6H, s), 4.80-4.93 (2H, m), 6.59 (2H, br), 6.91-7.27 (5H, m), 7.72 (1H, s), 8.54 (1H, s), 11.5 (1H, s).<br>[ESI+]: 577 |
| 24 | NMR-DMSO-$d_6$: 1.87 (2H, br), 2.00 (3H, s), 2.42 (2H, br), 3.05 (3H, s), 3.39 (2H, br), 3.74 (6H, s), 4.92 (2H, br), 6.61 (2H, br), 7.02-7.18 (5H, m), 8.61 (1H, s), 10.4 (1H, br).<br>[ESI+]: 563 |
| 25 | [FAB+]: 603 |
| 26 | NMR-DMSO-$d_6$: 1.45-1.53 (2H, m), 2.16-2.22 (2H, m), 2.69 (3H, s), 2.86 (6H, s), 3.30 (2H, br), 3.65-3.82 (6H, m), 4.75 (2H, s), 6.60-6.65 (2H, m), 6.97-7.46 (6H, m), 10.81 (1H, br).<br>[ESI+]: 611 |
| 27 | NMR-DMSO-$d_6$: 1.30-1.80 (2H, m), 2.34-2.40 (2H, m), 2.65-2.66 (3H, m), 2.86-2.87 (6H, m), 3.30-3.38 (2H, m), 3.74-3.76 (3H, m), 4.66-4.86 (2H, m), 5.50-5.58 (1H, m), 5.66-5.86 (1H, m), 6.70-6.85 (2H, m), 7.03-7.32 (6H, m), 10.81 (1H, br).<br>[ESI+]: 579 |
| 28 | NMR-DMSO-$d_6$: 1.40-1.80 (2H, m), 2.38-2.43 (2H, m), 2.64-2.65 (3H, m), 2.86-2.88 (6H, m), 3.30-3.42 (2H, m), 3.81-3.84 (3H, m), 4.64-4.89 (2H, m), 5.38-5.50 (1H, m), 5.76-5.97 (1H, m), 6.76-6.82 (1H, m), 7.07-7.28 (5H, m), 7.57-7.66 (1H, m), 8.11 (1H, s), 10.76 (1H, br).<br>[ESI+]: 562<br>mp: 178-179° C. |
| 29 | NMR-DMSO-$d_6$: 0.99-1.80 (6H, m), 2.20-2.24 (2H, m), 2.66 (3H, s), 2.86 (6H, s), 3.35-3.39 (2H, m), 4.65-4.80 (2H, m), 6.70-6.72 (2H, m), 6.97-7.25 (7H, m), 9.36 (1H, br), 10.82 (1H, s).<br>[ESI+]: 557 |

TABLE 120

| Ex | Data |
|---|---|
| 30 | NMR-DMSO-$d_6$: 1.04-1.74 (6H, m), 2.20-2.25 (2H, m), 2.67 (3H, s), 2.87 (6H, s), 3.32-3.38 (2H, m), 4.19 (2H, dt, J = 30.2 Hz, 3.5 Hz), 4.67-4.79 (4H, m), 6.91-7.23 (9H, m), 10.82 (1H, br).<br>[ESI+]: 603 |
| 31 | NMR-DMSO-$d_6$: 1.25-1.48 (6H, m), 2.18-2.22 (2H, m), 2.68 (3H, s), 2.87 (6H, s), 3.30-3.37 (2H, m), 3.76-3.80 (3H, m), 4.73-4.78 (2H, m), 6.92-7.36 (7H, m), 8.12-8.21 (1H, m), 10.85 (1H, br).<br>[ESI+]: 572<br>mp: 125-126° C. |
| 32 | [ESI+]: 533 |
| 33 | [ESI+]: 515 |
| 34 | [ESI+]: 561 |
| 35 | [ESI+]: 549 |
| 36 | [ESI+]: 625, 627 |
| 37 | [ESI+]: 567, 569 |
| 38 | [ESI+]: 577 |
| 39 | [ESI+]: 521 |
| 40 | [ESI+]: 566, 568 |
| 41 | [ESI+]: 549 |
| 42 | [ESI+]: 579 |
| 43 | [ESI+]: 563 |
| 44 | [ESI+]: 556 |
| 45 | [ESI+]: 555 |
| 46 | [ESI+]: 572, 574 |
| 47 | [ESI+]: 527 |
| 48 | [ESI+]: 558 |
| 49 | [ESI+]: 561 |
| 50 | [ESI+]: 589 |
| 51 | [ESI+]: 599 |
| 52 | [ESI+]: 593 |
| 53 | [ESI+]: 561 |
| 54 | [ESI+]: 543 |
| 55 | [ESI+]: 545 |
| 56 | [ESI+]: 571 |

TABLE 121

| Ex | Data |
|---|---|
| 57 | [ESI+]: 598 |
| 58 | [ESI+]: 621 |
| 59 | [ESI+]: 607 |
| 60 | [ESI+]: 573 |
| 61 | [ESI+]: 587 |
| 62 | NMR-DMSO-$d_6$: 1.80-2.03 (5H, m), 2.40-2.58 (2H, m), 3.41 (2H, br), 3.71-3.77 (6H, m), 4.55-4.82 (2H, m), 6.62-7.26 (7H, m), 7.71 (2H, br), 7.99 (1H, s), 12.12 (1H, br).<br>[ESI+]: 533<br>mp: 173-175° C. |
| 63 | NMR-DMSO-$d_6$: 1.79-2.04 (5H, m), 2.34-2.62 (5H, m), 3.26-3.45 (2H, m), 3.69-3.80 (6H, m), 4.51-4.86 (2H, m), 6.57-7.31 (7H, m), 7.78 (1H, s), 8.00 (1H, s), 12.14 (1H, brs).<br>[FAB+]: 547 |
| 64 | NMR-DMSO-$d_6$: 1.80-2.04 (5H, m), 2.36-2.64 (2H, m), 3.29-3.49 (2H, m), 3.75 (6H, s), 4.63-4.91 (2H, m), 6.59 (2H, s), 6.93 (1H, s), 7.00-7.30 (5H, m), 7.73 (1H, s), 12.27 (1H, s).<br>[ESI+]: 517 |
| 65 | [FAB+]: 629 |
| 66 | [ESI+]: 598 |
| 67 | [FAB+]: 613 |
| 68 | NMR-DMSO-$d_6$: 1.82-1.92 (2H, br), 2.01 (3H, s), 2.32-2.45 (2H, m), 2.88 (6H, s), 3.30-3.48 (2H, m), 3.75 (6H, s), 4.72-5.00 (2H, br), 6.54-6.74 (2H, br), 6.96-7.28 (5H, m), 8.57 (1H, s), 11.50 (1H, s)<br>[ESI+]: 561 |
| 69 | NMR-DMSO-$d_6$: 1.82-1.92 (2H, br), 2.00 (3H, s), 2.30-2.55 (2H, m), 3.30-3.50 (2H, m), 3.75 (6H, s), 4.70-5.00 (2H, m), 6.52-6.72 (2H, m), 6.94-7.28 (5H, m), 7.57 (2H, s), 8.52 (1H, s), 11.36 (1H, s).<br>[FAB+]: 533<br>mp: 147-150° C. |
| 70 | NMR-DMSO-$d_6$: 1.87 (2H, br), 2.01 (3H, s), 2.40 (2H, br), 2.54 (3H, d, J = 4.7 Hz), 3.3-3.45 (2H, m), 3.75 (6H, s), 4.80-5.01 (2H, m), 6.55-6.80 (2H, m), 6.93-7.25 (5H, m), 7.67 (1H, d, J = 4.77), 8.56 (1H, s), 11.4 (1H, s).<br>[ESI+]: 547 |

TABLE 122

| Ex | Data |
|---|---|
| 71 | NMR-DMSO-$d_6$: 1.06 (3H, t, J = 7.2), 1.87 (2H, br), 2.01 (3H, s), 2.41 (2H, br), 2.94-3.00 (2H, m), 3.40 (2H, br), 3.75 (6H, s), 4.92 (2H, br), 6.61 (2H, br), 6.91-7.37 (5H, m), 7.82 (1H, br), 8.55 (1H, s), 11.3 (1H, s).<br>[ESI+]: 561<br>mp: 143-144° C. |
| 72 | NMR-DMSO-$d_6$: 0.82 (3H, t, J = 7.4), 1.42-1.51 (2H, m), 1.87 (2H, br), 2.00 (3H, s), 2.41 (2H, br), 2.89 (2H, m), 3.40 (2H, br), 3.74 (6H, s), 4.92 (2H, br), 6.62 (2H, br), 6.95-7.31 (5H, m), 7.82 (1H, br), 8.53 (1H, s), 11.3 (1H, s).<br>[ESI+]: 575 |
| 73 | NMR-DMSO-$d_6$: 1.05-1.11 (6H, m), 1.86 (2H, br), 2.00 (3H, s), 2.39 (2H, br), 3.31-3.41 (1H, m), 3.44-3.54 (2H, m), 3.75 (6H, s), 4.80-4.92 (2H, m), 6.57-6.72 (2H, m), 6.99-7.20 (5H, m), 7.84 (1H, br), 8.54 (1H, s), 11.3 (1H, s).<br>[ESI+]: 575 |
| 74 | NMR-DMSO-$d_6$: 1.87 (2H, br), 2.00 (3H, s), 2.39 (2H, br), 3.08-3.15 (2H, m), 3.17 (3H, s), 3.36-3.45 (4H, m), 3.74 (6H, s), 4.80-4.95 (2H, m), 6.57-6.65 (2H, m), 7.00-7.17 (5H, m), 7.87 (1H, br), 8.54 (1H, s), 11.4 (1H, s).<br>[ESI+]: 591 ( ) |
| 75 | NMR-DMSO-$d_6$: 1.64-1.72 (2H, m), 1.87 (2H, br), 2.00 (3H, s), 2.34 (2H, br), 2.95-2.99 (2H, m), 3.16 (3H, s), 3.27-3.42 (4H, m), 3.75 (6H, s), 4.77-4.92 (2H, m), 6.61 (2H, br), 7.01-7.17 (5H, m), 7.86 (1H, br), 8.55 (1H, s), 11.4 (1H, s).<br>[FAB+]: 605 |
| 76 | NMR-DMSO-$d_6$: 0.53 (4H, m), 1.86 (2H, br), 2.00 (3H, s), 2.26-2.51 (3H, m), 3.23-3.50 (2H, m), 3.75 (6H, s), 4.80-4.93 (2H, m), 6.59-6.72 (2H, m), 6.99-7.15 (5H, m), 8.22 (1H, br), 8.57 (1H, s), 11.5 (1H, s).<br>[ESI+]: 573 |
| 77 | NMR-DMSO-$d_6$: 1.50 (2H, m), 1.85-2.05 (9H, m), 2.38 (2H, br), 3.78 (2H, br), 3.75 (7H, br), 4.81-4.94 (2H, m), 6.58 (2H, br), 6.98-7.14 (5H, m), 8.26 (1H, br), 8.53 (1H, s), 11.4 (1H, s).<br>[ESI+]: 587 |

TABLE 122-continued

| Ex | Data |
|---|---|
| 78 | NMR-DMSO-$d_6$: 1.85 (2H, br), 2.04 (3H, s), 2.37 (2H, br), 3.32 (2H, br), 3.74 (6H, s), 4.76-4.90 (2H, m), 6.57 (2H, br), 6.95-7.29 (11H, m), 8.48 (1H, s), 10.6 (1H, br), 12.0 (1H, s).<br>[FAB+]: 609 |

TABLE 123

| Ex | Data |
|---|---|
| 79 | NMR-DMSO-$d_6$: 1.80-2.05 (5H, m), 2.30-2.65 (2H, m), 3.20-3.50 (2H, m), 3.74 (6H, s), 4.57-4.99 (2H, m), 6.40-7.55 (9H, m), 7.74-8.10 (2H, m), 8.47 (1H, s).<br>[ESI+]: 610 |
| 80 | NMR-DMSO-$d_6$: 1.88 (2H, br), 2.00 (3H, s), 2.41 (2H, br), 3.37 (2H, br), 3.75 (6H, s), 4.17 (2H, d, J = 5.7 Hz), 4.80-4.99 (2H, m), 6.55-6.78 (2H, m), 7.14-7.32 (11H, m), 8.47 (1H, s), 11.4 (1H, s).<br>[FAB+]: 623 |
| 81 | NMR-DMSO-$d_6$: 1.86 (2H, br), 2.00 (3H, s), 2.36 (2H, br), 3.14-3.19 (2H, m), 3.29 (2H, br), 3.50 (2H, m), 3.73 (6H, s), 4.43 (3H, s), 4.89 (2H, br), 6.60 (2H, br), 7.03-7.34 (10H, m), 7.89 (1H, br), 8.52 (1H, s), 11.4 (1H, s).<br>[ESI+]: 667 |
| 82 | NMR-DMSO-$d_6$: 1.79-1.83 (4H, m), 1.83 (2H, br), 2.00 (3H, s), 2.34 (2H, br), 3.31-3.43 (5H, m), 3.75 (6H, s), 4.78-4.93 (2H, m), 6.59-6.70 (2H, m), 7.00-7.15 (5H, m), 8.57 (1H, s), 11.4 (1H, s).<br>[FAB+]: 587 |
| 83 | NMR-DMSO-$d_6$: 1.26 (3H, s), 1.70-2.10 (7H, m), 2.30-2.50 (2H, m), 3.20-3.80 (12H, m), 4.75-5.10 (3H, m), 6.55-7.30 (7H, m), 8.31 (1H, s), 11.36 (1H, s).<br>[ESI+]: 617 |
| 84 | NMR-DMSO-$d_6$: 1.37-1.50 (2H, m), 1.68-2.05 (7H, m), 2.30-2.75 (2H, m), 3.04-3.56 (10H, m), 3.75 (6H, s), 4.70-5.00 (2H, m), 6.50-7.33 (7H, m), 8.52 (1H, s), 11.51 (1H, s).<br>[ESI+]: 631 |
| 85 | NMR-DMSO-$d_6$: 1.79-2.05 (5H, m), 2.30-2.75 (6H, m), 3.20-3.60 (6H, m), 3.75 (6H, s), 4.70-5.00 (2H, m), 6.50-7.33 (7H, m), 8.51 (1H, s), 11.73 (1H, s).<br>[ESI+]: 619 |
| 86 | NMR-DMSO-$d_6$: 1.79-2.05 (5H, m), 2.30-2.70 (2H, m), 3.20-3.60 (6H, m), 3.75-3.80 (10H, m), 4.70-5.05 (2H, m), 6.45-7.40 (7H, m), 8.60 (1H, s), 12.00 (1H, brs).<br>[ESI+]: 651 |
| 87 | NMR-DMSO-$d_6$: 1.80-2.05 (5H, m), 2.30-2.75 (2H, m), 3.18-3.60 (6H, m), 3.75 (6H, s), 3.90 (2H, m), 4.70-5.00 (2H, m), 6.50-7.33 (7H, m), 8.09 (1H, s), 8.58 (1H, s), 11.87 (1H, brs).<br>[ESI+]: 616 |

TABLE 124

| Ex | Data |
|---|---|
| 88 | NMR-DMSO-$d_6$: 1.86 (2H, br), 2.00 (3H, s), 2.41 (2H, br), 3.20 (6H, s), 3.33-3.52 (10H, m), 3.74 (6H, s), 4.91 (2H, br), 6.59 (2H, br), 6.94-7.28 (5H, m), 8.53 (1H, s), 11.4 (1H, s).<br>[ESI+]: 649 |
| 89 | 1.82-1.95 (2H, br), 2.00 (3H, s), 2.31-2.62 (2H, m), 3.30-3.60 (5H, m), 3.70-3.78 (9H, m), 4.91 (2H, br), 6.61 (2H, br), 6.95-7.27 (5H, m), 7.61 (1H, s), 8.64 (1H, s).<br>[ESI+]: 605<br>mp: 135-137° C. |
| 90 | NMR-DMSO-$d_6$: 1.83-2.04 (5H, m), 2.30-2.67 (2H, m), 3.20-3.60 (2H, m), 3.71 (3H, s), 3.75 (6H, s), 4.81-5.00 (2H, m), 5.03 (2H, s), 6.54-6.76 (2H, m), 6.95-7.44 (10H, m), 8.63 (1H, s).<br>[ESI+]: 681 |
| 91 | NMR-DMSO-$d_6$: 1.81-2.03 (5H, m), 2.31-2.65 (2H, m), 3.20-3.60 (9H, m), 3.65-3.80 (9H, m), 4.70-5.00 (2H, m), 6.50-6.78 (2H, m), 6.91-7.31 (5H, m), 8.54 (1H, s).<br>[ESI+]: 649 |
| 92 | NMR-DMSO-$d_6$: 1.80-2.05 (5H, m), 2.20-2.70 (2H, m), 3.20-3.50 (4H, m), 3.62-3.80 (9H, m), 3.99-4.12 (2H, m), 4.36-4.55 (2H, m), 4.72-4.97 (2H, m), 6.51-6.74 (2H, m), 6.92-7.29 (5H, m), 8.46 (1H, s).<br>[ESI+]: 661 |

TABLE 124-continued

| Ex | Data |
|---|---|
| 93 | NMR-DMSO-$d_6$: 1.87 (2H, br), 2.00 (3H, s), 2.29-2.65 (2H, m), 3.20-3.50 (2H, m), 3.67-3.80 (9H, m), 4.41 (2H, d, J = 5.0), 4.75-4.97 (2H, m), 5.14-5.25 (2H, m), 5.88-6.00 (1H, m), 6.52-6.73 (2H, m), 6.93-7.32 (5H, m), 8.59 (1H, s).<br>[ESI+]: 631 |
| 94 | [ESI+]: 702 |
| 95 | [ESI+]: 648 |
| 96 | [ESI+]: 634 [EI-MS] |
| 97 | [ESI+]: 618 |
| 98 | [FAB+]: 621 |

TABLE 125

| Ex | Data |
|---|---|
| 99 | NMR-DMSO-$d_6$: 1.86 (2H, br), 2.00 (3H, s), 2.10 (3H, s), 2.30-2.68 (2H, m), 2.94 (3H, s), 3.17-3.50 (5H, m), 3.75 (6H, s), 4.72-5.04 (2H, m), 6.49-6.76 (2H, m), 6.91-7.29 (5H, m), 8.58 (1H, s).<br>[ESI+]: 618 |
| 100 | NMR-DMSO-$d_6$: 1.80-2.05 (5H, m), 2.30-2.60 (2H, m), 2.70 (3H, s), 2.92 (3H, s), 3.23-3.50 (2H, m), 3.65 (2H, dt, 27.3 Hz, 5.0 Hz), 3.75 (6H, s), 4.57 (2H, dt, 47.4 Hz, 5.0 Hz), 4.70-4.93 (2H, m), 6.50-7.35 (7H, m), 11.40 (1H, brs).<br>[ESI+]: 607 |
| 101 | NMR-DMSO-$d_6$: 1.80-2.05 (5H, m), 2.30-2.60 (2H, m), 2.70 (3H, s), 2.94 (3H, s), 3.22-3.50 (2H, m), 3.68-3.83 (8H, m), 4.70-4.93 (2H, m), 6.20 (1H, dt, 3.8 Hz, 55.3 Hz), 6.50-7.35 (7H, m), 11.35 (1H, s).<br>[ESI+]: 625 |
| 102 | NMR-DMSO-$d_6$: 1.86 (2H, br), 2.00 (3H, s), 2.12 (2H, br), 2.39 (2H, br), 2.85 (3H, s), 3.40 (2H, br), 3.48-3.55 (2H, m), 3.64 (2H, br), 3.75 (6H, s), 3.84-3.89 (1H, m), 4.63 (1H, br), 4.91 (1H, br), 6.61 (2H, m), 7.01-7.19 (5H, m), 8.54 (1H, s), 11.6 (1H, s).<br>[ESI+]: 617 |
| 103 | [ESI+]: 660 |
| 104 | NMR-DMSO-$d_6$: 1.88 (2H, br), 2.01 (3H, s), 2.35 (2H, br), 2.71 (3H, s), 3.40 (2H, br), 3.70 (3H, s), 3.75 (6H, s), 4.84 (2H, br), 6.60 (2H, br), 7.02-7.19 (5H, m), 10.3 (1H, s), 11.3 (1H, br).<br>[ESI+]: 577 |
| 105 | NMR-DMSO-$d_6$: 1.80-2.10 (5H, m), 2.30-2.60 (2H, m), 2.70 (3H, s), 2.92 (3H, s), 3.30-3.50 (4H, m), 3.58-3.80 (10H, m), 4.50 (2H, dt, J = 4.0, 48.0 Hz), 4.82 (2H, br), 6.60 (2H, br), 6.90-7.34 (5H, m), 10.90 (1H, brs).<br>[ESI+]: 651 |
| 106 | 1.88 (2H, br), 2.00 (3H, s), 2.41 (2H, br), 2.70 (3H, s), 3.36 (2H, br), 3.76 (6H, s), 4.12-4.22 (2H, m), 4.29-4.33 (2H, m), 4.85 (2H, br), 5.26-5.40 (1H, m), 6.60 (2H, br), 7.01-7.19 (5H, m).<br>[ESI+]: 605 |
| 107 | [ESI+]: 727 |

TABLE 126

| Ex | Data |
|---|---|
| 108 | NMR-DMSO-$d_6$: 1.87 (2H, br), 2.01 (3H, s), 2.31-2.52 (2H, m), 3.20-3.39 (5H, m), 3.75 (6H, s), 4.92 (2H, br), 6.58 (2H, s), 6.95-7.29 (5H, m), 8.58 (1H, s), 11.86 (1H, br).<br>[FAB+]: 532<br>mp: 133-134° C. |
| 109 | NMR-DMSO-$d_6$: 1.88 (2H, br), 2.01 (3H, s), 2.30-2.45 (2H, m), 2.71 (3H, s), 3.28-3.37 (5H, m), 3.75 (6H, s), 4.83 (2H, br), 6.59 (2H, s), 7.01-7.20 (5H, m), 11.18 (1H, br).<br>[FAB+]: 546<br>mp: 128-131° C. |
| 110 | NMR-DMSO-$d_6$: 1.89 (2H, br), 2.00 (3H, s), 2.54-2.82 (2H, m), 3.35-3.50 (2H, m), 3.76 (6H, brs), 4.72-4.98 (2H, m), 6.47-6.97 (4H, m), 7.61 (2H, s), 8.51 (1H, s), 11.34 (1H, br).<br>[FAB+]: 573, 575<br>mp: 154-156° C. |

TABLE 126-continued

| Ex | Data |
|---|---|
| 111 | 1.87 (2H, br), 2.00 (3H, s), 2.11 (3H, brs), 2.40 (2H, br), 3.38 (2H, br), 3.76 (6H, brs), 4.91 (2H, br), 5.71-5.99 (2H, m), 6.61 (2H, br), 7.61 (2H, s), 8.54 (1H, s), 11.34 (1H, br). [ESI+]: 537 |
| 112 | [ESI+]: 569 |
| 113 | NMR-DMSO-$d_6$: 1.86 (2H, br), 2.00 (3H, s), 2.40-2.54 (2H, m), 3.23-3.49 (2H, m), 3.75 (6H, s), 4.93 (2H, br), 6.55 (2H, br), 6.93-7.29 (4H, m), 7.61 (2H, s), 8.53 (1H, s), 11.33 (1H, s). [FAB+]: 551 mp: 145-146° C. |
| 114 | [FAB+]: 569 |
| 115 | [FAB+]: 569 |
| 116 | [FAB+]: 551 |
| 117 | NMR-DMSO-$d_6$: 1.78 (2H, br), 2.00 (3H, s), 2.67 (2H, br), 3.56 (2H, br), 3.74 (6H, s), 4.76-5.00 (2H, m), 6.46-6.76 (2H, m), 7.03-7.20 (2H, m), 7.34 (1H, br), 7.62 (1H, s), 8.54 (1H, s), 11.4 (1H, s). [ESI+]: 585 |
| 118 | [FAB+]: 558 |

TABLE 127

| Ex | Data |
|---|---|
| 119 | NMR-DMSO-$d_6$: 1.86 (2H, br), 2.00 (3H, s), 2.45 (2H, br), 2.87 (6H, s), 3.39 (2H, br), 3.74 (6H, s), 4.91 (2H, br), 6.57 (2H, br), 7.04-7.18 (4H, m), 8.55 (1H, s), 11.4 (1H, s). [ESI+]: 579 mp: 128-131° C. |
| 120 | [ESI+]: 564 |
| 121 | NMR-DMSO-$d_6$: 1.80-2.03 (5H, m), 2.39-2.63 (2H, m), 3.27-3.53 (2H, m), 3.74 (6H, s), 4.56-4.86 (2H, m), 6.53-6.71 (2H, m), 7.01-7.30 (5H, m), 7.57 (2H, s), 8.80 (1H, s), 11.64 (1H, s). [ESI+]: 517 mp: 136-141° C. |
| 122 | NMR-DMSO-$d_6$: 1.81-2.02 (5H, m), 2.34-2.64 (2H, m), 3.14-3.45 (2H, m), 3.74 (6H, s), 4.56-4.83 (2H, m), 6.54 (2H, s), 6.95-7.29 (5H, m), 7.46-7.57 (3H, m), 8.36 (1H, s), 11.69 (1H, s). [ESI+]: 532 |
| 123 | NMR-DMSO-$d_6$: 1.74-1.86 (2H, m), 2.00 (3H, s), 2.35-2.59 (2H, m), 3.18-3.41 (2H, m), 3.76 (6H, s), 4.44-4.77 (2H, m), 6.51-6.76 (3H, m), 6.97-7.30 (5H, m), 7.45-7.58 (3H, m), 11.77 (1H, s). [ESI+]: 516 |
| 124 | NMR-DMSO-$d_6$: 1.73-2.03 (5H, m), 2.29-2.62 (2H, m), 3.09-3.42 (2H, m), 3.64-3.80 (6H, m), 4.34-4.68 (2H, m), 6.10 (1H, s), 6.57 (2H, s), 6.94-7.41 (9H, m), 11.34 (1H, m). [FAB+]: 515 |
| 125 | [ESI+]: 633 |
| 126 | NMR-DMSO-$d_6$: 1.76-1.83 (2H, m), 2.49-2.57 (2H, m), 2.66-2.69 (3H, m), 2.87 (6H, s), 3.37-3.56 (4H, m), 3.70-3.74 (6H, m), 4.68-4.87 (2H, m), 6.45-6.53 (2H, m), 7.02-7.27 (6H, m), 10.78 (1H, br). [ESI+]: 575 mp: 132-135° C. |
| 127 | NMR-DMSO-$d_6$: 1.77-1.85 (2H, m), 2.00 (3H, s), 2.35-2.60 (2H, m), 3.20-3.40 (5H, m), 3.77 (6H, s), 4.49-4.73 (2H, m), 6.59-7.52 (9H, m), 12.13 (1H, br). [FAB+]: 515 |
| 128 | [ESI+]: 547 |
| 129 | [ESI+]: 559 |

TABLE 128

| Ex | Data |
|---|---|
| 130 | [ESI+]: 545 |
| 131 | NMR-DMSO-$d_6$: 0.75 (2H, br), 0.97 (2H, br), 1.87 (3H, brs), 2.46 (2H, br), 3.23-3.45 (2H, m), 3.71 (6H, s), 4.92 (2H, br), 6.57 (2H, br), 6.94-7.31 (5H, m), 7.60 (2H, s), 8.53 (1H, s), 11.33 (1H, br). [FAB+]: 559 mp: 147-149° C. |

TABLE 128-continued

| Ex | Data |
|---|---|
| 132 | [FAB+]: 599 |
| 133 | 1.02 (2H, br), 1.21 (2H, br), 1.34 (2H, br), 2.23 (2H, br), 2.69 (3H, s), 3.35 (2H, br), 3.73 (3H, s), 4.66 (2H, br), 6.87-7.26 (9H, m), 7.58 (2H, br), 10.6 (1H, s). [ESI+]: 543 |
| 134 | NMR-DMSO-$d_6$: 1.85 (2H, br), 2.39 (2H, br), 2.71 (3H, s), 3.43 (2H, br), 3.67 (3H, s), 3.75 (6H, s), 4.70-4.85 (2H, m), 6.48-6.56 (2H, m), 6.93-7.19 (5H, m), 10.3 (1H, s), 11.4 (1H, br). [ESI+]: 563 |
| 135 | NMR-DMSO-$d_6$: 1.82-1.95 (5H, m), 2.35-2.55 (5H, m), 2.71 (3H, s), 3.26-3.51 (2H, m), 3.71 (6H, s), 4.67-4.91 (3H, m), 5.21 (1H, s), 6.53-6.74 (2H, m), 6.96-7.28 (5H, m), 7.64 (1H, brs), 10.82 (1H, s). [ESI+]: 587 |
| 136 | NMR-DMSO-$d_6$: 1.84 (2H, br), 2.00 (3H, s), 2.21 (3H, s), 2.32 (2H, br), 2.54 (3H, d, J = 4.4 Hz), 3.32-3.45 (2H, m), 3.75 (6H, s), 4.79-4.93 (2H, m), 6.58-7.11 (6H, m), 7.64 (1H, br), 8.56 (1H, s), 11.4 (1H, s). [FAB+]: 561 |
| 137 | NMR-DMSO-$d_6$: 1.88 (2H, br), 2.01 (3H, s), 2.41-2.55 (5H, m), 3.36 (2H, br), 3.76 (6H, s), 4.81-4.93 (2H, m), 6.60-7.66 (5H, m), 8.55 (1H, s), 11.4 (1H, s). [ESI+]: 553 |
| 138 | [ESI+]: 580 |
| 139 | NMR-DMSO-$d_6$: 1.86 (2H, br), 1.99 (3H, s), 2.39 (2H, br), 2.53 (3H, br), 3.32 (2H, br), 3.74 (6H, s), 4.77-4.99 (2H, m), 6.50-7.00 (5H, m), 7.64 (1H, br), 8.56 (1H, s), 11.4 (1H, s). [ESI+]: 583 |
| 140 | NMR-DMSO-$d_6$: 1.86 (2H, br), 2.00 (3H, s), 2.33 (3H, s), 2.39 (2H, br), 2.54-2.75 (4H, m), 3.40 (2H, br), 3.76 (6H, s), 4.77-4.98 (2H, m), 6.35-6.74 (4H, m), 7.65 (1H, br), 8.56 (1H, s), 11.4 (1H, s). [ESI+]: 567 |

TABLE 129

| Ex | Data |
|---|---|
| 141 | NMR-DMSO-$d_6$: 1.03-1.08 (2H, m), 1.85 (2H, br), 2.00 (3H, s), 2.42 (2H, br), 2.71 (3H, m), 2.94-3.01 (2H, m), 3.48 (2H, br), 3.75 (6H, s), 4.83 (2H, br), 6.56 (2H, br), 6.97-7.22 (5H, m), 7.79 (1H, br), 10.8 (1H, s). [ESI+]: 593 |
| 142 | NMR-DMSO-$d_6$: 1.82 (2H, br), 2.00 (3H, s), 2.49-2.55 (8H, m), 3.44 (2H, br), 3.75 (6H, s), 4.90 (2H, br), 6.55-6.80 (3H, m), 7.12 (1H, br), 7.63 (1H, br), 8.55 (1H, s), 11.3 (1H, s). [ESI+]: 567 |
| 143 | [ESI+]: 591, 593 |
| 144 | NMR-DMSO-$d_6$: 1.80-1.92 (2H, m), 2.30-2.67 (2H, m), 3.26-3.54 (2H, m), 3.75 (6H, s), 4.64-4.95 (2H, m), 6.45-6.75 (3H, m), 6.89-7.36 (5H, m), 7.67 (2H, s), 11.32 (1H, s). [ESI+]: 553 |
| 145 | NMR-DMSO-$d_6$: 1.86 (2H, br), 2.32-2.60 (5H, m), 3.22-3.54 (2H, m), 3.75 (6H, s), 4.68-4.93 (2H, m), 6.45-6.62 (3H, m), 6.92-7.34 (5H, m), 11.76 (1H, br). [FAB+]: 552 mp: 113-114° C. |
| 146 | NMR-DMSO-$d_6$: 1.78-2.04 (5H, m), 2.34-2.65 (5H, m), 3.24-3.50 (2H, m), 3.55-3.82 (6H, m), 4.61-4.91 (2H, m), 6.61-6.63 (2H, m), 6.93-7.28 (5H, m), 7.59-8.09 (4H, m), 11.07 (1H, s). [FAB+]: 541 |
| 147 | [FAB+]: 537 |
| 148 | NMR-DMSO-$d_6$: 1.75-1.84 (2H, m), 2.00 (3H, s), 2.34-2.59 (5H, m), 3.21-3.42 (2H, m), 3.76 (6H, s), 4.43-4.78 (2H, m), 6.51-6.78 (3H, m), 6.95-7.31 (5H, m), 7.50 (1H, s), 7.63 (1H, d, J = 4.7 Hz), 11.72 (1H, s). [FAB+]: 541 |
| 149 | [ESI+]: 575 |
| 150 | [ESI+]: 573 |
| 151 | [ESI+]: 573 |
| 152 | [ESI+]: 591 |

TABLE 130

| Ex | Data |
|---|---|
| 153 | NMR-DMSO-$d_6$: 0.96-1.07 (5H, m), 1.88 (2H, br), 2.40 (2H, br), 2.47-2.64 (2H, m), 2.71 (3H, s), 3.29-3.50 (2H, m), 3.75 (6H, s), 4.61-4.92 (2H, m), 6.53-6.72 (2H, m), 6.92-7.32 (6H, m), 7.67 (1H, br), 10.83 (1H, br).<br>[ESI+]: 575<br>mp: 162-164° C. |
| 154 | NMR-DMSO-$d_6$: 1.85 (2H, br), 2.38 (2H, br), 2.44-2.63 (2H, m), 2.71 (3H, s), 3.22-3.50 (2H, m), 3.75 (6H, s), 4.60-4.93 (2H, m), 6.42-6.62 (2H, m), 6.91-7.29 (7H, m), 7.63 (1H, br), 10.83 (1H, brs).<br>[ESI+]: 587<br>mp: 112-113° C. |
| 155 | NMR-DMSO-$d_6$: 1.03-1.07 (3H, m), 1.85 (2H, br), 2.40-2.62 (2H, m), 2.71 (3H, br), 2.97 (3H, br), 3.29-3.48 (2H, m), 3.81 (6H, s), 4.67 (1H, br), 4.87 (2H, br), 6.66 (2H, br), 6.82-7.28 (5H, m), 7.77 (1H, br), 10.8 (1H, s).<br>[ESI+]: 611 |
| 156 | NMR-DMSO-$d_6$: 0.69-1.01 (4H, m), 1.82-1.92 (3H, m), 2.32-2.58 (5H, m), 2.71 (3H, s), 3.28-3.49 (2H, m), 3.71 (6H, s), 4.60-4.93 (2H, m), 6.46-6.72 (2H, m), 6.90-7.29 (5H, m), 7.64 (1H, brs), 10.81 (1H, s).<br>[ESI+]: 587 |
| 157 | [ESI+]: 613 |
| 158 | [FAB+]: 673 |
| 159 | [ESI+]: 575 |
| 160 | NMR-DMSO-$d_6$: 1.03 (2H, br), 1.22 (2H, br), 1.34 (2H, br), 2.23 (2H, br), 2.54 (3H, br), 2.68 (3H, s), 3.37 (2H, br), 3.73 (3H, s), 4.66 (2H, br), 6.87-7.25 (8H, m), 7.64 (1H, br), 10.7 (1H, s).<br>[FAB+]: 557 |
| 161 | NMR-DMSO-$d_6$: 1.88 (2H, br), 2.40 (2H, br), 2.71 (3H, s), 3.20 (3H, m), 3.49 (2H, br), 3.67 (3H, s), 3.76 (6H, s), 4.38 (2H, s), 4.70-4.87 (2H, m), 6.61-6.75 (2H, m), 7.00-7.18 (5H, m), 10.35 (1H, s).<br>[FAB+]: 607<br>mp: 151-153° C. |
| 162 | [FAB+]: 601 |
| 163 | [FAB+]: 595 |

TABLE 131

| Ex | Data |
|---|---|
| 164 | NMR-DMSO-$d_6$: 1.78 (3H, s), 1.87 (2H, br), 2.00 (3H, s), 2.39 (2H, br), 3.33 (2H, br), 3.75 (6H, br), 3.85 (2H, t, J = 5.4 Hz), 4.36 (2H, t, J = 5.4 Hz), 4.80-4.94 (2H, m), 6.58-6.73 (2H, m), 7.00-7.14 (5H, m), 8.59 (1H, s), 12.0 (1H, s).<br>[FAB+]: 604 |
| 165 | NMR-DMSO-$d_6$: 1.80-2.10 (5H, m), 2.30-2.50 (2H, m), 2.70 (3H, s), 2.92 (3H, s), 3.30-3.61 (10H, m), 3.75 (6H, s), 4.58 (1H, t, J = 5.3 Hz), 4.65-4.93 (2H, m), 6.55-7.30 (7H, m), 10.91 (1H, brs).<br>[ESI+]: 649 |
| 166 | NMR-DMSO-$d_6$: 2.04-2.16 (5H, m), 2.48-2.65 (2H, m), 2.87 (3H, m), 3.53 (2H, br), 3.91 (6H, s), 4.04-4.08 (2H, m), 4.27-4.31 (2H, m), 4.53-4.58 (1H, m), 5.00 (2H, br), 5.93-5.95 (1H, m), 6.76 (2H, br), 7.16-7.34 (5H, m), 11.09 (1H, br).<br>[ESI+]: 603 |
| 167 | NMR-DMSO-$d_6$: 1.87 (2H, br), 2.00 (3H, s), 2.39 (2H, br), 3.20 (2H, br), 3.47 (2H, br), 3.74 (8H, br), 4.78-4.92 (2H, m), 6.58-6.76 (2H, m), 7.01-7.14 (5H, m), 8.32 (1H, s).<br>[ESI+]: 562 |
| 168 | [FAB+]: 573 |
| 169 | NMR-DMSO-$d_6$: 1.87 (2H, br), 2.00 (3H, s), 2.36 (2H, br), 2.91 (3H, s), 3.30-3.46 (5H, m), 3.56 (2H, d, J = 5.9 Hz), 3.74 (6H, s), 4.91 (2H, br), 6.61 (2H, br), 7.03-7.19 (5H, m), 8.49 (1H, s), 11.4 (1H, br).<br>[ESI+]: 591 |
| 170 | NMR-DMSO-$d_6$: 1.11 (3H, t, J = 3.1 Hz), 1.87 (2H, br), 2.00 (3H, s), 2.40 (2H, br), 3.36-3.45 (6H, m), 3.54-3.57 (2H, m), 3.74 (6H, s), 4.91 (2H, br), 6.61 (2H, br), 7.02-7.19 (5H, m), 8.53 (1H, s), 11.5 (1H, br).<br>[ESI+]: 605<br>mp: 127-129° C. |

TABLE 131-continued

| Ex | Data |
|---|---|
| 171 | NMR-DMSO-$d_6$: 1.87 (2H, br), 2.01 (3H, s), 2.37 (2H, br), 2.70 (3H, s), 3.35 (2H, br), 3.41-3.44 (4H, m), 3.58 (4H, br), 3.75 (6H, s), 4.84-4.96 (2H, br), 6.60 (2H, br), 7.01-7.18 (5H, m), 11.1 (1H, s).<br>[FAB+]: 635 |

TABLE 132

| Ex | Data |
|---|---|
| 172 | NMR-DMSO-$d_6$: 1.65-1.72 (2H, m), 1.87 (2H, br), 2.01 (3H, s), 2.37 (2H, br), 2.68 (3H, s), 2.89 (3H, s), 3.30-3.44 (6H, m), 3.75 (6H, s), 4.83 (2H, br), 6.60 (2H, br), 7.01-7.19 (5H, m), 8.58 (1H, s), 10.9 (1H, br).<br>[ESI+]: 619 |
| 173 | NMR-DMSO-$d_6$: 1.88 (2H, br), 2.00 (3H, s), 2.42 (2H, br), 3.39 (2H, m), 3.75 (6H, s), 4.92 (2H, br), 6.61 (2H, m), 7.02-7.19 (5H, m), 8.60 (1H, s), 9.33 (1H, s), 9.77 (1H, s), 11.7 (1H, s).<br>[ESI+]: 549 |
| 174 | NMR-DMSO-$d_6$: 1.87 (2H, br), 2.01 (3H, s), 2.41 (2H, br), 2.70 (3H, s), 3.04 (2H, br), 3.42 (2H, br), 3.75 (6H, s), 4.85 (2H, br), 6.59 (2H, br), 6.93-7.18 (5H, m), 10.4 (1H, s), 11.8 (1H, br).<br>[ESI+]: 577 |
| 175 | NMR-DMSO-$d_6$: 1.21 (3H, d, J = 6.3 Hz), 1.88 (2H, br), 2.00 (3H, s), 2.42 (2H, br), 3.36-3.66 (4H, m), 3.74 (6H, s), 4.11-4.19 (1H, m), 4.91-5.05 (2H, m), 6.61 (2H, br), 7.01-7.19 (5H, m), 8.59 (1H, s), 11.5 (1H, s).<br>[ESI+]: 576 |
| 176 | NMR-DMSO-$d_6$: 1.34-1.77 (7H, m), 2.31-2.42 (2H, m), 2.68 (3H, s), 3.26-3.32 (2H, m), 3.73 (3H, s), 4.62-4.85 (2H, m), 5.23-5.81 (2H, m), 6.86-7.29 (9H, m), 7.58 (2H, br), 10.7 (1H, s).<br>[ESI+]: 533<br>mp: 120-121° C. |
| 177 | [ESI+]: 532 |
| 178 | NMR-DMSO-$d_6$: 1.84 (2H, br), 2.37 (2H, br), 2.70 (3H, s), 2.92 (3H, s), 3.32-3.35 (4H, m), 3.56 (2H, br), 3.75 (6H, s), 4.70-4.99 (2H, m), 6.47-6.55 (3H, m), 7.00 (1H, br), 7.18-7.29 (4H, m), 8.60 (1H, s), 11.0 (1H, s).<br>[ESI+]: 591 |
| 179 | [ESI+]: 572 |
| 180 | [ESI+]: 589 |
| 181 | [ESI+]: 585 |
| 182 | [ESI+]: 550 |
| 183 | [ESI+]: 587 |
| 184 | [ESI+]: 592, 594 |
| 185 | [ESI+]: 592, 594 |
| 186 | [ESI+]: 611 |

TABLE 133

| Ex | Data |
|---|---|
| 187 | [ESI+]: 590 |
| 188 | [ESI+]: 573 |
| 189 | [ESI+]: 572 |
| 190 | [ESI+]: 589 |
| 191 | [ESI+]: 570 |
| 192 | [ESI+]: 546 |
| 193 | [ESI+]: 596 |
| 194 | [ESI+]: 604 |
| 195 | [ESI+]: 544 |
| 196 | [ESI+]: 601 |
| 197 | [ESI+]: 575 |
| 198 | [ESI+]: 547 |
| 199 | [ESI+]: 578, 580 |
| 200 | [ESI+]: 576<br>NMR-DMSO-$d_6$: 1.26-1.28 (4H, m), 1.41-1.48 (2H, m), 2.15 (3H, s), 2.24 (2H, m), 2.63 (1H, m), 2.69 (3H, s), 2.87 (6H, s), 3.35 (1H, m), 3.77 (3H, s), 4.73-4.78 (2H, m), 5.72-5.95 (2H, m), 7.16-7.35 (2H, m), 8.18 (1H, m), 10.9 (1H, br). |
| 201 | [ESI+]: 548 |

TABLE 133-continued

| Ex | Data |
| --- | --- |
| 202 | [ESI+]: 589 |
| 203 | [ESI+]: 611 |
| 204 | [ESI+]: 591 |
| 205 | [ESI+]: 589 |
| 206 | [ESI+]: 585 |
| 207 | [ESI+]: 589 |
| 208 | [ESI+]: 590<br>NMR-DMSO-d$_6$: 1.23-1.31 (4H, m), 1.41-1.49 (2H, m), 2.20-2.28 (2H, m), 2.68 (3H, s), 2.87 (6H, s), 3.31-3.39 (2H, m), 3.79 (3H, s), 4.71-4.80 (2H, m), 6.73-6.80 (2H, m), 6.92-7.36 (4H, m), 8.19 (1H, br), 10.85 (1H, br).<br>mp: 114-115° C. |
| 209 | [ESI+]: 586 |
| 210 | [ESI+]: 590 |
| 211 | [ESI+]: 606 |
| 212 | [ESI+]: 589 |

TABLE 134

| Ex | Data |
| --- | --- |
| 213 | [ESI+]: 561 |
| 214 | [ESI+]: 597 |
| 215 | [ESI+]: 578 |
| 216 | [ESI+]: 550 |
| 217 | [ESI+]: 562 |
| 218 | [ESI+]: 622 |
| 219 | [ESI+]: 596, 598 |
| 220 | [ESI+]: 568 |
| 221 | [ESI+]: 562<br>NMR-DMSO-d$_6$: 1.26-1.28 (4H, m), 1.43-1.49 (2H, m), 2.28 (2H, m), 2.63 (1H, m), 2.69 (3H, s), 2.87 (6H, s), 3.35 (1H, m), 3.79 (3H, s), 4.73-4.77 (2H, m), 5.87-6.34 (2H, m), 7.16-7.49 (2H, m), 8.15 (1H, m), 10.8 (1H, br).<br>mp: 112-113° C. |
| 222 | [ESI+]: 562 |
| 223 | [ESI+]: 658 |
| 224 | [ESI+]: 600 |
| 225 | [ESI+]: 540 |
| 226 | [ESI+]: 512 |
| 227 | [ESI+]: 576 |
| 228 | [ESI+]: 604 |
| 229 | [ESI+]: 580 |
| 230 | [ESI+]: 577 |
| 231 | [ESI+]: 549 |
| 232 | [ESI+]: 578 |
| 233 | [ESI+]: 561 |
| 234 | [ESI+]: 612 |
| 235 | [ESI+]: 596 |
| 236 | [ESI+]: 612 |
| 237 | [ESI+]: 598 |
| 238 | [ESI+]: 532 |
| 239 | [ESI+]: 546 |
| 240 | [ESI+]: 615 |
| 241 | [ESI+]: 633 |
| 242 | [ESI+]: 647 |

TABLE 135

| Ex | Data |
| --- | --- |
| 243 | [ESI+]: 618 |
| 244 | [ESI+]: 565 |
| 245 | [ESI+]: 533 |
| 246 | [ESI+]: 591 |
| 247 | [ESI+]: 534 |
| 248 | [ESI+]: 533 |
| 249 | [ESI+]: 592 |
| 250 | [ESI+]: 579 |
| 251 | [ESI+]: 609 |
| 252 | [ESI+]: 551 |

TABLE 135-continued

| Ex | Data |
| --- | --- |
| 253 | [ESI+]: 579 |
| 254 | [ESI+]: 609 |
| 255 | [ESI+]: 547<br>NMR-DMSO-d$_6$: 1.32-1.77 (2H, m), 2.28-2.42 (2H, m), 2.52-2.56 (3H, s), 2.65-2.67 (3H, m), 3.27-3.34 (2H, m), 3.72-3.73 (3H, m), 4.62-4.86 (2H, m), 5.24-5.82 (2H, m), 6.85-6.91 (2H, m), 7.04-7.29 (7H, m), 7.63 (1H, br), 10.73 (1H, br). |
| 256 | [ESI+]: 567<br>NMR-DMSO-d$_6$: 1.40-1.82 (2H, m), 2.55-2.73 (5H, m), 2.86-2.87 (6H, m), 3.33-3.39 (2H, m), 3.73 (3H, s), 4.63-4.87 (2H, m), 5.28-5.85 (2H, m), 6.73-6.94 (4H, m), 7.20-7.31 (3H, m), 10.79 (1H, br).<br>mp: 118-120° C. |
| 257 | [ESI+]: 538 |
| 258 | [ESI+]: 597 |
| 259 | [ESI+]: 576 |
| 260 | [ESI+]: 589 |
| 261 | [ESI+]: 625, 627 |
| 262 | [ESI+]: 596, 598 |
| 263 | [ESI+]: 607 |
| 264 | [ESI+]: 576 |
| 265 | [ESI+]: 596, 598 |

TABLE 136

| Ex | Data |
| --- | --- |
| 266 | [ESI+]: 546<br>NMR-DMSO-d$_6$: 1.24 (3H, t, J = 7.4 Hz), 1.34-1.78 (2H, m), 2.30-2.40 (2H, m), 2.64-2.66 (3H, m), 3.35-3.50 (4H, m), 3.72-3.73 (3H, m), 4.62-4.86 (2H, m), 5.24-5.82 (2H, m), 6.86-6.90 (2H, m), 7.05-7.29 (7H, m), 11.11 (1H, br).<br>mp: 123-125° C. |
| 267 | [ESI+]: 558 |
| 268 | [ESI+]: 591 |
| 269 | [ESI+]: 550 |
| 270 | [ESI+]: 564 |
| 271 | [ESI+]: 564 |
| 272 | [ESI+]: 552<br>NMR-DMSO-d$_6$: 1.24 (3H, t, J = 7.3 Hz), 1.43-1.82 (2H, m), 2.55-2.73 (5H, m), 3.33-3.39 (2H, m), 3.44-3.51 (2H, m), 3.73 (3H, s), 4.63-4.87 (2H, m), 5.28-5.85 (2H, m), 6.74-6.94 (4H, m), 7.20-7.31 (3H, m), 11.09 (1H, br).<br>mp: 124-126° C. |
| 273 | [ESI+]: 576 |
| 274 | [ESI+]: 550 |
| 275 | [ESI+]: 550 |
| 276 | [ESI+]: 585 |
| 277 | [ESI+]: 550<br>NMR-DMSO-d$_6$: 1.22-1.81 (2H, m), 2.33-2.40 (2H, m), 2.66-2.68 (3H, m), 3.33-3.41 (5H, m), 3.74-3.76 (3H, m), 4.66-4.89 (2H, m), 5.50-5.86 (2H, m), 6.71-6.85 (2H, m), 7.05-7.31 (6H, m), 11.11 (1H, br).<br>mp: 121-123° C. |
| 278 | [ESI+]: 564<br>NMR-DMSO-d$_6$: 1.24 (3H, t, J = 7.3 Hz), 1.32-1.80 (2H, m), 2.32-2.40 (2H, m), 2.65-2.67 (3H, m), 3.32-3.50 (4H, m), 3.74-3.76 (3H, m), 4.66-4.90 (2H, m), 5.50-5.86 (2H, m), 6.71-6.85 (2H, m), 7.04-7.33 (6H, m), 11.10 (1H, br).<br>mp: 111-112° C. |
| 279 | [ESI+]: 633 |
| 280 | [ESI+]: 610, 612 |
| 281 | [ESI+]: 560 |

TABLE 137

| Ex | Data |
| --- | --- |
| 282 | [ESI+]: 565 |
| 283 | [ESI+]: 553<br>NMR-DMSO-d$_6$: 1.43-1.82 (2H, m), 2.52-2.73 (8H, m), 3.29-3.38 (2H, m), 3.73 (3H, s), 4.61-4.87 (2H, m), |

TABLE 137-continued

| Ex | Data |
|---|---|
| | 5.28-5.84 (2H, m), 6.73-6.93 (4H, m), 7.20-7.31 (3H, m), 7.62 (1H, br), 10.70 (1H, br). mp: 106-109° C. |
| 284 | [ESI+]: 565 NMR-DMSO-$d_6$: 1.33-1.82 (2H, m), 2.32-2.42 (2H, m), 2.53 (3H, s), 2.68 (3H, s), 3.34-3.42 (2H, m), 3.74-3.76 (3H, m), 4.64-4.92 (2H, m), 5.50-5.87 (2H, m), 6.69-6.86 (2H, m), 7.02-7.32 (6H, m), 7.62 (1H, br), 10.71 (1H, br). |
| 285 | [ESI+]: 560 NMR-DMSO-$d_6$: 1.30 (6H, d, J = 6.8 Hz), 1.35-1.76 (2H, m), 2.28-2.42 (2H, m), 2.63-2.65 (3H, m), 3.26-3.34 (2H, m), 3.72-3.81 (4H, m), 4.63-4.86 (2H, m), 5.24-5.83 (2H, m), 6.85-6.90 (2H, m), 7.04-7.29 (7H, m), 11.09 (1H, br). mp: 137-138° C. |
| 286 | [ESI+]: 607 |
| 287 | [ESI+]: 532 |
| 288 | [ESI+]: 601 |
| 289 | [ESI+]: 563 |
| 290 | [ESI+]: 561 NMR-DMSO-$d_6$: 1.32-1.78 (2H, m), 2.30-2.42 (2H, m), 2.73-2.65 (3H, m), 2.86-2.88 (6H, m), 3.27-3.32 (2H, m), 3.72-3.73 (3H, m), 4.62-4.86 (2H, m), 5.24-5.83 (2H, m), 6.86-6.90 (2H, m), 7.04-7.29 (7H, m), 10.82 (1H, br). mp: 110-112° C. |
| 291 | [ESI+]: 562 |
| 292 | [ESI+]: 575 |
| 293 | [ESI+]: 581, 583 |
| 294 | [ESI+]: 552, 554 |
| 295 | [ESI+]: 595, 597 |
| 296 | [ESI+]: 592 |
| 297 | [ESI+]: 576 |
| 298 | [ESI+]: 612, 614 |
| 299 | [ESI+]: 650, 652 |

TABLE 138

| Ex | Data |
|---|---|
| 300 | [ESI+]: 606, 608 |
| 301 | [ESI+]: 628 |
| 302 | [ESI+]: 576 |
| 303 | [ESI+]: 590 |
| 304 | [ESI+]: 590 |
| 305 | [ESI+]: 612 |
| 306 | [ESI+]: 561 NMR-DMSO-$d_6$: 1.01 (3H, t, J = 7.2), 1.86 (2H, br), 2.00 (3H, s), 2.32-2.64 (2H, m), 2.69-2.79 (2H, m), 3.28-3.51 (2H, br), 3.74 (6H, s), 4.66-4.97 (2H, m), 5.50 (1H, br), 6.51-6.85 (2H, m), 6.94-7.35 (5H, m), 7.83 (1H, s). mp: 203-205° C. |
| 307 | [ESI+]: 576 NMR-DMSO-$d_6$: 1.26-1.28 (4H, m), 1.41-1.48 (2H, m), 2.15 (3H, s), 2.19-2.26 (2H, m), 2.58 (6H, s), 2.60 (3H, s), 3.25-3.32 (2H, m), 3.78 (3H, s), 4.68 (2H, br), 5.72-5.96 (2H, m), 7.31-7.42 (2H, m), 8.15 (1H, br). |
| 308 | [ESI+]: 590 NMR-DMSO-$d_6$: 1.21-1.31 (4H, m), 1.40-1.49 (2H, m), 2.22-2.29 (2H, m), 2.58 (6H, s), 2.62 (3H, s), 3.23-3.29 (2H, m), 3.79 (3H, s), 6.76-6.82 (2H, m), 6.92-7.06 (1H, m), 7.19-7.41 (3H, m), 8.16 (1H, br). mp: 219-221° C. |

INDUSTRIAL APPLICABILITY

The compound of the formula (I) or a salt thereof has an antagonistic action against LPA receptor and can be used as an agent for preventing and/or treating diseases caused by LPA.

The invention claimed is:

1. A compound of the formula (I) or a salt thereof:

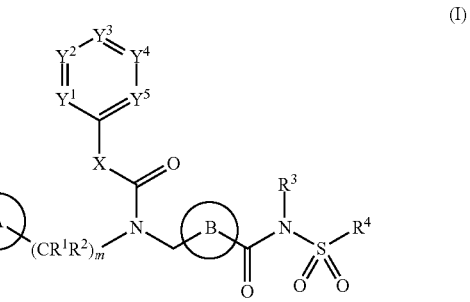

(I)

wherein
A is aryl which may be substituted or an aromatic hetero ring group which may be substituted,
B is a 5-membered aromatic hetero ring group which may be substituted,
X is a single bond or —$(CR^{X1}R^{X2})_n$—,
n is 1, 2, 3, or 4,
$R^{X1}$ and $R^{X2}$ are the same as or different from each other, and are H, halogen, OH, —O— (lower alkyl which may be substituted), or lower alkyl which may be substituted, or
$R^{X1}$ and $R^{X2}$ are combined with each other to form oxo (=O), or
$R^{X1}$ and $R^{X2}$ are combined with each other to form $C_{2-5}$ alkylene which may be
substituted,
in which when n is 2, 3, or 4, $R^{X1}$ may be combined with adjacent $R^{X1}$ to form a new bond,
$Y^1, Y^2, Y^3, Y^4$, and $Y^5$ are the same as or different from each other, and are $CR^Y$ or N,
$R^Y$'s are the same as or different from each other, and are H, OH, halogen, —O-(lower alkyl which may be substituted), —S-(lower alkyl which may be substituted), lower alkyl which may be substituted, lower alkenyl which may be substituted, or cycloalkyl which may be substituted,
$R^1$ and $R^2$ are the same as or different from each other, and are H, halogen, —O-(lower alkyl which may be substituted), or lower alkyl which may be substituted,
m is 1, 2, or 3,
$R^3$ is H, or lower alkyl which may be substituted,
$R^4$ is lower alkyl which may be substituted, lower alkenyl which may be substituted, cycloalkyl which may be substituted, aryl which may be substituted, a hetero ring group which may be substituted, or $NR^{101}R^{102}$, or
$R^3$ and $R^4$ may be combined with each other to form $C_{2-5}$ alkylene which may be substituted, and
$R^{101}$ and $R^{102}$ are the same as or different from each other, and are H, OH, —O-(lower alkyl which may be substituted), —C(=O)-(lower alkyl which may be substituted), —C(=O)—O-(lower alkyl which may be substituted), —NH—C(=O)-(lower alkyl which may be substituted), lower alkyl which may be substituted, lower alkenyl which may be substituted, cycloalkyl which may be substituted, aryl which may be substituted, or a hetero ring group which may be substituted, or
$R^{101}$ and $R^{102}$ may be combined with nitrogen atoms to which they are bonded to form nitrogen-containing monocyclic saturated hetero ring group,
in which when $R^4$ is $NR^{101}R^{102}$, at least one of $R^3$, $R^{101}$, and $R^{102}$ is H.

2. The compound or a salt thereof according to claim 1, wherein A is phenyl which may be substituted with halogen, or a 5-membered aromatic hetero ring which may be substituted with halogen or lower alkyl, and $R^4$ is lower alkyl which may be substituted, cycloalkyl which may be substituted, aryl which may be substituted, or a nitrogen-containing hetero ring group which may be substituted, or $NR^{101}R^{102}$.

3. The compound or a salt thereof according to claim 2, wherein B is

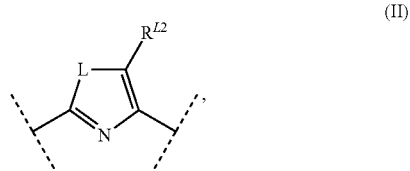

L is S, and
$R^{L2}$ represents H, halogen, or lower alkyl which may be substituted with halogen or OH.

4. The compound or a salt thereof according to claim 3, wherein
X is a single bond,
$Y^1$, $Y^2$, $Y^3$, $Y^4$, and $Y^5$ are $CR^Y$, and $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, $R^4$ is lower alkyl (in which the lower alkyl may be substituted with halogen, OH, or —O—C(O)-lower alkyl), a 5-membered nitrogen-containing hetero ring group which may be substituted with lower alkyl, cycloalkyl, aryl, or $NR^{101}R^{102}$, and $R^{101}$ and $R^{102}$ are the same as or different from each other, and are H, OH, O-(lower alkyl which may be substituted with halogen), lower alkyl (in which the lower alkyl may be substituted with halogen, OH, S-lower alkyl, or a hetero ring group), —C(=O)—O-(lower alkyl which may be substituted with aryl), a hetero ring group which may be substituted with lower alkyl, or lower alkenyl, m is 3, and $R^1$ and $R^2$ are the same as or different from each other, and are H, halogen, —O-(lower alkyl which may be substituted with halogen), or lower alkyl which may be substituted with halogen.

5. The compound or a salt thereof according to claim 4, wherein $Y^1$, $Y^2$, $Y^3$, $Y^4$, and $Y^5$ are $CR^Y$, and $R^Y$'s are the same as or different from each other, and are H, lower alkyl, or —O-(lower alkyl), and $R^3$ is H.

6. The compound or a salt thereof according to claim 5, wherein $R^4$ is $NR^{101}R^{102}$, $R^{101}$ is H, and $R^{102}$ is H, O-(lower alkyl which may be substituted with halogen), lower alkyl (in which the lower alkyl may be substituted with halogen, OH, S-lower alkyl, or a hetero ring group), —C(=O)—O-(lower alkyl which may be substituted with aryl), a hetero ring group which may be substituted with lower alkyl, or lower alkenyl.

7. The compound or a salt thereof according to claim 5, wherein $R^4$ is $NR^{101}R^{102}$, $R^{101}$ is H, and $R^{102}$ is lower alkyl, in which the lower alkyl may be substituted with halogen, OH, S-lower alkyl, or a hetero ring group.

8. The compound or a salt thereof according to claim 5, wherein $R^4$ is $NR^{101}R^{102}$, $R^{101}$ is H, and $R^{102}$ is methyl which may be substituted with a group selected from Group $G^2$, ethyl which may be substituted with a group selected from Group $G^2$, or propyl which may be substituted with a group selected from Group $G^2$, in which Group $G^2$ is halogen, OH, S-lower alkyl, or a hetero ring group.

9. The compound or a salt thereof according to claim 3, wherein X is a single bond, $Y^1$, $Y^2$, $Y^3$, $Y^4$, and $Y^5$ are $CR^Y$, and $R^Y$'s are the same as or different from each other, and are H, OH, halogen, —O-(lower alkyl which may be substituted with halogen or —O-lower alkyl), lower alkyl which may be substituted with halogen or —O-lower alkyl, or cycloalkyl which may be substituted with halogen or —O-lower alkyl, $R^3$ is H, $R^4$ is $NR^{101}R^{102}$, $R^{101}$ and $R^{102}$ are the same as or different from each other, and are H, —O-(lower alkyl which may be substituted with halogen), —C(=O)-(lower alkyl which may be substituted with halogen), —C(=O)—O-(lower alkyl which may be substituted with halogen), lower alkyl which may be substituted with halogen or OH, or hetero ring which may be substituted with halogen or OH, or $R^{101}$ and $R^{102}$ are combined with nitrogen atoms to which they are bonded to form a nitrogen-containing monocyclic saturated hetero ring, m is 3, and $R^1$ and $R^2$ are the same as or different from each other, and are H, halogen, —O-(lower alkyl which may be substituted with halogen), or lower alkyl which may be substituted with halogen.

10. The compound or a salt thereof according to claim 9, wherein $R^4$ is $NR^{101}R^{102}$, $R^{101}$ is H, and $R^{102}$ is H, methoxy, acetyl, methoxycarbonyl, methyl, ethyl, 2-fluoroethyl, 2-hydroxyethyl, or pyridin-2-yl.

11. The compound or a salt thereof according to claim 1, which is
N-(aminosulfonyl)-2-{[(3,5-dimethoxy-4-methylbenzoyl)(3-phenylpropyl)amino]methyl}-1,3-thiazole-4-carboxamide;
5-chloro-2-{[(3,5-dimethoxybenzoyl)(3-phenylpropyl)amino]methyl}-N-(methylsulfonyl)-1,3-thiazole-4-carboxamide;
2-{[(3,5-dimethoxy-4-methylbenzoyl)(3-phenylpropyl)amino]methyl}-N-[(ethylamino)sulfonyl]-1,3-thiazole-4-carboxamide;
2-{[(3,5-dimethoxybenzoyl)(3-phenylpropyl)amino]methyl}-5-methyl-N-[(methylamino)sulfonyl]-1,3-thiazole-4-carboxamide;
2-{[(4-ethyl-3,5-dimethoxybenzoyl)(3-phenylpropyl)amino]methyl}-5-methyl-N-[(methylamino)sulfonyl]-1,3-thiazole-4-carboxamide;
N-(dimethylsulfamoyl)-2-[({[1-(5-methoxypyridin-2-yl)cyclopropyl]carbonyl}[3-(5-methyl-2-furyl)propyl]amino)methyl]-5-methyl-1,3-thiazole-4-carboxamide, or
N-(dimethylsulfamoyl)-2-[([3-(3-fluorophenyl)propyl]{[1-(5-methoxypyridin-2-yl)cyclopropyl]carbonyl}amino)methyl]-5-methyl-1,3-thiazole-4-carboxamide.

12. The compound or a salt thereof according to claim 11, which is N-(aminosulfonyl)-2-{[(3,5-dimethoxy-4-methylbenzoyl)(3-phenylpropyl)amino]methyl}-1,3-thiazole-4-carboxamide.

13. The compound or a salt thereof according to claim 11, which is 2-{[(4-ethyl-3,5-dimethoxybenzoyl)(3-phenylpropyl)amino]methyl}-5-methyl-N-[(methylamino)sulfonyl]-1,3-thiazole-4-carboxamide.

14. The compound or a salt thereof according to claim 11, which is 2-{[(3,5-dimethoxy-4-methylbenzoyl)(3-phenylpropyl)amino]methyl}-N-[(ethylamino)sulfonyl]-1,3-thiazole-4-carboxamide.

15. A pharmaceutical composition comprising a compound or a salt thereof according to claim 12 and a pharmaceutically acceptable excipient.

16. A method for treating a disease caused by lysophosphatidic acid selected from the group consisting of benign prostatic hyperplasia, urinary dysfunction associated with benign prostatic hyperplasia, bladder neck sclerosis, and underactive bladder, comprising administering an effective amount of a compound or a salt thereof according to claim 11 to a subject in need thereof.

17. A method for treating a disease caused by lysophosphatidic acid selected from the group consisting of breast cancer, chronic renal diseases associated with fibrosis and idiopathic pulmonary fibrosis, comprising administering an effective amount of a compound or a salt thereof according to claim 11 to a subject in need thereof.

18. A method for treating urinary dysfunction associated with benign prostatic hyperplasia, comprising administering an effective amount of a compound or a salt thereof according to claim 12 to a subject in need thereof.

19. A method for treating urinary dysfunction associated with benign prostatic hyperplasia, comprising administering an effective amount of a compound or a salt thereof according to claim 13 to a subject in need thereof.

20. A method for treating urinary dysfunction associated with benign prostatic hyperplasia, comprising administering an effective amount of a compound or a salt thereof according to claim 14 to a subject in need thereof.

21. A method for treating urinary dysfunction associated with benign prostatic hyperplasia, comprising orally administering an effective amount of a compound or a salt thereof according to claim 12 to a subject in need thereof.

22. A method for treating urinary dysfunction associated with benign prostatic hyperplasia, comprising orally administering an effective amount of a compound or a salt thereof according to claim 13 to a subject in need thereof.

23. A method for treating urinary dysfunction associated with benign prostatic hyperplasia, comprising orally administering an effective amount of a compound or a salt thereof according to claim 14 to a subject in need thereof.

24. A method for treating benign prostatic hyperplasia, comprising administering an effective amount of a compound or a salt thereof according to claim 12 to a subject in need thereof.

25. A method for treating benign prostatic hyperplasia, comprising administering an effective amount of a compound or a salt thereof according to claim 13 to a subject in need thereof.

26. A method for treating benign prostatic hyperplasia, comprising administering an effective amount of a compound or a salt thereof according to claim 14 to a subject in need thereof.

* * * * *